United States Patent
Anand et al.

(10) Patent No.: US 8,796,258 B2
(45) Date of Patent: Aug. 5, 2014

(54) CYCLIC AZABENZIMIDAZOLE DERIVATIVES USEFUL AS ANTI-DIABETIC AGENTS

(75) Inventors: Rajan Anand, Fanwood, NJ (US); James M. Apgar, Highland Park, NJ (US); Tesfaye Biftu, Freehold, NJ (US); Ping Chen, Edison, NJ (US); Lin Chu, Scotch Plains, NJ (US); Vincent J. Colandrea, North Brunswick, NJ (US); Guizhen Dong, Dayton, NJ (US); James F. Dropinski, Colts Neck, NJ (US); Danqing Feng, Green Brook, NJ (US); Jacqueline D. Hicks, Scotch Plains, NJ (US); Jinlong Jiang, Scotch Plains, NJ (US); Alexander J. Kim, Morganville, NJ (US); Kenneth J. Leavitt, Plainsboro, NJ (US); Bing Li, Towaco, NJ (US); Xiaoxia Qian, New York, NY (US); Iyassu Sebhat, Jersey City, NJ (US); Lan Wei, Berkeley Heights, NJ (US); Robert R. Wilkening, Maplewood, NJ (US); Zhicai Wu, Montvale, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/812,536

(22) PCT Filed: Feb. 23, 2012

(86) PCT No.: PCT/US2012/026261
§ 371 (c)(1),
(2), (4) Date: Jan. 28, 2013

(87) PCT Pub. No.: WO2012/116145
PCT Pub. Date: Aug. 30, 2012

(65) Prior Publication Data
US 2013/0123237 A1     May 16, 2013

Related U.S. Application Data

(60) Provisional application No. 61/446,551, filed on Feb. 25, 2011.

(51) Int. Cl.
*A61K 31/00* (2006.01)
*C07D 513/02* (2006.01)

(52) U.S. Cl.
USPC ...... 514/210.21; 514/303; 514/253; 546/118; 544/362

(58) Field of Classification Search
USPC ............ 514/210.21, 303, 253; 546/118; 544/362
See application file for complete search history.

(56) References Cited

U.S. PATENT DOCUMENTS

| | | | |
|---|---|---|---|
| 6,312,662 B1 | 11/2001 | Erion et al. | |
| 6,489,476 B1 | 12/2002 | Dang et al. | |
| 7,799,782 B2 * | 9/2010 | Munson et al. | 514/234.5 |
| 2004/0186127 A1 * | 9/2004 | Daun et al. | 514/303 |
| 2005/0038068 A1 | 2/2005 | Iyengar et al. | |
| 2005/0148643 A1 | 7/2005 | Rui et al. | |
| 2006/0287356 A1 | 12/2006 | Iyengar et al. | |
| 2007/0015665 A1 | 1/2007 | Potluri et al. | |
| 2007/0032529 A1 | 2/2007 | Takagi et al. | |
| 2011/0142798 A1 * | 6/2011 | Qiu et al. | 424/85.4 |
| 2012/0101064 A1 * | 4/2012 | Howard et al. | 514/81 |

FOREIGN PATENT DOCUMENTS

| | | |
|---|---|---|
| DE | 33 16 095 A1 | 11/1983 |
| EP | 0 126 030 A2 | 11/1984 |
| EP | 0 126 030 A3 | 11/1984 |
| EP | 0 128 862 B1 | 12/1984 |
| EP | 0 129 506 B1 | 12/1984 |
| EP | 0 120 403 B1 | 6/1987 |
| JP | 6-298731 A | 10/1994 |
| WO | 93/07124 A1 | 4/1993 |
| WO | 95/29897 A1 | 11/1995 |
| WO | 98/39342 A1 | 9/1998 |
| WO | 98/39343 A1 | 9/1998 |
| WO | 00/03997 A1 | 1/2000 |
| WO | 00/14095 A1 | 3/2000 |
| WO | 01/53272 A1 | 7/2001 |
| WO | 01/53291 A1 | 7/2001 |
| WO | 02/40019 A1 | 5/2002 |
| WO | 02/092575 A1 | 11/2002 |
| WO | 03/018061 A1 | 3/2003 |

(Continued)

OTHER PUBLICATIONS

Kojima et al. CAS: 158: 243900, 2013.*

(Continued)

*Primary Examiner* — Rei-tsang Shiao
(74) *Attorney, Agent, or Firm* — Baerbel R. Brown; Catherine D. Fitch

(57) ABSTRACT

Novel compounds of structural formula (I) are activators of AMP-protein kinase and are useful in the treatment, prevention and suppression of diseases mediated by the AMPK-activated protein kinase. The compounds of the present invention are useful in the treatment of Type 2 diabetes, hyperglycemia, metabolic syndrome, obesity, hypercholesterolemia, and hypertension.

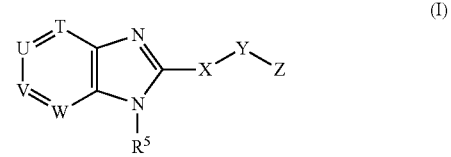

(I)

22 Claims, No Drawings

(56) References Cited

FOREIGN PATENT DOCUMENTS

| | | |
|---|---|---|
| WO | 2005/002520 A2 | 1/2005 |
| WO | 2005/002520 A3 | 1/2005 |
| WO | 2005/018672 A1 | 3/2005 |
| WO | 2005/020892 A2 | 3/2005 |
| WO | 2005/020892 A3 | 3/2005 |
| WO | 2005/051298 A2 | 9/2005 |
| WO | 2005/051298 A3 | 9/2005 |
| WO | 2006/094209 A2 | 9/2006 |
| WO | 2006/094209 A3 | 9/2006 |
| WO | 2008/006432 A1 | 1/2008 |
| WO | 2010/036613 A1 | 4/2010 |
| WO | 2010/047982 A1 | 4/2010 |
| WO | 2010/051176 A1 | 5/2010 |
| WO | 2010/051206 A1 | 5/2010 |
| WO | 2011/028455 A1 | 3/2011 |

OTHER PUBLICATIONS

Bergeron, R. et al., "Effect of 5-Aminoimidazole-4-Carboxamide-1-B-D-Ribofuranoside Infusion on In Vivo Glucose and Lipid Metabolism in Lean and Obese Zucker Rats", Diabetes, 2001, p. 1076-1082, vol. 50.

Blazquez, C. et al., "The AMP-Activated Protein Kinase Is Involved in the Regulation of Ketone Body Production by Astrocytes", Journal of Neurochemistry, 1999, p. 1674-1682, vol. 73.

Buhl, E. S. et al., "Long-Term AICAR Administration Reduces Metabolic Distrubances and Lowers Blood Pressure in Rats Displaying Features of the Insulin Resistance Syndrome", Diabetes, 2002, p. 2199-2206, vol. 51.

Butler, A. E. et al., "B-Cell Deficit and Increased B-Cell Apoptosis in Humans With Type 2 Diabetes", Diabetes, 2003, p. 102-110, vol. 52.

Carling, D. et al., "A common bicyclic protein kinase cascade inactivates the reulatory enzymes of fatty acid and cholesterol biosynthesis", Feb. 1987, p. 217-222, Vo. 223, No. 2.

Halseth, A. E. et al., "Acute and chronic treatment of ob/ob and db/db mice with AICAR decreases blood glucose concentrations", Biochemical and Biophysical Research Communications, 2002, p. 798-805, vol. 294.

Hardie, D. G. et al., "AMP-activated protein kinase: the energy charge hypothesis revisited", BioEssays, 2001, p. 1112-1119, vol. 23.

Kemp, B. E. et al., "AMP-activated protein kinase, super metabolic regulator", Biochemical Society, 2003, p. 162-168.

Leclerc, I. et al., "Hepatocyte Nuclear Factor-4a Involved in Type 1 Maturity-Onset Diabetes of the Young Is a Novel Target of AMP-Activated Protein Kinase", Diabetes, 2001, p. 1515-1521, vol. 50.

Lochhead, P. A. et al., "5-Aminoimidazole-4-Carboxamide Riboside Mimics the Effects of Insulin on the Expression of the 2 Key Gluconeogenic Genes PEPCK and Glucose-6-Phosphatase", Diabetes, 2000, p. 896-903, vol. 49.

Minokoshi, Y. et al., "Leptin Stimulates fatty-acid oxidation by activating AMP-activated protein kinase", Nature, 2002, p. 339-343, vol. 415.

Mu, J. et al., "A Role for AMP-Activated Protein Kinase in Contration- and Hypoxia-Regulated Glucose Transport in Skeletal Muscle", Molecular Cell, 2001, p. 1085-1094, vol. 7.

Muoio, D. M. et al., "AMP-activated kinase reciprocally regulates triacylglycerol synthesis and fatty acid oxidation in liver and muscle: evidence that sn-glycerol-3-phosphate acyltransferase is a novel target", Biochem J., 1999, p. 783-791, vol. 338.

Musi, N. et al., "Targeting the AMP-Activated Protein Kinase for the Treatment of Type 2 Diabetes", Current Drug Targets—Immune, Endocrine & Metabolic Disorders, 2002, p. 119-127, vol. 2.

Musi, N. et al., "Metformin Increases AMP-Activated Protein Kinase Activity in Skeletal Muscle of Subjects With Type 2 Diabetes", Diabetes, 2002, p. 2074-2081, vol. 51.

Polonsky, K. S., "Dynamics in insulin secretion in obesity and diabetes", International Journal of Obesity, 2000, p. S91-S31, vol. 24, Suppl. 2.

Song, X. M. et al., 5-Aminoimidazole-4-carboxamide ribonucleoside treatment improves glucose homeostasis in insulin-resistant diabetic (ob/ob) mice, Diabetologia, 2002, p. 56-65, vol. 45.

Zhou, M. et al., "UCP-3 expressionin skeletal muscle: effects of exercise, hypoxia, and AMP-activated protein kinase", Am J Physiol Endocrinol Metab, 2000, p. E622-E629, vol. 279.

Zhou, G. et al., "Role of AMP-activated protein kinase in mechanism of metformin action", The Journal of Clinical Investigation, 2001, p. 1167-1174, vol. 108, No. 8.

Chen, Z.P. et al., "AMP-activated protein kinase phosphorylation of endothelial NO synthase", FEBS Letters, 1999, p. 285-289, vol. 443.

* cited by examiner

CYCLIC AZABENZIMIDAZOLE DERIVATIVES USEFUL AS ANTI-DIABETIC AGENTS

CROSS-REFERENCE TO RELATED APPLICATIONS

This application is a U.S. National Phase application under 35 U.S.C. §371 of PCT Application No. PCT/US2012/026261, filed Feb. 23, 2012, which claims priority from and the benefit of U.S. Provisional Application No. 61/446,551, filed Feb. 25, 2011.

BACKGROUND OF THE INVENTION

Diabetes is characterized by elevated levels of plasma glucose (hyperglycemia) in the fasting state or after administration of glucose during an oral glucose tolerance test. In type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients having Type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, Int. J. Obes. Relat. Metab. Disord. 24 Suppl 2:S29-31, 2000). Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the beta cells within the pancreatic islets initially compensate for insulin resistance by increasing insulin output. The onset of Type 2 diabetes due to insufficient increases (or actual declines) in beta cell mass is apparently due to increased beta cell apoptosis relative to non-diabetic insulin resistant individuals (Butler et al., Diabetes 52:102-110, 2003).

Persistent or uncontrolled hyperglycemia is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or Metabolic Syndrome. Patients with Metabolic Syndrome have an increased risk of developing atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglitide); and (5) inhibitors of incretin hormone degradation (DPP-4 inhibitors, such as sitagliptin).

Many of the current treatments for diabetes have unwanted side effects. Phenformin and metformin can induce lactic acidosis, nausea/vomiting, and diarrhea. Metformin has a lower risk of side effects than phenformin and is widely prescribed for the treatment of Type 2 diabetes. The currently marketed PPAR gamma agonists are modestly effective in reducing plasma glucose and hemoglobinA1C, and do not greatly improve lipid metabolism or the lipid profile. Sulfonylureas and related insulin secretagogues can cause insulin secretion even if the glucose level is low, resulting in hypoglycemia, which can be fatal in severe cases. The administration of insulin secretagogues must therefore be carefully controlled. There remains a need for treatments for diabetes that work by novel mechanisms of action and that exhibit fewer side effects.

AMP-activated protein kinase (AMPK) has been identified as a regulator of carbohydrate and fatty acid metabolism that helps maintain energy balance in response to environmental and nutritional stress. There is evidence that activation of AMPK results in a number of beneficial effects on lipid and glucose metabolism by reducing glucogenesis and de novo lipogenesis (fatty acid and cholesterol synthesis), and by increasing fatty acid oxidation and skeletal muscle glucose uptake. Inhibition of ACC, by phosphorylation by AMPK, leads to a decrease in fatty acid synthesis and to an increase in fatty acid oxidation, while inhibition of HMG-CoA reductase, by phosphorylation by AMPK, leads to a decrease in cholesterol synthesis (Carling, D. et. al., FEBS Letters 223: 217 (1987)).

In the liver, AMPK activation results in a decrease in fatty acid and cholesterol synthesis, inhibiting hepatic glucose production and increasing fatty acid oxidation. It has been shown that AMP-activated protein kinase regulates triacylglycerol synthesis and fatty acid oxidation in liver and muscle via glycerol-3-phosphate acyltransferase (Muoio, D. M. et. al., Biochem. J. 338:783 (1999)). Another substance of AMPK, hepatocyte nuclear factor-4αa, has been shown to be involved in type-1 maturity onset diabetes (Leclerc, I. et. al., Diabetes 50:1515 (2001)). Additional processes believed to be regulated through AMPK activation include the stimulation of glucose transport in skeletal muscle and the regulation of key genes in fatty acid and glucose metabolism in the liver (Hardie, D. G. and Hawley, S. A., Bioessays 23: 1112 (2001), Kemp, B. E. et. al., Biochem. Soc. Transactions 31:162 (2003), Musi, N. and Goodyear, L. J. Current Drug Targets-Immune, Endocrine and Metabolic Disorders 2:119 (2002);

Lochhead, P. A. et. al., Diabetes 49:896 (2000); and Zhou, G. et. al., J. of Clin. Invest. 108: 1167 (2001).

In vivo studies have demonstrated the following beneficial effects of both acute and chronic administration of AICAR, an AMPK activator, in rodent models of obesity and type 2 diabetes: 1) an improvement in glucose homeostasis in insulin-resistant diabetic (ob/ob) mice; 2) a decrease in blood glucose concentrations in ob/ob and db/db mice and a blood glucose reduction of 35% following 8 weeks of administration; and 3) a reduction in metabolic disturbances and a reduction of blood pressure in rats displaying characteristics of insulin resistance syndrome (Bergeron, R. et. al., Diabetes 50:1076 (2001); Song, S. M. et. al., Diabetologia 45:56 (2002); Halseth, A. E. et. al., Biochem. and Biophys. Res. Comm. 294:798 (2002); and Buhl, E. S. et. al., Diabetes 51: 2199 (2002)). A further study of 7 week AICAR administration in obese Zucker (fa/fa) rats lead to a reduction in plasma triglycerides and free fatty acids; an increase in HDL cholesterol; and a normalization of glucose metabolism as assessed by an oral glucose tolerance test (Minokoshi, Y. et. al., Nature 415: 339 (2002)). Expression of dominant negative AMPK in skeletal muscle of transgenic mice has demonstrated that the AICAR effect on stimulation of glucose transport is dependent on AMPK activation (Mu, J. et. al., Molecular Cell 7: 1085 (2001)).

Recent data also suggest that AMPK activation is involved in the glucose and lipid-lowering effects of the anti-diabetic drug metformin. It has been shown that the diabetes drug metformin can activate AMPK in vivo at high concentrations (Zhou, G. et. al., J. of Clin. Invest. 108: 1167 (2001); Musi, N. et. al. Diabetes 51: 2074 (2002)).

Based on these studies, it is expected that the in vivo activation of AMPK in the liver may result in the reduction of hepatic glucose output, an improvement in overall glucose homeostasis, a decrease in fatty acid and cholesterol synthesis, and an increase in fatty acid oxidation. Stimulation of AMPK in skeletal muscle is expected to result in an increase in glucose uptake and fatty acid oxidation with resulting improvement of glucose homeostasis, and an improvement in insulin action. Finally, the resulting increase in energy expenditure should lead to a decrease in body weight. The lowering of blood pressure has also been reported to be a consequence of AMPK activation.

Increased fatty acid synthesis is a characteristic of many tumor cells, therefore decreasing the synthesis of fatty acids via AMPK activation may also be useful as a cancer therapy. Activation of AMPK may also be useful to treat ischemic events in the brain (Blazquez, C. et. al., J. Neurochem. 73: 1674 (1999)); to prevent damage from reactive oxygen species (Zhou, M. et. al., Am. J. Physiol. Endocrinol. Metab. 279: E622 (2000)); and to improve local circulatory systems (Chen, Z.-P., et. al. AMP-activated protein kinase phosphorylation of endothelial NO synthase. FEBS Letters 443: 285 (1999)).

Compounds that activate AMPK are expected to be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent AMPK activators that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. Nos. 6,312,662; 6,489,476; US 2005/0148643; DE 3 316 095; JP 6 298 731; EP 0 126 030; EP 0 128 862; EP 0 129 506; and EP 0 120 403. AMPK activators are disclosed in WO 08/006,432; WO 05/051298; WO 05/020892; US 2007/015665; US 2007/032529; US 2006/287356; and US 2005/038068.

SUMMARY OF THE INVENTION

The present invention is concerned with novel benzimidazole derivatives of structural Formula I:

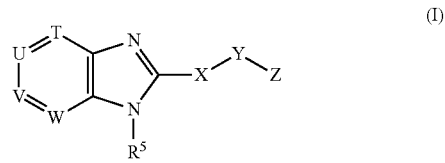

(I)

and pharmaceutically acceptable salts thereof. The compounds of structural formula I, and embodiments thereof, are activators of AMP-activated protein kinase (AMPK) and are useful in the treatment, prevention and suppression of diseases, disorders and conditions mediated by activation of AMP-activated protein kinase, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions responsive to activation of AMP-activated protein kinase in a subject in need thereof by administering the compounds and pharmaceutical compositions of the present invention. The present invention also relates to the use of compounds of the present invention for manufacture of a medicament useful in treating diseases, disorders and conditions responsive to the activation of AMP-activated protein kinase. The present invention is also concerned with treatment of these diseases, disorders and conditions by administering the compounds of the present invention in combination with a therapeutically effective amount of another agent known to be useful to treat the disease, disorder and condition. The invention is further concerned with processes for preparing the compounds of this invention.

DETAILED DESCRIPTION OF THE INVENTION

The present invention is concerned with novel compounds of structural Formula I:

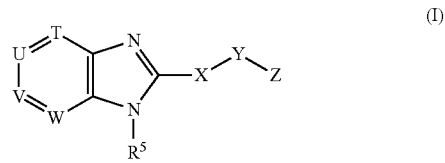

(I)

or a pharmaceutically acceptable salt thereof, wherein:
T is selected from the group consisting of: $CR^3$, N and N-oxide;

U is selected from the group consisting of: $CR^1$, N and N-oxide;

V is selected from the group consisting of: $CR^2$, N and N-oxide;

W is selected from the group consisting of: $CR^4$, N and N-oxide, provided that at least one of T, U, V and W is N or N-oxide;

X is absent or selected from:
- (1) —$CH_2$—,
- (2) —CHF—,
- (3) —$CF_2$—,
- (4) —S—,
- (5) —O—,
- (6) —O—$CH_2$—,
- (7) —NH—,
- (8) —C(O)—,
- (9) —NHC(O)—,
- (10) —C(O)NH—,
- (11) —$NHSO_2$—,
- (12) —$SO_2NH$—, and
- (13) —$CO_2$—, wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$-phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$-phenyl;

Y is selected from:
- (1) $C_{3-10}$cycloalkyl,
- (2) $C_{3-10}$cycloalkenyl,
- (3) $C_{2-10}$cycloheteroalkyl,
- (4) $C_{2-10}$cycloheteroalkenyl,
- (5) aryl, and
- (6) heteroaryl, wherein cycloalkyl, cycloalkenyl, cycloheteroalkyl, cycloheteroalkenyl, aryl and heteroaryl are unsubstituted or substituted with 1, 2, 3 or 4 substituents selected from $R^b$;

Z is selected from:
- (1) oxo,
- (2) —CN,
- (3) —$CF_3$,
- (4) —$C_{1-16}$alkyl,
- (5) —$(CH_2)_t$-halogen,
- (6) —$(CH_2)_nCOC_{1-6}$alkyl,
- (7) —$(CH_2)_nCO_2H$,
- (8) —$(CH_2)_nOCOH$,
- (9) —$(CH_2)_nCO_2R^i$,
- (10) —$(CH_2)_nOCOR^i$,
- (11) —$(CH_2)_nOH$,
- (12) —$(CH_2)_nC(O)N(R^g)_2$,
- (13) —$(CH_2)_nC(O)(CH_2)_nN(R^g)_2$,
- (14) —$(CH_2)_nOC(O)(CH_2)_nN(R^g)_2$,
- (15) —$(CH_2)_nNHC(O)C_{1-6}$alkyl,
- (16) —$(CH_2)_nNHSO_2R^i$,
- (17) —$(CH_2)_nSO_2C_{1-6}$alkyl,
- (18) —$(CH_2)_nSO_2NHR^g$,
- (19) —$(CH_2)_nSO_2NHC(O)R^i$,
- (20) —$(CH_2)_nSO_2NHCO_2R^i$,
- (21) —$(CH_2)_nSO_2NHCON(R^g)_2$,
- (22) —$(CH_2)_nC(O)NHSO_2R^i$,
- (23) —$(CH_2)_nNHC(O)N(R^g)_2$,
- (24) —$(CH_2)_nC_{3-10}$cycloalkyl-$CO_2R^e$,
- (25) heteroaryl,
- (26) —$C_{2-10}$cycloheteroalkenyl, and
- (27) —$C_{2-10}$cycloheteroalkyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$;

each $R^1$ and $R^2$ is independently selected from:
- (1) hydrogen,
- (2) halogen,
- (3) CN,
- (4) $CF_3$,
- (5) —$C_{1-6}$alkyl,
- (6) —$C_{2-6}$alkenyl,
- (7) —$C_{2-6}$alkynyl,
- (8) —$(CH_2)_pC_{3-10}$cycloalkyl,
- (9) —$(CH_2)_pC_{3-7}$cycloalkyl-aryl,
- (10) —$(CH_2)_pC_{3-7}$cycloalkyl-heteroaryl,
- (11) —$(CH_2)_pC_{4-10}$cycloalkenyl,
- (12) —$(CH_2)_pC_{4-7}$cycloalkenyl-aryl,
- (13) —$(CH_2)_pC_{4-7}$cycloalkenyl-heteroaryl,
- (14) —$(CH_2)_pC_{2-10}$cycloheteroalkyl,
- (15) —$(CH_2)_pC_{2-10}$cycloheteroalkenyl,
- (16) —$(CH_2)_p$aryl,
- (17) —$(CH_2)_p$aryl-$C_{1-8}$alkyl,
- (18) —$(CH_2)_p$aryl-$C_{2-8}$alkenyl,
- (19) —$(CH_2)_p$aryl-$C_{2-8}$alkynyl-$C_{1-8}$alkyl,
- (20) —$(CH_2)_p$aryl-$C_{2-8}$alkynyl-$C_{3-7}$cycloalkyl,
- (21) —$(CH_2)_p$aryl-$C_{2-8}$alkynyl-$C_{3-7}$cycloalkenyl,
- (22) —$(CH_2)_p$aryl-$C_{2-8}$alkynyl-$C_{2-10}$cycloheteroalkyl,
- (23) —$(CH_2)_p$aryl-$C_{2-8}$alkynyl-$C_{2-10}$cycloheteroalkenyl,
- (24) —$(CH_2)_p$aryl-$C_{2-8}$alkynyl-aryl,
- (25) —$(CH_2)_p$aryl-$C_{2-8}$alkynyl-heteroaryl,
- (26) —$(CH_2)_p$aryl-$C_{3-7}$cycloalkyl,
- (27) —$(CH_2)_p$aryl-$C_{2-10}$cycloheteroalkyl,
- (28) —$(CH_2)_p$aryl-$C_{2-10}$cycloheteroalkenyl,
- (29) —$(CH_2)_p$aryl-aryl,
- (30) —$(CH_2)_p$aryl-heteroaryl,
- (31) —$(CH_2)_p$heteroaryl,
- (32) —$C_{2-6}$alkenyl-alkyl,
- (33) —$C_{2-6}$alkenyl-aryl,
- (34) —$C_{2-6}$alkenyl-heteroaryl,
- (35) —$C_{2-6}$alkenyl-$C_{3-7}$cycloalkyl,
- (36) —$C_{2-6}$alkenyl-$C_{3-7}$cycloalkenyl,
- (37) —$C_{2-6}$alkenyl-$C_{2-7}$cycloheteroalkyl,
- (38) —$C_{2-6}$alkenyl-$C_{2-7}$cycloheteroalkenyl,
- (39) —$C_{2-6}$alkynyl-$(CH_2)_{1-3}$—O-aryl,
- (40) —$C_{2-6}$alkynyl-alkyl,
- (41) —$C_{2-6}$alkynyl-aryl,
- (42) —$C_{2-6}$alkynyl-heteroaryl,
- (43) —$C_{2-6}$alkynyl-$C_{3-7}$cycloalkyl,
- (44) —$C_{2-6}$alkynyl-$C_{3-7}$cycloalkenyl,
- (45) —$C_{2-6}$alkynyl-$C_{2-7}$cycloheteroalkyl,
- (46) —$C_{2-6}$alkynyl-$C_{2-7}$cycloheteroalkenyl, and
- (47) —C(O)NH—$(CH_2)_{0-3}$-phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl;

$R^3$ and $R^4$ are each independently selected from:
- (1) hydrogen,
- (2) halogen, (3) —$C_{1-6}$alkyl,
(4) —$C_{2-6}$alkenyl,
(5) —$C_{2-6}$alkynyl,
(6) —$C_{3-10}$cycloalkyl,
(7) —$C_{3-10}$cycloalkenyl,
(8) aryl,
(9) heteroaryl,
(10) —CN,
(11) —$CF_3$,
(12) —OH,
(13) —$OC_{1-6}$alkyl,
(14) —$NH_2$,
(15) —$NHC_{1-6}$alkyl,
(16) —$N(C_{1-6}alkyl)_2$,
(17) —$SC_{1-6}$alkyl,
(18) —$SOC_{1-6}$alkyl,
(19) —$SO_2C_{1-6}$alkyl,
(20) —$NHSO_2C_{1-6}$alkyl,
(21) —$NHC(O)C_{1-6}$alkyl,
(22) —$SO_2NHC_{1-6}$alkyl, and
(23) —$C(O)NHC_{1-6}$alkyl;

$R^5$ is selected from:
(1) hydrogen,
(2) —$C_{1-6}$alkyl,
(3) —$CH_2CO_2H$, and
(4) —$CH_2CO_2C_{1-6}$alkyl;

each $R^a$ is independently selected from the group consisting of:
(1) —$(CH_2)_m$-halogen,
(2) oxo,
(3) —$(CH_2)_m$OH,
(4) —$(CH_2)_mN(R^j)_2$,
(5) —$(CH_2)_mNO_2$,
(6) —$(CH_2)_m$CN,
(7) —$C_{1-6}$alkyl,
(8) —$(CH_2)_mCF_3$,
(9) —$(CH_2)_mOCF_3$,
(10) —O—$(CH_2)_m$—$OC_{1-6}$ alkyl,
(11) —$(CH_2)_mC(O)N(R^j)_2$,
(12) —$(CH_2)_mC(=N—OH)N(R^j)_2$,
(13) —$(CH_2)_mOC_{1-6}$alkyl,
(14) —$(CH_2)_mO$—$(CH_2)_m$—$C_{3-7}$cycloalkyl,
(15) —$(CH_2)_mO$—$(CH_2)_m$—$C_{2-7}$cycloheteroalkyl,
(16) —$(CH_2)_mO$—$(CH_2)_m$-aryl,
(17) —$(CH_2)_mO$—$(CH_2)_m$-heteroaryl,
(18) —$(CH_2)_mSC_{1-6}$alkyl,
(19) —$(CH_2)_mS(O)C_{1-6}$alkyl,
(20) —$(CH_2)_mSO_2C_{1-6}$alkyl,
(21) —$(CH_2)_mSO_2C_{3-7}$cycloakyl,
(22) —$(CH_2)_mSO_2C_{2-7}$cycloheteroalkyl,
(23) —$(CH_2)_mSO_2$-aryl,
(24) —$(CH_2)_mSO_2$-heteroaryl,
(25) —$(CH_2)_mSO_2NHC_{1-6}$alkyl,
(26) —$(CH_2)_mSO_2NHC_{3-7}$cycloalkyl,
(27) —$(CH_2)_mSO_2NHC_{2-7}$cycloheteroalkyl,
(28) —$(CH_2)_mSO_2NH$-aryl,
(29) —$(CH_2)_mSO_2NH$-heteroaryl,
(30) —$(CH_2)_mNHSO_2$—$C_{1-6}$alkyl,
(31) —$(CH_2)_mNHSO_2$—$C_{3-7}$cycloalkyl,
(32) —$(CH_2)_mNHSO_2$—$C_{2-7}$cycloheteroalkyl,
(33) —$(CH_2)_mNHSO_2$-aryl,
(34) —$(CH_2)_mNHSO_2NH$-heteroaryl,
(35) —$(CH_2)_mN(R^j)$—$C_{1-6}$alkyl,
(36) —$(CH_2)_mN(R^j)$—$C_{3-7}$cycloalkyl,
(37) —$(CH_2)_mN(R^j)$—$C_{2-7}$cycloheteroalkyl,
(38) —$(CH_2)_mN(R^j)$—$C_{2-7}$cycloheteroalkenyl,
(39) —$(CH_2)_mN(R^j)$-aryl,
(40) —$(CH_2)_mN(R^j)$-heteroaryl,
(41) —$(CH_2)_mC(O)R^f$,
(42) —$(CH_2)_mC(O)N(R^j)_2$,
(43) —$(CH_2)_mN(R^j)C(O)N(R^j)_2$,
(44) —$(CH_2)_mCO_2H$,
(45) —$(CH_2)_m$OCOH,
(46) —$(CH_2)_mCO_2R^f$,
(47) —$(CH_2)_mOCOR^f$,
(48) —$(CH_2)_mC_{3-7}$cycloalkyl,
(49) —$(CH_2)_mC_{3-7}$cycloalkenyl,
(50) —$(CH_2)_mC_{2-6}$cycloheteroalkyl,
(51) —$(CH_2)_mC_{2-6}$cycloheteroalkenyl,
(52) —$(CH_2)_m$aryl, and
(53) —$(CH_2)_m$heteroaryl, wherein each $CH_2$ is unsubstituted or substituted with 1 or 2 substituents selected from: oxo, —$(CH_2)_{0-3}$OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$-phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}$OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$SO_2C_{1-6}$alkyl, —$C_{3-7}$cycloalkyl, phenyl, $CH_2$-phenyl, heteroaryl and $CH_2$heteroaryl;

each $R^b$ is independently selected from:
(1) hydrogen,
(2) —$C_{1-6}$alkyl,
(3) —$C_{3-6}$cycloalkyl,
(4) —$C_{3-6}$cycloalkenyl,
(5) —$C_{2-6}$cycloheteroalkyl,
(6) —$C_{2-6}$cycloheteroalkenyl,
(7) aryl,
(8) heteroaryl,
(9) —$(CH_2)$t-halogen,
(10) —$(CH_2)$s-OH,
(11) —$NO_2$,
(12) —$NH_2$,
(13) —$NH(C_{1-6}alkyl)$,
(14) —$N(C_{1-6}alkyl)_2$,
(15) —$OC_{1-6}$alkyl,
(16) —$(CH_2)_qCO_2H$,
(17) —$(CH_2)_qCO_2C_{1-6}$alkyl,
(18) —$CF_3$,
(19) —CN,
(20) —$SO_2C_{1-6}$alkyl, and
(21) —$(CH_2)_sCON(R^e)_2$, wherein each $CH_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens; each $R^c$ is independently selected from:
(1) halogen,
(2) oxo,
(3) —$(CH_2)_r$OH,
(4) —$(CH_2)_rN(R^e)_2$,
(5) —$(CH_2)_r$CN,
(6) —$C_{1-6}$alkyl,
(7) —$CF_3$,
(8) —$C_{1-6}$alkyl-OH,
(9) —$OCH_2OC_{1-6}$alkyl,
(10) —$(CH_2)_rOC_{1-6}$alkyl,
(11) —$OCH_2$aryl,
(12) —$(CH_2)_rSC_{1-6}$alkyl,
(13) —$(CH_2)_rC(O)R^f$,

(14) —(CH$_2$)$_s$C(O)N(R$^e$)$_2$,
(15) —(CH$_2$)$_s$CO$_2$H,
(16) —(CH$_2$)$_s$CO$_2$R$^f$,
(17) —(CH$_2$)$_s$C$_{3-7}$cycloalkyl,
(18) —(CH$_2$)$_s$C$_{2-6}$cycloheteroalkyl,
(19) —(CH$_2$)$_s$aryl, and
(20) —(CH$_2$)$_s$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;

each R$^e$, R$^g$ and R$^h$ is independently selected from:
(1) hydrogen,
(2) —C$_{1-6}$alkyl, and
(3) —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^1$ is independently selected from:
(1) hydrogen,
(2) C$_{1-6}$alkyl,
(3) C$_{3-6}$cycloalkyl,
(4) —C(O)R$^i$, and
(5) —SO$_2$R$^i$, wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^f$, and R$^i$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;

n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4; and
t is 0, 1, 2, 3 or 4.

In one embodiment of the present invention, the present invention is concerned with novel compounds of structural Formula I:

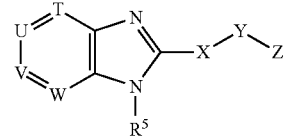

or a pharmaceutically acceptable salt thereof, wherein:
T is selected from the group consisting of: CR$^3$, N and N-oxide;
U is selected from the group consisting of: CR$^1$, N and N-oxide;
V is selected from the group consisting of: CR$^2$, N and N-oxide;
W is selected from the group consisting of: CR$^4$, N and N-oxide,
provided that at least one of T, U, V and W is N or N-oxide;
X is absent or selected from: —CH$_2$—, —CHF—, —CF$_2$—, —S—, —O—, —O—CH$_2$—, —NH—, —C(O)—, —NHC(O)—, —C(O)NH—, —NHSO$_2$—, —SO$_2$NH—, and —CO$_2$—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, COC$_{1-6}$alkyl, phenyl and —CH$_2$-phenyl, and wherein each NH is unsubstituted or substituted with 1 substituent selected from: C$_{1-6}$alkyl, CO$_2$H, CO$_2$C$_{1-6}$alkyl, COC$_{1-6}$alkyl, phenyl and —CH$_2$-phenyl;
Y is selected from: C$_{3-10}$cycloalkyl, C$_{3-10}$cycloalkenyl, C$_{2-10}$cycloheteroalkyl, C$_{2-10}$cycloheteroalkenyl, aryl, and heteroaryl, wherein cycloalkyl, cycloalkenyl, cycloheteroalkyl, cycloheteroalkenyl, aryl and heteroaryl are unsubstituted or substituted with 1, 2, 3 or 4 substituents selected from R$^b$;
Z is selected from: oxo, —CN, —CF$_3$, —C$_{1-6}$alkyl, —(CH$_2$)$_r$-halogen, —(CH$_2$)$_n$COC$_{1-6}$alkyl, —(CH$_2$)$_n$CO$_2$H, —(CH$_2$)$_n$OCOH, —(CH$_2$)$_n$CO$_2$R$^i$, —(CH$_2$)$_n$OCOR$^i$, —(CH$_2$)$_n$OH, —(CH$_2$)$_n$C(O)N(R$^g$)$_2$, —(CH$_2$)$_n$C(O)(CH$_2$)$_n$N(R$^g$)$_2$, —(CH$_2$)$_n$OC(O)(CH$_2$)$_n$N(R$^g$)$_2$, —(CH$_2$)$_n$NHC(O)C$_{1-6}$alkyl, —(CH$_2$)$_n$NHSO$_2$R$^i$, —(CH$_2$)$_n$SO$_2$C$_{1-6}$alkyl, —(CH$_2$)$_n$SO$_2$NHR$^g$, —(CH$_2$)$_n$SO$_2$NHC(O)R$^i$, —(CH$_2$)$_n$SO$_2$NHCO$_2$R$^i$, —(CH$_2$)$_n$SO$_2$NHCON(R$^g$)$_2$, —(CH$_2$)$_n$C(O)NHSO$_2$R$^i$, —(CH$_2$)$_n$NHC(O)N(R$^g$)$_2$, —(CH$_2$)$_n$C$_{3-10}$cycloalkyl-CO$_2$R$^e$, heteroaryl, —C$_{2-10}$cycloheteroalkenyl, and —C$_{2-10}$cycloheteroalkyl, wherein each CH$_2$ is unsubstituted or substituted with 1 or 2 substituents selected from C$_{1-6}$alkyl, —OH and —NH$_2$, wherein each NH is unsubstituted or substituted with 1 substituent selected from R$^c$, and wherein each alkyl, cycloalkyl, cycloheteroalkyl, cycloheteroalkenyl, aryl and heteroaryl is unsubstituted or substituted with 1, 2, 3 or 4 substituents selected from R$^c$;
each R$^1$ and R$^2$ is independently selected from: hydrogen, halogen, CN, CF$_3$, —C$_{1-6}$alkyl, —C$_{2-6}$alkenyl, —C$_{2-6}$alkynyl, —(CH$_2$)$_p$C$_{3-10}$cycloalkyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{3-7}$cycloalkyl, —(CH$_2$)$_p$aryl-C$_{2-7}$cycloheteroalkyl, —(CH$_2$)$_p$aryl-aryl, —(CH$_2$)$_p$aryl-heteroaryl, —(CH$_2$)$_p$heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkyl, —C$_{2-6}$alkenyl-C$_{2-7}$cycloheteroalkyl, —C$_{2-6}$alkenyl-C$_{2-7}$cycloheteroalkenyl, —C$_{2-6} $ alkynyl-(CH$_2$)$_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—(CH$_2$)$_{0-3}$-phenyl, wherein each CH$_2$ is unsubstituted or substituted with 1 or 2 substituents selected from: halogen, CF$_3$, —OH, —NH$_2$, —$C_{1-6}$alkyl, —OC$_{1-6}$alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —$C_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, provided that at least one of and only one of R$^1$ and R$^2$ is selected from the group consisting of: hydrogen, halogen, —CN, —CF$_3$, —$C_{1-6}$alkyl, —$C_{2-6}$alkenyl and —$C_{2-6}$alkynyl;

R$^3$ and R$^4$ are each independently selected from: hydrogen, halogen, —$C_{1-6}$alkyl, —$C_{2-6}$alkenyl, $C_{2-6}$alkynyl, —$C_{3-10}$cycloalkyl, —$C_{3-10}$cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl;

R$^5$ is selected from: hydrogen, —$C_{1-6}$alkyl, —CH$_2$CO$_2$H, and —CH$_2$CO$_2$C$_{1-6}$alkyl;

each R$^a$ is independently selected from the group consisting of: halogen, oxo, —(CH$_2$)$_m$OH, —(CH$_2$)$_m$N(R$^j$)$_2$, —(CH$_2$)$_m$NO$_2$, —(CH$_2$)$_m$CN, —$C_{1-6}$alkyl, —(CH$_2$)$_m$CF$_3$, —(CH$_2$)$_m$OCF$_3$, —OCH$_2$OC$_{1-6}$ alkyl, —(CH$_2$)$_m$C(O)N(R$^j$)$_2$, —(CH$_2$)$_m$C(=N—OH)N(R$^j$)$_2$, —(CH$_2$)$_m$OC$_{1-6}$alkyl, —(CH$_2$)$_m$O—(CH$_2$)$_m$—$C_{3-7}$cycloalkyl, —(CH$_2$)$_m$O—(CH$_2$)$_m$—$C_{2-7}$cycloheteroalkyl, —(CH$_2$)$_m$O—(CH$_2$)$_m$-aryl, —(CH$_2$)$_m$O—(CH$_2$)$_m$-heteroaryl, —(CH$_2$)$_m$SC$_{1-6}$alkyl, —(CH$_2$)$_m$S(O)C$_{1-6}$alkyl, —(CH$_2$)$_m$SO$_2$C$_{1-6}$alkyl, —(CH$_2$)$_m$SO$_2$C$_{3-7}$cycloalkyl, —(CH$_2$)$_m$SO$_2$C$_{2-7}$cycloheteroalkyl, —(CH$_2$)$_m$SO$_2$-aryl, —(CH$_2$)$_m$SO$_2$-heteroaryl, —(CH$_2$)$_m$SO$_2$NHC$_{1-6}$alkyl, —(CH$_2$)$_m$SO$_2$NHC$_{3-7}$cycloalkyl, —(CH$_2$)$_m$SO$_2$NHC$_{2-7}$cycloheteroalkyl, —(CH$_2$)$_m$SO$_2$NH-aryl, —(CH$_2$)$_m$SO$_2$NH-heteroaryl, —(CH$_2$)$_m$NHSO$_2$—$C_{1-6}$alkyl, —(CH$_2$)$_m$NHSO$_2$—$C_{3-7}$cycloalkyl, —(CH$_2$)$_m$NHSO$_2$—$C_{2-7}$cycloheteroalkyl, —(CH$_2$)$_m$NHSO$_2$-aryl, —(CH$_2$)$_m$NHSO$_2$NH-heteroaryl, —(CH$_2$)$_m$C(O)R$^f$, —(CH$_2$)$_m$C(O)N(R$^j$)$_2$, —(CH$_2$)$_m$N(R$^j$)C(O)N(R$^j$)$_2$, —(CH$_2$)$_m$CO$_2$H, —(CH$_2$)$_m$OCOH, —(CH$_2$)$_m$CO$_2$R$^f$, —(CH$_2$)$_m$OCOR$^f$, —(CH$_2$)$_m$C$_{3-7}$cycloalkyl, —(CH$_2$)$_m$C$_{3-7}$cycloalkenyl, —(CH$_2$)$_m$C$_{2-6}$cycloheteroalkyl, —(CH$_2$)$_m$C$_{2-6}$cycloheteroalkenyl, —(CH$_2$)$_m$aryl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —$C_{1-6}$alkyl, —OC$_{1-6}$alkyl, halogen, —CH$_2$F, —CHF$_2$, —CF$_3$, —CO$_2$H, —CO$_2$C$_{1-6}$alkyl, —$C_{3-7}$cycloalkyl, phenyl, CH$_2$-phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —$C_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —$C_{3-7}$cycloalkyl, phenyl, CH$_2$-phenyl, heteroaryl and CH$_2$heteroaryl;

each R$^b$ is independently selected from: hydrogen, —$C_{1-6}$alkyl, —$C_{3-6}$cycloalkyl, —$C_{3-6}$cycloalkenyl, —$C_{2-6}$cycloheteroalkyl, —$C_{2-6}$cycloheteroalkenyl, aryl, heteroaryl, —(CH$_2$)$_t$-halogen, —(CH$_2$)$_s$—OH, —NO$_2$, —NH$_2$, —NH(C$_{1-6}$alkyl), —N(C$_{1-6}$alkyl)$_2$, —OC$_{1-6}$alkyl, —(CH$_2$)$_q$CO$_2$H, —(CH$_2$)$_q$CO$_2$C$_{1-6}$alkyl, —CF$_3$, —CN, —SO$_2$C$_{1-6}$alkyl, and —(CH$_2$)$_s$CON(R$^e$)$_2$, wherein each CH$_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens;

each R$^c$ is independently selected from: halogen, oxo, —(CH$_2$)$_r$OH, —(CH$_2$)$_r$N(R$^e$)$_2$, —(CH$_2$)$_r$CN, —$C_{1-6}$alkyl, —CF$_3$, —$C_{1-6}$alkyl-OH, —OCH$_2$OC$_{1-6}$alkyl, —(CH$_2$)$_r$OC$_{1-6}$alkyl, —OCH$_2$aryl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, —(CH$_2$)$_r$CO$_2$R$^f$, —(CH$_2$)$_r$C$_{3-7}$cycloalkyl, —(CH$_2$)$_r$C$_{2-6}$cycloheteroalkyl, —(CH$_2$)$_r$aryl, and —(CH$_2$)$_r$heteroaryl, wherein each CH$_2$ is unsubstituted or substituted with 1 or 2 substituents selected from: oxo, —OH, —CN, —N(R$^h$)$_2$, —$C_{1-6}$alkyl, —OC$_{1-6}$alkyl, halogen, —CH$_2$F, —CHF$_2$, —CF$_3$, —CO$_2$H, —CO$_2$C$_{1-6}$alkyl, —$C_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —$C_{1-6}$alkyl, —OC$_{1-6}$alkyl, halogen, —CH$_2$F, —CHF$_2$, —CF$_3$, —CO$_2$H, —CO$_2$C$_{1-6}$alkyl, —$C_{3-7}$cycloalkyl and heteroaryl;

each R$^e$, R$^g$ and R$^h$ is independently selected from: hydrogen, —$C_{1-6}$alkyl, and —O—$C_{1-6}$alkyl, wherein alkyl is unsubstituted or substituted with 1, 2, 3 or 4 substituents selected from: —OH, oxo, halogen, $C_{1-6}$alkyl, —OC$_{1-6}$alkyl, —NH$_2$, —NH(C$_{1-6}$alkyl), and —N(C$_{1-6}$alkyl)$_2$;

each R$^j$ is independently selected from: hydrogen, C$_{1-6}$alkyl, C$_{3-6}$cycloalkyl, —C(O)R$^i$, and —SO$_2$R$^i$, wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^f$, and R$^i$ is independently selected from: C$_{1-6}$alkyl, C$_{4-7}$cycloalkyl, C$_{4-7}$cycloalkenyl, C$_{3-7}$cycloheteroalkyl, C$_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;

n is 0, 1, 2, 3 or 4; m is 0, 1, 2, 3 or 4; p is 0, 1, 2, or 3; q is 0, 1, 2, 3 or 4; r is 0, 1 or 2; s is 0, 1, 2, 3 or 4; and t is 0, 1, 2, 3 or 4.

In another embodiment of the present invention, T is selected from the group consisting of: —CR$^3$—, N, and N-oxide. In a class of this embodiment, T is —CR$^3$—. In another class of this embodiment, T is selected from the group consisting of: N, and N-oxide. In another class of this embodiment, T is N. In another class of this embodiment, T is N-oxide.

In another embodiment of the present invention, U is selected from the group consisting of —CR$^1$—, N, and N-oxide. In a class of this embodiment, U is —CR$^1$—. In another class of this embodiment, U is selected from the group consisting of: N, and N-oxide. In another class of this embodiment, U is N. In another class of this embodiment, U is selected from the group consisting of: N-oxide.

In another embodiment of the present invention, V is selected from the group consisting of: —CR$^2$—, N, and N-oxide. In a class of this embodiment, V is —CR$^2$—. In another class of this embodiment, V is selected from the group consisting of: N, and N-oxide. In another class of this embodiment, V is N. In another class of this embodiment, V is N-oxide.

In another embodiment of the present invention, W is selected from the group consisting of: —$CR^4$—, N, and N-oxide. In a class of this embodiment, W is selected from the group consisting of: —$CR^4$—, In another class of this embodiment, W is selected from the group consisting of: N, and N-oxide. In another class of this embodiment, W is N. In another class of this embodiment, W is N-oxide.

In another embodiment of the present invention, one of T and W is N or N-oxide, U is $CR^1$ and V is $CR^2$, provided that if W is N or N-oxide then $R^1$ is selected from hydrogen, halogen, —CN, —$CF_3$, —$C_{1-6}$alkyl, —$C_{2-6}$alkenyl and —$C_{2-6}$alkynyl, and if T is N or N-oxide then $R^2$ is selected from hydrogen, halogen, —CN, —$CF_3$, —$C_{1-6}$alkyl, —$C_{2-6}$alkenyl and —$C_{2-6}$alkynyl.

In another embodiment of the present invention, one of T and W is N or N-oxide, U is $CR^1$ and V is $CR^2$, provided that if W is N or N-oxide then $R^1$ is halogen, and if T is N or N-oxide then $R^2$ is halogen.

In another embodiment of the present invention, T is N or N-oxide; U is —$CR^1$—; V is —$CR^2$—; and W is —$CR^4$—. In a class of this embodiment, T is N or N-oxide; U is —$CR^1$—; V is —$CR^2$—, wherein $R^2$ is halogen; and W is —$CR^4$—. In another class of this embodiment, T is N; U is —$CR^1$—; V is —$CR^2$—, wherein $R^2$ is halogen; and W is —$CR^4$—.

In another embodiment of the present invention, one of T and W is N or N-oxide, U is $CR^1$ and V is $CR^2$, provided that if W is N or N-oxide then $R^1$ is halogen, and if T is N or N-oxide then $R^2$ is chloride.

In another embodiment of the present invention, T is N or N-oxide, U is $CR^1$, V is $CR^2$, and W is $CR^4$. In a subclass of this class, T is N, U is $CR^1$, V is $CR^2$, and W is $CR^4$. In another subclass of this class, T is N, U is $CR^1$, V is $CR^2$, W is $CR^4$, and $R^2$ is halogen. In another subclass of this class, T is N, U is $CR^1$, V is $CR^2$, W is $CR^4$, and $R^2$ is chloride. In another subclass of this class, T is N, U is $CR^1$, V is $CR^2$, W is $CR^4$, $R^2$ is chloride, and $R^4$ is hydrogen.

In another embodiment of the present invention, X is absent.

In another embodiment of the present invention, X is selected from: —$CH_2$—, —CHF—, —$CF_2$—, —S—, —O—, —O—$CH_2$—, —NH—, —C(O)—, —NHC(O)—, —C(O)NH—, —$NHSO_2$—, —$SO_2NH$—, and —$CO_2$—, wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$-phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$-phenyl. In a class of this embodiment, X is absent or selected from: —$CH_2$—, —CHF—, —$CF_2$—, —S—, —O—, —O—$CH_2$—, and —NH—. In another class of this embodiment, X is absent or selected from: —$CH_2$—, —O—, and —O—$CH_2$—. In another class of this embodiment, X is absent or selected from: —O—, and —O—$CH_2$—. In another class of this embodiment, X is selected from: —O—, and —O—$CH_2$—. In another class of this embodiment, X is —O—. In another class of this embodiment, X is —O—$CH_2$—. In another class of this embodiment, X is absent or selected from: —C(O)—, —NHC(O)—, —C(O)NH—, —$NHSO_2$—, —$SO_2NH$—, and —$CO_2$—.

In another embodiment of the present invention, X is —O—.

In another embodiment of the present invention, Y is selected from: $C_{3-10}$cycloalkyl, $C_{3-10}$cycloalkenyl, $C_{2-10}$cycloheteroalkyl, $C_{2-10}$cycloheteroalkenyl, aryl, and heteroaryl, wherein cycloalkyl, cycloalkenyl, cycloheteroalkyl, cycloheteroalkenyl, aryl and heteroaryl are unsubstituted or substituted with 1, 2, 3 or 4 substituents selected from $R^b$. In a class of this embodiment, Y is selected from: $C_{3-10}$cycloalkyl, $C_{2-10}$cycloheteroalkyl, and aryl, wherein cycloalkyl, cycloheteroalkyl and aryl are unsubstituted or substituted with 1, 2, 3 or 4 substituents selected from $R^b$. In another class of this embodiment, Y is selected from: $C_{3-10}$cycloalkyl, $C_{2-10}$cycloheteroalkyl, and phenyl, wherein cycloalkyl, cycloheteroalkyl and phenyl are unsubstituted or substituted with 1, 2, 3 or 4 substituents selected from $R^b$. In another class of this embodiment, Y is selected from: cyclohexyl, cyclobutyl, cyclopropyl, cyclopentyl, pyrrolidine, piperidine, tetrahydrofuran, tetrahydropyran and phenyl, wherein cycloalkyl, cycloheteroalkyl and phenyl are unsubstituted or substituted with 1, 2, 3 or 4 substituents selected from $R^b$.

In another class of this embodiment, Y is selected from: $C_{3-7}$cycloalkyl, and aryl, wherein each cycloalkyl and aryl is unsubstituted or substituted with 1, 2, 3 or 4 substituents selected from $R^b$. In a subclass of this class, Y is selected from: cyclohexyl, and phenyl, wherein each cycloalkyl, and phenyl is unsubstituted or substituted with 1, 2, 3 or 4 substituents selected from $R^b$.

In another class of this embodiment, Y is aryl, wherein each aryl is unsubstituted or substituted with 1, 2, 3 or 4 substituents selected from $R^b$. In a subclass of this class, Y is phenyl, wherein each phenyl is unsubstituted or substituted with 1, 2, 3 or 4 substituents selected from $R^b$.

In another class of this embodiment, Y is selected from: $C_{3-10}$cycloalkyl, wherein each cycloalkyl is unsubstituted or substituted with 1, 2, 3 or 4 substituents selected from $R^b$. In a subclass of this class, Y is cyclohexyl, wherein each cyclohexyl is unsubstituted or substituted with 1, 2, 3 or 4 substituents selected from $R^b$.

In another embodiment of the present invention, Y is selected from: $C_{3-7}$cycloalkyl, $C_{2-10}$cycloheteroalkyl, and phenyl, wherein each cycloalkyl, cycloheteroalkyl, and phenyl is unsubstituted or substituted with 1, 2, 3 or 4 substituents selected from $R^b$. In a class of this embodiment, Y is selected from: cyclobutyl, cyclohexyl, 1,4:3,6-dianhydro-D-mannitol, tetrahydropyran, and phenyl, wherein each cyclobutyl, cyclohexyl, tetrahydropyran, and phenyl is unsubstituted or substituted with 1, 2, 3 or 4 substituents selected from $R^b$. In another class of this embodiment, Y is selected from: cyclobutyl, cyclohexyl, 1,4:3,6-dianhydro-D-mannitol, 2,3,3a,5,6,6a-hexahydrofuro[3,2-b]furan, tetrahydropyran, and phenyl, wherein each cyclobutyl, cyclohexyl, tetrahydropyran, and phenyl is unsubstituted or substituted with 1, 2, 3 or 4 substituents selected from $R^b$. In another class of this embodiment, Y is selected from: cyclobutyl, cyclohexyl, 2,3,3a,5,6,6a-hexahydrofuro[3,2-b]furan, tetrahydropyran, and phenyl, wherein each cyclobutyl, cyclohexyl, tetrahydropyran, and phenyl is unsubstituted or substituted with 1, 2, 3 or 4 substituents selected from $R^b$.

In another embodiment of the present invention, Y is selected from: $C_{2-10}$cycloheteroalkyl, wherein each cycloheteroalkyl is unsubstituted or substituted with 1, 2, 3 or 4 substituents selected from $R^b$. In a class of this embodiment, Y is hexahydrofuro[3,2-b]furan. In another class of this embodiment, Y is 2,3,3a,5,6,6a-hexahydrofuro[3,2-b]furan.

In another embodiment of the present invention, Z is selected from: oxo, —CN, —$CF_3$, —$C_{1-6}$alkyl, —$(CH_2)_r$-halogen, —$(CH_2)_nCOC_{1-6}$alkyl, —$(CH_2)_nCO_2H$, —$(CH_2)_n$OCOH, —$(CH_2)_nCO_2R^i$, —$(CH_2)_nOCOR^i$, —$(CH_2)_nOH$, —$(CH_2)_nC(O)N(R^g)_2$, —$(CH_2)_nC(O)(CH_2)_nN(R^g)_2$, —$(CH_2)_nOC(O)(CH_2)_nN(R^g)_2$, —$(CH_2)_nNHC(O)C_{1-6}alkyl$, —$(CH_2)_nNHSO_2R^i$, —$(CH_2)_nSO_2C_{1-6}alkyl$, —$(CH_2)_nSO_2NHR^g$, —$(CH_2)_nSO_2NHC(O)R^i$, —$(CH_2)_nSO_2NHCO_2R^i$, —$(CH_2)_nSO_2NHCON(R^g)_2$, —$(CH_2)_nC(O)NHSO_2R^i$, —$(CH_2)_nNHC(O)N(R^g)_2$, —$(CH_2)_nC_{3-10}$cycloalkyl-$CO_2R^e$, heteroaryl, —$C_{2-10}$cycloheteroalkenyl, and —$C_{2-10}$cycloheteroalkyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$.

In a class of this embodiment, Z is selected from: oxo, —CN, —$CF_3$, —$C_{1-6}$alkyl, —$(CH_2)_t$-halogen, —$(CH_2)_n$COC$_{1-6}$alkyl, —$(CH_2)_nCO_2H$, —$(CH_2)_nOCOH$, —$(CH_2)_nCO_2R^i$, —$(CH_2)_nOCOR^i$, —$(CH_2)_nOH$, —$(CH_2)_nC(O)N(R^g)_2$, —$(CH_2)_nC(O)(CH_2)_nN(R^g)_2$, —$(CH_2)_nOC(O)(CH_2)_nN(R^g)_2$, —$(CH_2)_nNHC(O)C_{1-6}alkyl$, —$(CH_2)_nNHSO_2R^i$, —$(CH_2)_nSO_2C_{1-6}alkyl$, —$(CH_2)_nSO_2NHR^g$, —$(CH_2)_nSO_2NHC(O)R^i$, —$(CH_2)_nSO_2NHCO_2R^i$, —$(CH_2)_nSO_2NHCON(R^g)_2$, —$(CH_2)_nC(O)NHSO_2R^i$, —$(CH_2)_nNHC(O)N(R^g)_2$, —$(CH_2)_nC_{3-10}$cycloalkyl-$CO_2R^e$, heteroaryl, —$C_{2-10}$cycloheteroalkenyl, and —$C_{2-10}$cycloheteroalkyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, and heteroaryl is unsubstituted or substituted with 1, 2, 3 or 4 substituents selected from $R^c$.

In another class of this embodiment of the present invention, Z is selected from: oxo, —$CF_3$, —$C_{1-6}$alkyl, —$(CH_2)_t$-halogen, —$(CH_2)_nCOC_{1-6}alkyl$, —$(CH_2)_nCO_2H$, —$(CH_2)_nOH$, —$(CH_2)_nC(O)N(R^g)_2$, —$(CH_2)_nC(O)(CH_2)_nN(R^g)_2$, —$(CH_2)_nSO_2C_{1-6}alkyl$, and heteroaryl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl and heteroaryl is unsubstituted or substituted with 1, 2, 3 or 4 substituents selected from $R^c$.

In another class of this embodiment of the present invention, Z is selected from: oxo, —$CF_3$, —$C_{1-6}$alkyl, —$(CH_2)_t$-halogen, —$(CH_2)_nCOC_{1-6}alkyl$, —$(CH_2)_nOCOH$, —$(CH_2)_nCO_2H$, —$(CH_2)_nOH$, —$(CH_2)_nC(O)N(R^g)_2$, —$(CH_2)_nC(O)(CH_2)_nN(R^g)_2$, —$(CH_2)_nOC(O)(CH_2)_nN(R^g)_2$, and —$(CH_2)_nSO_2C_{1-6}alkyl$, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl is unsubstituted or substituted with 1, 2, 3 or 4 substituents selected from $R^c$.

In another class of this embodiment of the present invention, Z is selected from: oxo, —$CF_3$, —$CH_3$, —$CH_2F$, —$COCH_3$, —$CO_2H$, —OH, —$CH_2OH$, —$CH(CH_3)OH$, —$C(CH_3)_2OH$, —$C(O)N(OCH_3)(CH_3)$, —$C(O)(CH_2)NH_2$, ), —$OC(O)CH(CH_3)NH_2$, and —$SO_2CH_3$, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl is unsubstituted or substituted with 1, 2, 3 or 4 substituents selected from $R^c$.

In another class of this embodiment of the present invention, Z is selected from: oxo, —$CF_3$, —$C_{1-6}$alkyl, —$(CH_2)_t$-halogen, —$(CH_2)_nCO_2H$, —$(CH_2)_nOH$, and —$(CH_2)_nSO_2C_{1-6}alkyl$, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl is unsubstituted or substituted with 1, 2, 3 or 4 substituents selected from $R^c$. In another class of this embodiment of the present invention, Z is selected from: oxo, —$CF_3$, —$CH_3$, —$CH_2F$, —$CO_2H$, —OH, —$CH_2OH$, —$CH(CH_3)OH$, —$C(CH_3)_2OH$, and —$SO_2CH_3$, wherein each $CH_2$ is unsubstituted or substituted with 1 or 2 substituents selected from $C_{1-6}$alkyl, —OH and —$NH_2$, and wherein each alkyl is unsubstituted or substituted with 1, 2, 3 or 4 substituents selected from $R^c$.

In another class of this embodiment of the present invention, Z is selected from: oxo, —$CF_3$, —$CH_3$, —$CH_2F$, —$CO_2H$, —OH, —$CH_2OH$, —$CH(CH_3)OH$, —$C(CH_3)_2$OH, and —$SO_2CH_3$.

In another class of this embodiment, Z is selected from: oxo, CN, —$(CH_2)_nCO_2H$, —$(CH_2)_nCO_2R^i$, and —$(CH_2)_n$OH. In a subclass of this class, Z is selected from: oxo, CN, —$CO_2H$, —$CO_2R^i$, and —OH.

In another class of this embodiment, Z is selected from: —$(CH_2)_nCO_2H$, and —$(CH_2)_nCO_2R^i$. In a subclass of this class, Z is selected from: —$CO_2H$, and —$CO_2R^i$.

In another embodiment of this invention, Z is selected from: —$(CH_2)_nCO_2H$, and —$(CH_2)_n$OH, wherein each $CH_2$ is unsubstituted or substituted with 1 or 2 substituents selected from $C_{1-6}$alkyl, —OH and —$NH_2$, and wherein each NH is unsubstituted or substituted with 1 substituent selected from $R^c$. In a class of this embodiment, Z is selected from: —$(CH_2)_nCO_2H$, and —$(CH_2)_n$OH, wherein each $CH_2$ is unsubstituted or substituted with 1 or 2 substituents selected from $C_{1-6}$alkyl, and —OH. In another class of this embodiment, Z is selected from: —$(CH_2)_nCO_2H$, and —$(CH_2)_n$OH. In another class of this embodiment, Z is selected from: —$CO_2H$, —OH, —$CH_2OH$, and —$C(CH_3)_2OH$. In another class of this embodiment, Z is selected from: —$CO_2H$, —$CH_2OH$, and —$C(CH_3)_2OH$.

In another embodiment of the present invention, Z is —$CO_2H$.

In another embodiment of the present invention, Z is selected from: —$(CH_2)_n$OH, wherein each $CH_2$ is unsubstituted or substituted with 1 or 2 substituents selected from $C_{1-6}$alkyl, —OH and —$NH_2$, and wherein each NH is unsubstituted or substituted with 1 substituent selected from $R^c$. In a class of this embodiment, Z is selected from: —$(CH_2)_n$OH, wherein each $CH_2$ is unsubstituted or substituted with 1 or 2 substituents selected from $C_{1-6}$alkyl, and —OH. In another class of this embodiment Z is selected from: —$(CH_2)_n$OH. In another class of this embodiment, Z is selected from: —OH, —$CH_2OH$, and —$C(CH_3)_2OH$.

In another embodiment of the present invention, Z is selected from: —$(CH_2)_t$-halogen, and —$(CH_2)_n$OH, wherein each $CH_2$ is unsubstituted or substituted with 1 or 2 substituents selected from $C_{1-6}$alkyl, —OH and —$NH_2$. In a class of this embodiment, Z is selected from: —$(CH_2)_t$-halogen, and —$(CH_2)_n$OH. In a class of this embodiment, Z is selected from: -halogen and —OH.

In another class of this embodiment, Z is selected from: fluorine and —OH. In another class of this embodiment, Z is halogen. In another class of this embodiment, Z is fluorine. In another class of this embodiment, Z is —OH.

In another embodiment of this invention, Z is selected from: —$(CH_2)_nCO_2H$, —$(CH_2)_t$-halogen, and —$(CH_2)_n$OH, wherein each $CH_2$ is unsubstituted or substituted with 1 or 2 substituents selected from $C_{1-6}$alkyl, —OH and —$NH_2$, and wherein each NH is unsubstituted or substituted with 1 substituent selected from $R^c$. In a class of this embodiment, Z is selected from: —$(CH_2)_nCO_2H$, —$(CH_2)_t$-halogen, and —(CH$_2$)$_n$OH, wherein each CH$_2$ is unsubstituted or substituted with 1 or 2 substituents selected from C$_{1-6}$alkyl, and —OH. In another class of this embodiment, Z is selected from: —(CH$_2$)$_n$CO$_2$H, halogen and —(CH$_2$)$_n$OH. In another class of this embodiment, Z is selected from: —CO$_2$H, F, —OH, —CH$_2$OH, and —C(CH$_3$)$_2$OH. In another class of this embodiment, Z is selected from: —CO$_2$H, F, —OH, —CH$_2$OH, and —C(CH$_3$)$_2$OH.

In another embodiment of the present invention, each R$^1$ and R$^2$ is independently selected from: hydrogen, halogen, CN, CF$_3$, —C$_{1-6}$alkyl, —C$_{2-6}$alkenyl, —C$_{2-6}$alkynyl, —(CH$_2$)$_p$C$_{3-10}$cycloalkyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{3-7}$cycloalkyl, —(CH$_2$)$_p$aryl-C$_{2-7}$cycloheteroalkyl, —(CH$_2$)$_p$aryl-aryl, —(CH$_2$)$_p$aryl-heteroaryl, —(CH$_2$)$_p$heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$ alkynyl-(CH$_2$)$_{1-3}$-O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$-phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, provided that at least one of and only one of R$^1$ and R$^2$ is selected from the group consisting of: hydrogen, halogen, —CN, —CF$_3$, —C$_{1-6}$alkyl, —C$_{2-6}$alkenyl and —C$_{2-6}$alkynyl. In a class of this embodiment of the present invention, each R$^1$ and R$^2$ is independently selected from: halogen, —(CH$_2$)$_p$C$_{4-10}$cycloalkenyl, —(CH$_2$)$_p$aryl, —(CH$_2$)$_p$aryl-C$_{3-7}$cycloalkyl, —(CH$_2$)$_p$aryl-C$_{2-7}$cycloheteroalkyl, —(CH$_2$)$_p$aryl-aryl, —(CH$_2$)$_p$aryl-heteroaryl, —(CH$_2$)$_p$heteroaryl, —C$_{2-6}$alkynyl-aryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of halogen.

In another class of this embodiment of the present invention, each R$^1$ and R$^2$ is independently selected from: halogen, —C$_{4-10}$cycloalkenyl, -aryl, -aryl-C$_{3-7}$cycloalkyl, -aryl-C$_{2-7}$cycloheteroalkyl, -aryl-aryl, -aryl-heteroaryl, -heteroaryl, —C$_{2-6}$alkynyl-aryl, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of halogen. In another class of this embodiment of the present invention, each R$^1$ and R$^2$ is independently selected from: halogen, —C$_{4-10}$cycloalkenyl, -phenyl, -phenyl-C$_{3-7}$cycloalkyl, -phenyl-C$_{2-7}$cycloheteroalkyl, -phenyl-heteroaryl, -heteroaryl, —C$_{2-6}$alkynyl-phenyl, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, phenyl and heteroaryl is unsubstituted or substituted with 1, 2, 3 or 4 substituents independently selected from R$^a$, provided that at least one of and only one of R$^1$ and R$^2$ is selected from the group consisting of halogen. In another class of this embodiment of the present invention, each R$^1$ and R$^2$ is independently selected from: Cl, F, cyclohexenyl, -phenyl, phenyl-cyclopropyl, phenyl-piperazine, phenyl-pyrrolidine, -phenyl-phenyl, phenyl-triazole, phenyl-thiazole, phenyl-pyrazole, phenyl-oxadiazole, phenyl-furan, -pyridine, benzodioxole, indole, azaindole, benzofuran, benzopyrazole, benzodioxane, tetrahydroisoquinoline, azabenzimidazole, —C$_2$-alkynyl-phenyl, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, phenyl and heteroaryl is unsubstituted or substituted with 1, 2, 3 or 4 substituents independently selected from R$^a$, provided that at least one of and only one of R$^1$ and R$^2$ is selected from the group consisting of Cl and F. In another class of this embodiment of the present invention, each R$^1$ and R$^2$ is independently selected from: Cl, cyclohexenyl, -phenyl, phenyl-cyclopropyl, phenyl-piperazine, phenyl-pyrrolidine, -phenyl-phenyl, phenyl-triazole, phenyl-thiazole, phenyl-pyrazole, phenyl-oxadiazole, phenyl-furan, -pyridine, benzodioxole, indole, azaindole, benzofuran, benzopyrazole, benzodioxane, tetrahydroisoquinoline, —C$_2$-alkynyl-phenyl, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, phenyl and heteroaryl is unsubstituted or substituted with 1, 2, 3 or 4 substituents independently selected from R$^a$, provided that at least one of and only one of R$^1$ and R$^2$ is Cl.

In another class of this embodiment of the present invention, R$^1$ is independently selected from: —(CH$_2$)$_p$C$_{4-10}$cycloalkenyl, —(CH$_2$)$_p$aryl, —(CH$_2$)$_p$aryl-C$_{3-7}$cycloalkyl, —(CH$_2$)$_p$aryl-C$_{2-7}$cycloheteroalkyl, —(CH$_2$)$_p$aryl-aryl, —(CH$_2$)$_p$aryl-heteroaryl, —(CH$_2$)$_p$heteroaryl, —C$_{2-6}$alkynyl-aryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, aryl and heteroaryl is unsubstituted or substituted with 1, 2, 3 or 4 substituents independently selected from R$^a$, and R$^2$ is selected from the group consisting of halogen. In another class of this embodiment of the present invention, R$^1$ is independently selected from: —C$_{4-10}$cycloalkenyl, -aryl, -aryl-C$_{3-7}$cycloalkyl, -aryl-C$_{2-7}$cycloheteroalkyl, -aryl-aryl, -aryl-heteroaryl, -heteroaryl, —C$_{2-6}$alkynyl-aryl, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, aryl and heteroaryl is unsubstituted or substituted with 1, 2, 3 or 4 substituents independently selected from $R^a$, and $R^2$ is selected from the group consisting of halogen. In another class of this embodiment of the present invention, $R^1$ is independently selected from: —$C_{4-10}$cycloalkenyl, -phenyl, -phenyl-$C_{3-7}$cycloalkyl, -phenyl-$C_{2-7}$cycloheteroalkyl, -phenyl-heteroaryl, -heteroaryl, —$C_{2-6}$alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl and heteroaryl is unsubstituted or substituted with 1, 2, 3 or 4 substituents independently selected from $R^a$, and $R^2$ is selected from the group consisting of halogen. In another class of this embodiment of the present invention, $R^1$ is independently selected from: cyclohexenyl, -phenyl, phenyl-cyclopropyl, phenyl-piperazine, phenyl-pyrrolidine, -phenyl-phenyl, phenyl-triazole, phenyl-thiazole, phenyl-pyrazole, phenyl-oxadiazole, phenyl-furan, -pyridine, benzodioxole, indole, azaindole, benzofuran, benzopyrazole, benzodioxane, tetrahydroisoquinoline, —$C_2$-alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl and heteroaryl is unsubstituted or substituted with 1, 2, 3 or 4 substituents independently selected from $R^a$, and $R^2$ is selected from the group consisting of Cl and F. In another class of this embodiment of the present invention, $R^1$ is independently selected from: cyclohexenyl, -phenyl, phenyl-cyclopropyl, phenyl-piperazine, phenyl-pyrrolidine, -phenyl-phenyl, phenyl-triazole, phenyl-thiazole, phenyl-pyrazole, phenyl-oxadiazole, phenyl-furan, -pyridine, benzodioxole, indole, azaindole, benzofuran, benzopyrazole, benzodioxane, tetrahydroisoquinoline, —$C_2$-alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl and heteroaryl is unsubstituted or substituted with 1, 2, 3 or 4 substituents independently selected from $R^a$, and $R^2$ is Cl.

In another embodiment of the present invention, each $R^1$ and $R^2$ is independently selected from: halogen, —$C_{4-10}$cycloalkenyl, -phenyl, -phenyl-$C_{3-7}$cycloalkyl, -phenyl-$C_{2-7}$cycloheteroalkyl, -phenyl-aryl, -phenyl-heteroaryl, -heteroaryl, and —$C_{2-6}$alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of halogen. In another class of the embodiment, each $R^1$ and $R^2$ is independently selected from: halogen, -phenyl-$C_{2-7}$cycloheteroalkyl, and -phenyl-aryl, wherein each cycloheteroalkyl, aryl and phenyl is unsubstituted or substituted with 1, 2, 3 or 4 substituents independently selected from $R^a$, provided that at least one of and only one of $R^1$ and $R^2$ is selected from the group consisting of halogen; or a pharmaceutically acceptable salt thereof. In another class of the embodiment, each $R^1$ and $R^2$ is independently selected from: halogen, -phenyl-pyrrolidine, and -phenyl-phenyl, wherein each pyrrolidine and phenyl is unsubstituted or substituted with 1, 2, 3 or 4 substituents independently selected from $R^a$, provided that at least one of and only one of $R^1$ and $R^2$ is selected from the group consisting of halogen; or a pharmaceutically acceptable salt thereof. In another class of the embodiment, each $R^1$ is independently selected from: -phenyl-$C_{2-7}$cycloheteroalkyl, and -phenyl-aryl, wherein each cycloheteroalkyl, aryl and phenyl is unsubstituted or substituted with 1, 2, 3 or 4 substituents independently selected from $R^a$, and $R^2$ is selected from the group consisting of halogen; or a pharmaceutically acceptable salt thereof. In another class of the embodiment, each $R^1$ is independently selected from: -phenyl-$C_{2-7}$cycloheteroalkyl, and -phenyl-phenyl, wherein each cycloheteroalkyl and phenyl is unsubstituted or substituted with 1, 2, 3 or 4 substituents independently selected from $R^a$, and $R^2$ is selected from the group consisting of halogen; or a pharmaceutically acceptable salt thereof. In another class of the embodiment, each $R^1$ is independently selected from: -phenyl-pyrrolidine, and -phenyl-phenyl, wherein each pyrrolidine and phenyl is unsubstituted or substituted with 1, 2, 3 or 4 substituents independently selected from $R^a$, and $R^2$ is selected from the group consisting of halogen; or a pharmaceutically acceptable salt thereof.

In another class of this embodiment of the present invention, $R^2$ is independently selected from: —$(CH_2)_pC_{4-10}$cycloalkenyl, —$(CH_2)_p$aryl, —$(CH_2)_p$aryl-$C_{3-7}$cycloalkyl, —$(CH_2)_p$aryl-$C_{2-7}$cycloheteroalkyl, —$(CH_2)_p$aryl-aryl, —$(CH_2)_p$aryl-heteroaryl, —$(CH_2)_p$heteroaryl, —$C_{2-6}$alkynyl-aryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, aryl and heteroaryl is unsubstituted or substituted with 1, 2, 3 or 4 substituents independently selected from $R^a$, and $R^1$ is selected from the group consisting of halogen. In another class of this embodiment of the present invention, $R^2$ is independently selected from: —$C_{4-10}$cycloalkenyl, -aryl, -aryl-$C_{3-7}$cycloalkyl, -aryl-$C_{2-7}$cycloheteroalkyl, -aryl-aryl, -aryl-heteroaryl, -heteroaryl, —$C_{2-6}$alkynyl-aryl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, aryl and heteroaryl is unsubstituted or substituted with 1, 2, 3 or 4 substituents independently selected from $R^a$, and $R^1$ is selected from the group consisting of halogen. In another class of this embodiment of the present invention, $R^2$ is independently selected from: —$C_{4-10}$cycloalkenyl, -phenyl, -phenyl-$C_{3-7}$cycloalkyl, -phenyl-$C_{2-7}$cycloheteroalkyl, -phenyl-phenyl, -phenyl-heteroaryl, -heteroaryl, —$C_{2-6}$alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl and heteroaryl is unsubstituted or substituted with 1, 2, 3 or 4 substituents independently selected from $R^a$, and $R^1$ is selected from the group consisting of halogen. In another class of this embodiment of the present invention, $R^2$ is independently selected from: cyclohexenyl, -phenyl, phenyl-cyclopropyl, phenyl-piperazine, phenyl-pyrrolidine, -phenyl-phenyl, phenyl-triazole, phenyl-thiazole, phenyl-pyrazole, phenyl-oxadiazole, phenyl-furan, -pyridine, benzodioxole, indole, azaindole, benzofuran, benzopyrazole, benzodioxane, tetrahydroisoquinoline, —$C_2$-alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl and heteroaryl is unsubstituted or substituted with 1, 2, 3 or 4 substituents independently selected from $R^a$, and $R^1$ is selected from the group consisting of Cl and F. In another class of this embodiment of the present invention, $R^2$ is independently selected from: cyclohexenyl, -phenyl, phenyl-cyclopropyl, phenyl-piperazine, phenyl-pyrrolidine, -phenyl-phenyl, phenyl-triazole, phenyl-thiazole, phenyl-pyrazole, phenyl-oxadiazole, phenyl-furan, -pyridine, benzodioxole, indole, azaindole, benzofuran, benzopyrazole, benzodioxane, tetrahydroisoquinoline, —$C_2$-alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, phenyl and heteroaryl is unsubstituted or substituted with 1, 2, 3 or 4 substituents independently selected from $R^a$, and $R^1$ is Cl.

In another embodiment of the present invention, each $R^1$ is independently selected from: —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-6}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, and —$(CH_2)_p$aryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, paryl and heteroaryl is unsubstituted or substituted with 1, 2, 3 or 4 substituents independently selected from $R^a$.

In another embodiment of the present invention, each $R^1$ is independently selected from: —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{2-10}$cycloheteroalkyl, —$(CH_2)_p$aryl-$C_{2-10}$cycloheteroalkenyl, —$(CH_2)_p$aryl-aryl, and —$(CH_2)_p$aryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkynyl, cycloalkyl, cycloheteroalkyl, cycloheteroalkenyl, aryl and heteroaryl is unsubstituted or substituted with 1, 2, 3 or 4 substituents independently selected from $R^a$.

In another embodiment of the present invention, each $R^1$ is independently selected from: -phenyl-$C_{2-8}$alkynyl-$C_{1-8}$alkyl, -phenyl-$C_{2-3}$alkynyl-$C_{3-7}$cycloalkyl, -phenyl-$C_{2-3}$alkynyl-$C_{2-10}$cycloheteroalkyl, -phenyl-$C_{2-10}$cycloheteroalkenyl, biphenyl, and -phenyl-heteroaryl, wherein each alkyl, alkynyl, cycloalkyl, cycloheteroalkyl, cycloheteroalkenyl, phenyl, biphenyl and heteroaryl is unsubstituted or substituted with 1, 2, 3 or 4 substituents independently selected from $R^a$.

In another embodiment of the present invention, each $R^1$ is independently selected from: -phenyl-$C_2$alkynyl$C_{1-5}$alkyl, -phenyl-$C_{2-3}$alkynyl-$C_{3-7}$cycloalkyl, -phenyl-$C_{2-3}$alkynyl-$C_{2-10}$cycloheteroalkyl, -phenyl-$C_{2-10}$cycloheteroalkenyl, biphenyl, and -phenyl-heteroaryl, wherein each alkyl, alkynyl, cycloalkyl, cycloheteroalkyl, phenyl, biphenyl, cycloheteroalkenyl and heteroaryl is unsubstituted or substituted with 1, 2, 3 or 4 substituents independently selected from $R^a$. In another embodiment of the present invention, each $R^1$ is independently selected from: phenyl-$C_2$alkynyl$C_{1-5}$alkyl, phenyl-$C_{2-3}$alkynyl-$C_{3-7}$cycloalkyl, phenyl-$C_{2-3}$alkynyl-$C_{2-10}$cycloheteroalkyl, phenyl-dihydropyrrolo[3,4-c]pyrazole, biphenyl, phenyl-pyridine, wherein each alkyl, alkynyl, cycloalkyl, cycloheteroalkyl, phenyl, biphenyl dihydropyrrolo[3,4-c]pyrazole and pyridine is unsubstituted or substituted with 1, 2, 3 or 4 substituents independently selected from $R^a$. In another embodiment of the present invention, each $R^1$ is independently selected from: phenyl-$C_2$alkynyl-CH(OH)$CH_3$, phenyl-$C_2$alkynyl-$CH_2CH_2OH$, phenyl-$C_2$alkynyl-$C(CH_3)_2OH$, phenyl-$C_2$alkynyl-$CH_2OH$, phenyl-$C_2$alkynyl-$CH_2CH_2CH_2OH$, phenyl-$C_2$alkynyl-$(CH_2)_4$—$CH_3$, phenyl-$C_2$alkynyl-$CH_2CH_2$—NH-pyrimidine, and phenyl-$C_2$alkynyl-$CH_2OCH_2CH_2OCH_3$, phenyl-$C_2$alkynyl-cyclopentyl, phenyl-$C_2$alkynyl-cyclopentyl-OH, phenyl-$C_3$alkynyl-cyclopentyl, phenyl-$C_2$alkynyl-cyclohexyl, phenyl-$C_3$alkynyl-morpholine, phenyl-$C_2$alkynyl-piperidine, phenyl-$C_3$alkynyl-pyrrolidine-OH, phenyl-$C_3$alkynyl-piperazine-$CH_3$, phenyl-4,6-dihydropyrrolo[3,4-c]pyrazole, phenyl-4,6-dihydropyrrolo[3,4-c]pyrazole-$CH_2C(CH_3)_2$OH, phenyl-4,6-dihydropyrrolo[3,4-c]pyrazole-$CH_2C(CH_3)_2$F, phenyl-4,6-dihydropyrrolo[3,4-c]pyrazole-$CH_2$cyclopropyl, phenyl-4,6-dihydropyrrolo[3,4-c]pyrazole-$CH_2CF_3$, and phenyl-4,6-dihydropyrrolo[3,4-c]pyrazole-$SO_2NH$-cyclopropyl, biphenyl, biphenyl-pyrazole, biphenyl-pyrazole-$CH_3$, biphenyl-pyrazole-cyclopropyl, biphenyl-pyrazole-$CH_2C(CH_3)_2OH$, biphenyl-imidazole, biphenyl-imidazole-$CH_3$, biphenyl-oxazole, biphenyl-oxadiazole, biphenyl-oxadiazole-$CH_3$, biphenyl-oxadiazole-cyclopropyl, biphenyl-oxadiazole-$CF_3$, biphenyl-oxadiazole-OH, biphenyl-thiazole, biphenyl-triazole, biphenyl-tetrazole, biphenyl-dihydroimidazole, biphenyl-tetrahydropyrimidine, phenyl-pyridine, phenyl-pyridine-triazole, phenyl-pyridine-tetrazole, phenyl-pyridine-pyrazole, and phenyl-pyridine-pyrazole-$CH_2C(CH_3)_2OH$.

In another embodiment of the present invention, each $R^1$ is independently selected from: -phenyl-$C_{2-10}$cycloheteroalkenyl, biphenyl, -phenyl-heteroaryl, wherein each cycloheteroalkenyl, phenyl, biphenyl and heteroaryl is unsubstituted or substituted with 1, 2, 3 or 4 substituents independently selected from $R^a$. In a class of this embodiment, each $R^1$ is independently selected from: -phenyl-dihydropyrrolo[3,4-c]pyrazole, biphenyl, -phenyl-pyridine, wherein each phenyl, dihydropyrrolo[3,4-c]pyrazole, biphenyl, and pyridine, is unsubstituted or substituted with 1, 2, 3 or 4 substituents independently selected from $R^a$. In a subclass of this class, each $R^1$ is independently selected from: phenyl-4,6-dihydropyrrolo[3,4-c]pyrazole, phenyl-4,6-dihydropyrrolo[3,4-c]pyrazole-$CH_2C(CH_3)_2OH$, phenyl-4,6-dihydropyrrolo[3,4-c]pyrazole-$CH_2C(CH_3)_2F$, phenyl-4,6-dihydropyrrolo[3,4-c]pyrazole-$CH_2$cyclopropyl, phenyl-4,6-dihydropyrrolo[3,4-c]pyrazole-$CH_2CF_3$, and phenyl-4,6-dihydropyrrolo[3,4-c]pyrazole-$SO_2NH$-cyclopropyl, biphenyl, biphenyl-pyrazole, biphenyl-pyrazole-$CH_3$, biphenyl-pyrazole-cyclopropyl, biphenyl-pyrazole-$CH_2C(CH_3)_2OH$, biphenyl-imidazole, biphenyl-imidazole-$CH_3$, biphenyl-oxazole, biphenyl-oxadiazole, biphenyl-oxadiazole-$CH_3$, biphenyl-oxadiazole-cyclopropyl, biphenyl-oxadiazole-$CF_3$, biphenyl-oxadiazole-OH, biphenyl-thiazole, biphenyl-triazole, biphenyl-tetrazole, biphenyl-dihydroimidazole, biphenyl-tetrahydropyrimidine, phenyl-pyridine, phenyl-pyridine-triazole, phenyl-pyridine-tetrazole, phenyl-pyridine-pyrazole, and phenyl-pyridine-pyrazole-$CH_2C(CH_3)_2OH$.

In another embodiment of the present invention, each $R^1$ and $R^2$ is independently selected from: halogen, —$C_{4-10}$cycloalkenyl, -phenyl, phenyl-$C_{2-8}$alkynyl-$C_{1-8}$alkyl, phenyl-$C_{2-3}$alkynyl-$C_{3-7}$cycloalkyl, phenyl-$C_{2-3}$alkynyl-$C_{2-10}$cycloheteroalkyl, -phenyl-$C_{3-7}$cycloalkyl, -phenyl-$C_{2-7}$cycloheteroalkyl, phenyl-$C_{2-10}$cycloheteroalkenyl, -phenyl-aryl, -phenyl-heteroaryl, -heteroaryl, and —$C_{2-6}$alkynyl-phenyl, and wherein each alkyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from halogen; or a pharmaceutically acceptable salt thereof.

In another embodiment of the present invention, $R^1$ is independently selected from: —$C_{4-10}$cycloalkenyl, -phenyl, phenyl-$C_2$alkynyl$C_{1-5}$alkyl, phenyl-$C_{2-3}$alkynyl-$C_{3-7}$cycloalkyl, phenyl-$C_{2-3}$alkynyl-$C_{2-10}$cycloheteroalkyl, -phenyl-$C_{3-7}$cycloalkyl, -phenyl-$C_{2-7}$cycloheteroalkyl, phenyl-$C_{2-10}$ cycloheteroalkenyl, -phenyl-phenyl, -phenyl-heteroaryl, -heteroaryl, and —$C_{2-6}$alkynyl-phenyl, wherein each alkyl, alkynyl, cycloalkyl, cycloalkenyl, cycloheteroalkyl, cycloheteroalkenyl, phenyl and heteroaryl is unsubstituted or substituted with 1, 2, 3 or 4 substituents independently selected from $R^a$. In another embodiment of the present invention, $R^1$ is independently selected from: -phenyl-$C_{2-7}$cycloheteroalkyl, -phenyl-$C_{2-10}$cycloheteroalkenyl, -phenyl-phenyl, and -phenyl-heteroaryl, wherein each cycloheteroalkyl, cycloheteroalkenyl, heteroaryl and phenyl is unsubstituted or substituted with 1, 2, 3 or 4 substituents independently selected from $R^a$, In another embodiment of the present invention, $R^3$ and $R^4$ are each independently selected from: hydrogen, halogen, —$C_{1-6}$alkyl, —$C_{2-6}$alkenyl, —$C_{2-6}$alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl.

In another embodiment of the present invention, each $R^3$ is absent or independently selected from: hydrogen, halogen, —$C_{1-6}$ alkyl, —$C_{2-6}$ alkenyl, —$C_{2-6}$ alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, each $R^3$ is independently selected from: hydrogen, halogen, —$C_{1-6}$ alkyl, —$C_{2-6}$ alkenyl, —$C_{2-6}$ alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In another class of this embodiment, each $R^3$ is independently selected from: hydrogen, halogen, —$C_{1-6}$ alkyl, —$C_{2-6}$ alkenyl, —$C_{2-6}$ alkynyl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In another class of this embodiment, each $R^3$ is independently selected from: hydrogen, halogen, —$C_{1-6}$ alkyl, —CN, —$CF_3$, —OH, —$OC_{1-6}$alkyl, —$NH_2$, —$NHC_{1-6}$alkyl, and —$N(C_{1-6}$alkyl$)_2$. In another class of this embodiment, each $R^3$ is independently selected from: hydrogen, halogen, —$C_{1-6}$ alkyl, —CN, —$CF_3$, —OH, and —$OC_{1-6}$alkyl.

In another class of this embodiment, each $R^3$ is independently selected from: hydrogen, and —$C_{1-6}$alkyl. In another class of this embodiment, each $R^3$ is hydrogen. In another class of this embodiment, each $R^3$ is —$C_{1-6}$ alkyl.

In another embodiment of the present invention, $R^3$ is hydrogen or absent. In a class of this embodiment, $R^3$ is hydrogen. In another class of this embodiment of the present invention, $R^3$ is absent.

In another embodiment of the present invention, each $R^4$ is absent or independently selected from: hydrogen, halogen, —$C_{1-6}$ alkyl, —$C_{2-6}$ alkenyl, —$C_{2-6}$ alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, each $R^4$ is independently selected from: hydrogen, halogen, —$C_{1-6}$ alkyl, —$C_{2-6}$ alkenyl, —$C_{2-6}$ alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In another class of this embodiment, each $R^4$ is independently selected from: hydrogen, halogen, —$C_{1-6}$ alkyl, —$C_{2-6}$ alkenyl, —$C_{2-6}$ alkynyl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In another class of this embodiment, each $R^4$ is independently selected from: hydrogen, halogen, —$C_{1-6}$ alkyl, —CN, —$CF_3$, —OH, —$OC_{1-6}$alkyl, —$NH_2$, —$NHC_{1-6}$alkyl, and —$N(C_{1-6}$alkyl$)_2$. In another class of this embodiment, each $R^4$ is independently selected from: hydrogen, halogen, —$C_{1-6}$alkyl, —CN, —$CF_3$, —OH, and —$OC_{1-6}$alkyl.

In another class of this embodiment, each $R^4$ is independently selected from: hydrogen, and —$C_{1-6}$alkyl. In another class of this embodiment, each $R^4$ is hydrogen. In another class of this embodiment, each $R^4$ is —$C_{1-6}$alkyl.

In another embodiment of the present invention, $R^4$ is hydrogen or absent. In a class of this embodiment, $R^4$ is hydrogen. In another class of this embodiment of the present invention, $R^4$ is absent.

In another embodiment of the present invention, $R^5$ is selected from the group consisting of: hydrogen, —$C_{1-6}$alkyl, —$CH_2CO_2H$, and —$CH_2CO_2C_{1-6}$alkyl. In a class of this embodiment, $R^5$ is selected from the group consisting of: hydrogen, and —$C_1$-alkyl. In another class of this embodiment, $R^5$ is hydrogen.

In another embodiment of the present invention, $R^a$ is independently selected from the group consisting of: —$(CH_2)_m$-halogen, oxo, —$(CH_2)_mOH$, —$(CH_2)_mN(R^j)_2$, —$(CH_2)_mNO_2$, —$(CH_2)_mCN$, —$C_{1-6}$alkyl, —$(CH_2)_mCF_3$, —$(CH_2)_mOCF_3$, —O—$(CH_2)_m$—$OC_{1-6}$alkyl, —$(CH_2)_mC(O)N(R^j)_2$, —$(CH_2)_mC(=N-OH)N(R^j)_2$, —$(CH_2)_mOC_{1-6}$alkyl, —$(CH_2)_mO$—$(CH_2)_m$—$C_{3-7}$cycloalkyl, —$(CH_2)_mO$—$(CH_2)_m$—$C_{2-7}$cycloheteroalkyl, —$(CH_2)_mO$—$(CH_2)_m$-aryl, —$(CH_2)_mO$—$(CH_2)_m$-heteroaryl, —$(CH_2)_mSC_{1-6}$alkyl, —$(CH_2)_mS(O)C_{1-6}$alkyl, —$(CH_2)_mSO_2C_{1-6}$alkyl, —$(CH_2)_mSO_2C_{3-7}$cycloalkyl, —$(CH_2)_mSO_2C_{2-7}$cycloheteroalkyl, —$(CH_2)_mSO_2$-aryl, —$(CH_2)_mSO_2$-heteroaryl, —$(CH_2)_mSO_2NHC_{1-6}$alkyl, —$(CH_2)_mSO_2NHC_{3-7}$cycloalkyl, —$(CH_2)_mSO_2NHC_{2-7}$cycloheteroalky, —$(CH_2)_mSO_2NH$-aryl, —$(CH_2)_mSO_2NH$-heteroaryl, —$(CH_2)_mNHSO_2$—$C_{1-6}$alkyl, —$(CH_2)_mNHSO_2$—$C_{3-7}$cycloalkyl, —$(CH_2)_mNHSO_2$—$C_{2-7}$cycloheteroalkyl, —$(CH_2)_mNHSO_2$-aryl, —$(CH_2)_mNHSO_2NH$-heteroaryl, —$(CH_2)_mN(R^j)$—$C_{1-6}$alkyl, —$(CH_2)_mN(R^j)$—$C_{3-7}$cycloalkyl, —$(CH_2)_mN(R^j)$—$C_{2-7}$cycloheteroalkyl, —$(CH_2)_mN(R^j)$—$C_{2-7}$cycloheteroalkenyl, —$(CH_2)_mN(R^j)$-aryl, —(CH$_2$)$_m$N(R$^j$)-heteroaryl, —(CH$_2$)$_m$C(O)R$^f$, —(CH$_2$)$_m$C(O)N(R$^j$)$_2$, —(CH$_2$)$_m$N(R$^j$)C(O)N(R$^j$)$_2$, —(CH$_2$)$_m$CO$_2$H, —(CH$_2$)$_m$OCOH, —(CH$_2$)$_m$CO$_2$R$^f$, —(CH$_2$)$_m$OCOR$^f$, —(CH$_2$)$_m$C$_{3-7}$cycloalkyl, —(CH$_2$)$_m$C$_{3-7}$cycloalkenyl, —(CH$_2$)$_m$C$_{2-6}$cycloheteroalkyl, —(CH$_2$)$_m$C$_{2-6}$cycloheteroalkenyl, —(CH$_2$)$_m$aryl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl.

In another embodiment of the present invention, each R$^a$ is independently selected from the group consisting of: halogen, oxo, —(CH$_2$)$_m$OH, —(CH$_2$)$_m$N(R$^j$)$_2$, —(CH$_2$)$_m$NO$_2$, —(CH$_2$)$_m$CN, —C$_{1-6}$alkyl, —(CH$_2$)$_m$CF$_3$, —(CH$_2$)$_m$OCF$_3$, —OCH$_2$OC$_{1-6}$ alkyl, —(CH$_2$)$_m$C(O)N(R$^j$)$_2$, —(CH$_2$)$_m$C(=N—OH)N(R$^j$)$_2$, —(CH$_2$)$_m$OC$_{1-6}$alkyl, —(CH$_2$)$_m$O—(CH$_2$)$_m$—C$_{3-7}$cycloalkyl, —(CH$_2$)$_m$O—(CH$_2$)$_m$—C$_{2-7}$cycloheteroalkyl, —(CH$_2$)$_m$O—(CH$_2$)$_m$-aryl, —(CH$_2$)$_m$O—(CH$_2$)$_m$-heteroaryl, —(CH$_2$)$_m$SC$_{1-6}$alkyl, —(CH$_2$)$_m$S(O)C$_{1-6}$alkyl, —(CH$_2$)$_m$SO$_2$C$_{1-6}$alkyl, —(CH$_2$)$_m$SO$_2$C$_{3-7}$cycloalkyl, —(CH$_2$)$_m$SO$_2$C$_{2-7}$cycloheteroalkyl, —(CH$_2$)$_m$SO$_2$-aryl, —(CH$_2$)$_m$SO$_2$-heteroaryl, —(CH$_2$)$_m$SO$_2$NHC$_{1-6}$alkyl, —(CH$_2$)$_m$SO$_2$NHC$_{3-7}$cycloalkyl, —(CH$_2$)$_m$SO$_2$NHC$_{2-7}$cycloheteroalkyl, —(CH$_2$)$_m$SO$_2$NH-aryl, —(CH$_2$)$_m$SO$_2$NH-heteroaryl, —(CH$_2$)$_m$NHSO$_2$—C$_{1-6}$alkyl, —(CH$_2$)$_m$NHSO$_2$—C$_{3-7}$cycloalkyl, —(CH$_2$)$_m$NHSO$_2$—C$_{2-7}$cycloheteroalkyl, —(CH$_2$)$_m$NHSO$_2$-aryl, —(CH$_2$)$_m$NHSO$_2$NH-heteroaryl, —(CH$_2$)$_m$C(O)R$^f$, —(CH$_2$)$_m$C(O)N(R$^j$)$_2$, —(CH$_2$)$_m$N(R$^j$)C(O)N(R$^j$)$_2$, —(CH$_2$)$_m$CO$_2$H, —(CH$_2$)$_m$OCOH, —(CH$_2$)$_m$CO$_2$R$^f$, —(CH$_2$)$_m$OCOR$^f$, —(CH$_2$)$_m$C$_{3-7}$cycloalkyl, —(CH$_2$)$_m$C$_{3-7}$cycloalkenyl, —(CH$_2$)$_m$C$_{2-6}$cycloheteroalkyl, —(CH$_2$)$_m$C$_{2-6}$cycloheteroalkenyl, —(CH$_2$)$_m$aryl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl.

In a class of this embodiment, each R$^a$ is independently selected from the group consisting of: halogen, —(CH$_2$)$_m$OH, —(CH$_2$)$_m$N(R$^j$)$_2$, —(CH$_2$)$_m$CN, —C$_{1-6}$alkyl, —(CH$_2$)$_m$CF$_3$, —(CH$_2$)$_m$OCF$_3$, —(CH$_2$)$_m$C(O)N(R$^j$)$_2$, —(CH$_2$)$_m$OC$_{1-6}$alkyl, —(CH$_2$)$_m$O—(CH$_2$)$_m$—C$_{3-7}$cycloalkyl, —(CH$_2$)$_m$O—(CH$_2$)$_m$—C$_{2-7}$cycloheteroalkyl, —(CH$_2$)$_m$SO$_2$C$_{1-6}$alkyl, —(CH$_2$)$_m$SO$_2$C$_{2-7}$cycloheteroalkyl, —(CH$_2$)$_m$SO$_2$NHC$_{1-6}$alkyl, —(CH$_2$)$_m$SO$_2$NHC$_{3-7}$cycloalkyl, —(CH$_2$)$_m$NHSO$_2$—C$_{1-6}$alkyl, —(CH$_2$)$_m$C(O)R$^f$, —(CH$_2$)$_m$CO$_2$H, —(CH$_2$)$_m$CO$_2$R$^f$, —(CH$_2$)$_m$C$_{3-7}$cycloalkyl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, and cycloheteroalkyl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl.

In another class of this embodiment, each R$^a$ is independently selected from the group consisting of: halogen, —(CH$_2$)$_m$OH, —N(R$^j$)$_2$, —CN, —C$_{1-6}$alkyl, —(CH$_2$)$_m$CF$_3$, —OCF$_3$, —(CH$_2$)$_m$C(O)N(R$^j$)$_2$, —(CH$_2$)$_m$OC$_{1-6}$alkyl, —(CH$_2$)$_m$O—(CH$_2$)$_m$—C$_{3-7}$cycloalkyl, —(CH$_2$)$_m$O—(CH$_2$)$_m$—C$_{2-7}$cycloheteroalkyl, —SO$_2$C$_{1-6}$alkyl, —SO$_2$C$_{2-7}$cycloheteroalkyl, —SO$_2$NHC$_{1-6}$alkyl, —SO$_2$NHC$_{3-7}$cycloalkyl, —NHSO$_2$—C$_{1-6}$alkyl, —C(O)R$^f$, —CO$_2$H, —CO$_2$R$^f$, —C$_{3-7}$cycloalkyl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl and cycloheteroalkyl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl.

In another class of this embodiment, each R$^a$ is independently selected from the group consisting of: halogen, —(CH$_2$)$_m$OH, —N(R$^j$)$_2$, —CN, —C$_{1-6}$alkyl, —(CH$_2$)$_m$CF$_3$, —OCF$_3$, —(CH$_2$)$_m$C(O)N(R$^j$)$_2$, —(CH$_2$)$_m$OC$_{1-6}$alkyl, —(CH$_2$)$_m$O—(CH$_2$)$_m$—C$_{3-7}$cycloalkyl, —(CH$_2$)$_m$O—(CH$_2$)$_m$—C$_{2-7}$cycloheteroalkyl, —SO$_2$C$_{1-6}$alkyl, —SO$_2$C$_{2-7}$cycloheteroalkyl, —SO$_2$NHC$_{1-6}$alkyl, —SO$_2$NHC$_{3-7}$cycloalkyl, —NHSO$_2$—C$_{1-6}$alkyl, —C(O)R$^f$, —CO$_2$H, —CO$_2$R$^f$, —C$_{3-7}$cycloalkyl, wherein each CH$_2$ is unsubstituted or substituted with 1 or 2 substituents selected from: —OH, —C$_{1-6}$alkyl, —OC-6alkyl and halogen, and wherein alkyl, cycloalkyl and cycloheteroalkyl are unsubstituted or substituted with 1, 2, 3 or 4 substituents selected from: —C$_{1-6}$alkyl, halogen, —SO$_2$C$_{1-6}$alkyl, and —C$_{3-7}$cycloalkyl.

In another class of this embodiment, each R$^a$ is independently selected from the group consisting of: F, Cl, Br, —C(CH$_3$)$_2$OH, —OH, —CH$_2$OH, —CH(OH)CHF$_2$, CH(OH)CF$_3$, —(CH$_2$)$_2$C(CH$_3$)$_2$—OH, —N(CH$_3$)$_2$, —CN, —CH$_3$, —CH$_2$CH$_3$, —C(CH$_3$)$_3$—CF$_3$, —CH$_2$CF$_3$—OCF$_3$—C(O)NH-cyclopropyl —OCH$_2$CH$_3$, —OCH$_3$, —O(CH$_2$)$_3$—SO$_2$CH$_3$, OCH$_2$CH$_2$F, —CH$_2$OCH$_3$—O-cyclobutyl, —O-cyclopentyl, —O-azetidine, —O—CH$_2$-dioxolane, —SO$_2$CH(CH$_3$)$_2$, —SO$_2$CH$_3$—SO$_2$-pyrrolidine, —SO$_2$-azetidine —SO$_2$NHCH$_3$, —SO$_2$NHC(CH$_3$)$_3$, —SO$_2$NH-cyclopropyl, —NHSO$_2$—CH$_3$, —C(O)CH(CH$_3$)$_2$, C(O)-pyrrolidine, —C(O)-morpholine, —CO$_2$H, —CO$_2$—CH(CH$_3$)$_2$, —CO$_2$—C(CH$_3$)$_3$, and cyclopropyl, wherein each CH$_2$ is unsubstituted or substituted with 1 or 2 substituents selected from: —OH, —C$_{1-6}$alkyl, —OC$_{1-6}$alkyl and halogen, and wherein alkyl, cycloalkyl and cycloheteroalkyl are unsubstituted or substituted with 1, 2, 3 or 4 substituents selected from: —C$_{1-6}$alkyl, halogen, —SO$_2$C$_{1-6}$alkyl, and —C$_{3-7}$cycloalkyl.

In another class of this embodiment, each R$^a$ is independently selected from the group consisting of: F, Cl, Br, —C(CH$_3$)$_2$OH, —OH, —CH$_2$OH, —CH(OH)CHF$_2$, CH(OH)CF$_3$, —(CH$_2$)$_2$C(CH$_3$)$_2$—OH, —N(CH$_3$)$_2$, —CN, —CH$_3$, —CH$_2$CH$_3$, —C(CH$_3$)$_3$—CF$_3$, —CH$_2$CF$_3$—OCF$_3$—C(O)NH-cyclopropyl —OCH$_2$CH$_3$, —OCH$_3$, —O(CH$_2$)$_3$—SO$_2$CH$_3$, OCH$_2$CH$_2$F, —CH$_2$OCH$_3$—O-cyclobutyl, —O-cyclopentyl, —O-azetidine, —O—CH$_2$-dioxolane, —SO$_2$CH(CH$_3$)$_2$, —SO$_2$CH$_3$—SO$_2$-pyrrolidine, —SO$_2$-azetidine —SO$_2$NHCH$_3$, —SO$_2$NHC(CH$_3$)$_3$, —SO$_2$NH-cyclopropyl, —NHSO$_2$—CH$_3$, —C(O)CH (CH$_3$)$_2$, C(O)-pyrrolidine, —C(O)-morpholine, —CO$_2$H, —CO$_2$—CH(CH$_3$)$_2$, —CO$_2$—C(CH$_3$)$_3$, and cyclopropyl.

In another embodiment of the present invention, R$^a$ is independently selected from the group consisting of: halogen, oxo, —(CH$_2$)$_m$OH, —(CH$_2$)$_m$N(R$^j$)$_2$, —(CH$_2$)$_m$NO$_2$, —(CH$_2$)$_m$CN, —C$_{1-6}$alkyl, —(CH$_2$)$_m$CF$_3$, —(CH$_2$)$_m$OCF$_3$, —OCH$_2$OC$_{1-6}$alkyl, —OCH$_2$-aryl, —(CH$_2$)$_m$C(=N—OH)N(R$^j$)$_2$, —(CH$_2$)$_m$OC$_{1-6}$alkyl, —(CH$_2$)$_m$O-aryl, —(CH$_2$)$_m$SC$_{1-6}$alkyl, —(CH$_2$)$_m$S(O)C$_{1-6}$alkyl, —(CH$_2$)$_m$SO$_2$C$_{1-6}$alkyl, —(CH$_2$)$_m$SO$_2$C$_{3-7}$cycloalkyl, —(CH$_2$)$_m$SO$_2$C$_{2-7}$cycloheteroalkyl, —(CH$_2$)$_m$SO$_2$-aryl, —(CH$_2$)$_m$SO$_2$-heteroaryl, —(CH$_2$)$_m$SO$_2$NHC$_{1-6}$alkyl, —(CH$_2$)$_m$SO$_2$NHC$_{3-7}$cycloalkyl, —(CH$_2$)$_m$SO$_2$NHC$_{2-7}$cycloheteroalkyl, —(CH$_2$)$_m$SO$_2$NH-aryl, —(CH$_2$)$_m$SO$_2$NH-heteroaryl, —(CH$_2$)$_m$NHSO$_2$—C$_{1-6}$alkyl, —(CH$_2$H$_2$)$_m$NHSO$_2$—C$_{3-7}$cycloalkyl, —(CH$_2$)$_m$NHSO$_2$—C$_{2-7}$cycloheteroalkyl, —(CH$_2$)$_m$NHSO$_2$-aryl, —(CH$_2$)$_m$NHSO$_2$NH-heteroaryl, —(CH$_2$)$_m$C(O)R$^f$, —(CH$_2$)$_m$C(O)N(R$^j$)$_2$, —(CH$_2$)$_m$N(R$^j$)C(O)N(R$^j$)$_2$, —(CH$_2$)$_m$CO$_2$H, —(CH$_2$)$_m$OCOH, —(CH$_2$)$_m$CO$_2$R$^f$, —(CH$_2$)$_m$OCOR$^f$, —(CH$_2$)$_m$C$_{3-7}$cycloalkyl, —(CH$_2$)$_m$C$_{3-7}$cycloalkenyl, —(CH$_2$)$_m$C$_{2-6}$cycloheteroalkyl, —(CH$_2$)$_m$C$_{2-6}$cycloheteroalkenyl, —(CH$_2$)$_m$aryl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl.

In a class of this embodiment, each R$^a$ is independently selected from the group consisting of: halogen, —(CH$_2$)$_m$OH, —(CH$_2$)$_m$N(R$^j$)$_2$, —(CH$_2$)$_m$CN, —C$_{1-6}$alkyl, —(CH$_2$)$_m$CF$_3$, —(CH$_2$)$_m$OC$_{1-6}$alkyl, —(CH$_2$)$_m$SO$_2$C$_{1-6}$alkyl, —(CH$_2$)$_m$SO$_2$C$_{2-7}$cycloheteroalkyl, —(CH$_2$)$_m$SO$_2$NHC$_{1-6}$alkyl, —(CH$_2$)$_m$SO$_2$NHC$_{3-7}$cycloalkyl, —(CH$_2$)$_m$NHSO$_2$—C$_{1-6}$alkyl, —(CH$_2$)$_m$C(O)R$^f$, and —(CH$_2$)$_m$CO$_2$H, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, and cycloheteroalkyl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl.

In a subclass of this class, each R$^a$ is independently selected from the group consisting of: halogen, —(CH$_2$)$_m$OH, —N(R$^j$)$_2$, —CN, —C$_{1-6}$alkyl, —CF$_3$, —OC$_{1-6}$alkyl, —SO$_2$C$_{1-6}$alkyl, —SO$_2$C$_{2-7}$cycloheteroalkyl, —SO$_2$NHC$_{1-6}$alkyl, —SO$_2$NHC$_{3-7}$cycloalkyl, —NHSO$_2$—C$_{1-6}$alkyl, —C(O)R$^f$, and —CO$_2$H, wherein each alkyl, cycloalkyl, and cycloheteroalkyl is unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In another subclass of this class, each R$^a$ is independently selected from the group consisting of: F, Cl, —CH$_2$OH, —OH, —N(CH$_3$)$_2$, —CN, —CH$_3$, —CF$_3$, —OCH$_3$, —OCH$_2$CH$_3$, —C(OH)(CH$_3$)$_2$, —CH(OH)CHF$_2$, —CH(OCH$_3$)CH$_3$, —SO$_2$CH$_3$, —SO$_2$CH(CH$_3$)$_2$, —SO$_2$-azetidine, —SO$_2$-pyrrolidine, —SO$_2$NH-tert-butyl, —SO$_2$NH-cyclopropyl, —NHSO$_2$CH$_3$, —C(O)CH(CH$_3$)$_2$, and —CO$_2$H, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, and cycloheteroalkyl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a subclass of this class, each R$^a$ is independently selected from the group consisting of: F, Cl, —CH$_2$OH, —OH, —N(CH$_3$)$_2$, —CN, —CH$_3$, —CF$_3$, —OCH$_3$, —OCH$_2$CH$_3$, —C(OH)(CH$_3$)$_2$, —CH(OH)CHF$_2$, —CH(OCH$_3$)CH$_3$, —SO$_2$CH$_3$, —SO$_2$CH(CH$_3$)$_2$, —SO$_2$-azetidine, —SO$_2$-pyrrolidine, —SO$_2$NH-tert-butyl, —SO$_2$NH-cyclopropyl, —NHSO$_2$CH$_3$, —C(O)CH(CH$_3$)$_2$, and —CO$_2$H. In another class of this embodiment, each R$^a$ is independently selected from the group consisting of: —SO$_2$C$_{1-6}$alkyl, and —NHSO$_2$—C$_{1-6}$alkyl, wherein alkyl is unsubstituted or substituted with 1, 2, or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this class, each R$^a$ is independently selected from the group consisting of: —SO$_2$CH$_3$, —SO$_2$CH(CH$_3$)$_2$, and —NHSO$_2$CH$_3$, wherein each alkyl is unsubstituted or substituted with 1, 2, or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In another subclass of this class, each R$^a$ is independently selected from the group consisting of: —SO$_2$CH$_3$, —SO$_2$CH(CH$_3$)$_2$, and —NHSO$_2$CH$_3$. In another subclass of this class, each R$^a$ is independently selected from the group consisting of: —SO$_2$CH$_3$ and —NHSO$_2$CH$_3$.

In another embodiment of the present invention, each R$^a$ is independently selected from the group consisting of: —(CH$_2$)$_m$CN, —(CH$_2$)$_m$NHSO$_2$—C$_{1-6}$alkyl, and —(CH$_2$)$_m$SO$_2$C$_{1-6}$alkyl. In a class of this embodiment, each R$^a$ is independently selected from the group consisting of: —CN, —NHSO$_2$—C$_{1-6}$alkyl, and —SO$_2$C$_{1-6}$alkyl. In another class of this embodiment, each R$^a$ is independently selected from the group consisting of: —CN, —NHSO$_2$CH$_3$, and —SO$_2$C$_{1-6}$alkyl.

In another embodiment of the present invention, each R$^a$ is independently selected from the group consisting of: —(CH$_2$)$_m$CN, —(CH$_2$)$_m$NHSO$_2$—C$_{1-6}$alkyl, and —(CH$_2$)$_m$SO$_2$C$_{1-6}$alkyl. In a class of this embodiment, each R$^a$ is independently selected from the group consisting of —CN, —NHSO$_2$—C$_{1-6}$alkyl, and —SO$_2$C$_{1-6}$alkyl. In another class of this embodiment, each R$^a$ is independently selected from the group consisting of: —CN, —NHSO$_2$CH$_3$, —SO$_2$CH$_3$, and —SO$_2$CH(CH$_3$)$_2$. In another class of this embodiment, each R$^a$ is independently selected from the group consisting of: —CN, —NHSO$_2$CH$_3$ and —SO$_2$CH$_3$.

In another embodiment of the present invention, each R$^a$ is independently selected from the group consisting of: —(CH$_2$)$_m$CN, and —(CH$_2$)$_m$SO$_2$C$_{1-6}$alkyl. In a class of this embodiment, each R$^a$ is independently selected from the group consisting of: —CN, and —SO$_2$C$_{1-6}$alkyl. In another class of this embodiment, each R$^a$ is independently selected from the group consisting of: —CN and —SO$_2$CH$_3$.

In another embodiment of the present invention, R$^a$ is independently selected from the group consisting of: —(CH$_2$)$_m$-halogen, —(CH$_2$)$_m$OH, —(CH$_2$)$_m$CF$_3$, —O—(CH$_2$)$_m$—OC$_{1-6}$alkyl, —(CH$_2$)$_m$SO$_2$NHC$_{3-7}$cycloalkyl, —(CH$_2$)$_m$N(R$^j$)-heteroaryl, —(CH$_2$)$_m$C$_{3-7}$cycloalkyl, —(CH$_2$)$_m$C$_{2-6}$cycloheteroalkenyl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein alkyl, cycloalkyl, cycloheteroalkenyl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl. In a class of this embodiment, each CH$_2$ is unsubstituted or substituted with 1 or 2 substituents selected from: —C$_{1-6}$alkyl, and each alkyl, cycloalkyl, cycloheteroalkenyl and heteroaryl is unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl. In another class of this embodiment, each CH$_2$ is unsubstituted or substituted with 1 or 2 substituents selected from: —C$_{1-6}$alkyl, and each alkyl, cycloalkyl, cycloheteroalkenyl and heteroaryl is unsubstituted or substituted with 1, 2, 3 or 4 substituents selected from: oxo, —(CH$_2$)$_{0-5}$OH, —C$_{1-6}$alkyl, —CF$_3$, and —C$_{3-7}$cycloalkyl. In another class of this embodiment, each CH$_2$ is unsubstituted or substituted with 1 or 2 substituents selected from: —CH$_3$, and each alkyl, cycloalkyl, cycloheteroalkenyl and heteroaryl is unsubstituted or substituted with 1, 2, 3 or 4 substituents selected from: —OH, —CH$_2$C(CH$_3$)$_2$OH, —CH$_3$, CH$_2$CH$_3$, CH(CH$_3$)$_2$, —CF$_3$, cyclopropyl, cyclohexyl, and cyclopentyl. In another class of this embodiment, each heteroaryl is unsubstituted or substituted with 1, 2, 3 or 4 substituents selected from: —CH$_2$C(CH$_3$)$_2$OH.

In another embodiment of the present invention, R$^a$ is independently selected from the group consisting of: —CH$_2$CH$_2$F, —OH, —CH$_2$CH$_2$OH, —CH$_2$C(CH$_3$)$_2$OH, —CH$_2$CF$_3$, —OCH$_2$CH$_2$OCH$_3$, —SO$_2$NHcyclopropyl, —NH-pyrimidine, —CH$_2$cyclopropyl, 2,5 dihydro 1H imidazole, 1,4,5,6-tetrahydropyrimidine, imidazole, oxazole, thiazole, triazole, tetrazole, and oxadiazole, wherein each CH$_2$ is unsubstituted or substituted with 1 or 2 substituents selected from: —C$_{1-6}$alkyl, and wherein alkyl, cycloalkyl, cycloheteroalkenyl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl. In a class of this embodiment, each CH$_2$ is unsubstituted or substituted with 1 or 2 substituents selected from: —C$_{1-6}$alkyl, and each alkyl, cycloalkyl, cycloheteroalkenyl and heteroaryl is unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl. In another class of this embodiment, each CH$_2$ is unsubstituted or substituted with 1 or 2 substituents selected from: —C$_{1-6}$alkyl, and each alkyl, cycloalkyl, cycloheteroalkenyl and heteroaryl is unsubstituted or substituted with 1, 2, 3 or 4 substituents selected from: oxo, —(CH$_2$)$_{0-5}$OH, —C$_{1-6}$alkyl, —CF$_3$, and —C$_{3-7}$cycloalkyl. In another class of this embodiment, each CH$_2$ is unsubstituted or substituted with 1 or 2 substituents selected from: —CH$_3$, and each alkyl, cycloalkyl, cycloheteroalkenyl and heteroaryl is unsubstituted or substituted with 1, 2, 3 or 4 substituents selected from: —OH, —CH$_2$C(CH$_3$)$_2$OH, —CH$_3$, CH$_2$CH$_3$, CH(CH$_3$)$_2$, —CF$_3$, cyclopropyl, cyclohexyl, and cyclopentyl. In another class of this embodiment, each heteroaryl is unsubstituted or substituted with 1, 2, 3 or 4 substituents selected from: —CH$_2$C(CH$_3$)$_2$OH.

In another embodiment of the present invention, R$^a$ is independently selected from the group consisting of: —(CH$_2$)$_m$OH, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl, and wherein heteroaryl is unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl. In a class of this embodiment, each CH$_2$ is unsubstituted or substituted with 1 or 2 substituents selected from: —C$_{1-6}$alkyl, and each heteroaryl is unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$-phenyl, heteroaryl and CH$_2$heteroaryl. In another class of this embodiment, each CH$_2$ is unsubstituted or substituted with 1 or 2 substituents selected from: —C$_{1-6}$alkyl, and each heteroaryl is unsubstituted or substituted with 1, 2, 3 or 4 substituents selected from: oxo, —(CH$_2$)$_{0-5}$OH, —C$_{1-6}$alkyl, —CF$_3$, and —C$_{3-7}$cycloalkyl. In another class of this embodiment, each CH$_2$ is unsubstituted or substituted with 1 or 2 substituents selected from: —CH$_3$, and each heteroaryl is unsubstituted or substituted with 1, 2, 3 or 4 substituents selected from: —OH, —CH$_2$C(CH$_3$)$_2$OH, —CH$_3$, CH$_2$CH$_3$, CH(CH$_3$)$_2$, —CF$_3$, cyclopropyl, cyclohexyl, and cyclopentyl. In another class of this embodiment, each heteroaryl is unsubstituted or substituted with 1, 2, 3 or 4 substituents selected from: —CH$_2$C(CH$_3$)$_2$OH.

In another embodiment of the present invention, R$^a$ is independently selected from the group consisting of: —OH, —CH$_2$CH$_2$OH, —CH$_2$C(CH$_3$)$_2$OH, pyrazole, imidazole, oxazole, thiazole, triazole, tetrazole, and oxadiazole, wherein each CH$_2$ is unsubstituted or substituted with 1 or 2 substituents selected from: oxo, —(CH$_2$)$_{0-3}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —$C_{3-7}$cycloalkyl, phenyl, CH$_2$-phenyl, heteroaryl and CH$_2$heteroaryl, and wherein heteroaryl are unsubstituted or substituted with 1, 2, 3 or 4 substituents selected from: oxo, —(CH$_2$)$_{0-5}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —SO$_2C_{1-6}$alkyl, —$C_{3-7}$cycloalkyl, phenyl, CH$_2$-phenyl, heteroaryl and CH$_2$heteroaryl. In a class of this embodiment, each CH$_2$ is unsubstituted or substituted with 1 or 2 substituents selected from: —$C_{1-6}$alkyl, and each heteroaryl is unsubstituted or substituted with 1, 2, 3 or 4 substituents selected from: oxo, —(CH$_2$)$_{0-5}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —SO$_2C_{1-6}$alkyl, —$C_{3-7}$cycloalkyl, phenyl, CH$_2$-phenyl, heteroaryl and CH$_2$heteroaryl. In another class of this embodiment, each CH$_2$ is unsubstituted or substituted with 1 or 2 substituents selected from: —$C_{1-6}$alkyl, and each heteroaryl is unsubstituted or substituted with 1, 2, 3 or 4 substituents selected from: oxo, —(CH$_2$)$_{0-5}$OH, —$C_{1-6}$alkyl, —CF$_3$, and —$C_{3-7}$cycloalkyl.

In another class of this embodiment, each CH$_2$ is unsubstituted or substituted with 1 or 2 substituents selected from: —CH$_3$, and each heteroaryl is unsubstituted or substituted with 1, 2, 3 or 4 substituents selected from: —OH, —CH$_2$C(CH$_3$)$_2$OH, —CH$_3$, CH$_2$CH$_3$, CH(CH$_3$)$_2$, —CF$_3$, cyclopropyl, cyclohexyl, and cyclopentyl. In another class of this embodiment, each heteroaryl is unsubstituted or substituted with 1, 2, 3 or 4 substituents selected from: —CH$_2$C(CH$_3$)$_2$OH.

In another embodiment of the present invention, R$^a$ is independently selected from the group consisting of: —(CH$_2$)$_m$-halogen, —(CH$_2$)$_m$OH, —(CH$_2$)$_m$—N(R$^j$)$_2$, —(CH$_2$)$_m$—CN, —(CH$_2$)$_m$ $C_{1-6}$alkyl, —(CH$_2$)$_m$OCF$_3$, —(CH$_2$)$_m$C(O)N(R$^j$)$_2$, —(CH$_2$)$_m$O—(CH$_2$)$_m$—$C_{3-7}$cycloalkyl, —(CH$_2$)$_m$O—(CH$_2$)$_m$—$C_{2-7}$cycloheteroalkyl, —(CH$_2$)$_m$ SO$_2C_{1-6}$alkyl, —(CH$_2$)$_m$ SO$_2C_{2-7}$cycloheteroalkyl, —(CH$_2$)$_m$ SO$_2$NHC$_{1-6}$alkyl, —(CH$_2$)$_m$ NHSO$_2$—$C_{1-6}$alkyl, —(CH$_2$)$_m$ C(O)R$^f$, —(CH$_2$)$_m$ CO$_2$H, —(CH$_2$)$_m$ CO$_2$R$^f$, —(CH$_2$)$_m$CF$_3$, —O—(CH$_2$)$_m$—OC$_{1-6}$alkyl, —(CH$_2$)$_m$SO$_2$NHC$_{3-7}$cycloalkyl, —(CH$_2$)$_m$N(R$^j$)-heteroaryl, —(CH$_2$)$_m$$C_{3-7}$cycloalkyl, —(CH$_2$)$_m$$C_{2-6}$cycloheteroalkenyl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —$C_{3-7}$cycloalkyl, phenyl, CH$_2$-phenyl, heteroaryl and CH$_2$heteroaryl, and wherein each alkyl, cycloalkyl, cycloheteroalkyl, cycloheteroalkenyl and heteroaryl are unsubstituted or substituted with 1, 2, 3 or 4 substituents selected from: oxo, —(CH$_2$)$_{0-5}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —SO$_2C_{1-6}$alkyl, —$C_{3-7}$cycloalkyl, phenyl, CH$_2$-phenyl, heteroaryl and CH$_2$heteroaryl. In a class of this embodiment, each R$^a$ is independently selected from the group consisting of: F, Cl, Br, —C(CH$_3$)$_2$OH, —OH, —CH$_2$OH, —CH$_2$CH$_2$OH, —CH$_2$C(CH$_3$)$_2$OH, —CH(OH)CHF$_2$, CH(OH)CF$_3$, —(CH$_2$)$_2$C(CH$_3$)$_2$—OH, —N(CH$_3$)$_2$, —CN, —CH$_3$, —CH$_2$CH$_3$, —C(CH$_3$)$_3$—CF$_3$, —CH$_2$CF$_3$—OCF$_3$—C(O)NH-cyclopropyl —OCH$_2$CH$_3$, —OCH$_3$, —O(CH$_2$)$_3$—SO$_2$CH$_3$, OCH$_2$CH$_2$F, —CH$_2$OCH$_3$—O-cyclobutyl, —O-cyclopentyl, —O-azetidine, —O—CH$_2$-dioxolane, —SO$_2$CH(CH$_3$)$_2$, —SO$_2$CH$_3$—SO$_2$-pyrrolidine, —SO$_2$-azetidine —SO$_2$NHCH$_3$, —SO$_2$NHC(CH$_3$)$_3$, —SO$_2$NH-cyclopropyl, —NHSO$_2$—CH$_3$, —C(O)CH(CH$_3$)$_2$, C(O)-pyrrolidine, —C(O)-morpholine, —CO$_2$H, —CO$_2$—CH(CH$_3$)$_2$, —CO$_2$—C(CH$_3$)$_3$, cyclopropyl, pyrazole, imidazole, oxazole, thiazole, triazole, tetrazole, and oxadiazole, wherein each heteroaryl is unsubstituted or substituted with 1, 2, 3 or 4 substituents selected from: oxo, —(CH$_2$)$_{0-5}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —SO$_2C_{1-6}$alkyl, —$C_{3-7}$cycloalkyl, phenyl, CH$_2$-phenyl, heteroaryl and CH$_2$heteroaryl.

In another embodiment of the present invention, R$^a$ is independently selected from the group consisting of: —(CH$_2$)$_m$-halogen, N(R$^j$)$_2$, —CN, —$C_{1-6}$alkyl, —(CH$_2$)$_m$OH, —(CH$_2$)$_m$CF$_3$, —O—(CH$_2$)$_m$—OC$_{1-6}$alkyl, —C(O)R$^f$, —CO$_2$H, —(CH$_2$)$_m$SO$_2$NHC$_{3-7}$cycloalkyl, —NHSO$_2$—$C_{1-6}$alkyl, —(CH$_2$)$_m$N(R$^j$)-heteroaryl, —(CH$_2$)$_m$$C_{3-7}$cycloalkyl, —(CH$_2$)$_m$$C_{2-6}$cycloheteroalkenyl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —$C_{3-7}$cycloalkyl, phenyl, CH$_2$-phenyl, heteroaryl and CH$_2$heteroaryl, and wherein alkyl, cycloalkyl, cycloheteroalkyl cycloheteroalkenyl and heteroaryl are unsubstituted or substituted with 1, 2, 3 or 4 substituents selected from: oxo, —(CH$_2$)$_{0-5}$OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —SO$_2C_{1-6}$alkyl, —$C_{3-7}$cycloalkyl, phenyl, CH$_2$-phenyl, heteroaryl and CH$_2$heteroaryl. In a class of this embodiment, each R$^a$ is independently selected from the group consisting of: F, Cl, —OH, —CH$_2$OH, —CH$_2$CH$_2$OH, —CH$_2$C(CH$_3$)$_2$OH, —N(CH$_3$)$_2$, —CN, —CH$_3$, —CF$_3$, —OCH$_3$, —OCH$_2$CH$_3$, —C(OH)(CH$_3$)$_2$, —CH(OH)CHF$_2$, —CH(OCH$_3$)CH$_3$, —SO$_2$CH$_3$, —SO$_2$CH(CH$_3$)$_2$, —SO$_2$-azetidine, —SO$_2$-pyrrolidine, —SO$_2$NH-tert-butyl, —SO$_2$NH-cyclopropyl, —NHSO$_2$CH$_3$, —C(O)CH(CH$_3$)$_2$, —CO$_2$H, pyrazole, imidazole, oxazole, thiazole, triazole, tetrazole, and oxadiazole, wherein each CH$_2$ is unsubstituted or substituted with 1 or 2 substituents selected from: —$C_{1-6}$alkyl, and each heteroaryl is unsubstituted or substituted with 1, 2, 3 or 4 substituents selected from: oxo, —(CH$_2$)$_{0-5}$OH, —$C_{1-6}$alkyl, —CF$_3$, and —$C_{3-7}$cycloalkyl.

In another embodiment of the present invention, R$^a$ is independently selected from the group consisting of: —(CH$_2$)$_m$OH, —(CH$_2$)$_m$CN, —(CH$_2$)$_m$NHSO$_2$—$C_{1-6}$alkyl, —(CH$_2$)$_m$SO$_2C_{1-6}$alkyl and —(CH$_2$)$_m$heteroaryl, wherein each CH$_2$ is unsubstituted or substituted with 1 or 2 substituents selected from: —$C_{1-6}$alkyl, and each heteroaryl is unsubstituted or substituted with 1, 2, 3 or 4 substituents selected from: oxo, —(CH$_2$)$_{0-5}$OH, —$C_{1-6}$alkyl, —CF$_3$, and —$C_{3-7}$cycloalkyl.

In another embodiment of the present invention, R$^a$ is independently selected from the group consisting of: —OH, —CH$_2$CH$_2$OH, —CH$_2$C(CH$_3$)$_2$OH, —CN, —NHSO$_2$CH$_3$ and —SO$_2$CH$_3$, pyrazole, imidazole, oxazole, thiazole, triazole, tetrazole, and oxadiazole, wherein each CH$_2$ is unsubstituted or substituted with 1 or 2 substituents selected from: —$C_{1-6}$alkyl, and each heteroaryl is unsubstituted or substituted with 1, 2, 3 or 4 substituents selected from: oxo, —(CH$_2$)$_{0-5}$OH, —$C_{1-6}$alkyl, —CF$_3$, and —$C_{3-7}$cycloalkyl.

In another embodiment of the present invention, each R$^b$ is independently selected from: hydrogen, —$C_{1-6}$alkyl, —$C_{3-6}$cycloalkyl, —$C_{3-6}$cycloalkenyl, —$C_{2-6}$cycloheteroalkyl, —$C_{2-6}$cycloheteroalkenyl, aryl, heteroaryl, —(CH$_2$)$_t$-halogen, —(CH$_2$)$_s$—OH, —NO$_2$, —NH$_2$, —NH ($C_{1-6}$alkyl), —N($C_{1-6}$alkyl)$_2$, —O$C_{1-6}$alkyl, —(CH$_2$)$_q$CO$_2$H, —(CH$_2$)$_q$CO$_2$C$_{1-6}$alkyl, —CF$_3$, —CN, —SO$_2$C$_{1-6}$alkyl, and —(CH$_2$)$_s$CON(R$^e$)$_2$, wherein each CH$_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens.

In a class of this embodiment, each R$^b$ is independently selected from: hydrogen, —C$_{1-6}$alkyl, —(CH$_2$)$_t$-halogen, —(CH$_2$)$_s$—OH, —NO$_2$, —NH$_2$, —NH(C$_{1-6}$alkyl), —N(C$_{1-6}$alkyl)$_2$, —OC$_{1-6}$alkyl, —(CH$_2$)$_q$CO$_2$H, —(CH$_2$)$_q$CO$_2$C$_{1-6}$alkyl, —CF$_3$, —CN, —SO$_2$C$_{1-6}$alkyl, and —(CH$_2$)$_s$CON(R$^e$)$_2$, wherein each CH$_2$ is unsubstituted or substituted with 1 or 2 halogens, and wherein each alkyl is unsubstituted or substituted with 1, 2 or 3 halogens. In a class of this embodiment, each R$^b$ is independently selected from: hydrogen, —C$_{1-6}$alkyl, —(CH$_2$)$_t$-halogen, —(CH$_2$)$_s$—OH, —NO$_2$, —NH$_2$, —NH(C$_{1-6}$alkyl), —N(C$_{1-6}$alkyl)$_2$, —OC$_{1-6}$alkyl, —(CH$_2$)$_q$CO$_2$H, —(CH$_2$)$_q$CO$_2$C$_{1-6}$alkyl, —CF$_3$, —CN, —SO$_2$C$_{1-6}$alkyl, and —(CH$_2$)$_s$CON(R$^e$)$_2$, wherein each CH$_2$ is unsubstituted or substituted with 1 or 2 halogens, and wherein each alkyl is unsubstituted or substituted with 1, 2 or 3 halogens. In another class of this embodiment, each R$^b$ is independently selected from: hydrogen, —C$_{1-6}$alkyl, —(CH$_2$)$_t$-halogen, —(CH$_2$)$_s$—OH, —CO$_2$H, and —CO$_2$C$_{1-6}$alkyl, wherein each CH$_2$ is unsubstituted or substituted with 1 or 2 halogens, and wherein each alkyl is unsubstituted or substituted with 1, 2 or 3 halogens. In another class of this embodiment, each R$^b$ is independently selected from: hydrogen, —C$_{1-6}$alkyl, —(CH$_2$)$_t$-halogen, —(CH$_2$)$_s$—OH, —CO$_2$H, and —CO$_2$C$_{1-6}$alkyl, wherein each CH$_2$ is unsubstituted or substituted with 1 or 2 halogens, and wherein each alkyl is unsubstituted or substituted with 1, 2 or 3 halogens. In another class of this embodiment, each R$^b$ is independently selected from: hydrogen, —CH$_3$, —CH$_2$F, —CH$_2$OH, —C(CH$_3$)$_2$—OH, —CO$_2$H and —CO$_2$C(CH$_3$)$_3$, wherein each CH$_2$ is unsubstituted or substituted with 1 or 2 halogens, and wherein each alkyl is unsubstituted or substituted with 1, 2 or 3 halogens.

In another embodiment of the present invention, each R$^b$ is independently selected from: hydrogen, —C$_{1-6}$alkyl, and —(CH$_2$)$_s$—OH. In a class of this embodiment, each R$^b$ is independently selected from: hydrogen, —CH$_3$, —OH, and —CH$_2$OH. In a class of this embodiment, each R$^b$ is independently selected from: hydrogen, —CH$_3$, and —CH$_2$OH.

In another embodiment of the present invention, each R$^c$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, —C$_{1-6}$alkyl-OH, —OCH$_2$OC$_{1-6}$alkyl, —(CH$_2$)$_r$OC$_{1-6}$alkyl, —OCH$_2$aryl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, —(CH$_2$)$_r$CO$_2$R$^f$, —(CH$_2$)$_r$C$_{3-7}$cycloalkyl, —(CH$_2$)$_r$C$_{2-6}$cycloheteroalkyl, —(CH$_2$)$_r$aryl, and —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl. In a class of this embodiment, each R$^c$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, —C$_{1-6}$alkyl-OH, —OCH$_2$OC$_{1-6}$alkyl, —(CH$_2$)$_r$OC$_{1-6}$alkyl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, and —(CH$_2$)$_r$CO$_2$R$^f$, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl is unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a class of this embodiment, each R$^c$ is independently selected from: halogen, oxo, —OH, —N(R$^e$)$_2$, —CN, —C$_{1-6}$alkyl, —CF$_3$, —C$_{1-6}$alkyl-OH, —OC$_{1-6}$alkyl, —SC$_{1-6}$alkyl, —C(O)R$^f$, —C(O)N(R$^e$)$_2$, —CO$_2$H, and —CO$_2$R$^f$, wherein alkyl is unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In another class of this embodiment, each R$^c$ is independently selected from: halogen, oxo, —OH, —N(R$^e$)$_2$, —CN, —C$_{1-6}$alkyl, —CF$_3$, —C$_{1-6}$alkyl-OH, and —OC$_{1-6}$alkyl, wherein alkyl is unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl.

In another embodiment of the present invention, each R$^e$, R$^g$ and R$^h$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment of the present invention, each R$^e$, R$^g$ and R$^h$ is independently selected from: hydrogen, —CH$_3$, and —OCH$_3$, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^e$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment of the present invention, each R$^e$ is independently selected from: hydrogen, —CH$_3$, and —OCH$_3$, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^g$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment of the present invention, each R$^g$ is independently selected from: hydrogen, —CH$_3$, and —OCH$_3$, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^h$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment of the present invention, each R$^h$ is independently selected from: hydrogen, —CH$_3$, and —OCH$_3$, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^e$, R$^g$ and R$^h$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a class of this embodiment, each $R^e$ is independently selected from: hydrogen, and $C_{1-6}$alkyl, wherein alkyl is unsubstituted or substituted with 1, 2 or 3 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a subclass of this class, $R^e$ is hydrogen. In another subclass of this class, $R^e$ is $C_{1-6}$alkyl. In another class of this embodiment, each $R^g$ is independently selected from: hydrogen, and $C_{1-6}$alkyl, wherein alkyl is unsubstituted or substituted with 1, 2 or 3 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a subclass of this class, $R^g$ is hydrogen. In another subclass of this class, $R^g$ is $C_{1-6}$alkyl. In another class of this embodiment, each $R^h$ is independently selected from: hydrogen, and $C_{1-6}$alkyl, wherein alkyl is unsubstituted or substituted with 1, 2 or 3 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$.

In a subclass of this class, $R^h$ is hydrogen. In another subclass of this class, $R^h$ is $C_{1-6}$alkyl.

In another embodiment of the present invention, each $R^j$ is independently selected from: hydrogen, $C_{1-6}$alkyl, $C_{3-6}$cycloalkyl, —C(O)$R^i$, and —$SO_2R^i$, wherein alkyl and cycloalkyl are unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a class of this embodiment, each $R^j$ is independently selected from: hydrogen, $C_{1-6}$alkyl, and $C_{3-6}$cycloalkyl, wherein alkyl and cycloalkyl are unsubstituted or substituted with 1, 2, 3 or 4 substituents selected from: —OH, oxo, halogen, $C_{1-6}$alkyl, —$OC_{1-6}$alkyl, —$NH_2$, —NH($C_1$-alkyl), and —N($C_{1-6}$alkyl)$_2$. In another class of this embodiment, each $R^j$ is independently selected from: hydrogen, —$CH_3$ and cyclopropyl, wherein methyl and cyclopropyl are unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$.

In another embodiment of the present invention, each $R^j$ is independently selected from: hydrogen, $C_{1-6}$alkyl, $C_{3-6}$cycloalkyl, —C(O)$R^j$, and —$SO_2R^j$, wherein alkyl and cycloalkyl are unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a class of this embodiment, each $R^j$ is independently selected from: hydrogen, $C_{1-6}$alkyl, —C(O)$R^j$, and —$SO_2R^j$, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$.

In another class of this embodiment, each $R^j$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —OC16alkyl, —$NH_2$, —NH($C_{1-6}$alkyl), and —N($C_{1-6}$alkyl)$_2$. In another class of this embodiment, each $R^j$ is independently selected from: hydrogen, and $C_{1-6}$alkyl. In another class of this embodiment, $R^j$ is hydrogen. In another class of this embodiment, $R^j$ is $C_{1-6}$alkyl, wherein alkyl is unsubstituted or substituted with 1, 2 or 3 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In another class of this embodiment, $R^j$ is $C_{1-6}$alkyl.

In another embodiment of the present invention, each $R^f$, and $R^i$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, each $R^f$, and $R^i$ is independently selected from: $C_{1-6}$alkyl, and $C_{3-7}$cycloheteroalkyl, wherein alkyl and cycloheteroalkyl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In another class of this embodiment, each $R^f$, and $R^i$ is independently selected from: $C_{1-6}$alkyl, and $C_{3-7}$cycloheteroalkyl, wherein alkyl and cycloheteroalkyl are unsubstituted or substituted with 1, 2 or 3 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$ and —$CO_2C_{1-6}$alkyl. In another class of this embodiment, each $R^f$, and $R^i$ is independently selected from: —CH($CH_3$)$_2$, —C($CH_3$, morpholine, pyrrolidine, and piperazine, wherein each alky, morpholine, pyrrolidine, and piperazine is unsubstituted or substituted with 1, 2 or 3 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$ and —$CO_2C_{1-6}$alkyl.

In another embodiment of the present invention, each $R^f$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, each $R^f$ is independently selected from: $C_{1-6}$alkyl, and $C_{3-7}$cycloheteroalkyl, wherein alkyl and cycloheteroalkyl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In another class of this embodiment, each $R^f$ is independently selected from: $C_{1-6}$alkyl, and $C_{3-7}$cycloheteroalkyl, wherein alkyl and cycloheteroalkyl are unsubstituted or substituted with 1, 2 or 3 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$ and —$CO_2C_{1-6}$alkyl. In another class of this embodiment, each $R^f$ is independently selected from: —CH($CH_3$)$_2$, —C($CH_3$, morpholine, pyrrolidine, and piperazine, wherein each alkyl, morpholine, pyrrolidine, and piperazine is unsubstituted or substituted with 1, 2 or 3 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$ and —$CO_2C_{1-6}$alkyl.

In another embodiment of the present invention, each $R^1$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, each $R^i$ is independently selected from: $C_{1-6}$alkyl, and $C_{3-7}$cycloheteroalkyl, wherein alkyl and cycloheteroalkyl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl. In another class of this embodiment, each R$^i$ is independently selected from: C$_{1-6}$alkyl, and C$_{3-7}$cycloheteroalkyl, wherein alkyl and cycloheteroalkyl are unsubstituted or substituted with 1, 2 or 3 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H and —CO$_2$C$_{1-6}$alkyl. In another class of this embodiment, each R$^i$ is independently selected from: —CH(CH$_3$)$_2$, —C(CH$_3$, morpholine, pyrrolidine, and piperazine, wherein each alky, morpholine, pyrrolidine, and piperazine is unsubstituted or substituted with 1, 2 or 3 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H and —CO$_2$C$_{1-6}$alkyl.

In another class of this embodiment, each R$^f$, and R$^i$ is independently selected from: C$_{1-6}$alkyl, wherein alkyl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl. In another class of this embodiment, each R$^f$, and R$^i$ is independently selected from: C$_{4-7}$cycloalkyl, C$_{4-7}$cycloalkenyl, C$_{3-7}$cycloheteroalkyl, C$_{3-7}$cycloheteroalkenyl, aryl, and heteroaryl, wherein cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl.

In another embodiment of the present invention, n is 0, 1, 2, 3 or 4. In a class of this embodiment, n is 1, 2 or 3. In another class of this embodiment, n is 0, 1 or 2. In another class of this embodiment, n is 0. In another class of this embodiment, n is 1. In another class of this embodiment, n is 2.

In another embodiment of the present invention, m is 0, 1, 2, 3, or 4. In a class of this embodiment, m is 0, 1, 2 or 3. In another class of this embodiment, m is 1, 2 or 3. In another class of this embodiment, m is 0, 1 or 2. In another class of this embodiment, m is 0 or 1. In another class of this embodiment, m is 0. In another class of this embodiment, m is I.

In another embodiment of the present invention, p is 0, 1, 2 or 3. In a class of this embodiment, p is 1, 2 or 3. In another class of this embodiment, p is 0, 1 or 2. In another class of this embodiment, p is 0 or 2. In another class of this embodiment, p is 0. In another class of this embodiment, p is 1. In another class of this embodiment, p is 2.

In another embodiment of the present invention, q is 0, 1, 2, 3 or 4. In a class of this embodiment, q is 1, 2 or 3. In another class of this embodiment, q is 0, 1 or 2. In another class of this embodiment, q is 1 or 2. In another class of this embodiment, q is 0. In another class of this embodiment, q is 1. In another class of this embodiment, q is 2.

In another embodiment of the present invention, r is 0, 1 or 2. In a class of this embodiment, r is 0 or 1. In another class of this embodiment, r is 0. In another class of this embodiment, r is 1. In another class of this embodiment, r is 2.

In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, t is 0, 1, 2, 3 or 4. In a class of this embodiment, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3.

Another embodiment of the present invention relates to compounds of structural formula I wherein:
T is N;
U is —CR$^1$—;
V is —CR$^2$—;
W is —CR$^4$—;
X is selected from:
  (1) —O—, and
  (2) —O—CH$_2$—;
Y is selected from:
  (1) C$_{3-10}$cycloalkyl,
  (2) C$_{2-10}$cycloheteroalkyl, and
  (3) phenyl,
wherein cycloalkyl, cycloheteroalkyl and phenyl are unsubstituted or substituted with 1, 2, 3 or 4 substituents selected from R$^b$;
Z is selected from:
  (1) oxo,
  (2) —CF$_3$,
  (3) —C$_{1-6}$alkyl,
  (4) —(CH$_2$)$_t$-halogen,
  (5) —(CH$_2$)$_n$CO$_2$H,
  (6) —(CH$_2$)$_n$OH, and
  (7) —(CH$_2$)$_n$SO$_2$C$_{1-6}$alkyl,
wherein each CH$_2$ is unsubstituted or substituted with 1 or 2 substituents selected from C$_{1-6}$alkyl, —OH and —NH$_2$, and wherein each alkyl is unsubstituted or substituted with 1, 2, 3 or 4 substituents selected from R$^c$;
R$^1$ is independently selected from:
  (1) —C$_{4-10}$cycloalkenyl,
  (2) -phenyl,
  (3) phenyl-C$_2$alkynylC$_{1-5}$alkyl,
  (4) phenyl-C$_{2-3}$alkynyl-C$_{3-7}$cycloalkyl,
  (5) phenyl-C$_{2-3}$ alkynyl-C$_{2-10}$cycloheteroalkyl,
  (6)-phenyl-C$_{3-7}$cycloalkyl,
  (7) -phenyl-C$_{2-7}$cycloheteroalkyl,
  (8) phenyl-C$_{2-10}$cycloheteroalkenyl,
  (9) -phenyl-phenyl,
  (10)-phenyl-heteroaryl,
  (11)-heteroaryl, and
  (12) —C$_{2-6}$alkynyl-phenyl,
wherein each alkyl, alkynyl, cycloalkyl, cycloalkenyl, cycloheteroalkyl, cycloheteroalkenyl, phenyl and heteroaryl is unsubstituted or substituted with 1, 2, 3 or 4 substituents independently selected from R$^a$;
R$^2$ is selected from halogen;
R$^4$ is hydrogen; and
R$^5$ is hydrogen;
or a pharmaceutically acceptable salt thereof.

Another embodiment of the present invention relates to compounds of structural formula I wherein:
T is N;
U is —CR$^1$—;
V is —CR$^2$—;
W is —CR$^4$—;
X is —O—;

Y is selected from $C_{2-10}$cycloheteroalkyl, wherein each cycloheteroalkyl is unsubstituted or substituted with 1, 2, 3 or 4 substituents selected from $R^b$;
Z is selected from: —$(CH_2)_t$-halogen, and —$(CH_2)_n$OH;
$R^1$ is independently selected from:
- (1) phenyl-$C_{2-8}$alkynyl-$C_{1-8}$alkyl,
- (2) phenyl-$C_{2-3}$alkynyl-$C_{3-7}$cycloalkyl,
- (3) phenyl-$C_{2-3}$alkynyl-$C_{2-10}$cycloheteroalkyl,
- (4) phenyl-$C_{2-10}$cycloheteroalkenyl,
- (5) biphenyl, and
- (6) phenyl-heteroaryl, wherein each alkyl, alkynyl, cycloalkyl, cycloheteroalkyl, cycloheteroalkenyl, phenyl, biphenyl and heteroaryl is unsubstituted or substituted with 1, 2, 3 or 4 substituents independently selected from $R^a$;
$R^2$ is selected from halogen;
$R^4$ is hydrogen; and
$R^5$ is hydrogen;
or a pharmaceutically acceptable salt thereof.

Another embodiment of the present invention relates to compounds of structural formula I wherein:
T is N;
U is —$CR^1$—;
V is —$CR^2$—;
W is —$CR^4$—;
X is selected from:
- (1) —O—, and
- (2) —O—$CH_2$—;

Y is selected from:
- (1) $C_{3-10}$cycloalkyl,
- (2) $C_{2-10}$cycloheteroalkyl, and
- (3) phenyl, wherein cycloalkyl, cycloheteroalkyl and phenyl are unsubstituted or substituted with 1, 2, 3 or 4 substituents selected from $R^b$;
Z is selected from:
- (1) oxo,
- (2) —$CF_3$,
- (3) —$C_{1-6}$alkyl,
- (4) —$(CH_2)_t$-halogen,
- (5) —$(CH_2)_n CO_2 H$,
- (6) —$(CH_2)_n$OH, and
- (7) —$(CH_2)_n SO_2 C_{1-6}$alkyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl is unsubstituted or substituted with 1, 2, 3 or 4 substituents selected from $R^c$;
$R^1$ is independently selected from:
- (1) —$C_{4-10}$cycloalkenyl,
- (2) -phenyl,
- (3) -phenyl-$C_{3-7}$cycloalkyl,
- (4) -phenyl-$C_{2-7}$cycloheteroalkyl,
- (5) -phenyl-phenyl,
- (6) -phenyl-heteroaryl,
- (7) -heteroaryl, and
- (8) —$C_{2-6}$alkynyl-phenyl, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloalkenyl, cycloheteroalkyl, phenyl and heteroaryl is unsubstituted or substituted with 1, 2, 3 or 4 substituents independently selected from $R^a$;
$R^2$ is selected from: halogen;
$R^4$ is hydrogen; and
$R^5$ is hydrogen;
or a pharmaceutically acceptable salt thereof.

Another embodiment of the present invention relates to compounds of structural formula I wherein:
T is N;
U is —$CR^1$—;
V is —$CR^2$—;
W is —$CR^4$—;
X is —O—;
Y is selected from:
- (1) $C_{3-7}$cycloalkyl,
- (2) $C_{2-10}$cycloheteroalkyl, and
- (3) phenyl, wherein each cycloalkyl, cycloheteroalkyl and phenyl is unsubstituted or substituted with 1, 2, 3 or 4 substituents selected from $R^b$;
Z is selected from:
- (1) —$(CH_2)_n CO_2 H$,
- (2) —$(CH_2)_t$-halogen, and
- (3) —$(CH_2)_n$OH, wherein each $CH_2$ is unsubstituted or substituted with 1 or 2 substituents selected from $C_{1-6}$alkyl, and —OH; or a pharmaceutically acceptable salt thereof $R^1$ is independently selected from:
- (1) -phenyl-$C_{2-7}$cycloheteroalkyl,
- (2) phenyl-$C_{2-10}$cycloheteroalkenyl,
- (3) -phenyl-phenyl, and
- (4) phenyl-heteroaryl, wherein each cycloheteroalkyl, cycloheteroalkenyl, heteroaryl and phenyl is unsubstituted or substituted with 1, 2, 3 or 4 substituents independently selected from $R^a$;
$R^2$ is selected from halogen;
$R^4$ is hydrogen; and
$R^5$ is hydrogen;
or a pharmaceutically acceptable salt thereof.

Another embodiment of the present invention relates to compounds of structural formula I wherein:
T is N;
U is —$CR^1$—;
V is —$CR^2$—;
W is —$CR^4$—;
X is —O—;
Y is selected from $C_{2-10}$cycloheteroalkyl, wherein each cycloheteroalkyl is unsubstituted or substituted with 1, 2, 3 or 4 substituents selected from $R^b$;
Z is selected from: —$(CH_2)_n$OH;
$R^1$ is independently selected from:
- (1) -phenyl-$C_{2-10}$ cycloheteroalkenyl,
- (2) biphenyl, and
- (3) phenyl-heteroaryl, wherein each cycloheteroalkenyl, phenyl, biphenyl and heteroaryl is unsubstituted or substituted with 1, 2, 3 or 4 substituents independently selected from $R^a$;
$R^2$ is selected from halogen;
$R^4$ is hydrogen; and
$R^5$ is hydrogen;
or a pharmaceutically acceptable salt thereof.

Another embodiment of the present invention relates to compounds of structural formula I wherein:
T is N;
U is —$CR^1$—;
V is —$CR^2$—;
W is —$CR^4$—;
X is —O—;

Y is selected from:
(1) $C_{3-7}$cycloalkyl,
(2) $C_{2-10}$cycloheteroalkyl, and
(3) phenyl,
wherein each cycloalkyl, cycloheteroalkyl and phenyl is unsubstituted or substituted with 1, 2, 3 or 4 substituents selected from $R^b$;
Z is selected from:
(1) —$(CH_2)_nCO_2H$, and
(2) —$(CH_2)_nOH$,
wherein each $CH_2$ is unsubstituted or substituted with 1 or 2 substituents selected from $C_{1-6}$alkyl, and —OH;
$R^1$ is selected from:
(1)-phenyl-$C_{2-7}$cycloheteroalkyl, and
(2) -phenyl-phenyl,
wherein each cycloheteroalkyl and phenyl is unsubstituted or substituted with 1, 2, 3 or 4 substituents independently selected from $R^a$;
$R^2$ is selected from: halogen;
$R^4$ is hydrogen; and
$R^5$ is hydrogen;
or a pharmaceutically acceptable salt thereof.

In another embodiment of the present invention, the invention relates to compounds of structural formula Ia:

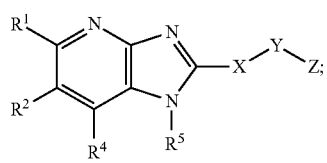
(Ia)

or a pharmaceutically acceptable salt thereof.

In another embodiment of the present invention, the invention relates to compounds of structural formula Ib:

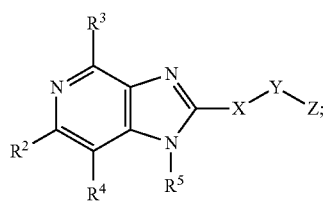
(Ib)

or a pharmaceutically acceptable salt thereof.

In another embodiment of the present invention, the invention relates to compounds of structural formula Ic:

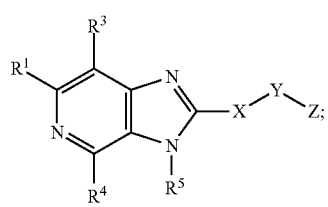
(Ic)

or a pharmaceutically acceptable salt thereof.

In another embodiment of the present invention, the invention relates to compounds of structural formula Id:

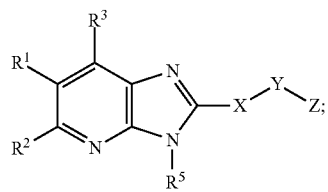
(Id)

or a pharmaceutically acceptable salt thereof.

The compound of structural formula I, includes the compounds of structural formulas Ia, Ib, Ic and Id, and pharmaceutically acceptable salts, hydrates and solvates thereof.

Illustrative, but non-limiting, examples of the compounds of the present invention that are useful as activators of AMP-protein kinase are the following compounds:

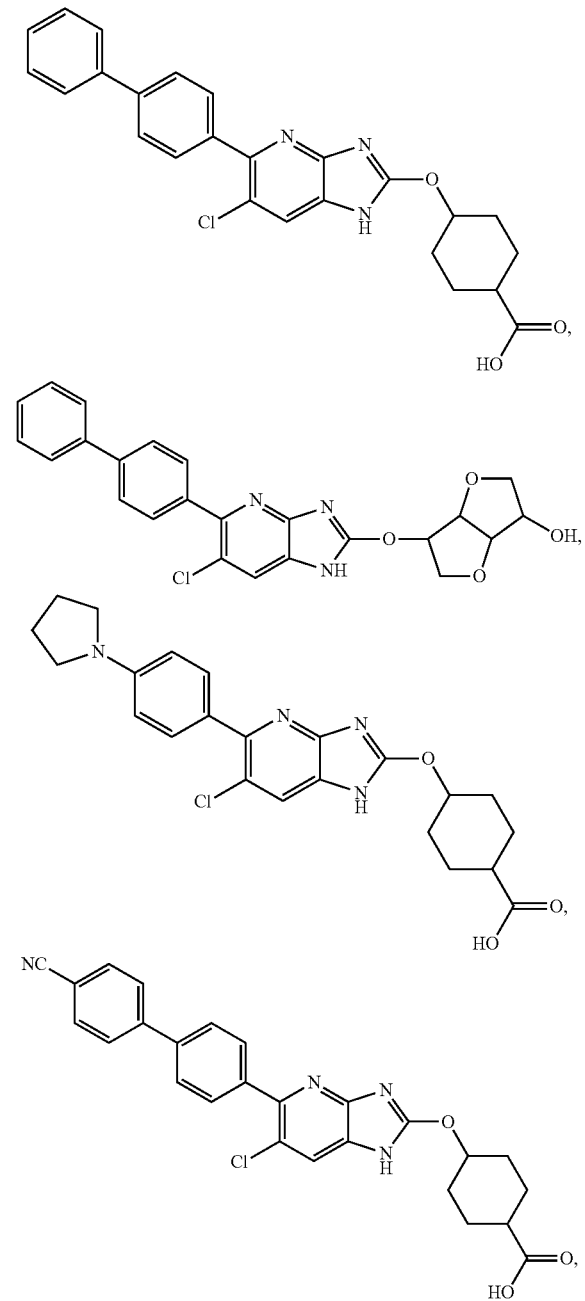

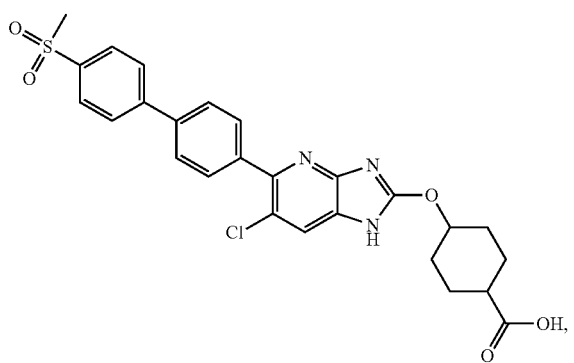
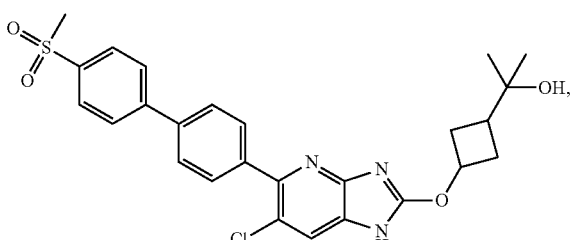
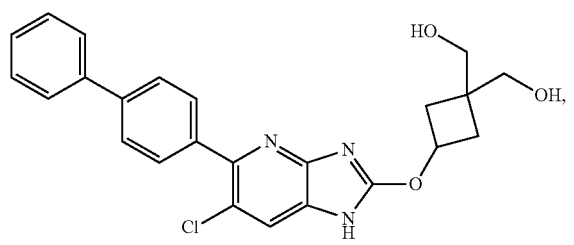
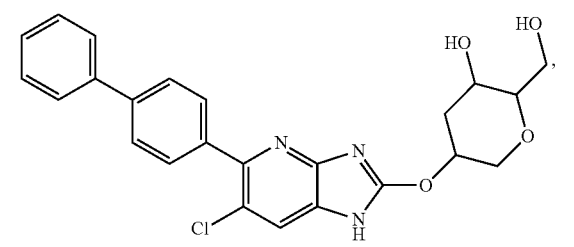
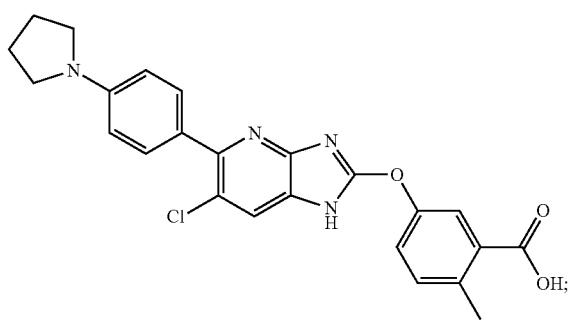
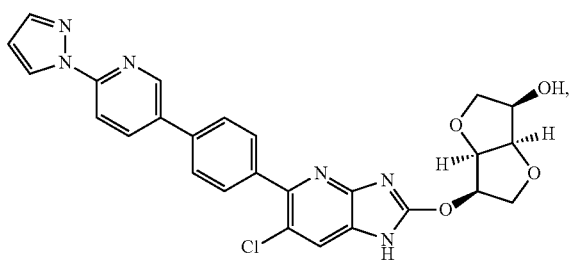

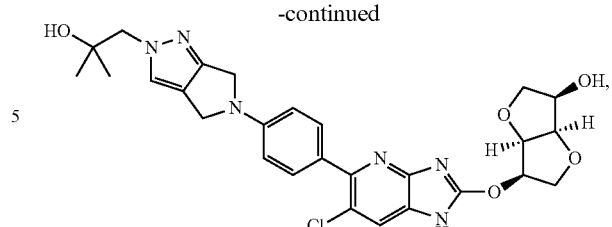
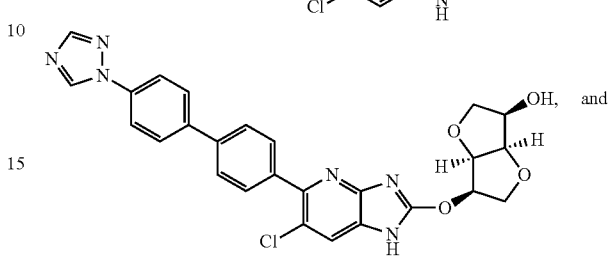
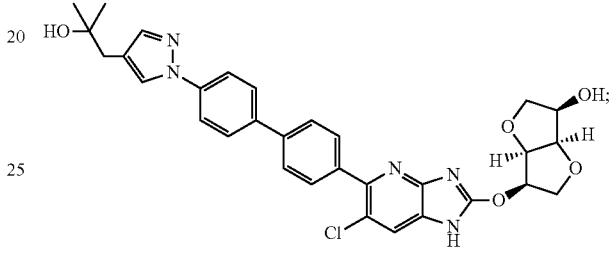

and pharmaceutically acceptable salts thereof.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is vinyl.

"Alkynyl" means carbon chains up to 10 carbons which contain at least one carbon-carbon triple bond, and which may be linear or branched or combinations thereof. In one embodiment, $C_{2-8}$alkynyl means a carbon chain with 2 to 8 carbons that contains one carbon-carbon triple bond. Examples of alkynyl include ethynyl, propargyl, 3-methyl-1-pentynyl, 2-heptynyl and the like. In one embodiment of the present invention, alkynyl is ethynyl. In another embodiment, alkynyl is propargyl.

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like. In one embodiment of the present invention, cycloalkyl is selected from cyclopentyl and cyclohexyl. In another embodiment of the present invention, cycloalkyl is selected from cyclopropyl, cyclopentyl, and cyclohexyl.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. In one embodiment, $C_{2-10}$cycloheteroalkyl means non-aromatic, mono- or bicyclic or bridged saturated carbocyclic rings, having from 2 to 10 carbon atoms and containing, 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from piperidine, pyrrolidine, oxazolidine, 1,3-oxazolidine-2,4-dione, thiazolidine, 1,3-thiazolidine-2,4-dione, imidazolidine, and hydantoin, and the like. In another embodiment of the present invention cycloheteroalkyl is selected from: morpholine, pyrrolidine, piperazine, and piperidine. In another embodiment of the present invention, cycloheteroalkyl is pyrrolidine.

In another embodiment, $C_{2-10}$cycloheteroalkyl is a non-aromatic, bicyclic saturated carbocyclic ring having from 2 to 10 carbon atoms, and containing 1 or 2 heteroatoms selected from O. In another embodiment of the present invention, cycloheteroalkyl is dianhydro-mannitol. In another embodiment of the present invention, cycloheteroalkyl is 1,4:3,6-dianhydro-mannitol. In another embodiment of the present invention, cycloheteroalkyl is 1,4:3,6-dianhydro-D-mannitol. In another embodiment of the present invention, cycloheteroalkyl is hexahydrofuro[3,2-b]furan. In a class of this embodiment, cycloheteroalkyl is 2,3,3a,5,6,6a-hexahydrofuro[3,2-b]furan.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine.

In another embodiment, $C_{2-10}$cycloheteroalkenyl is a non-aromatic, bicyclic carbocyclic ring having from 2 to 10 carbon atoms, and containing 1, 2 or 3 heteroatoms selected from N, and NH. In a class of this embodiment, cycloheteroalkenyl is dihydropyrrolo[3,4-c]pyrazole. In another class of this embodiment, cycloheteroalkenyl is 4,6-dihydropyrrolo[3,4-c]pyrazole.

In another embodiment, $C_{2-6}$cycloheteroalkenyl is a non-aromatic, bicyclic carbocyclic ring having from 2 to 6 carbon atoms, and containing 1 or 2 heteroatoms selected from N, and NH. In a class of this embodiment, cycloheteroalkenyl is dihydroimidazole or tetrahydropyrimidine. In another class of this embodiment, cycloheteroalkenyl is 2,5 dihydro-1H-imidazole or 1,4,5,6-tetrahydropyrimidine. In another class of this embodiment, cycloheteroalkenyl is dihydroimidazole. In another class of this embodiment, cycloheteroalkenyl is 2,5 dihydro-1H-imidazole. In another class of this embodiment, cycloheteroalkenyl is tetrahydropyrimidine. In another class of this embodiment, cycloheteroalkenyl is 1,4,5,6-tetrahydropyrimidine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as acycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, oxazole, furan, benzoxazole, isoxazole, indoline, isoindoline, tetrazole, imidazole, oxadiazole, thiadiazole, triazole, benzothiazole, benzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment of the present invention, heteroaryl is selected from: imidazole, pyrazole, pyridine, pyrazine, pyrimidine, thiazole, thiophene, benzoimidazole, quinoline, isoquinoline, indole, indazole, carbazole, benzotriazole, benzofuran, benzothiazole, benzo[b]thiophene, benzo[d]isooxazole, 3,4-dihydro-2H-benzo[1,4]oxazine, benzo[1,3]dioxole, benzo[1,4]dioxine, 1H-pyrrolo[2,3-b]pyridine, 1,6-dihydro-pyridine, [1,2,4]triazolo[4,3-a]pyridine, 3,4 dihydropyrido[3,2-b][1,4] oxazine, 3,4-dihydro-2H-1,4-benzoxazine, 2,3-dihydro-1H-indole, 2,3-dihydro-1H-isoindole, 2,3-dihydrobenzoimidazole, 1,2-dihydroquinoline, 1,2,3,4-tetrahydroisoquinoline, 1,2,3,4-tetrahydrocyclopenta[b]indole, 1,2,3,4-tetrahydroquinoxaline, and 1,2,3,6-tetrahydropyridine. In another embodiment of the present invention, heteroaryl is tetrazole. In another embodiment, heteroaryl is selected from: pyrazole, pyridine, pyrimidine, isoxazole, imidazole, oxazole, triazole, tetrazole, oxadiazole, thiazole, thiadiazole, and benzoxazole. In another embodiment of this invention, heteroaryl is tetrazole.

"Halogen" includes fluorine, chlorine, bromine and iodine. In one embodiment of the present invention, halogen is selected from fluorine, chlorine, and bromine. In another embodiment of the present invention, halogen is selected from fluorine, and chlorine. In another embodiment of the present invention, halogen is fluorine. In another embodiment of the present invention, halogen is chlorine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

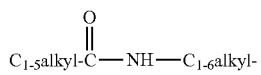

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, trifluoroacetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are activators of the AMP-activated protein kinase. The methods of treatment of this invention comprises a method of activating AMPK-activated protein kinase and treating AMPK-activated protein kinase mediated diseases by administering to a patient in need of such treatment a non-toxic therapeutically effective amount of a compound of this invention that activate AMPK-activated protein kinase.

AMP-activated protein kinase (AMPK) is a heterotrimeric enzyme composed of a catalytic α subunit and regulatory β and γ subunits. There are two genes encoding isoforms of both the α and β subunits (α11, α2, β31 and β2) and three genes encoding isoforms of the γ subunit (γ1, γ2 and γ3) leading to 12 possible heterotrimeric combinations. The α2 isoform is predominately found in skeletal and cardiac muscle AMPK; both the α1 and α2 isoforms are found in hepatic AMPK; while in pancreatic islet β-cells the al isoform AMPK predominates. In particular, the compounds of structural formula I are activators of at least one heterotrimeric isoform of AMP-activated protein kinase.

An "activator" is a compound that either increases the activity (phosphorylation of downstream substrates) of fully phosphorylated AMPK or that increases the phosphorylation of AMPK.

The compounds of the present invention are efficacious in the treatment and prevention of diseases, disorders and conditions responsive to the activation of AMP-activated protein kinase, including but not limited to: type 2 diabetes, insulin resistance, hyperglycemia, obesity, hyperinsulinemia, glucose intolerance, atherosclerosis, Metabolic Syndrome, hypertension, high hepatic glucose output, high blood glucose concentrations, nonalcoholic steatohepatitis, protection against ischemia and reperfusion damage, and lipid disorders, such as dyslipidemia, elevated levels of plasma triglycerides, elevated levels of free fatty acids, elevated levels of cholesterol, high levels of low density lipoprotein (LDL) and low levels of high density lipoprotein (HDL). The compounds are also useful for the treatment of cancer, hypoxia and glucocorticoid-induced apoptosis.

One or more of the following diseases may be treated by the administration of a therapeutically effective amount of a compound of Formula I, or a pharmaceutically acceptable salt thereof, to a patient in need of treatment: (1) non-insulin dependent diabetes mellitus (Type 2 diabetes); (2) hyperglycemia; (3) Metabolic Syndrome; (4) obesity; (5) hypercholesterolemia; (6) hypertriglyceridemia (elevated levels of triglyceride-rich-lipoproteins); (7) mixed or diabetic dyslipidemia; (8) low HDL cholesterol; (9) high LDL cholesterol; (10) atherosclerosis; and (11) hypertension.

Also, the compounds of Formula I may be used for the manufacture of a medicament for treating one or more of the above diseases.

One embodiment of the uses of the compounds is directed to the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; and (6) hypertension.

The compounds may also be used for manufacturing a medicament for use in the treatment of one or more of the above diseases.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, methods and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others. By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with Type 2 diabetes from needing insulin therapy.

Other possible outcomes of treatment with the compounds of the present invention include, but are not limited to: 1) a decrease in fatty acid synthesis; 2) an increase in fatty acid oxidation and ketogenesis; 3) a decrease in cholesterol synthesis, lipogenesis, and triglyceride synthesis; 4) a decrease in blood glucose levels and concentration; 5) an improvement in glucose homeostasis; 6) a normalization of glucose metabolism; 7) a decrease in blood pressure; 8) an increase in HDL; 9) a decrease in plasma triglycerides; 10) a decrease in free fatty acids; 11) a decrease in hepatic glucose output; 12) an improvement in insulin action; 13) a decrease in blood pressure; 14) an improvement in insulin sensitivity; 15) a suppression of hepatic glucose output; 15) an inhibition of de novo lipogenesis; 16) stimulation of muscle glucose uptake; 17) modulation of insulin secretion by pancreatic P cells; and 16) a decrease in body weight.

The compounds generally may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example anacetrapib, torcetrapib, and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

The present invention also relates to methods and medicaments for the treatment, control, or prevention of Type 2 diabetes by administering the compounds and pharmaceutical compositions of the present invention. The present invention also relates to methods and medicaments for the treatment, control, or prevention of Type 2 diabetes by administering the compounds of the present invention in combination with a therapeutically effective amount of another agent known to be useful to treat the condition. The present invention also relates to methods and medicaments for the treatment, control, or prevention of diabetes related disorders by administering the compounds and pharmaceutical compositions of the present invention alone, or in combination. The present invention also relates to methods and medicaments for the treatment and prevention of diabetes in pre-diabetic subject by administering the compounds and pharmaceutical compositions of the present invention alone, or in combination.

The present invention also relates to methods and medicaments for the treatment, control, or prevention of obesity by administering the compounds and pharmaceutical compositions of the present invention. The present invention also relates to methods and medicaments for the treatment, control, or prevention of obesity by administering the compounds of the present invention in combination with a therapeutically effective amount of another agent known to be useful to treat the condition. The present invention also relates to methods and medicaments for the treatment, control, or prevention of obesity related disorders by administering the compounds and pharmaceutical compositions of the present invention alone, or in combination. The present invention also relates to methods and medicaments for the treatment and prevention of obesity in overweight subject by administering the compounds and pharmaceutical compositions of the present invention alone, or in combination. The compounds are also useful for the treatment of obesity related disorders, or eating disorders associated with excessive food intake, and complications associated therewith, including left ventricular hypertrophy, as well as treating or preventing obesity in other mammalian species, including canines and felines.

The present invention also relates to methods and medicaments for the treatment, control, or prevention of hyperglycemia by administering the compounds and pharmaceutical compositions of the present invention. The present invention also relates to methods and medicaments for the treatment, control, or prevention of hyperglycemia by administering the compounds of the present invention in combination with a therapeutically effective amount of another agent known to be useful to treat the condition.

The present invention also relates to methods and medicaments for the treatment, control, or prevention of insulin resistance by administering the compounds and pharmaceutical compositions of the present invention. The present invention also relates to methods and medicaments for the treatment, control, or prevention of insulin resistance by administering the compounds of the present invention in combination with a therapeutically effective amount of another agent known to be useful to treat the condition.

The present invention also relates to methods and medicaments for the treatment, control, or prevention of lipid disorders by administering the compounds and pharmaceutical compositions of the present invention. The present invention also relates to methods and medicaments for the treatment, control, or prevention of lipid disorders by administering the compounds of the present invention in combination with a therapeutically effective amount of another agent known to be useful to treat the condition. The present invention also relates to methods and medicaments for the treatment, control, or prevention of dyslipidemia related disorders and lipid disorder-related disorders by administering the compounds and pharmaceutical compositions of the present invention alone, or in combination.

The present invention also relates to methods and medicaments for the treatment, control, or prevention of atherosclerosis by administering the compounds and pharmaceutical compositions of the present invention. The present invention also relates to methods and medicaments for the treatment, control, or prevention of atherosclerosis by administering the compounds of the present invention in combination with a therapeutically effective amount of another agent known to be useful to treat the condition. The present invention also relates to methods and medicaments for the treatment, control, or prevention of atherosclerosis related disorders by administering the compounds and pharmaceutical compositions of the present invention alone, or in combination.

The present invention also relates to methods and medicaments for the treatment, control, or prevention of hypertension by administering the compounds and pharmaceutical compositions of the present invention. The present invention also relates to methods and medicaments for the treatment, control, or prevention of hypertension by administering the compounds of the present invention in combination with a therapeutically effective amount of another agent known to be useful to treat the condition. The present invention also relates to methods and medicaments for the treatment, control, or prevention of hypertension related disorders by administering the compounds and pharmaceutical compositions of the present invention alone, or in combination.

The present invention also relates to methods and medicaments for the treatment and prevention of hypertension in pre-hypertensive subject by administering the compounds and pharmaceutical compositions of the present invention alone, or in combination.

The present invention also relates to methods and medicaments for the treatment, control, or prevention of Metabolic Syndrome by administering the compounds and pharmaceutical compositions of the present invention. The present invention also relates to methods and medicaments for treating Metabolic Syndrome by administering the compounds of the present invention in combination with a therapeutically effective amount of another agent known to be useful to treat the condition.

The compounds of the present invention wherein at least one of T, U, V and W is N or N-oxide have the unexpected benefit of increased potency in enzyme activation assays using recombinant human AMPK complex (see Biological Example 1) compared to compounds wherein T is $CR^3$, U is $CR^1$—, V is $CR^2$ and W is $CR^4$.

Additionally, the compounds of the present invention wherein at least one of T, U, V and W is N or N-oxide have the unexpected benefit of reduced binding to human plasma proteins compared to compounds wherein T is $CR^3$, U is $CR^1$—, V is $CR^2$ and W is $CR^4$. Pharmacological activity in vivo is associated with the concentration of drug unbound to plasma proteins. Plasma proteins, by virtue of their high concentration, control the concentration of drug unbound to plasma proteins in plasma and in compartments in equilibrium with plasma, thereby, effectively attenuating drug potency in vivo (See Trainor, G. L. (2007), Expert Opin. Drug Discov. 2(1), 51-64). A higher concentration of drug unbound to plasma proteins results in an increase in pharmacological activity in vivo. Due to their increased potency and their higher unbound fraction in plasma, the compounds of the present invention are expected to exhibit glucose lowering efficacy at reduced plasma exposures.

The term "diabetes," as used herein, includes both insulin-dependent diabetes mellitus (i.e., IDDM, also known as type I diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention are useful for treating both Type 1 and Type 2 diabetes. The term "diabetes associated with obesity" refers to diabetes caused by obesity or resulting from obesity. The compositions are especially effective for treating Type 2 diabetes. The compositions of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. An overweight subject is a subject at risk of obesity. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus-type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

Left ventricular hypertrohpy (LVH) is identified based on left ventricular mass index (LVMI) and relative wall thickness (RWT). Left ventricular mass index is defined as left ventricular mass in grams divided by body surface area in meters$^2$. Relative wall thickness is defined as 2× posterior wall thickness/left ventricular end diastolic diameter. Normal LVMI values are typically 85 and normal RWT approximately 0.36. A male subject with LVH has a LVMI greater than 131 g/m$^2$; a female subject with LVH has a LVMI greater than 100 g/m$^2$. A subject with an elevated LVMI value is a male subject with a LVMI between 85 g/m$^2$ and 131 g/m$^2$, or a female subject with a LVMI between 85 g/m$^2$ and 100 g/m$^2$.

Treatment of cardiac hypertrophy, or left ventricular hypertrophy, refers to the administration of the combinations of the present invention to a subject with cardiac hypertrophy or left ventricular hypertrophy. Prevention of cardiac hypertrophy, or left ventricular hypertrophy, refers to the administration of the combinations of the present invention to decrease or maintain the LVMI in a subject with an elevated LVMI value or to prevent the increase of LVMI in a subject with a normal LVMI value.

One outcome of treatment of cardiac hypertrophy or left ventricular hypertrophy may be a decrease in ventricular mass. Another outcome of treatment of cardiac hypertrophy or left ventricular hypertrophy may be a decrease in the rate of increase of ventricular mass. Another outcome of treatment of cardiac hypertrophy or left ventricular hypertrophy may be a decrease in ventricular wall thickness. Another outcome of treatment of cardiac hypertrophy of left ventricular hypertrophy may be the decrease in the rate of increase in ventricular wall thickness.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or a companion animal such as a dog or cat, with an effective dosage of a compound of the present invention. For example, oral, rectal, topical, parenteral, ocular, pulmonary, and nasal routes of administration, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL | Tablet | mg/tablet |
|---|---|---|---|
| Compound of Formula I | 10 | Compound of Formula I | 25 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 43.5 |
| Benzalkonium chloride | 1.0 | Magnesium Stearate | 2.5 |
| Water for injection to a total volume of 1 mL | | | 500 |

| Capsule | mg/capsule | Aerosol | Per canister |
|---|---|---|---|
| Compound of Formula I | 25 | Compound of Formula I | 24 mg |
| Lactose Powder | 573.5 | Lecithin, NF Liq. Conc. | 1.2 mg |
| Magnesium Stearate | 1.5 | Trichlorofluoromethane, NF | 4.025 g |
| | 600 | Dichlorodifluoromethane, NF | 12.15 g |

Compounds of Formula I may be used in combination with other drugs that are used in the treatment/prevention/suppression or amelioration of the diseases, disorders or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: other anti-diabetic agents, anti-dylipidemic agents, and anti-hypertensive agents, anti-obesity agents, and anorectic agents, which may be administered separately or in the same pharmaceutical compositions.

The present invention also provides a method for the treatment or prevention of an AMPK-activated protein kinase (AMPK) mediated disease, which method comprises administration to a patient in need of such treatment or at risk of developing an AMPK mediated disease of an amount of an AMPK activator and an amount of one or more active ingredients, such that together they give effective relief.

In a further aspect of the present invention, there is provided a pharmaceutical composition comprising an AMPK activator and one or more active ingredients, together with at least one pharmaceutically acceptable carrier or excipient.

Thus, according to a further aspect of the present invention there is provided the use of an AMPK activator and one or more active ingredients for the manufacture of a medicament for the treatment or prevention of an AMPK mediated disease. In a further or alternative aspect of the present invention, there is therefore provided a product comprising an AMPK activator and one or more active ingredients as a combined preparation for simultaneous, separate or sequential use in the treatment or prevention of an AMPK mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

Suitable pharmaceutical agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, pelgiltazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY$^{26}$, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphosphohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-t H-indene-1-yl] oxy]phenyl]isothiazole-3-ol 1-oxide, 5-(4-((3-(2,6-dimethyl-4-(3-(methylsulfonyl)propoxy)phenyl)phenyl) methoxy)phenyl)iso, 5-(4-((3-(2-methyl-6-(3-hydroxypropoxy)pyridine-3-yl)-2-methylphenyl)methoxy) phenyl)isothiazole-3-ol 1-oxide, and 5-[4-[[3-[4-(3-aminopropoxy)-2,6-dimethylphenyl]phenyl]methoxy] phenyl]isothiazole-3-ol 1-oxide), and those disclosed in WO 11/078,371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A -cholesterol acyl transferase (ACAT) inhibitors such as avasimibe, eflucimibe, pactimibe (KY$^{505}$), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO151828 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI 143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and $RNH_{6270}$, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), O1691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl) carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1' receptor (MCH1R) antagonists, such as T-226296 (Takeda), T71 (TakedalAmgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) $MCH_2R$ (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081x, GW-548118x; FR 235,208; FR226928, FR 240662, FR252384; 1229U91, GI-264879A, CGP71683A, C-75 (Fasgen) LY-377897, LY366377, PD-160170, SR-120562A, SR-120819A,S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR$^{10}$A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) 133 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2)inhibitors; (31) FAS (fatty acid synthase) inhibitors, such as Cerulenin and C75; (32) PDE (phosphodiesterase) inhibitors, such as theophylline, pentoxifylline, zaprinast, sildenafil, aminone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptideYY and PYY agonists such as PYY336 (Nastech/Merck), AC162352 (IC Innovations/Curis/Amylin), TM30335/TM30338 (7™ Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC 137 (Amylin); (59) *Hoodia* and *trichocaulon* extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H- tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl) [3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl)[3-(1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl]-2-fluoro-2-methylpropyl)-5-fluorobenzonitrile, 3-((S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl) [3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1, 2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl] azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b] pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3' H)-isobenzofuran]-4-carboxamide, trans-3-oxo-N-(5-phenyl-2-pyrazinyl)spiro[4-azaiso-benzofuran-1 (3H), 1'-cyclohexane]-4'-carboxamide, trans-N-[5-(3-fluorophenyl)-2-pyrimidinyl]-3-oxospiro[5-azaisobenzofuran(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro [7-azaisobenzofuran-1(3H), 1'-cyclohexane]-4'-carboxamide, trans-3-oxo-N-(1-phenyl-4-pyrazolyl)spiro[4-azaisobenzofuran-(3H)),1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1 (3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy] phenyl}-4-[(4-fluorobenzyl)oxy]pyridin-2(1H)-one, 4-[(4-fluorobenzyl)oxy]-1-{-4-[(1-isopropylazetidin-3-yl)oxy] phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl) oxy]phenyl}pyridin-2(1H)-one, 4-[(5-chloropyridin-2-yl) methoxy]-1-{4-[(1-propylazetidin-3-yl)oxy] phenyl}pyridin-2(1H)-one, and 4-[(5-chloropyridin-2-yl) methoxy]-1-(4-{[(2S)-1-ethylazetidin-2-yl] methoxy}phenyl)pyridin-2(1H)-one, or a pharmaceutically acceptable salt thereof.

Specific DP-IV inhibitors of use in combination with a compound of the present invention are selected from Januvia, 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl) butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2, 3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl] propoxy}phenyl)pyrido[2,3-d]pyrimidin-4(3H)-one 2-methyl-3-(4-{3-[(3S)-3-methylpiperidin-1-yl] propoxy}phenyl)pyrido[4,3-d]pyrimidin-4(3H)-one, 3-{4-[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl})-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4, 3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methylpropane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; R067319; R1124; R1204; SSR146977; SSR240600; T-2328; and T2763; or a pharmaceutically acceptable salts thereof.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of structural formula I of the present invention can be prepared according to the procedures of the following Schemes, Intermediates and Examples, using appropriate materials and are further exemplified by the following specific examples. Moreover, by utilizing the procedures described in the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those previously described herein. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N.Y., 1991. CBZ and BOC are commonly used protecting groups in organic synthesis, and their removal conditions are known to those skilled in the art. All temperatures are degrees Celsius unless otherwise noted. Mass spectra (MS) were measured by electron-spray ion-mass spectroscopy.

Abbreviations used in the description of the preparation of the compounds of the present invention: ACN is acetonitrile; AcOH is acetic acid; C is carbon; CV is column volume(s); DAST is (diethylamino)sulfur trifluoride; DBU is 1,8-diazabicyclo[5.4.0]undec-7-ene; DIBAL-H is di-isobutyl aluminum hydride; DCM is dichloromethane; DIPEA is diisopropylethyl amine; DMA is dimethyl acetal; DME is 1,2-dimethoxyethane; DMF is dimethyl formamide; DMSO is dimethyl sulfoxide; dppf DCM complex is 1,1'-bis(diphenylphosphino)ferrocene dichloromethane complex; $Et_2O$ is diethyl ether; EtOAc is ethyl acetate; dppf is 1,1'-Bis(diphenyl-phosphino)ferrocene; EtOH is ethanol; $Et_3N$ is triethyl amine; h is hour(s); HPLC is high pressure liquid chromatography; ISCO $R_f$ is the Rf determined via medium pressure liquid chromatography using a Teledyne ISCO RediSep® column; isomannide is 1,4:3,6-Di-anhydro-mannitol; KOAc is potassium acetate; L is liter; LC/MS and LC-MS is liquid chromatography/mass spectroscopy; KOTMS is potassium trimethylsilanolate; LAH is lithium aluminum hydride; M is molar; ml and mL is milliliter; Me is methyl, MeCN is acetonitrile; MeI is methyl iodide; MeMgBr is methyl magnesium bromide; MeOH is methanol; MgBr is magnesium bromide; min is minutes; mmol is millimole(s); m-CPBA is meta chloro per benzoic acid; MTBE is tert-butyl methyl ether; N is normal; NaOAc is sodium acetate; NBS is N-bromo succinamide; NIS is N-iodo succinamide; $PPh_3$ is triphenyl phosphine; PhSiH is phenyl silane; wt % is weight percent; psi is pounds per square inch; RT and rt is room temperature; Rt is retention time; Rochelles' Salt is potassium sodium tartrate; SEM is 2-(trimethylsilyl)ethoxymethyl; SEMC1 is 2-(trimethylsilyl)-ethoxymethyl chloride; TBAF is tetrabutyl ammonium fluoride; TMS is trimethylsilyl; TFA is trifluoro acetic acid; and THF is tetrahydrofuran.

Microwave (MW) reactions were performed with a single mode operating Biotage Emrys Optimizer in sealed reaction vials at the indicated fixed temperature held constant for the designated reaction time. The medium pressure liquid chromatography (MPLC) purifications were performed with Teledyne ISCORediSep® normal-phase columns pre-packed with 35-60 micron silica gel. The LC-MS system contained an Applied Biosystems API50EX MS operating in a positive ion mode receiving 0.1 mL/min flowrate with a Shimadzu UV detector receiving 0.1 mL/min flowrate. Unless specified, the LC conditions were solvent A=0.03% TFA in acetonitrile; solvent B=0.05% TFA in water; flowrate=10 mL/min; column: Chromolith Performance RP-18e, 100×4.6 mm; gradient program: min (% B) 0 (95), 1.6 (5), 2.6 (5), 2.7 (95), 3.0 (95). Unless specified, the $^1$H NMRs were obtained in DMSO-$d_6$ at 300 or 500 MHz and spectra were recorded in units δ with $CD_2HS(O)CD_3$ (δ 2.504) as the reference line internal standard. C, H, N microanalyses were performed by Robertson Microlit Laboratories, Inc., Madison, N.J.

The following reaction schemes illustrate methods which may be employed for the synthesis of the compounds of structural formula I described in this invention. All substituents are as defined above unless indicated otherwise. Several strategies based upon synthetic transformations known in the literature of organic synthesis may be employed for the preparation of the title compounds of general formula I.

GENERAL SCHEME

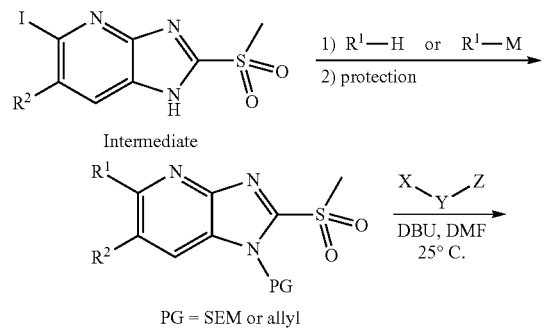

PG = SEM or allyl

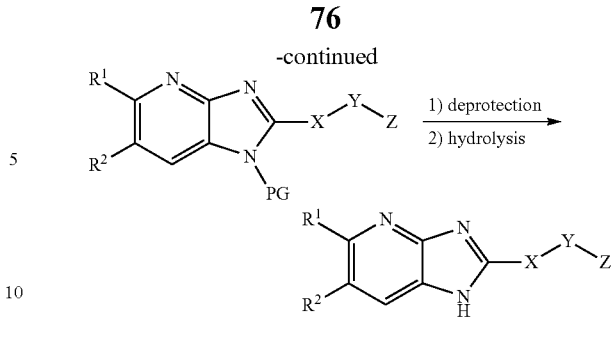

INTERMEDIATE 1

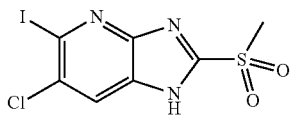

6-chloro-5-iodo-2-(methylsulfonyl)-1H-imidazo[4,5-b]pyridine

Step A 5,6-dichloro-3-nitropyridin-2-amine. To a solution of 5-chloro-3-nitropyridin-2-amine (16 g, 92 mmol) in AcOH (70 mL) was added N-chlorosuccinimide (14.8 g 111 mmol). The mixture was stirred overnight at 80° C. for 3 h, cooled to rt, diluted with MeOH (30 mL) and filtered. The solid residue was washed with AcOH, water, and then dried to afford the desired product as a white solid, which was used in the next step without further purification. LC-MS: calculated for $C_5H_3Cl_2N_3O_2$ 208.0, observed m/e: 208.07 (M+H)$^+$ (Rt 1.48/5 min).

Step B 5-chloro-6-iodo-3-nitropyridin-2-amine. To a solution of 5,6-dichloro-3-nitropyridin-2-amine (15 g, 72.1 mmol) in AcOH (70 mL) was added sodium iodide (43.2 g 149.9 mmol). The mixture was stirred at 90° C. for 2 h, cooled to rt, diluted with water (70 mL) and filtered. The solid residue was washed with water, and then dried under vacuum to afford the desired product as a pale yellow solid, which was used in the next step without further purification. LC-MS: calculated for $C_5H_3ClIN_3O$ 2299.45, observed m/e: 299.94 (M+H)$^+$ (Rt 2.18/5 min).

Step C 5-chloro-6-iodopyridine-2,3-diamine. To a suspension of 5-chloro-6-iodo-3-nitropyridin-2-amine (18.9 g, 63.1 mmol) in EtOH (100 mL) was added tin (II) chloride dihydrate (57 g, 252 mmol). The mixture was heated at 70° C. for 0.5 h. The rxn was warmed to rt and treated with a slurry of 150 mL water and 60 g KF and stirred for 0.5 h. The mixture was then partitioned between ethyl acetate (300 mL) and water (300 mL). The ethyl acetate layer was washed with brine, dried over magnesium sulfate and filtered through a 100 g pad of silica gel. The filtrate was concentrated and dried under vacuum to give an off-white solid, which was used in next step without further purification. LC-MS: calculated for $C_5H_5ClIN_3$ 269.47, observed m/e: 269.99 (M+H)$^+$ (Rt 1.35/5 min).

Step D 6-chloro-5-iodo-1,3-dihydro-2H-imidazo[4,5-b]pyridine-2-thione. DMAP (15.4 g, 126 mmol) was added to a THF (200 mL) solution of 5-chloro-6-iodopyridine-2,3-diamine (17 g, 63.1 mmol). Thiophosgene (4.9 mL, 63.1 mmol) was then added drop-wise via addition funnel under nitrogen and allowed to stir at rt for 1 h. The mixture was then partitioned between ethyl acetate (500 mL) and 2N HCl (100 mL). The ethyl acetate layer was washed with brine, dried over magnesium sulfate and concentrated to give the desired product as a white powder, which was used in the next step without further purification. LC-MS: calculated for $C_6H_3ClIN_3S$ 311.5, observed m/e: 311.91 (M+H)$^+$ (Rt 1.69/5 min).

Step E 6-chloro-5-iodo-2-(methsulfanyl)-1H-imidazo[4,5-b]pyridine. A suspension of 6-chloro-5-iodo-1,3-dihydro-2H-imidazo[4,5-b]pyridine-2-thione (11.0 g, 35.3 mmol) and KOH (2.38 g, 42.4 mmol) in ethanol (200 mL) was stirred at rt for 0.5 h. Iodomethane (2.2 mL, 35.3 mmol) was then added and the reaction was allowed to stir for 1 h at rt. The ethanol was removed in vacuo and the resulting residue was partitioned between ethyl acetate (250 mL) and 2N HCl (50 mL). The ethyl acetate layer was washed with brine, dried over magnesium sulfate, filtered through a 100 g pad of silica gel and concentrated to give the desired product as a white solid. LC-MS: calculated for $C_7H_5ClIN_3S$ 325.56, observed m/e: 325.88 (M+H)$^+$ (Rt 2.05/5 min).

Step F 6-chloro-5-iodo-2-(methysulfonyl)-1H-imidazo[45-b]pyridine. Oxone (20.8 g, 33.8 mmol) was added to an acetonitrile (100 mL)/water (100 mL) suspension of 6-chloro-5-iodo-2-(methylsulfanyl)-1H-imidazo[4,5-b]pyridine (5.0 g, 15.4 mmol) and the reaction was allowed to stir for 18 h at rt. The suspension was filtered through a sintered glass funnel and the filtrate was partitioned between ethyl acetate and saturated sodium bisulfate. The ethyl acetate layer was washed with brine, dried over magnesium sulfate and concentrated to afford the title compound as a white solid that was used in subsequent steps without further purification. Solubility precludes purification and this was used as is. LC-MS: calculated for $C_7H_5ClIN_3O_2S$ 357.56, observed m/e: 357.07 (M+H)$^+$ (Rt 1.36/4 min) $^1$H NMR δ (ppm) (DMSO-$d_6$): 8.44 (1H, s), 3.53 (3H, s).

INTERMEDIATE 2

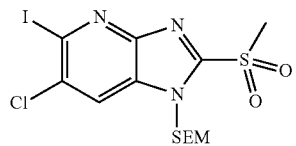 [SMILES: C[Si](C)(C)CCOCn1c(S(C)(=O)=O)nc2nc(I)c(Cl)cc21]

6-chloro-5-iodo-2-(methylsulfonyl)-1-{[2-(trimethylsilyl)ethoxy]methyl}-imidazo[4,5-b]pyridine SEM-Cl (2.48 mL, 14 mmol) was added to a THF (100 mL) solution of Intermediate 1 (5.0 g, 14 mmol) and triethylamine (2.92 mL, 21 mmol) at 0° C. under nitrogen atmosphere. The reaction was warmed to rt over 30 min. The reaction was partitioned between ethyl acetate and saturated aqueous ammonium chloride. The organic layer was washed with water, brine, dried over magnesium sulfate and concentrated. Flash chromatography of the resulting residue utilizing a Biotage™ 100G SNAP cartridge and employing a linear gradient: 0-20% EtOAc/hexane and then 20-100% EtOAc/hexane; afforded the title compound as a clear oil. LC-MS: calculated for $C_{13}H_{19}ClN_3O_3SSi$ 487.8, observed m/e: 428.9 (M+H)$^+$ (Rt 2.54/4 min).

INTERMEDIATE 3

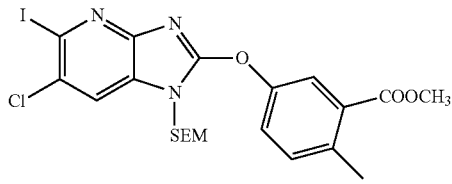 [SMILES: COC(=O)c1cc(Oc2nc3nc(I)c(Cl)cc3n2COCC[Si](C)(C)C)ccc1C]

Methyl 5-[6-chloro-5-iodo-1-{[2-(trimethylsily)ethoxy]methyl}-1H imidazo[4,5-b]pyridin-2-yl)oxy]-2-methylbenzoate. Cesium carbonate (2.67 g, 8.2 mmol) was added to a DMA (10 mL) solution of Intermediate 2 (1.6 g, 3.28 mmol) and methyl 5-hydroxy-2-methylbenzoate (0.82 g, 4.92 mmol) at rt under a nitrogen atmosphere. The reaction was stirred for 15 min, then partitioned between ethyl acetate and 10% aqueous citric acid. The organic layer was washed with water, brine, dried over magnesium sulfate and concentrated. Flash chromatography of the resulting residue utilizing a Biotage™ 100G SNAP cartridge and employing a linear gradient: 0-100% EtOAc/hexane afforded the title compound as a white solid. LC-MS: calculated for $C_{21}H_{25}ClN_3O_4Si$ 573.89, observed m/e: 573.93 (M+H)$^+$ (Rt 2.92/4 min).

INTERMEDIATE 4

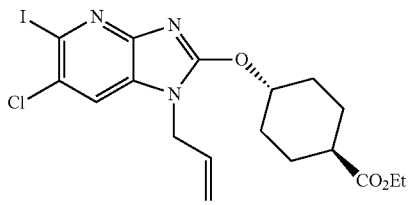 [SMILES: C=CCn1c(O[C@H]2CC[C@H](C(=O)OCC)CC2)nc2nc(I)c(Cl)cc21]

Ethyl trans-4-[(6-chloro-5-iodo-1-{prop-2-en-1-yl}-1H imidazo[4,5-b]pyridin-2-yl]oxy}cyclohexanecarboxylate. Sodium hydride (475 mg, 19.8 mmol) was added to a DMF solution of Intermediate 1 (5.9 g, 16.5 mmol) and allyl bromide (1.7 mL, 19.8 mmol) at rt. The reaction was allowed to stir at rt for 16 h. The reaction was then treated sequentially with ethyl-4-hydroxycyclohexanecarboxylate (10.64 mL, 66 mmol) and DBU (9.95 mL, 66 mmol). The reaction was partitioned between EtOAc and 10% aqueous citric acid. The EtOAc layer was washed with water, brine, dried over magnesium sulfate and concentrated. Flash chromatography of the resulting residue utilizing a Biotage™ 100 g SNAP cartridge and employing a gradient: 0-20% EtOAc/hexane afforded the title compound as a colorless oil, which solidified after overnight vacuum drying. LC-MS: calculated for $C_{18}H_{21}ClN_3O_3$ 489.7, observed: m/e: 489.9 (M+H)$^+$ (Rt 2.75/4 min).

INTERMEDIATE 5

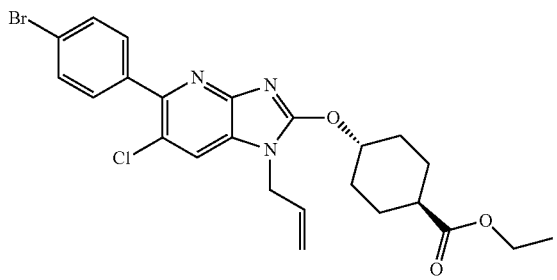 [SMILES: C=CCn1c(O[C@H]2CC[C@H](C(=O)OCC)CC2)nc2nc(-c3ccc(Br)cc3)c(Cl)cc21]

Ethyl trans-4-{([(5-(4-bromophenyl)-6-chloro-1-{prop-2-en-1-yl}-1H imidazo[4,5-b]pyridin-2-yl]oxy}cyclohexane-carboxylate. 1,1'-bis(diphenylphosphinoferrocene-Palladium (II) dichloride dichloromethane complex (183 mg, 0.22 mmol) was added to a DMSO (5 mL) solution of Intermediate 4 (550 mg, 1.12 mmol), 4-bromophenylboronic acid (271 mg, 1.35 mmol) and cesium carbonate (1.1 g, 3.37 mmol) at rt under a nitrogen atmosphere. The reaction was heated to 90° C. for 3 h, then partitioned between EtOAc and 10% aqueous citric acid. The organic layer was washed with water and brine, dried over magnesium sulfate and concentrated. Flash chromatography of the resulting residue utilizing a Biotage™ 50G SNAP cartridge and employing a linear gradient: 0-100% EtOAc/hexane afforded the title compound as a white solid. LC-MS: calculated for $C_{24}H_{25}BrClN_3O_3$ 518.8, observed m/e: 520.3 (M+H)+ (Rt 1.4/2 min).

INTERMEDIATE 6

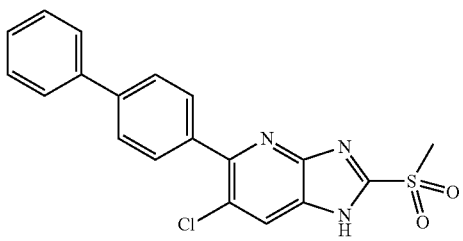 [SMILES: CS(=O)(=O)c1nc2nc(-c3ccc(-c4ccccc4)cc3)c(Cl)cc2[nH]1]

5-(biphenyl-4-yl)-6-chloro-2-(methlsulfonyl)-1H-imidazo-4,5-b]pyridine

Intermediate 1 (50 g, 140 mmol), 4-Biphenylboronic acid (33.2 g, 168 mmol) and tripotassium phosphate (89 g, 212.3 mmol) were dissolved in THF (500 mL) and water (50 mL), then sparged with $N_2$ for 20 min. A solution of palladium acetate (3.14 g, 14.0 mmol) and n-butyldiadamantylphosphine (Catacxium A, 10 g, 28 mmol) in THF (30 mL) was sparged with $N_2$ for 20 minutes, and then added to the mixture of Intermediate 1, biphenylboronic acid and base. The reaction was heated to 45° C. for 18 h. An additional aliquot of palladium acetate (3.14 g, 14.0 mmol) and n-butyldiadamantylphosphine (Catacxium A, 10 g, 28 mmol) in THF (30 mL) was sparged with $N_2$ for 20 minutes and added to the reaction mixture. After 24 h at 45° C., the reaction was cooled to rt and diluted with EtOAc and brine. The organic layer was concentrated and triturated with THF/MTBE to provide the title compound as a tan solid. LC-MS: calculated for $C_{19}H_{14}ClN_3O_2S$ 383.05; observed m/e: 383.9 (M+H)+ (Rt 2.01/4 min).

SCHEME 1

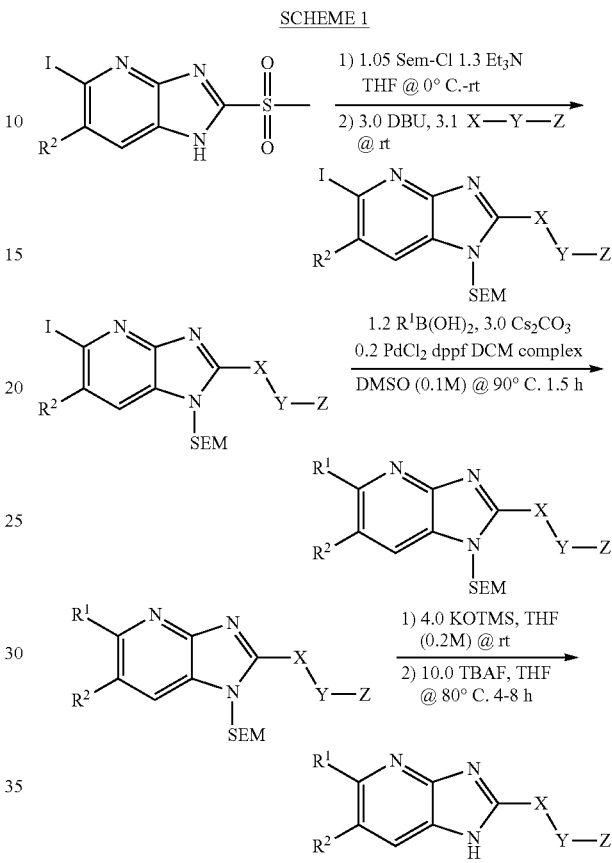

EXAMPLE 1

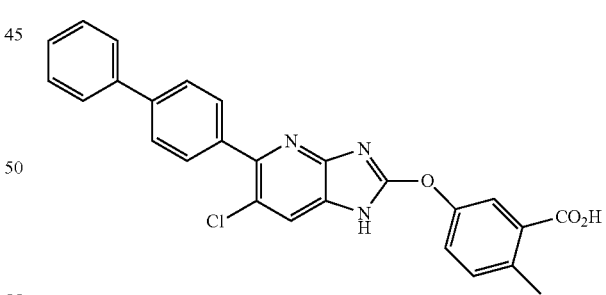

5-{[5-(biphenyl-4-yl)-6-chloro-1-H imidazo[4,5-b] pyridin-2-yl]oxy}-2-methylbenzoic acid Step A. 1,1'-Bis(diphenylphosphinoferrocene-Palladium (II) dichloride dichloromethane complex (142 mg, 0.17 mmol) was added to a dioxane (1.8 mL)/water (0.2 mL) solution of Intermediate 3 (200 mg, 0.35 mmol), 4-biphenylboronic acid (104 mg, 0.52 mmol) and lithium hydroxide (20 mg, 0.87 mmol) at rt under a nitrogen atmosphere. The reaction was heated to 80° C. for 20 min, then partitioned between ethyl acetate and 10% aqueous citric acid. The organic layer was washed with water, brine, dried over magnesium sulfate and concentrated. Flash chromatography of the resulting residue utilizing a Biotage™ 10G SNAP cartridge and employing a linear gradient: 0-100% EtOAc/hexane afforded methyl 5-{[5-(biphenyl-4-yl)-6-chloro-1-{[2-(trimethylsilyl)ethoxy]methyl}-1H imidazo[4,5-b]pyridin-2-yl]oxy}-2-methylbenzoate as a white solid. LC-MS: calculated for $C_{33}H_{34}ClN_3O_4Si$ 600.18, observed m/e: 600.93 (M+H)+(Rt 3.2/4 min), Step B. A formic acid (2.7 mL, 70.4 mmol) solution of methyl 5-{[5-(biphenyl-4-yl)-6-chloro-1-{[2-(trimethylsilyl)ethoxy]methyl}-1H imidazo[4,5-b]pyridin-2-yl]oxy}-2-methylbenzoate (140 mg, 0.23 mmol) and saturated potassium bisulfate (0.27 mL) was stirred at 80° C. for 1 h. The reaction was partitioned between EtOAc and brine. The organic layer was separated, and concentrated to give methyl 5-{[5-(biphenyl-4-yl)-6-chloro-1-H imidazo[4,5-b]pyridin-2-yl]oxy}-2-methylbenzoate as a white solid, which was used in the next step without further purification. LC-MS: calculated for $C_{27}H_{20}ClN_3O_3$ 456.89, observed m/e: 470.2 (M+H)+

Step C. 2N KOH (1.1 mL, 2.2 mmol) was added to a methanol (10 mL) solution of methyl 5-{[5-(biphenyl-4-yl)-6-chloro-1-H imidazo[4,5-b]pyridin-2-yl]oxy}-2-methylbenzoate (104 mg, 0.22 mmol) and the reaction was stirred at 80° C. for 2 h. The reaction was partitioned between EtOAc and 10% aqueous citric acid. The organic layer was separated, washed with brine, dried over magnesium sulfate and concentrated. Flash chromatography of the resulting residue utilizing a Biotage™ 10G SNAP cartridge and employing a gradient: 0-100% EtOAc/hexane afforded the title compound as a white solid. LC-MS: calculated for $C_{26}H_{18}ClN_3O_3$ 455.89, observed m/e: 456.2 (M+H)+ (Rt 2.0/4 min). $^1$H NMR δ (ppm) (DMSO-$d_6$): 8.00 (1H, s), 7.82 (1H, m) 7.79-7.69 (7H, m), 7.48 (2H, m), 7.38 (2H, m), 2.56 (3H, s).

TABLE 1

| | Compounds prepared according to the methods described in Example 1. | |
| --- | --- | --- |
| Example Number | Structure | HPLC-mass spectrum m/e |
| 2 | | 419.93 |
| 3 | | 448.13 |
| 4 | | 464.1 |

TABLE 1-continued

Compounds prepared according to the methods described in Example 1.

| Example Number | Structure | HPLC-mass spectrum m/e |
|---|---|---|
| 5 | 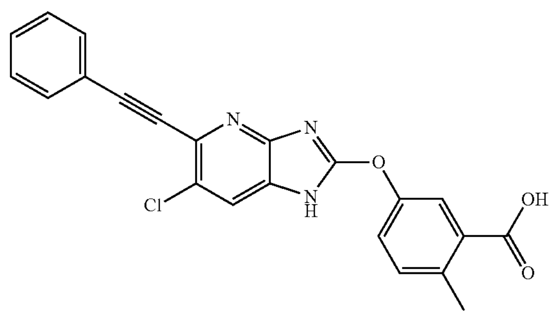 [SMILES: Cc1ccc(Oc2nc3nc(C#Cc4ccccc4)c(Cl)cc3[nH]2)cc1C(=O)O] | 404.05 |
| 6 | 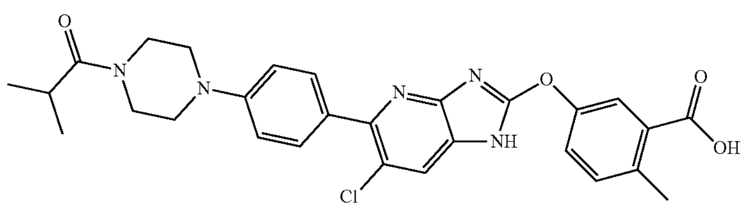 [SMILES: Cc1ccc(Oc2nc3nc(-c4ccc(N5CCN(C(=O)C(C)C)CC5)cc4)c(Cl)cc3[nH]2)cc1C(=O)O] | 534.09 |
| 7 | 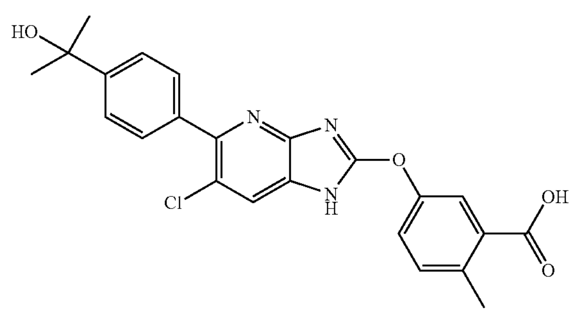 [SMILES: Cc1ccc(Oc2nc3nc(-c4ccc(C(C)(C)O)cc4)c(Cl)cc3[nH]2)cc1C(=O)O] | 437.92 |
| 8 | 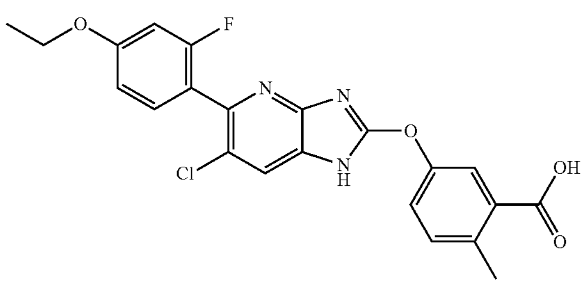 [SMILES: CCOc1ccc(-c2nc3nc(Oc4ccc(C)c(C(=O)O)c4)[nH]c3cc2Cl)c(F)c1] | 441.83 |
| 9 | 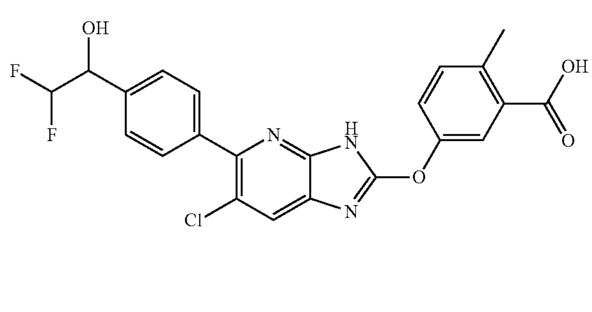 [SMILES: Cc1ccc(Oc2nc3cc(Cl)c(-c4ccc(C(O)C(F)F)cc4)nc3[nH]2)cc1C(=O)O] | 460.0 |

TABLE 1-continued

Compounds prepared according to the methods described in Example 1.

| Example Number | Structure | HPLC-mass spectrum m/e |
|---|---|---|
| 10 | 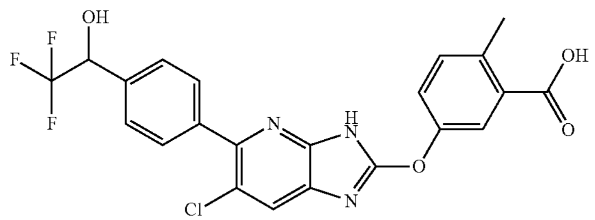 [SMILES: Cc1ccc(Oc2nc3cc(Cl)c(-c4ccc(C(O)C(F)(F)F)cc4)nc3[nH]2)cc1C(=O)O] | 478.0 |
| 11 | 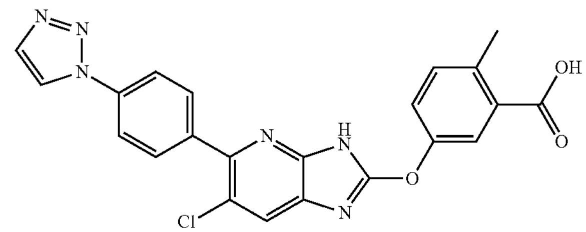 [SMILES: Cc1ccc(Oc2nc3cc(Cl)c(-c4ccc(-n5ccnn5)cc4)nc3[nH]2)cc1C(=O)O] | 447.1 |
| 12 | 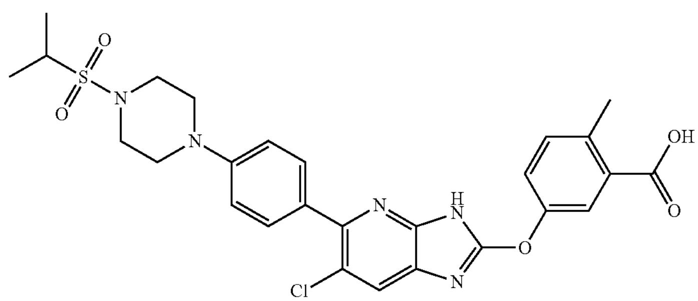 [SMILES: Cc1ccc(Oc2nc3cc(Cl)c(-c4ccc(N5CCN(S(=O)(=O)C(C)C)CC5)cc4)nc3[nH]2)cc1C(=O)O] | 570.2 |
| 13 | 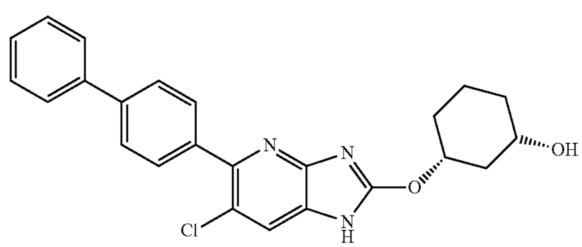 | 420.25 |
| 14 | 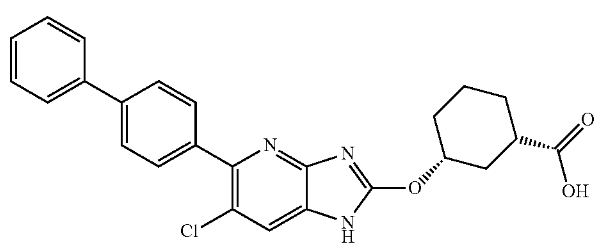 | 448.31 |
| 15 | 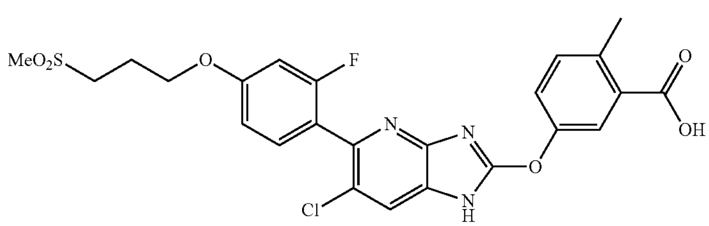 [SMILES: Cc1ccc(Oc2nc3nc(-c4ccc(OCCCS(C)(=O)=O)cc4F)c(Cl)cc3[nH]2)cc1C(=O)O] | 534.11 |

TABLE 1-continued

Compounds prepared according to the methods described in Example 1.

| Example Number | Structure | HPLC-mass spectrum m/e |
|---|---|---|
| 16 | 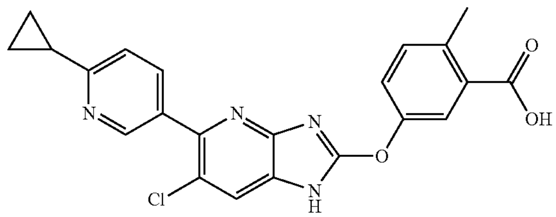 [SMILES: Cc1ccc(Oc2nc3nc(-c4ccc(C5CC5)nc4)c(Cl)cc3[nH]2)cc1C(=O)O] | 421.05 |
| 17 | 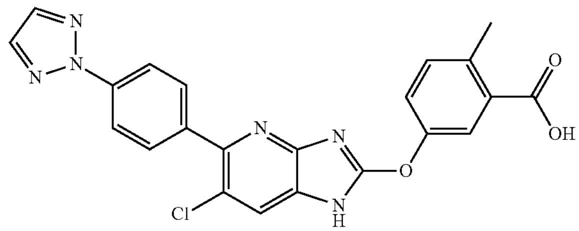 [SMILES: Cc1ccc(Oc2nc3nc(-c4ccc(-n5nccn5)cc4)c(Cl)cc3[nH]2)cc1C(=O)O] | 447.12 |
| 18 | 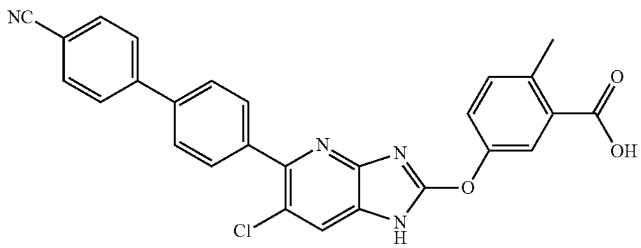 [SMILES: Cc1ccc(Oc2nc3nc(-c4ccc(-c5ccc(C#N)cc5)cc4)c(Cl)cc3[nH]2)cc1C(=O)O] | 481.19 |
| 19 | 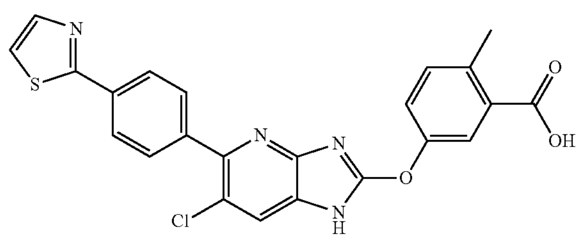 [SMILES: Cc1ccc(Oc2nc3nc(-c4ccc(-c5nccs5)cc4)c(Cl)cc3[nH]2)cc1C(=O)O] | 463.12 |
| 20 | 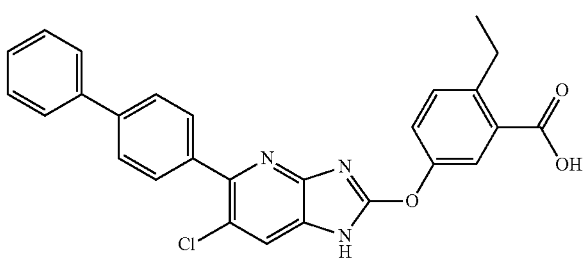 [SMILES: CCc1ccc(Oc2nc3nc(-c4ccc(-c5ccccc5)cc4)c(Cl)cc3[nH]2)cc1C(=O)O] | 470.02 |
| 21 | 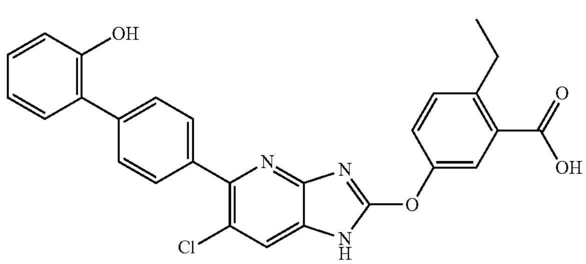 [SMILES: CCc1ccc(Oc2nc3nc(-c4ccc(-c5ccccc5O)cc4)c(Cl)cc3[nH]2)cc1C(=O)O] | 485.95 |

TABLE 1-continued

Compounds prepared according to the methods described in Example 1.

| Example Number | Structure | HPLC-mass spectrum m/e |
|---|---|---|
| 22 | 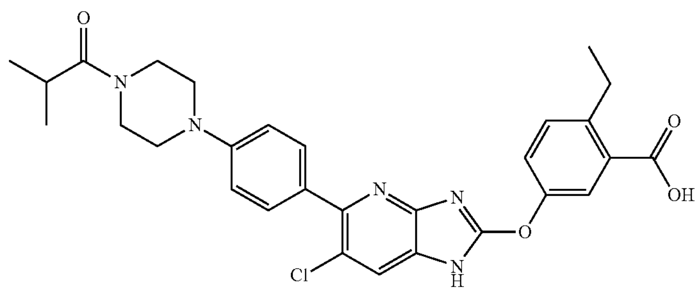 [SMILES: CCc1ccc(Oc2nc3nc(-c4ccc(N5CCN(C(=O)C(C)C)CC5)cc4)c(Cl)cc3[nH]2)cc1C(=O)O] | 548.01 |
| 23 | 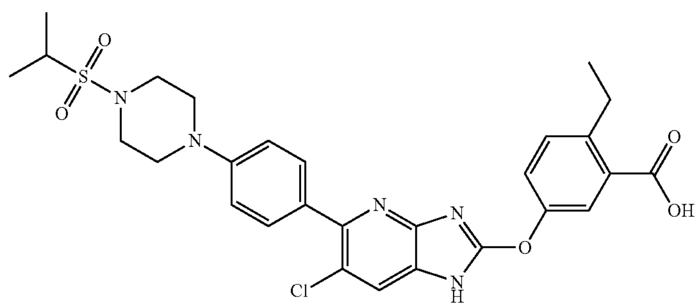 [SMILES: CCc1ccc(Oc2nc3nc(-c4ccc(N5CCN(S(=O)(=O)C(C)C)CC5)cc4)c(Cl)cc3[nH]2)cc1C(=O)O] | 584.06 |
| 24 | 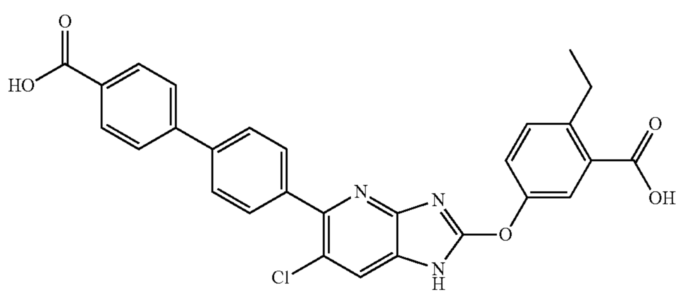 [SMILES: CCc1ccc(Oc2nc3nc(-c4ccc(-c5ccc(C(=O)O)cc5)cc4)c(Cl)cc3[nH]2)cc1C(=O)O] | 514.04 |
| 25 | 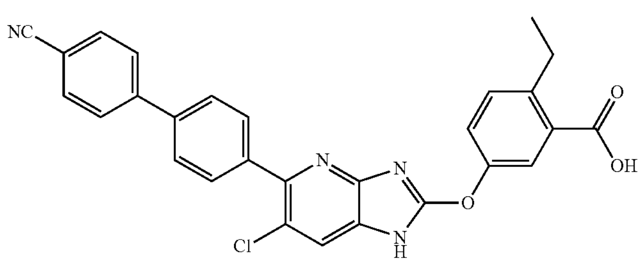 [SMILES: CCc1ccc(Oc2nc3nc(-c4ccc(-c5ccc(C#N)cc5)cc4)c(Cl)cc3[nH]2)cc1C(=O)O] | 494.88 |
| 26 | 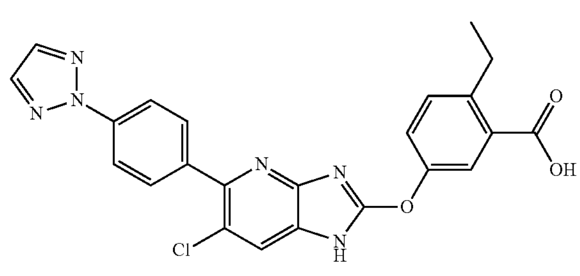 [SMILES: CCc1ccc(Oc2nc3nc(-c4ccc(-n5nccn5)cc4)c(Cl)cc3[nH]2)cc1C(=O)O] | 461.05 |

TABLE 1-continued

Compounds prepared according to the methods described in Example 1.

| Example Number | Structure | HPLC-mass spectrum m/e |
|---|---|---|
| 27 | 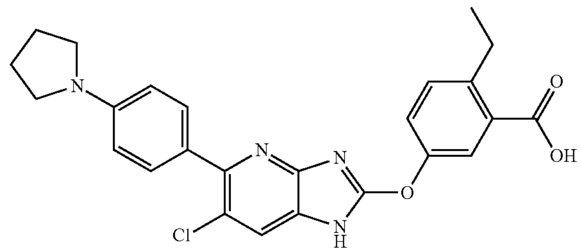 [SMILES: CCc1ccc(Oc2nc3nc(-c4ccc(N5CCCC5)cc4)c(Cl)cc3[nH]2)cc1C(=O)O] | 463.09 |
| 28 | 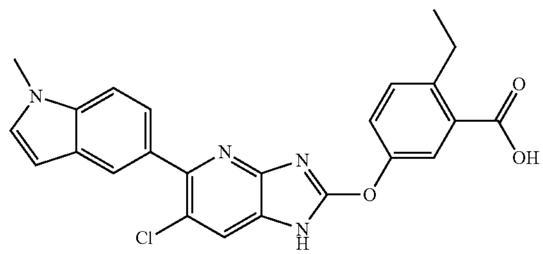 [SMILES: CCc1ccc(Oc2nc3nc(-c4ccc5c(ccn5C)c4)c(Cl)cc3[nH]2)cc1C(=O)O] | 447.03 |

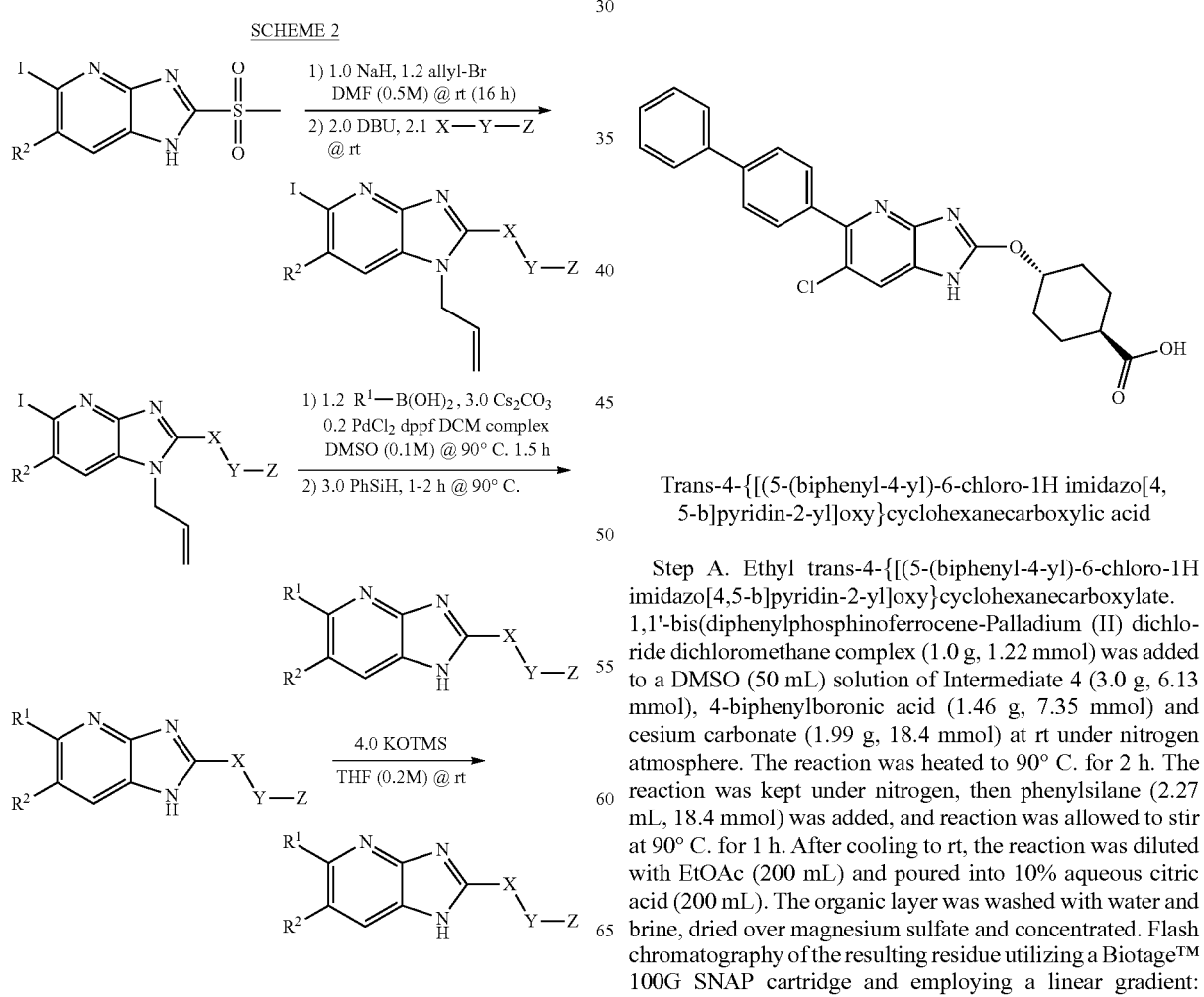

EXAMPLE 29

Trans-4-{[(5-(biphenyl-4-yl)-6-chloro-1H imidazo[4,5-b]pyridin-2-yl]oxy}cyclohexanecarboxylic acid Step A. Ethyl trans-4-{[(5-(biphenyl-4-yl)-6-chloro-1H imidazo[4,5-b]pyridin-2-yl]oxy}cyclohexanecarboxylate. 1,1'-bis(diphenylphosphinoferrocene-Palladium (II) dichloride dichloromethane complex (1.0 g, 1.22 mmol) was added to a DMSO (50 mL) solution of Intermediate 4 (3.0 g, 6.13 mmol), 4-biphenylboronic acid (1.46 g, 7.35 mmol) and cesium carbonate (1.99 g, 18.4 mmol) at rt under nitrogen atmosphere. The reaction was heated to 90° C. for 2 h. The reaction was kept under nitrogen, then phenylsilane (2.27 mL, 18.4 mmol) was added, and reaction was allowed to stir at 90° C. for 1 h. After cooling to rt, the reaction was diluted with EtOAc (200 mL) and poured into 10% aqueous citric acid (200 mL). The organic layer was washed with water and brine, dried over magnesium sulfate and concentrated. Flash chromatography of the resulting residue utilizing a Biotage™ 100G SNAP cartridge and employing a linear gradient:

0-100% ethyl acetate/hexane afforded ethyl trans-4-{[(5-(biphenyl-4-yl)-6-chloro-1H imidazo[4,5-b]pyridin-2-yl]oxy}cyclohexanecarboxylate as a crystalline white solid. LC-MS: calculated for $C_{27}H_{26}ClN_3O_3$ 476.9, observed m/e: 476.4 (M+H)+(Rt 1.5/2 min).

Step B Potassium trimethylsilanolate (1.48 g, 11.5 mmol) was added to a THF (10 mL) solution of ethyl trans-4-{[(5-(biphenyl-4-yl)-6-chloro-1H imidazo[4,5-b]pyridin-2-yl]oxy}cyclohexanecarboxylate (2.5 g, 5.25 mmol), and the reaction was stirred at rt for 16 h. The reaction mixture was then partitioned between EtOAc and 10% aqueous citric acid. The organic layer was washed with brine, dried over magnesium sulfate and concentrated rinsing with THF (40 mL). The combined organic layers were concentrated, and then triturated with acetonitrile (50 mL) to afford the title compound as an off-white solid. LC-MS: calculated for $C_{25}H_{22}ClN_3O_3$ 447.9, observed m/e: 448.4 (M+H)+ (Rt 1.15/2 min). $^1$H NMR δ (ppm) (DMSO-$d_6$): 7.91 (1 H, s), 7.78-7.71 (6 H, m), 7.49 (2 H, t, J=7.60 Hz), 7.39 (1 H, t, J=7.38 Hz), 5.02-4.95 (1 H, m), 2.35-2.27 (1 H, m), 2.24 (2 H, m), 1.99 (2 H, m), 1.57-1.46 (4 H, m).

TABLE 2

Compounds prepared according to the methods described in Example 29.

| Example Number | Structure | HPLC-mass spectrum m/e |
|---|---|---|
| 30 | 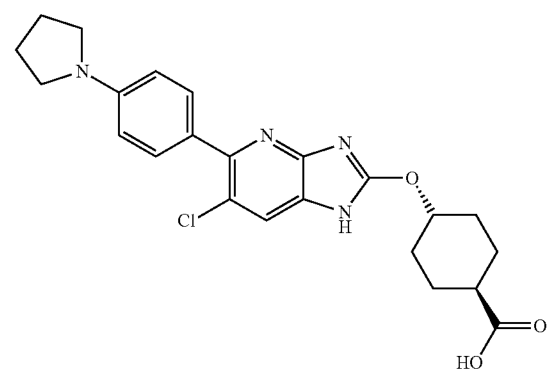 | 441.15 |
| 31 | 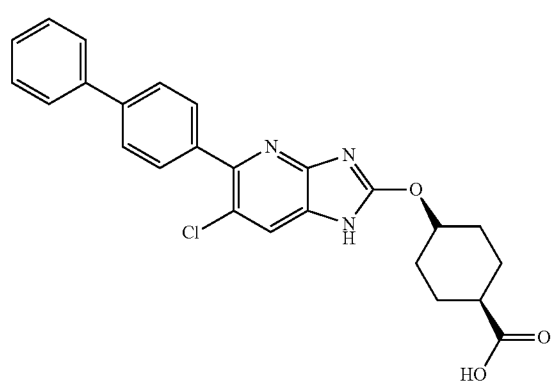 | 448.3 |
| 32 | 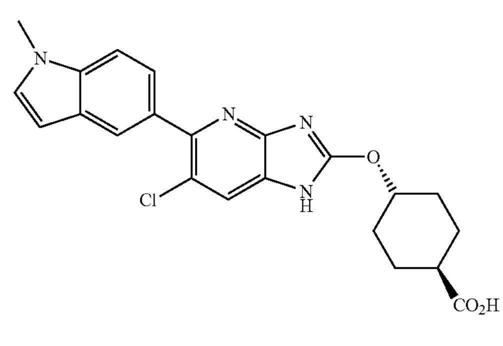 | 425.9 |

TABLE 2-continued

Compounds prepared according to the methods described in Example 29.

| Example Number | Structure | HPLC-mass spectrum m/e |
|---|---|---|
| 33 | 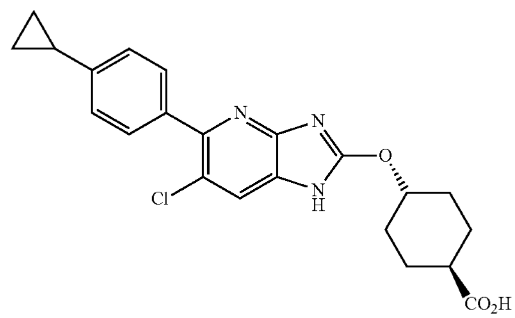 | 412.1 |
| 34 | 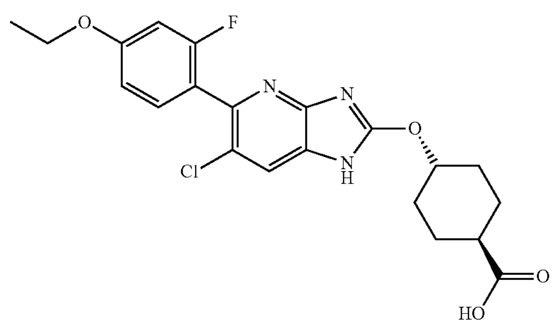 | 434.3 |
| 35 | 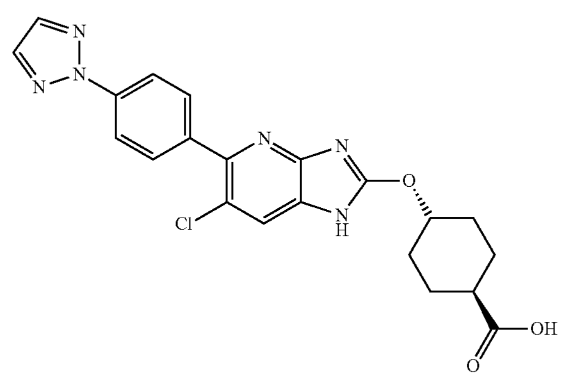 | 439.3 |
| 36 | 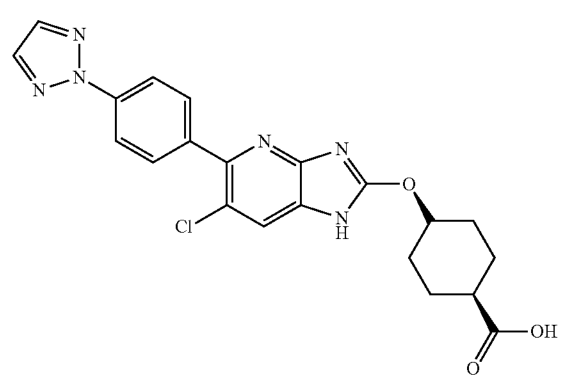 | 439.3 |

TABLE 2-continued
Compounds prepared according to the methods described in Example 29.
| Example Number | Structure | HPLC-mass spectrum m/e |
|---|---|---|
| 37 | 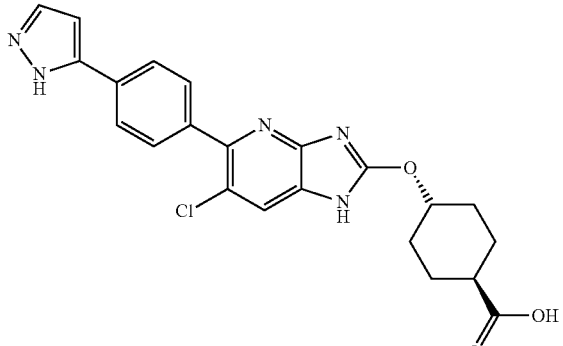 | 438.3 |
| 38 | 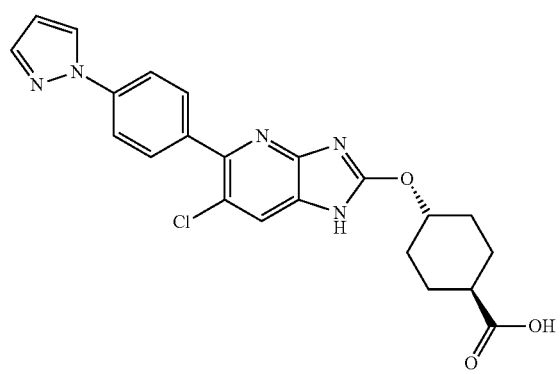 | 438.4 |
| 39 | 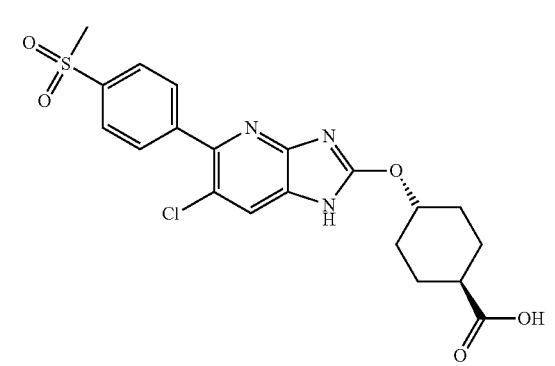 | 450.2 |
| 40 | 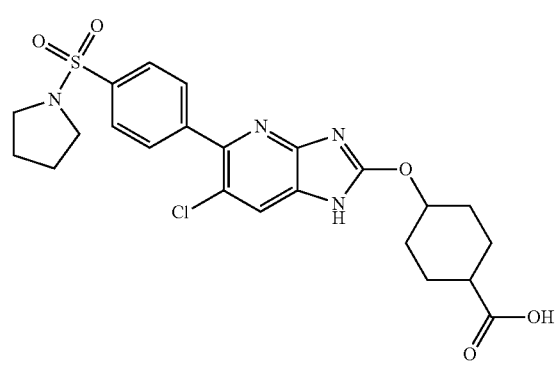 [SMILES: O=C(O)C1CCC(Oc2nc3nc(-c4ccc(S(=O)(=O)N5CCCC5)cc4)c(Cl)cc3[nH]2)CC1] | 505.3 |

TABLE 2-continued

Compounds prepared according to the methods described in Example 29.

| Example Number | Structure | HPLC-mass spectrum m/e |
|---|---|---|
| 41 | 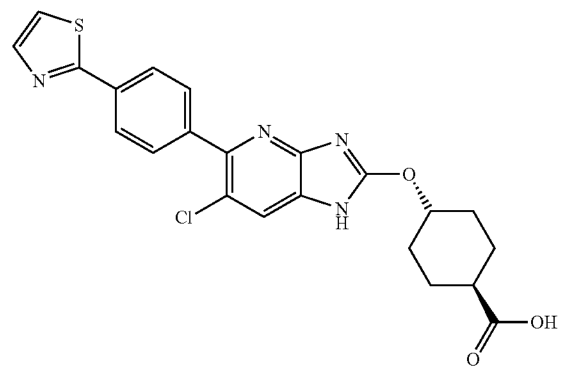 | 455.3 |
| 42 | 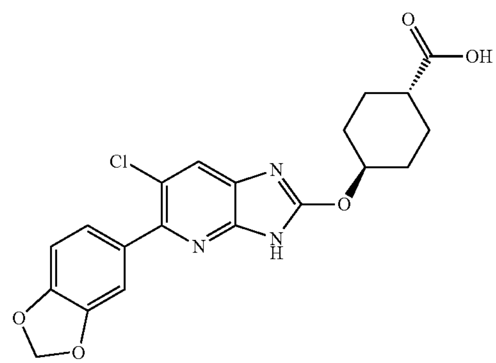 [SMILES: O=C(O)[C@H]1CC[C@H](Oc2nc3cc(Cl)c(-c4ccc5c(c4)OCO5)nc3[nH]2)CC1] | 416.4 (402.1 strong fragment) |
| 43 | 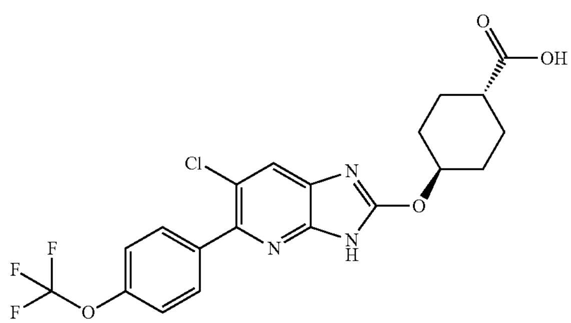 [SMILES: O=C(O)[C@H]1CC[C@H](Oc2nc3cc(Cl)c(-c4ccc(OC(F)(F)F)cc4)nc3[nH]2)CC1] | 456.4 |
| 44 | 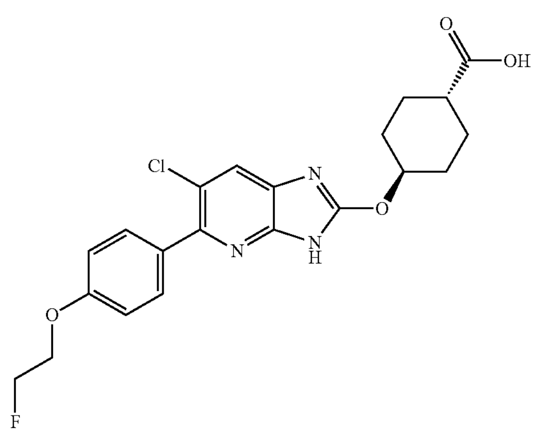 [SMILES: O=C(O)[C@H]1CC[C@H](Oc2nc3cc(Cl)c(-c4ccc(OCCF)cc4)nc3[nH]2)CC1] | 420.4 (M—CH$_2$ fragment strong) |

TABLE 2-continued

Compounds prepared according to the methods described in Example 29.

| Example Number | Structure | HPLC-mass spectrum m/e |
|---|---|---|
| 45 | 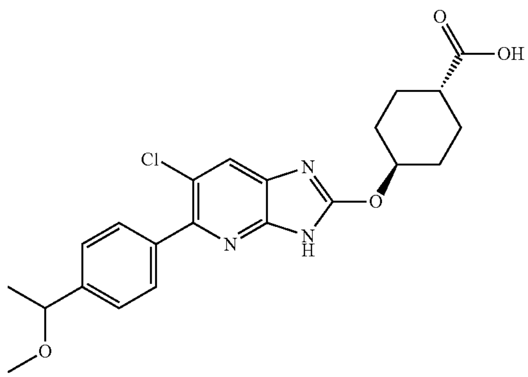 [SMILES: COC(C)c1ccc(-c2nc3[nH]c(O[C@H]4CC[C@H](C(=O)O)CC4)nc3cc2Cl)cc1] | 430.4 |
| 46 | 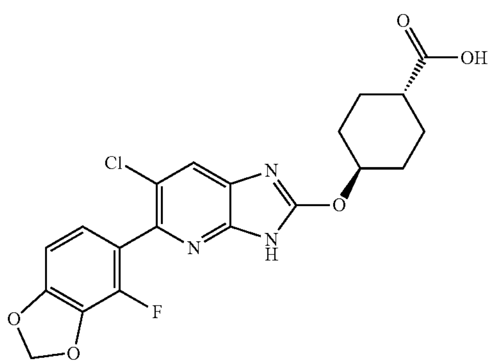 [SMILES: O=C(O)[C@H]1CC[C@H](Oc2nc3cc(Cl)c(-c4ccc5c(c4F)OCO5)nc3[nH]2)CC1] | 434.4 |
| 47 | 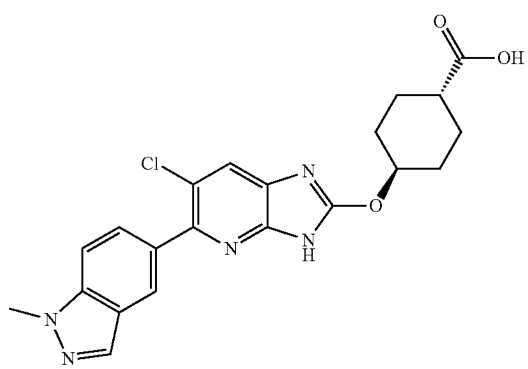 [SMILES: Cn1ncc2cc(-c3nc4[nH]c(O[C@H]5CC[C@H](C(=O)O)CC5)nc4cc3Cl)ccc21] | 426.3 |
| 48 | 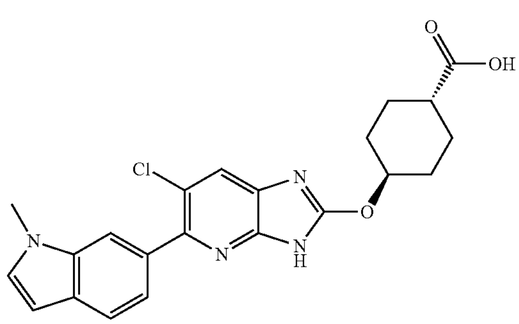 [SMILES: Cn1ccc2ccc(-c3nc4[nH]c(O[C@H]5CC[C@H](C(=O)O)CC5)nc4cc3Cl)cc21] | 425.4 |

TABLE 2-continued

Compounds prepared according to the methods described in Example 29.

| Example Number | Structure | HPLC-mass spectrum m/e |
|---|---|---|
| 49 | (structure) | 454.3 |
| 50 | (structure) | 416.3 |
| 51 | (structure) | 430.3 |
| 52 | (structure) | 430.4 |

TABLE 2-continued

Compounds prepared according to the methods described in Example 29.

| Example Number | Structure | HPLC-mass spectrum m/e |
|---|---|---|
| 53 | 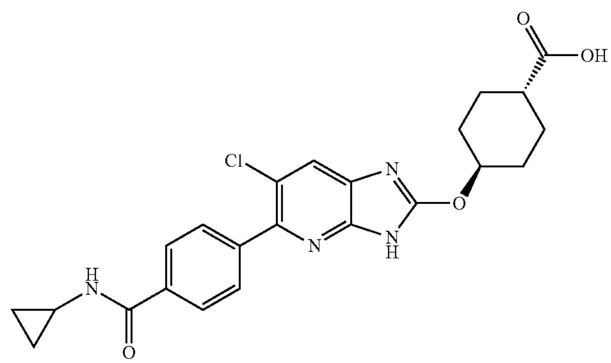 [SMILES: O=C(NC1CC1)c1ccc(-c2nc3[nH]c(O[C@H]4CC[C@H](C(=O)O)CC4)nc3cc2Cl)cc1] | 455.3 |
| 54 | 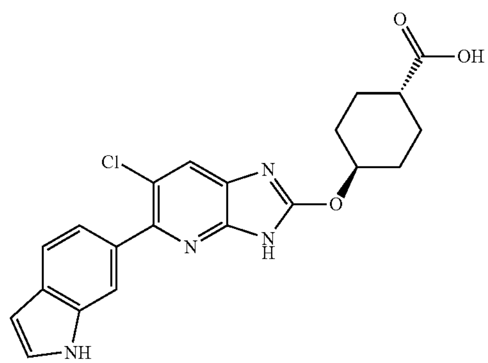 [SMILES: O=C(O)[C@H]1CC[C@H](Oc2nc3cc(Cl)c(-c4ccc5cc[nH]c5c4)nc3[nH]2)CC1] | 411.3 |
| 55 | 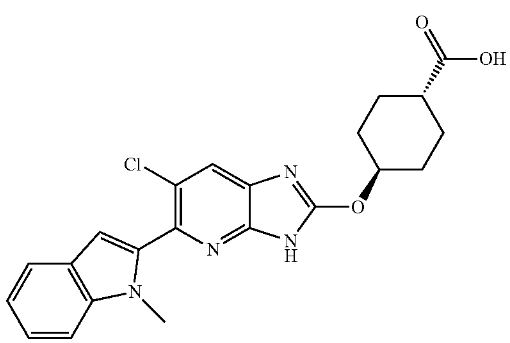 [SMILES: Cn1c(-c2nc3[nH]c(O[C@H]4CC[C@H](C(=O)O)CC4)nc3cc2Cl)cc2ccccc21] | 425.4 |
| 56 | 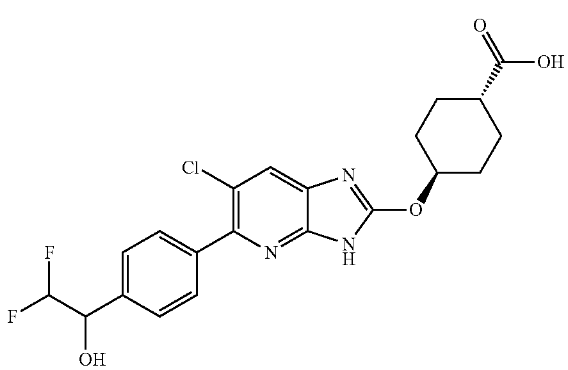 [SMILES: O=C(O)[C@H]1CC[C@H](Oc2nc3cc(Cl)c(-c4ccc(C(O)C(F)F)cc4)nc3[nH]2)CC1] | 452.3 |

TABLE 2-continued

Compounds prepared according to the methods described in Example 29.

| Example Number | Structure | HPLC-mass spectrum m/e |
|---|---|---|
| 57 | 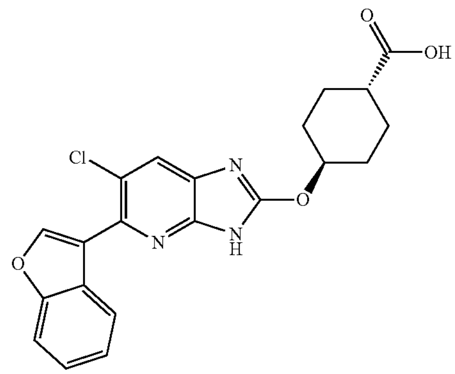 [SMILES: O=C(O)[C@H]1CC[C@H](Oc2nc3cc(Cl)c(-c4coc5ccccc45)nc3[nH]2)CC1] | 432.4 |
| 58 | 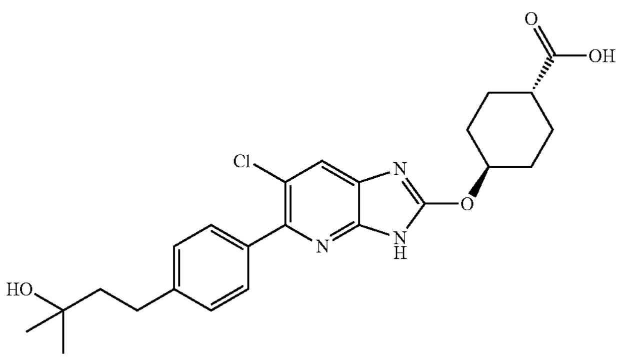 [SMILES: CC(C)(O)CCc1ccc(-c2nc3[nH]c(O[C@H]4CC[C@H](C(=O)O)CC4)nc3cc2Cl)cc1] | 458.4 |
| 59 | 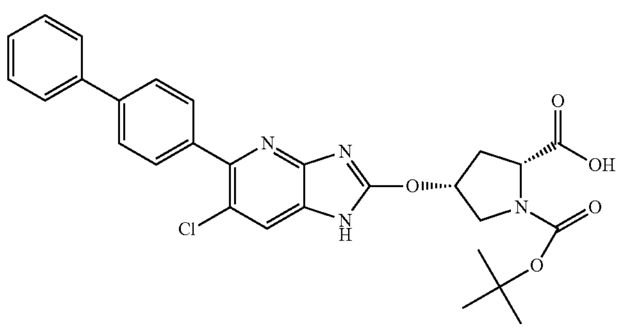 [SMILES: CC(C)(C)OC(=O)N1C[C@H](Oc2nc3nc(-c4ccc(-c5ccccc5)cc4)c(Cl)cc3[nH]2)C[C@@H]1C(=O)O] | 535.19 |
| 60 | 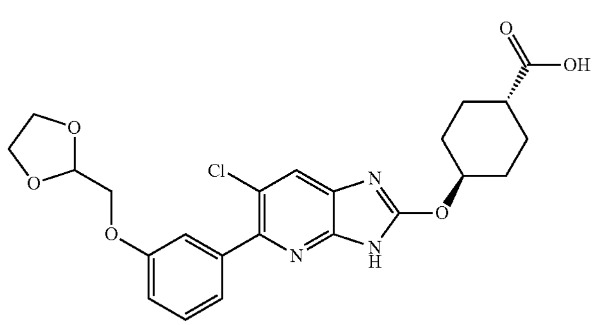 [SMILES: O=C(O)[C@H]1CC[C@H](Oc2nc3cc(Cl)c(-c4cccc(OCC5OCCO5)c4)nc3[nH]2)CC1] | 474.1 |

TABLE 2-continued

Compounds prepared according to the methods described in Example 29.

| Example Number | Structure | HPLC-mass spectrum m/e |
| --- | --- | --- |
| 61 | 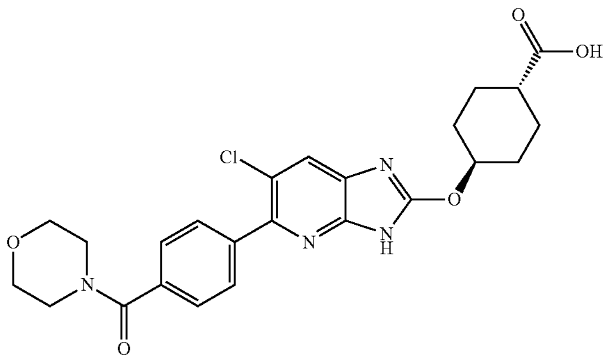 [SMILES: O=C(c1ccc(-c2nc3[nH]c(O[C@H]4CC[C@H](C(=O)O)CC4)nc3cc2Cl)cc1)N1CCOCC1] | 485.1 |
| 62 | 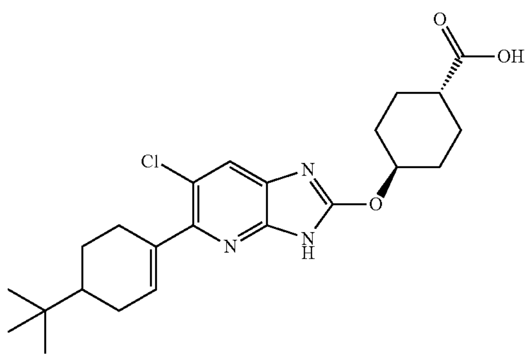 [SMILES: CC(C)(C)C1CC=C(c2nc3[nH]c(O[C@H]4CC[C@H](C(=O)O)CC4)nc3cc2Cl)CC1] | 478.1 |
| 63 | 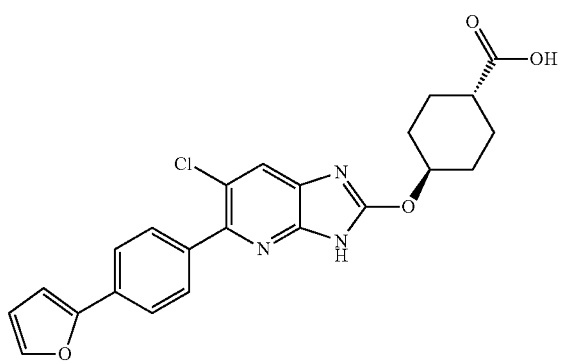 [SMILES: O=C(O)[C@H]1CC[C@H](Oc2nc3cc(Cl)c(-c4ccc(-c5ccco5)cc4)nc3[nH]2)CC1] | 455.1 |
| 64 | 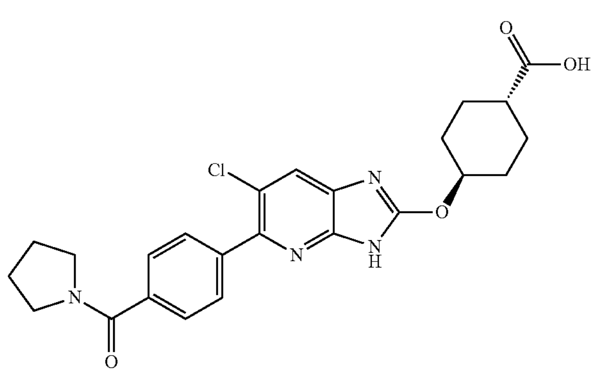 [SMILES: O=C(c1ccc(-c2nc3[nH]c(O[C@H]4CC[C@H](C(=O)O)CC4)nc3cc2Cl)cc1)N1CCCC1] | 486.1 |

TABLE 2-continued

Compounds prepared according to the methods described in Example 29.

| Example Number | Structure | HPLC-mass spectrum m/e |
|---|---|---|
| 65 | 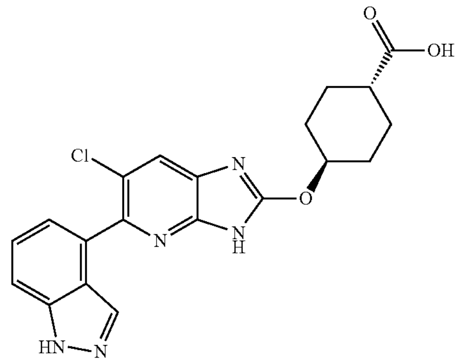 [SMILES: O=C(O)[C@H]1CC[C@H](Oc2nc3cc(Cl)c(-c4cccc5[nH]ncc45)nc3[nH]2)CC1] | 412.1 |
| 66 | 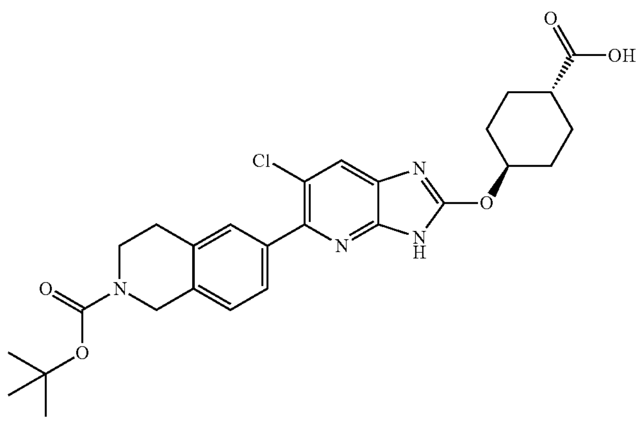 [SMILES: CC(C)(C)OC(=O)N1CCc2cc(-c3nc4[nH]c(O[C@H]5CC[C@H](C(=O)O)CC5)nc4cc3Cl)ccc2C1] | 528.1 |
| 67 | 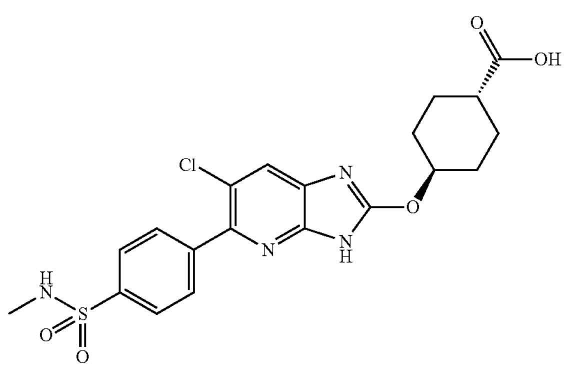 [SMILES: CNS(=O)(=O)c1ccc(-c2nc3[nH]c(O[C@H]4CC[C@H](C(=O)O)CC4)nc3cc2Cl)cc1] | 465.1 |
| 68 | 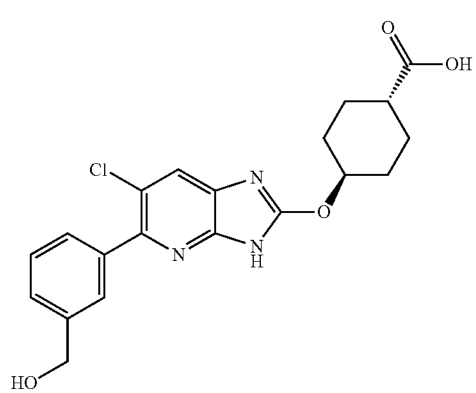 [SMILES: O=C(O)[C@H]1CC[C@H](Oc2nc3cc(Cl)c(-c4cccc(CO)c4)nc3[nH]2)CC1] | 402.1 |

TABLE 2-continued

Compounds prepared according to the methods described in Example 29.

| Example Number | Structure | HPLC-mass spectrum m/e |
|---|---|---|
| 69 | 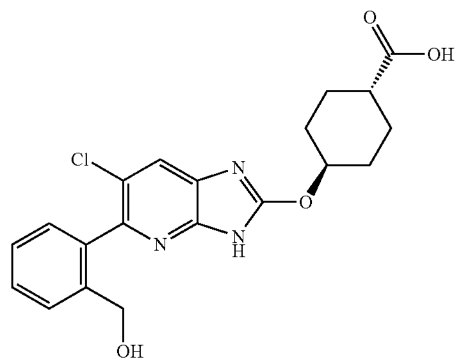 [SMILES: O=C(O)[C@H]1CC[C@H](Oc2nc3cc(Cl)c(-c4ccccc4CO)nc3[nH]2)CC1] | 402.1 |
| 70 | 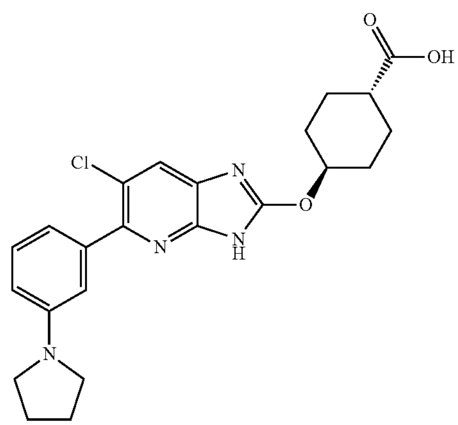 [SMILES: O=C(O)[C@H]1CC[C@H](Oc2nc3cc(Cl)c(-c4cccc(N5CCCC5)c4)nc3[nH]2)CC1] | 441.1 |
| 71 | 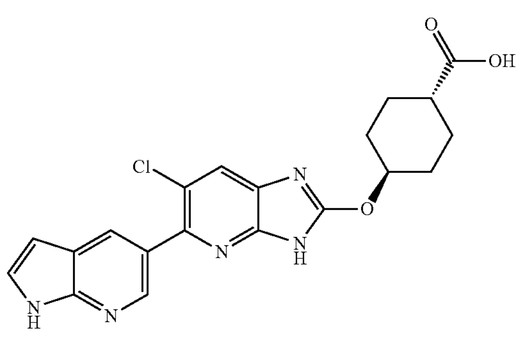 [SMILES: O=C(O)[C@H]1CC[C@H](Oc2nc3cc(Cl)c(-c4cnc5[nH]ccc5c4)nc3[nH]2)CC1] | 412.1 |
| 72 | 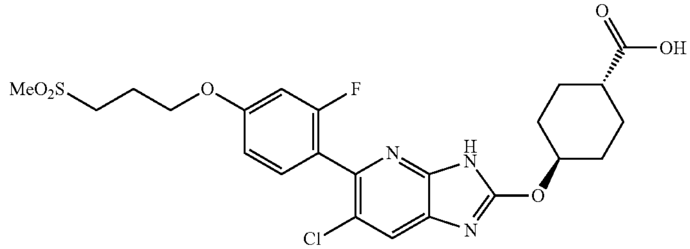 [SMILES: CS(=O)(=O)CCCOc1ccc(-c2nc3[nH]c(O[C@H]4CC[C@H](C(=O)O)CC4)nc3cc2Cl)c(F)c1] | 526.01 |

TABLE 2-continued

Compounds prepared according to the methods described in Example 29.

| Example Number | Structure | HPLC-mass spectrum m/e |
|---|---|---|
| 73 | 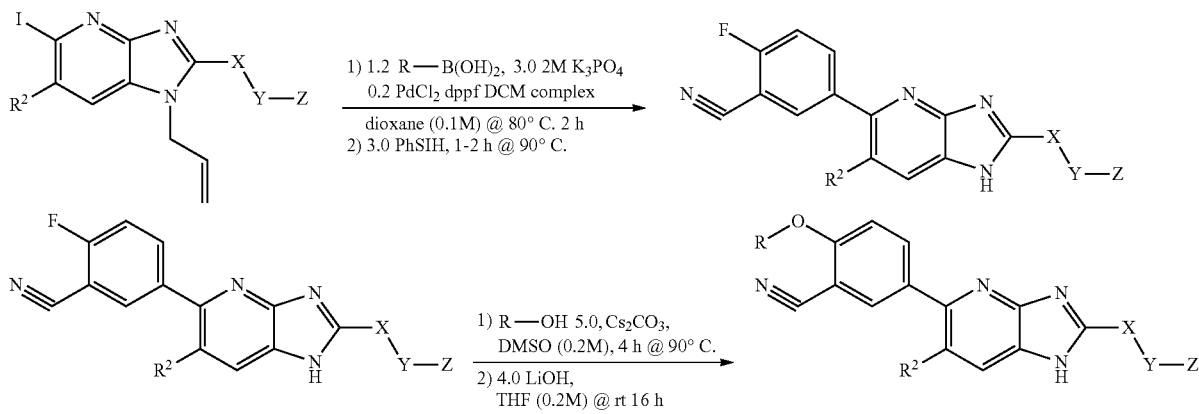 | 464.24 |

SCHEME 3

EXAMPLE 74

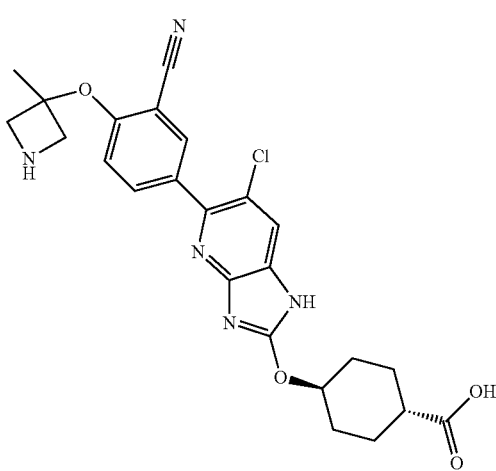 [SMILES: CC1(Oc2ccc(-c3nc4nc(O[C@H]5CC[C@H](C(=O)O)CC5)[nH]c4cc3Cl)cc2C#N)CNC1]

Trans-4-[(6-chloro-5-{3-cyano-4-[(3-ethylazetidin-3-yl)oxy]phenyl}-1H-imidazo[4,5-b]pyridin-2-yl)oxy] cyclohexanecarboxylic acid Step A. Intermediate 4 was dissolved in DMSO (3.7 mL) and cesium carbonate (1996 mg, 6.13 mmol), then 3-cyano-4-fluorophenylboronic acid (674 mg, 4.08 mmol) and 1,1'-bis (diphenylphosphinoferrocene-Palladium (II) dichloride dichloromethane complex (149 mg, 0.204 mmol) were added. The reaction was heated to 80° C. and stirred for 4 h. The reaction was quenched with citric acid (3 mL, 10% w/v). The organic layer was collected, concentrated in vacuo and then purified via flash chromatography (40 g column, 0-50% EtOAc/hexane) to afford ethyl trans-4-{[6-chloro-5-(3-cyano-4-fluorophenyl)-1-(prop-2-en-1-yl)-1H-imidazo[4,5-b]pyridin-2-yl]oxy}cyclohexanecarboxylate as a tan solid.

Step B. To a solution of ethyl trans-4-{[6-chloro-5-(3-cyano-4-fluorophenyl)-1-(prop-2-en-1-yl)-1H-imidazo[4,5-b]pyridin-2-yl]oxy}cyclohexanecarboxylate (980 mg, 2.029 mmol) in DMSO (4 mL) was added 1,1'-bis(diphenylphosphinoferrocene-Palladium (II) dichloride dichloromethane complex (148 mg, 0.203 mmol) followed by phenylsilane (220 mg, 2.029 mmol). The reaction was heated at 90° C. for 1 h. The reaction was then cooled, quenched with citric acid (10% w/v, 5 mL) and then extracted with EtOAc (2×10 mL). The organic layers were collected, dried and then concentrated in vacuo. The residue was purified via flash chromatography (40 g column, 40 mL/min flow, 0-100% EtOAc/hexane to afford ethyl trans-4-{[6-chloro-5-(3-cyano-4-fluorophenyl)-1H-imidazo[4,5-b]pyridin-2-yl]oxy}-cyclohexanecarboxylate as a yellow foam.

Step C. To a solution of ethyl trans-4-{[6-chloro-5-(3-cyano-4-fluorophenyl)-1H-imidazo[4,5-b]pyridin-2-yl]oxy}cyclohexanecarboxylate (30 mg, 0.075 mmol) in DMSO (400 µL) was added cesium carbonate (48.9 mg, 0.150 mmol) and 3-methylazetidin-3-ol (2.55 mg, 0.150 mmol). The reaction was heated to 90° C. over 4 h. The reaction was cooled, then quenched with citric acid, and extracted with EtOAc. LiOH (100 µL, 0.200 mmol) was added and the reaction was stirred overnight. The reaction was then quenched with citric acid (2 mL, 10% w/v) and extracted with EtOAc (2×5 mL). The organic layers were combined and concentrated in vacuo to give a crude residue, which was purified via reverse phase HPLC to afford the title compound as white powder. LC-MS: calculated for $C_{24}H_{24}ClN_5O_4$ 481.2, observed m/e: 482.1 $(M+H)^+$ (Rt 0.8/2 min).

TABLE 3

Compounds prepared according to the methods described in Example 74.

| Example Number | Structure | HPLC-mass spectrum m/e |
|---|---|---|
| 75 | 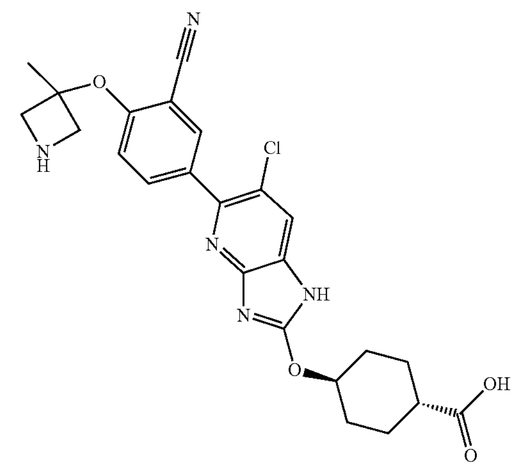 [SMILES: CC1(Oc2ccc(-c3nc4nc(O[C@H]5CC[C@H](C(=O)O)CC5)[nH]c4cc3Cl)cc2C#N)CNC1] | 482.1 |
| 76 | 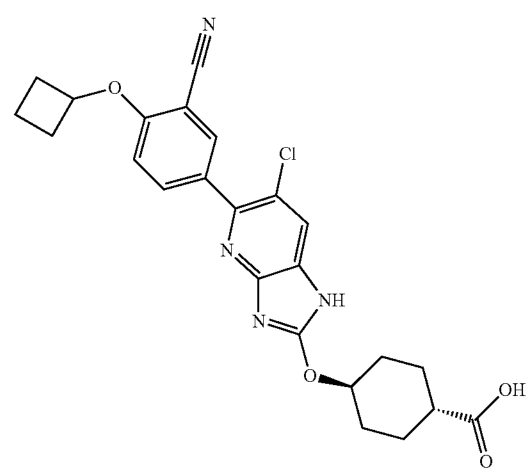 [SMILES: N#Cc1cc(-c2nc3nc(O[C@H]4CC[C@H](C(=O)O)CC4)[nH]c3cc2Cl)ccc1OC1CCC1] | 467.1 |

TABLE 3-continued
Compounds prepared according to the methods described in Example 74.
| Example Number | Structure | HPLC-mass spectrum m/e |
|---|---|---|
| 77 | 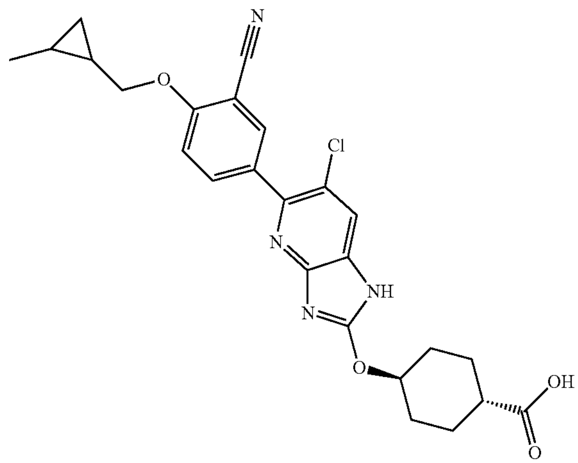 [SMILES: CC1CC1COc1ccc(-c2nc3nc(O[C@H]4CC[C@H](C(=O)O)CC4)[nH]c3cc2Cl)cc1C#N] | 481.1 |
| 78 | 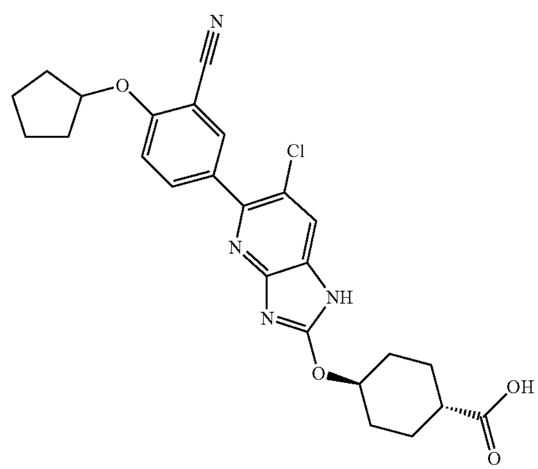 [SMILES: N#Cc1cc(-c2nc3nc(O[C@H]4CC[C@H](C(=O)O)CC4)[nH]c3cc2Cl)ccc1OC1CCCC1] | 481.1 |
SCHEME 4
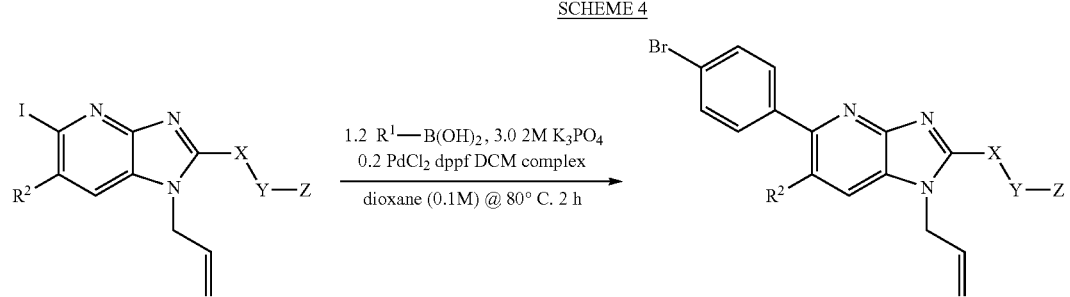

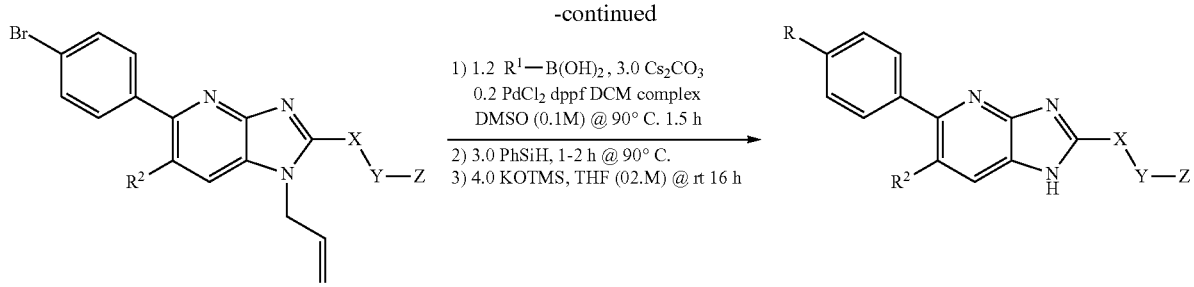

EXAMPLE 79

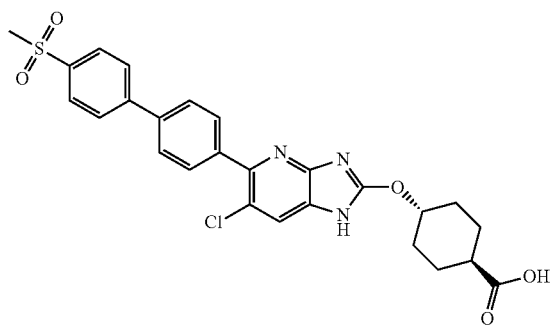 [SMILES: CS(=O)(=O)c1ccc(-c2ccc(-c3nc4nc(O[C@H]5CC[C@H](C(=O)O)CC5)[nH]c4cc3Cl)cc2)cc1]

Trans-4-({6-chloro-5-[4'-(methylsulfonyl)biphenyl-4-yl]-1H-imidazo[4,5-b]pyridin-2-yl}oxy)cyclohexanecarboxylic acid Step A. 1,1'-bis(diphenylphosphinoferrocene-Palladium (II) dichloride dichloromethane complex (260 mg, 0.32 mmol) was added to a dioxane (6 mL) solution of Intermediate 5 (550 mg, 1.06 mmol), 4-(methylsulfonyl)phenylboronic acid (233 mg, 1.17 mmol) and 2 M potassium phosphate tribasic (1.59 mL, 3.18 mmol) at rt under nitrogen atmosphere. The reaction was heated to 80° C. for 4 h. Then phenylsilane (688 mg, 6.36 mmol) was added and reaction was stirred at 80° C. for 1 h. After cooling to rt, the reaction was diluted with EtOAc (200 mL) and poured into 10% aqueous citric acid (200 mL). The organic layer was separated, washed with water and brine, dried over magnesium sulfate and concentrated. Flash chromatography of the resulting residue utilizing a Biotage™ 50G SNAP cartridge and eluting with 0-100% EtOAc/hexane afforded ethyl trans-4-({6-chloro-5-[4'-(methylsulfonyl)-biphenyl-4-yl]-1H imidazo[4,5-b]pyridin-2-yl}oxy)cyclohexanecarboxylate as a pale yellow oil. LC-MS: calculated for $C_{28}H_{28}ClN_3O_5S$ 554.05, observed m/e: 555.04 (M+H)+ (Rt 2.2/4 min).

Step B. Potassium trimethylsilanolate (278 mg, 2.16 mmol) was added to a tetrahydrofuran (3 mL) solution of ethyl trans-4-({6-chloro-5-[4'-(methylsulfonyl)biphenyl-4-yl]-1H imidazo[4,5-b]pyridin-2-yl}oxy)cyclohexanecarboxylate (240 mg, 0.43 mmol), and the mixture was stirred at rt for 16 h. The reaction mixture was partitioned between EtOAc and 10% aqueous citric acid. The organic layer was separated, washed with brine, dried over magnesium sulfate and concentrated. Trituration of the resulting crude product with acetonitrile (10 mL) provided the title compound as an off-white solid. LC-MS: calculated for $C_{26}H_{24}ClN_3O_5S$ 526.0, observed m/e: 526.3 (M+H)+ (Rt 0.8/2 min). $^1$H NMR δ (ppm) (DMSO-$d_6$): 8.03-7.99 (5 H, m), 7.86 (2 H, d, J=8.16 Hz), 7.79 (2 H, d, J=8.12 Hz), 5.01-4.97 (1 H, m), 2.30 (1 H, m), 2.24 (3 H, d, J=10.17 Hz), 2.00 (3 H, m), 1.58-1.49 (4 H, m).

TABLE 4

Compounds prepared according to the methods described in Example 79.

| Example Number | Structure | HPLC-mass spectrum m/e |
|---|---|---|
| 80 | 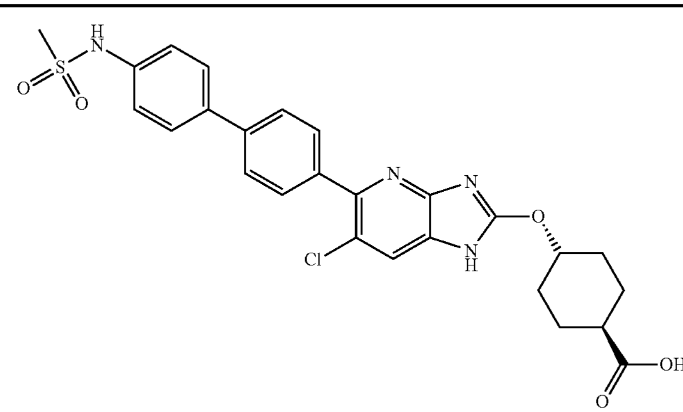 | 541.1 |

TABLE 4-continued

Compounds prepared according to the methods described in Example 79.

| Example Number | Structure | HPLC-mass spectrum m/e |
|---|---|---|
| 81 | 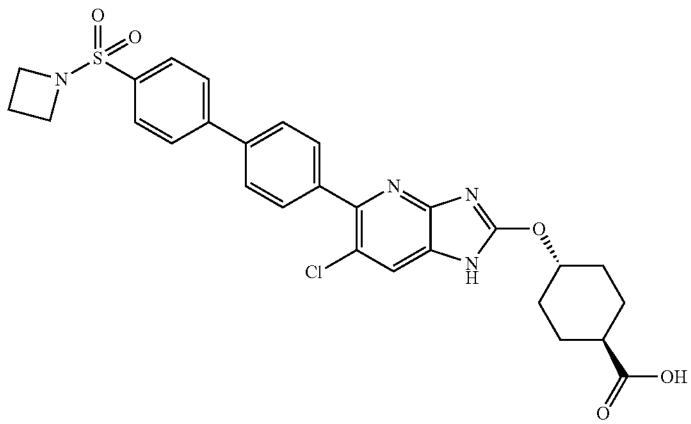 [SMILES: O=C(O)[C@H]1CC[C@H](Oc2nc3nc(-c4ccc(-c5ccc(S(=O)(=O)N6CCC6)cc5)cc4)c(Cl)cc3[nH]2)CC1] | 567.3 |
| 82 | 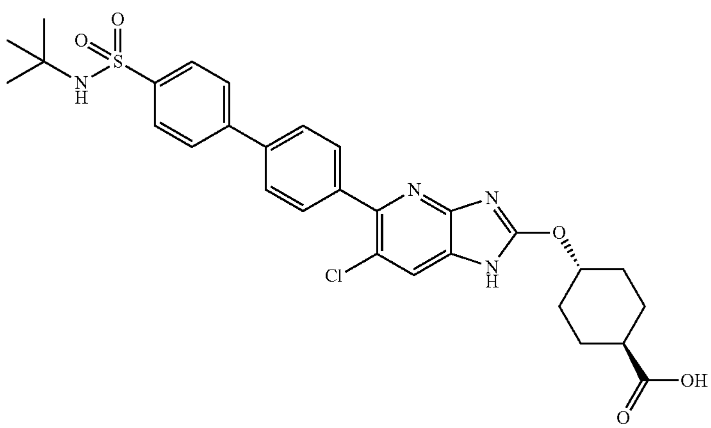 [SMILES: CC(C)(C)NS(=O)(=O)c1ccc(-c2ccc(-c3nc4nc(O[C@H]5CC[C@H](C(=O)O)CC5)[nH]c4cc3Cl)cc2)cc1] | 583.4 |
| 83 | 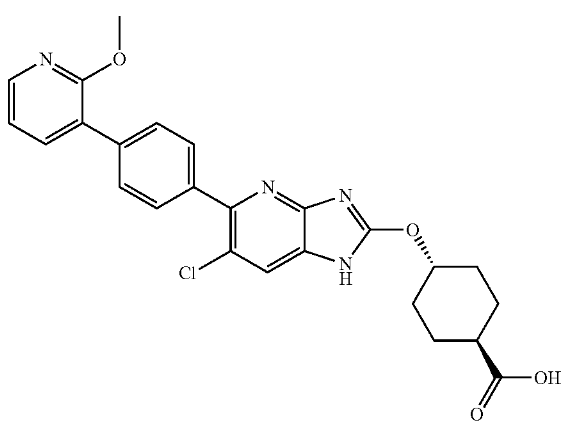 [SMILES: COc1ncccc1-c1ccc(-c2nc3nc(O[C@H]4CC[C@H](C(=O)O)CC4)[nH]c3cc2Cl)cc1] | 479.3 |

TABLE 4-continued

Compounds prepared according to the methods described in Example 79.

| Example Number | Structure | HPLC-mass spectrum m/e |
|---|---|---|
| 84 | 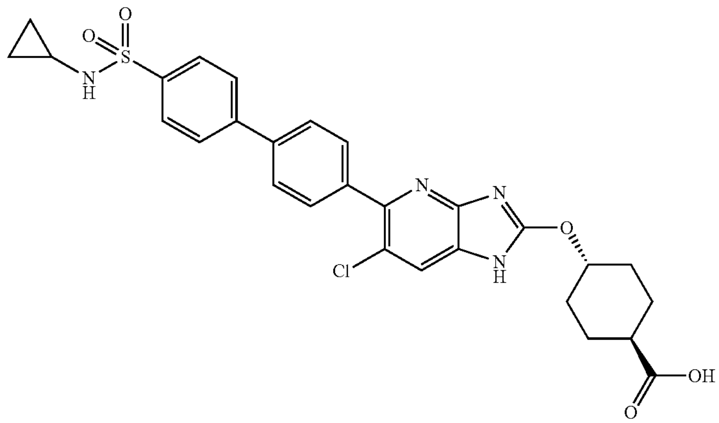 [SMILES: O=C(O)[C@H]1CC[C@H](Oc2nc3nc(-c4ccc(-c5ccc(S(=O)(=O)NC6CC6)cc5)cc4)c(Cl)cc3[nH]2)CC1] | 567.8 |
| 85 | 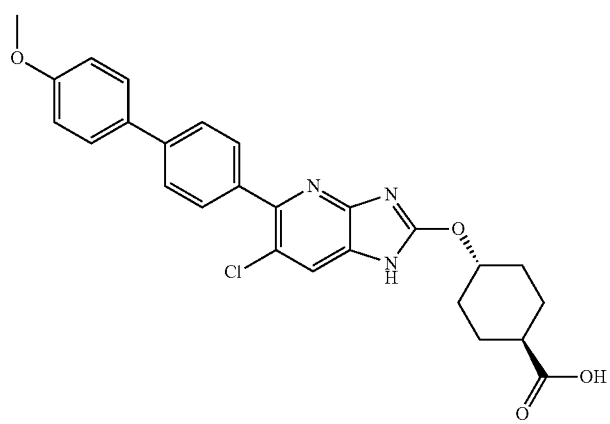 [SMILES: COc1ccc(-c2ccc(-c3nc4nc(O[C@H]5CC[C@H](C(=O)O)CC5)[nH]c4cc3Cl)cc2)cc1] | 478.3 |
| 86 | 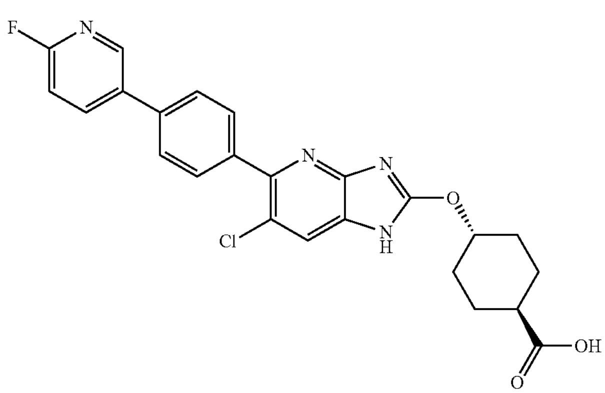 [SMILES: O=C(O)[C@H]1CC[C@H](Oc2nc3nc(-c4ccc(-c5ccc(F)nc5)cc4)c(Cl)cc3[nH]2)CC1] | 467.3 |

TABLE 4-continued

Compounds prepared according to the methods described in Example 79.

| Example Number | Structure | HPLC-mass spectrum m/e |
|---|---|---|
| 87 | 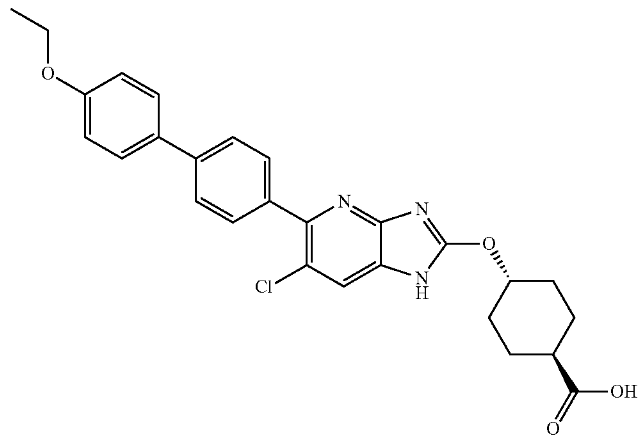 [SMILES: CCOc1ccc(-c2ccc(-c3nc4nc(O[C@H]5CC[C@H](C(=O)O)CC5)[nH]c4cc3Cl)cc2)cc1] | 492.3 |
| 88 | 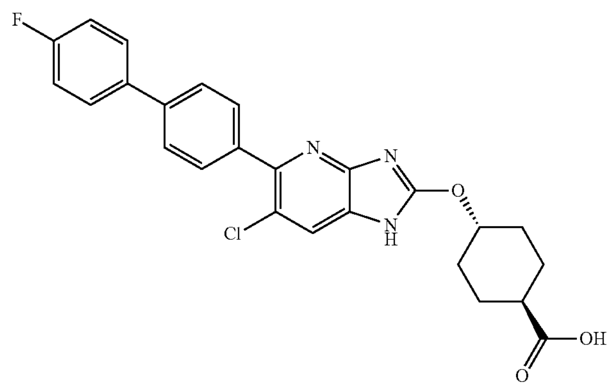 [SMILES: O=C(O)[C@H]1CC[C@H](Oc2nc3nc(-c4ccc(-c5ccc(F)cc5)cc4)c(Cl)cc3[nH]2)CC1] | 466.3 |
| 89 | 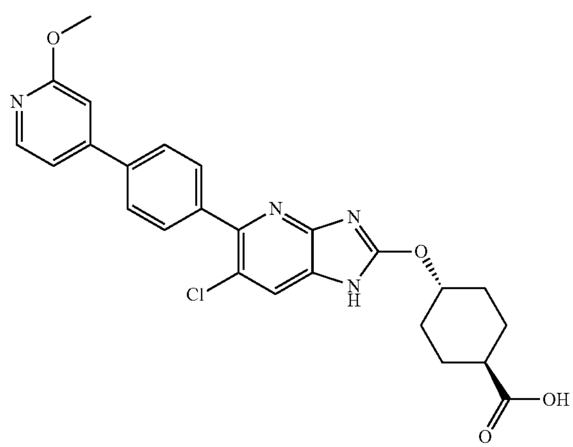 [SMILES: COc1cc(-c2ccc(-c3nc4nc(O[C@H]5CC[C@H](C(=O)O)CC5)[nH]c4cc3Cl)cc2)ccn1] | 479.3 |

TABLE 4-continued

Compounds prepared according to the methods described in Example 79.

| Example Number | Structure | HPLC-mass spectrum m/e |
|---|---|---|
| 90 | 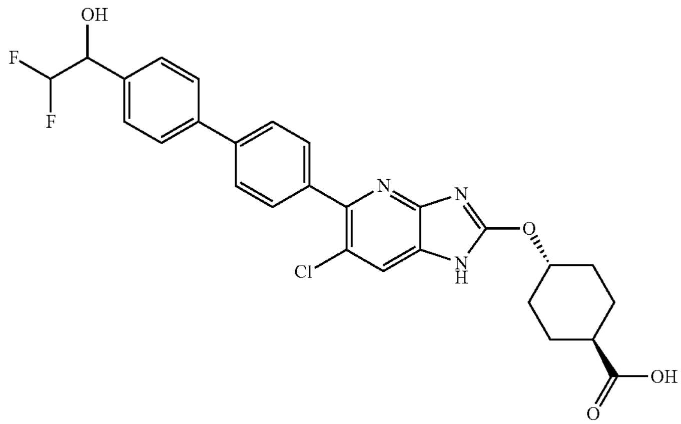 [SMILES: O=C(O)[C@H]1CC[C@H](Oc2nc3nc(-c4ccc(-c5ccc(C(O)C(F)F)cc5)cc4)c(Cl)cc3[nH]2)CC1] | 527.1 |
| 91 | 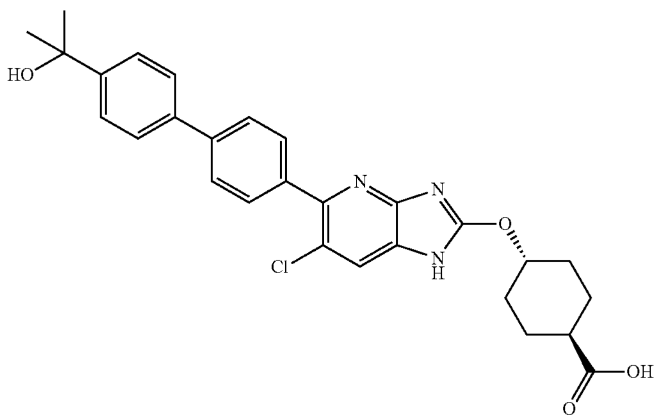 [SMILES: CC(C)(O)c1ccc(-c2ccc(-c3nc4nc(O[C@H]5CC[C@H](C(=O)O)CC5)[nH]c4cc3Cl)cc2)cc1] | 506.3 |
| 92 | 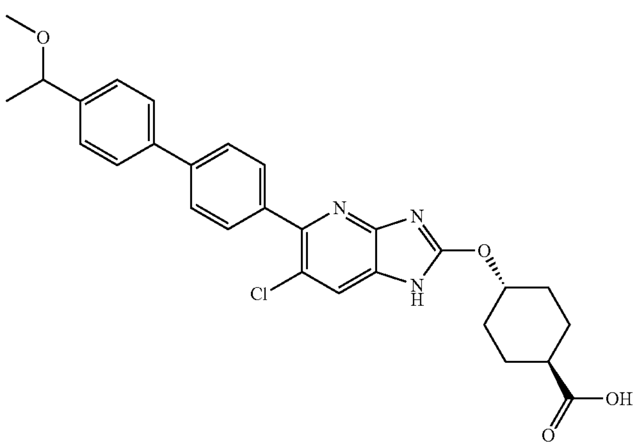 [SMILES: COC(C)c1ccc(-c2ccc(-c3nc4nc(O[C@H]5CC[C@H](C(=O)O)CC5)[nH]c4cc3Cl)cc2)cc1] | 506.4 |

TABLE 4-continued

Compounds prepared according to the methods described in Example 79.

| Example Number | Structure | HPLC-mass spectrum m/e |
|---|---|---|
| 93 | 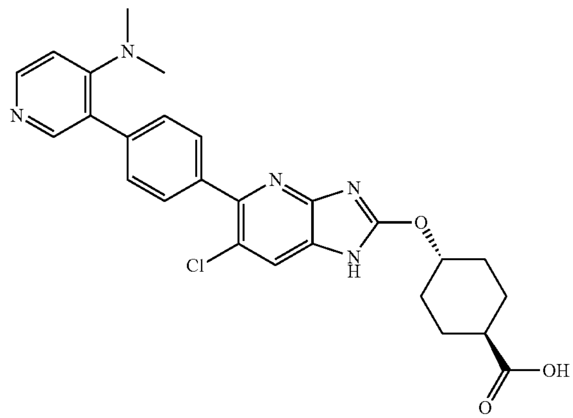 [SMILES: CN(C)c1ccncc1-c1ccc(-c2nc3nc(O[C@H]4CC[C@H](C(=O)O)CC4)[nH]c3cc2Cl)cc1] | 492.3 |
| 94 | 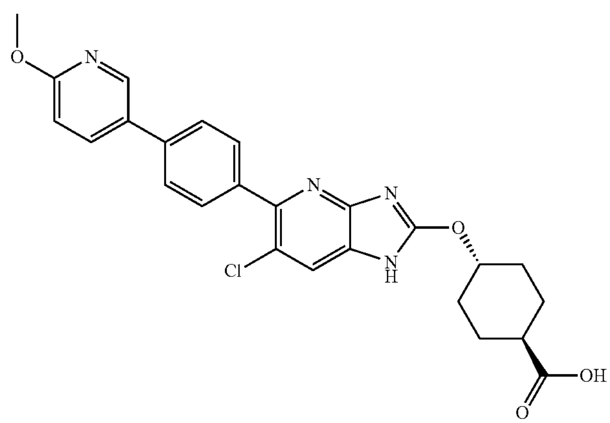 [SMILES: COc1ccc(-c2ccc(-c3nc4nc(O[C@H]5CC[C@H](C(=O)O)CC5)[nH]c4cc3Cl)cc2)cn1] | 479.3 |
| 95 | 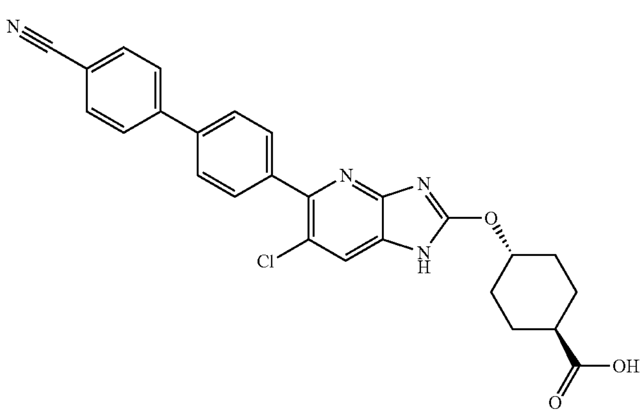 [SMILES: N#Cc1ccc(-c2ccc(-c3nc4nc(O[C@H]5CC[C@H](C(=O)O)CC5)[nH]c4cc3Cl)cc2)cc1] | 473.3 |

TABLE 4-continued

Compounds prepared according to the methods described in Example 79.

| Example Number | Structure | HPLC-mass spectrum m/e |
|---|---|---|
| 96 | 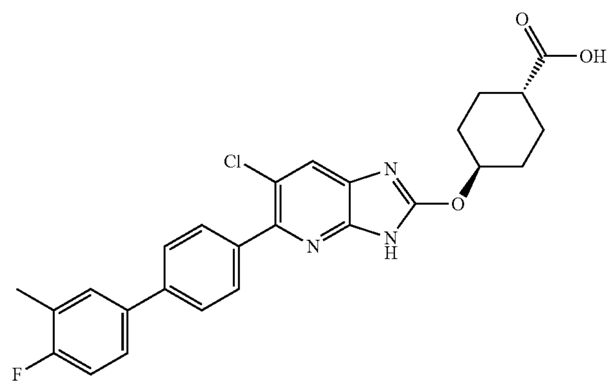 [SMILES: Cc1cc(-c2ccc(-c3nc4[nH]c(O[C@H]5CC[C@H](C(=O)O)CC5)nc4cc3Cl)cc2)ccc1F] | 480.3 |
| 97 | 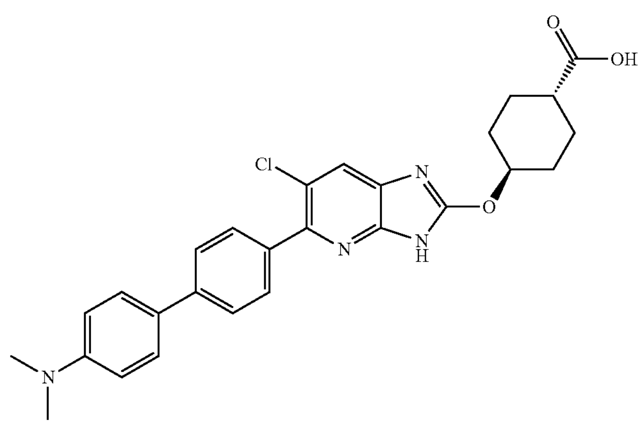 [SMILES: CN(C)c1ccc(-c2ccc(-c3nc4[nH]c(O[C@H]5CC[C@H](C(=O)O)CC5)nc4cc3Cl)cc2)cc1] | 491.4 |
| 98 | 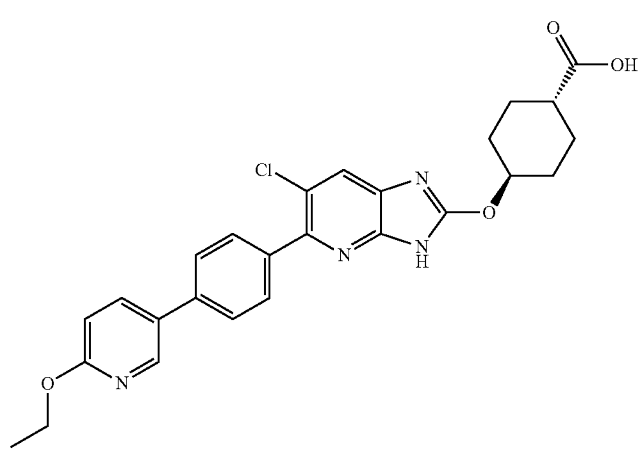 [SMILES: CCOc1ccc(-c2ccc(-c3nc4[nH]c(O[C@H]5CC[C@H](C(=O)O)CC5)nc4cc3Cl)cc2)cn1] | 493.3 |

TABLE 4-continued

Compounds prepared according to the methods described in Example 79.

| Example Number | Structure | HPLC-mass spectrum m/e |
|---|---|---|
| 99 | 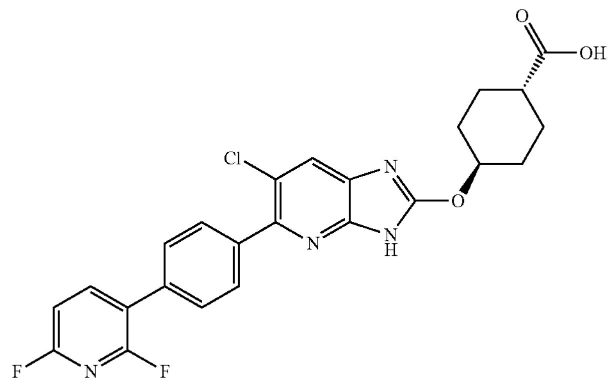 [SMILES: O=C(O)[C@H]1CC[C@H](Oc2nc3cc(Cl)c(-c4ccc(-c5ccc(F)nc5F)cc4)nc3[nH]2)CC1] | 485.3 |
| 100 | 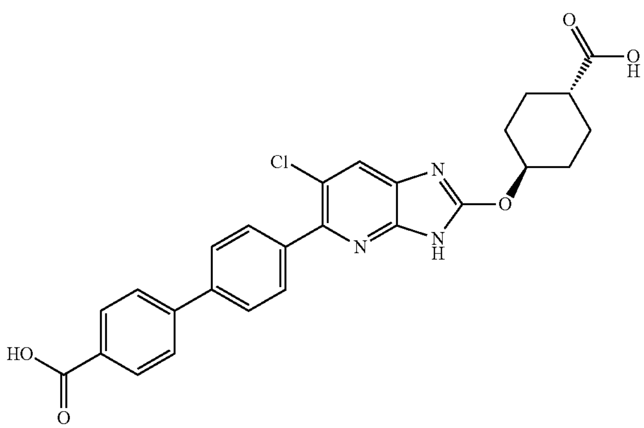 [SMILES: O=C(O)c1ccc(-c2ccc(-c3nc4[nH]c(O[C@H]5CC[C@H](C(=O)O)CC5)nc4cc3Cl)cc2)cc1] | 492.3 |
| 101 | 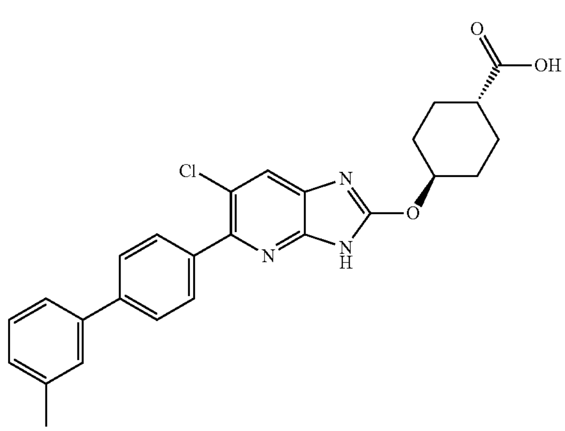 [SMILES: Cc1cccc(-c2ccc(-c3nc4[nH]c(O[C@H]5CC[C@H](C(=O)O)CC5)nc4cc3Cl)cc2)c1] | 462.3 |

TABLE 4-continued

Compounds prepared according to the methods described in Example 79.

| Example Number | Structure | HPLC-mass spectrum m/e |
|---|---|---|
| 102 | 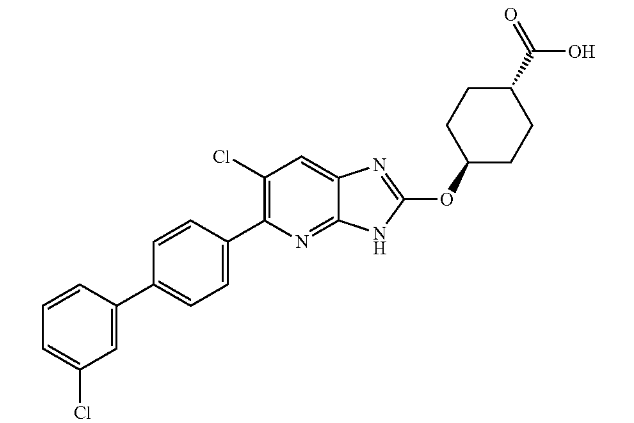 [SMILES: O=C(O)[C@H]1CC[C@H](Oc2nc3cc(Cl)c(-c4ccc(-c5cccc(Cl)c5)cc4)nc3[nH]2)CC1] | 483.4 |
| 103 | 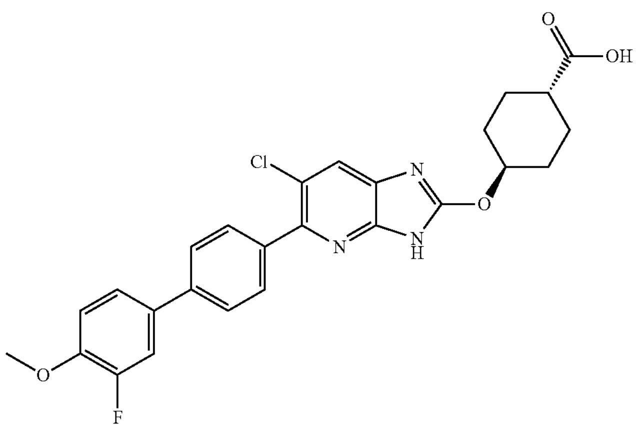 [SMILES: COc1ccc(-c2ccc(-c3nc4[nH]c(O[C@H]5CC[C@H](C(=O)O)CC5)nc4cc3Cl)cc2)cc1F] | 496.1 |
| 104 | 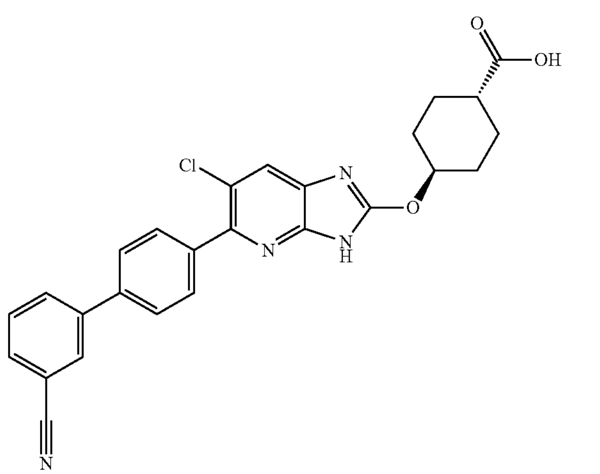 [SMILES: N#Cc1cccc(-c2ccc(-c3nc4[nH]c(O[C@H]5CC[C@H](C(=O)O)CC5)nc4cc3Cl)cc2)c1] | 473.3 |

TABLE 4-continued
Compounds prepared according to the methods described in Example 79.
| Example Number | Structure | HPLC-mass spectrum m/e |
|---|---|---|
| 105 | 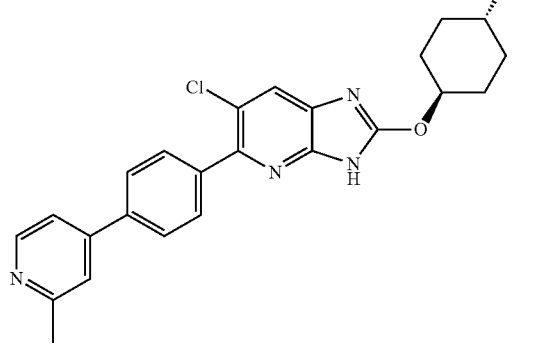 | 463.3 |
| 106 | 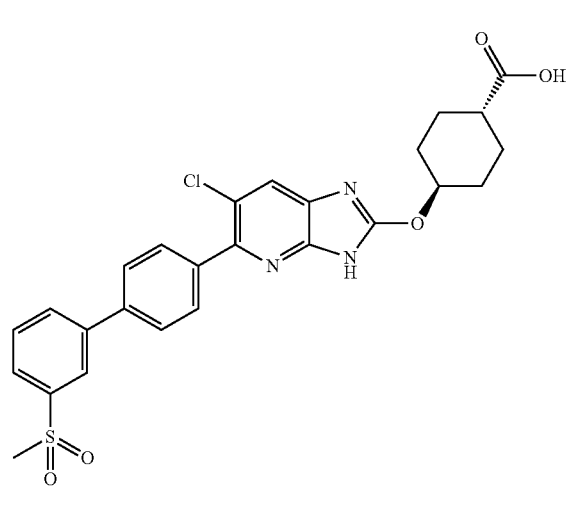 [SMILES: CS(=O)(=O)c1cccc(-c2ccc(-c3nc4[nH]c(O[C@H]5CC[C@H](C(=O)O)CC5)nc4cc3Cl)cc2)c1] | 527.3 |
| 107 | 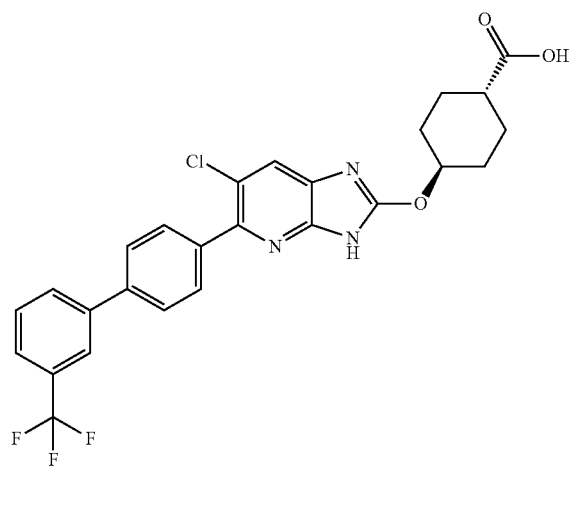 [SMILES: O=C(O)[C@H]1CC[C@H](Oc2nc3cc(Cl)c(-c4ccc(-c5cccc(C(F)(F)F)c5)cc4)nc3[nH]2)CC1] | 516.3 |

TABLE 4-continued
Compounds prepared according to the methods described in Example 79.
| Example Number | Structure | HPLC-mass spectrum m/e |
|---|---|---|
| 108 | 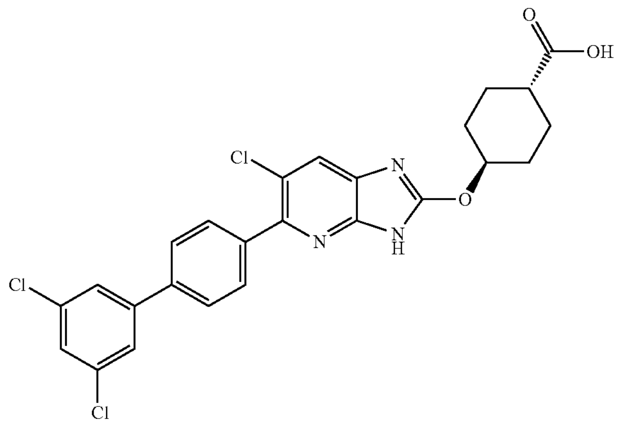 [SMILES: O=C(O)[C@H]1CC[C@H](Oc2nc3cc(Cl)c(-c4ccc(-c5cc(Cl)cc(Cl)c5)cc4)nc3[nH]2)CC1] | 517.1 |
| 109 | 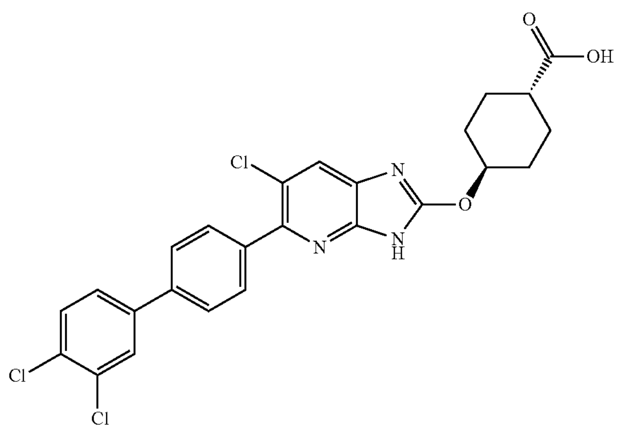 [SMILES: O=C(O)[C@H]1CC[C@H](Oc2nc3cc(Cl)c(-c4ccc(-c5ccc(Cl)c(Cl)c5)cc4)nc3[nH]2)CC1] | 517.1 |
| 110 | 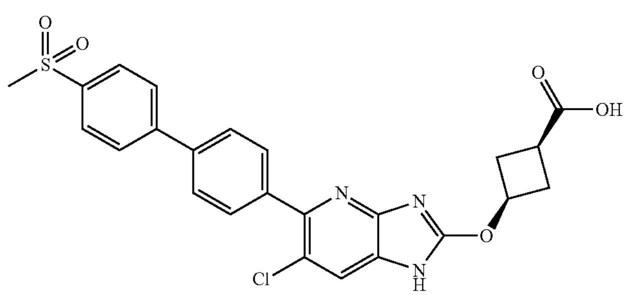 [SMILES: CS(=O)(=O)c1ccc(-c2ccc(-c3nc4nc(O[C@H]5C[C@@H](C(=O)O)C5)[nH]c4cc3Cl)cc2)cc1] | 498.1 |
SCHEME 5
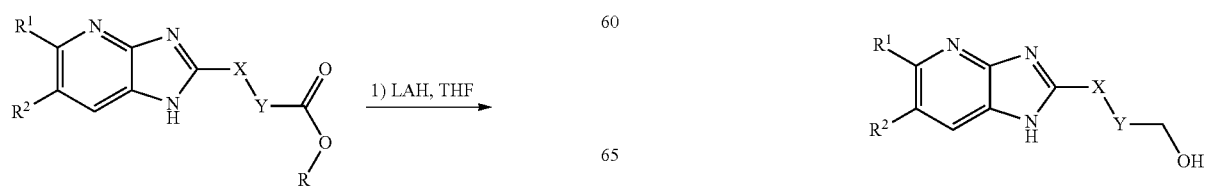

EXAMPLE 111

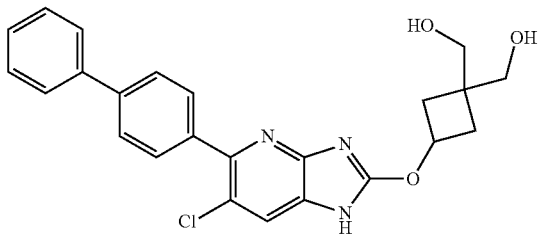 [SMILES: OCC1(CO)CC(Oc2nc3nc(-c4ccc(-c5ccccc5)cc4)c(Cl)cc3[nH]2)C1]

(3-{5-(biphenyl-4-yl)-6-chloro-1H-imidazo[4,5-b]pyridin-2-yl]oxy}cyclobutane-1,1-diyl)dimethanol To a stirred solution of diethyl 2,2'-(3-{[5-(biphenyl-4-yl)-6-chloro-1H-imidazo[4,5-b]pyridin-2-yl]oxy}cyclobutane-1,1-diyl)diacetate (ester precursor to example 73, 590 mg, 1.14 mmol) in anhydrous THF (13.0 mL) under nitrogen at ambient temperature was added lithium aluminum hydride (215 mg, 5.67 mmol) in one portion. The mixture exhibited an exotherm and was allowed to stir at ambient temperature for 45 minutes. The mixture was diluted with anhydrous THF (20 mL) and cooled to 5° C. Saturated aqueous ammonium chloride was added dropwise until gas evolution ceased. The mixture was then diluted with a saturated aqueous solution of Rochelle's salt (50 mL) and stirred for 2 hours. The mixture was extracted with ethyl acetate (3×150 mL). The organic layers were combined and washed with a saturated aqueous solution of Rochelle's salt (3×70 mL) and brine (100 mL). The organic layer was filtered through a thin pad of Celite™ and concentrated under reduced pressure. The resultant white solid was dried under high vacuum at 50° C. for 1 hour to provide the title compound. LC-MS: calculated for $C_{24}H_{22}ClN_3O_3$ 435.13, observed m/e: 436.19 (M+H)$^+$ (Rt 2.0/4.0 min). $^1$H NMR δ (ppm) (DMSO-d$_6$): 7.90 (1H, s), 7.77-7.72 (6H, m), 7.49 (2H, t, J=7.6 Hz), 7.39 (1H, 6, J=7.2 Hz), 5.27 (1H, t, 7.1Hz), 4.74 (1H, t, 5.4 Hz), 4.67 (1H, t, 5.5 Hz), 3.41 (2H, d, 5.3 Hz), 3.34 (2H, d, 5.3 Hz), 2.30 (2H, m), 2.07 (2H, m).

TABLE 5

Compounds prepared according to the methods in Example 111.

| Example Number | Structure | HPLC-mass spectrum m/e |
|---|---|---|
| 112 | 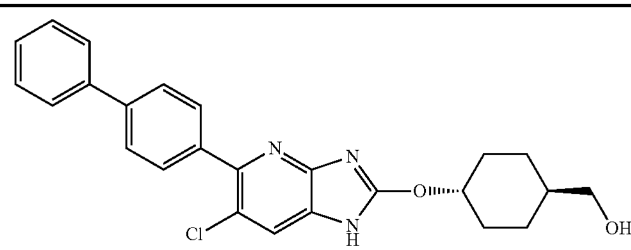 | 434.16 |
| 113 | 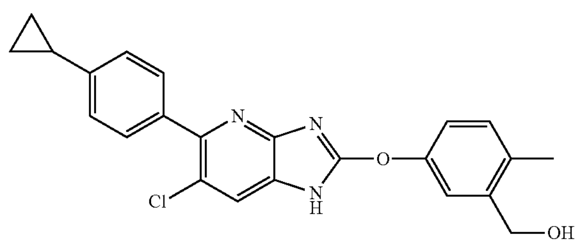 [SMILES: Cc1ccc(Oc2nc3nc(-c4ccc(C5CC5)cc4)c(Cl)cc3[nH]2)cc1CO] | 406.19 |
| 114 | 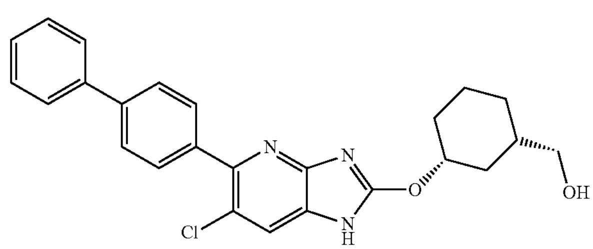 | 434.30 |
| 115 | 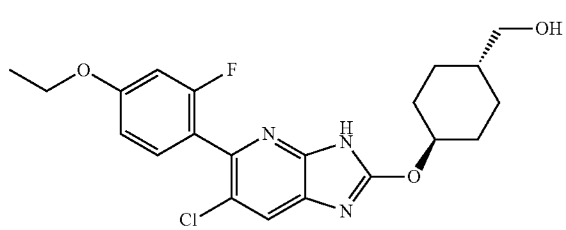 [SMILES: CCOc1ccc(-c2nc3[nH]c(O[C@H]4CC[C@H](CO)CC4)nc3cc2Cl)c(F)c1] | 420.18 |

TABLE 5-continued

Compounds prepared according to the methods in Example 111.

| Example Number | Structure | HPLC-mass spectrum m/e |
|---|---|---|
| 116 | 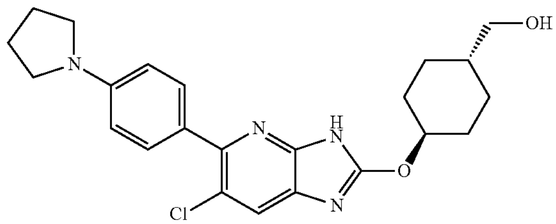 [SMILES: OC[C@H]1CC[C@H](Oc2nc3cc(Cl)c(-c4ccc(N5CCCC5)cc4)nc3[nH]2)CC1] | 427.23 |
| 117 | 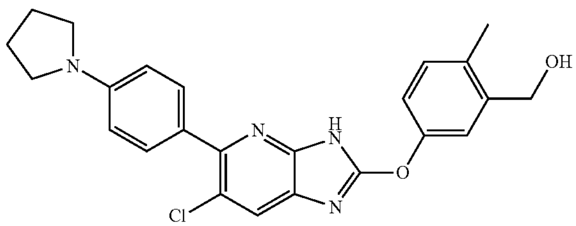 [SMILES: Cc1ccc(Oc2nc3cc(Cl)c(-c4ccc(N5CCCC5)cc4)nc3[nH]2)cc1CO] | 435.22 |
| 118 | 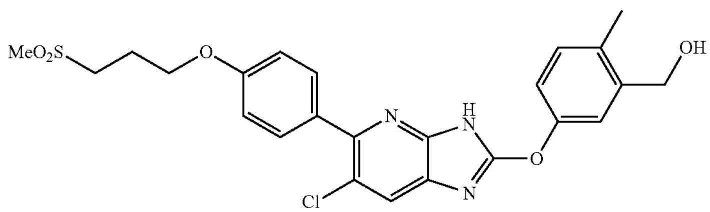 [SMILES: Cc1ccc(Oc2nc3cc(Cl)c(-c4ccc(OCCCS(C)(=O)=O)cc4)nc3[nH]2)cc1CO] | 520.10 |
| 119 | 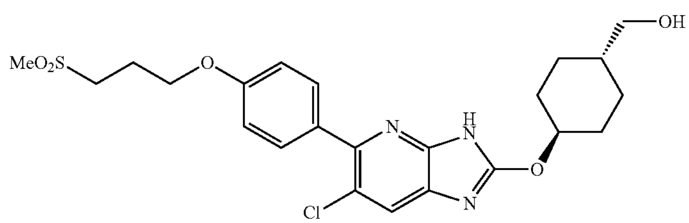 [SMILES: CS(=O)(=O)CCCOc1ccc(-c2nc3[nH]c(O[C@H]4CC[C@H](CO)CC4)nc3cc2Cl)cc1] | 512.14 |
| 120 | 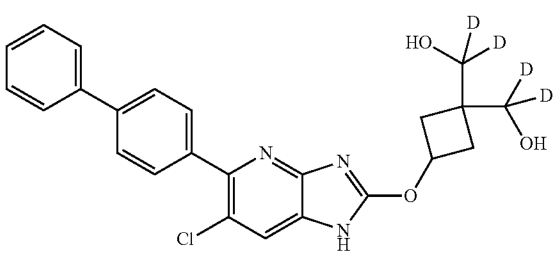 [SMILES: [2H]C([2H])(O)C1(C([2H])([2H])O)CC(Oc2nc3nc(-c4ccc(-c5ccccc5)cc4)c(Cl)cc3[nH]2)C1] | 440.25 |
| 121 | 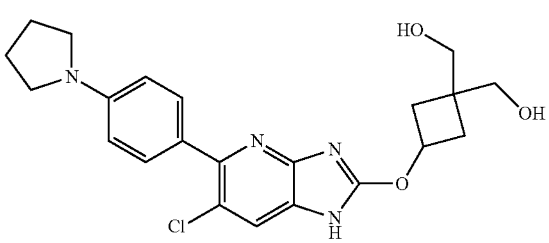 [SMILES: OCC1(CO)CC(Oc2nc3nc(-c4ccc(N5CCCC5)cc4)c(Cl)cc3[nH]2)C1] | 429.27 |

TABLE 5-continued

Compounds prepared according to the methods in Example 111.

| Example Number | Structure | HPLC-mass spectrum m/e |
|---|---|---|
| 122 | 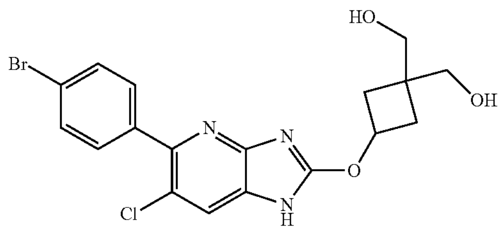 [SMILES: OCC1(CO)CC(Oc2nc3nc(-c4ccc(Br)cc4)c(Cl)cc3[nH]2)C1] | 440.11 |
| 123 | 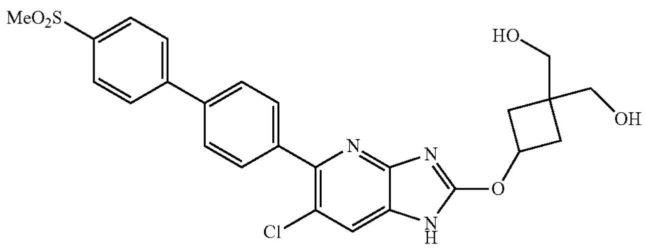 [SMILES: CS(=O)(=O)c1ccc(-c2ccc(-c3nc4nc(OC5CC(CO)(CO)C5)[nH]c4cc3Cl)cc2)cc1] | 514.27 |
| 124 | 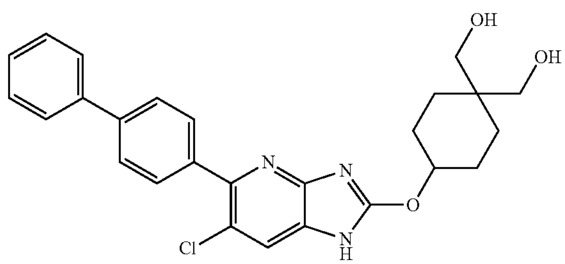 [SMILES: OCC1(CO)CCC(Oc2nc3nc(-c4ccc(-c5ccccc5)cc4)c(Cl)cc3[nH]2)CC1] | 464.07 |
| 125 | 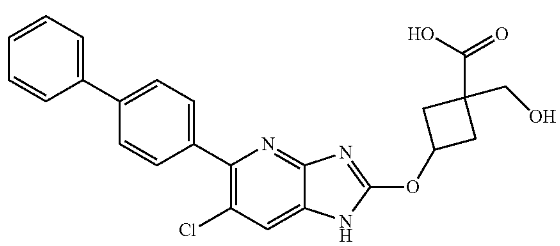 [SMILES: O=C(O)C1(CO)CC(Oc2nc3nc(-c4ccc(-c5ccccc5)cc4)c(Cl)cc3[nH]2)C1] | 450.30 |
| 126 | 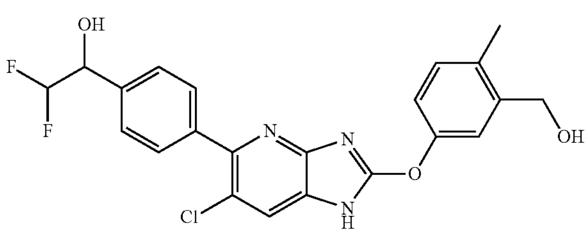 [SMILES: Cc1ccc(Oc2nc3nc(-c4ccc(C(O)C(F)F)cc4)c(Cl)cc3[nH]2)cc1CO] | 446.08 |
| 127 | 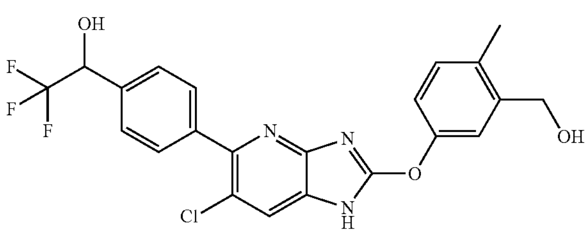 [SMILES: Cc1ccc(Oc2nc3nc(-c4ccc(C(O)C(F)(F)F)cc4)c(Cl)cc3[nH]2)cc1CO] | 464.06 |

TABLE 5-continued

Compounds prepared according to the methods in Example 111.

| Example Number | Structure | HPLC-mass spectrum m/e |
|---|---|---|
| 128 | 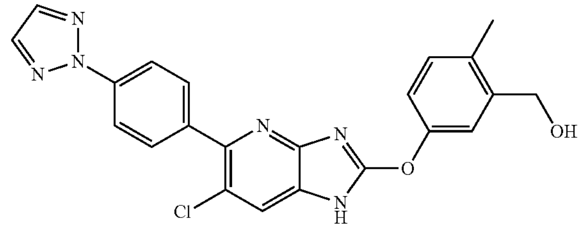 [SMILES: Cc1ccc(Oc2nc3nc(-c4ccc(-n5nccn5)cc4)c(Cl)cc3[nH]2)cc1CO] | 433.26 |
| 129 | 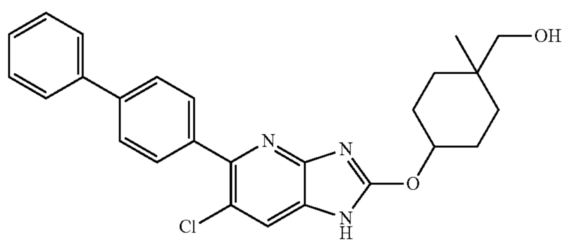 [SMILES: CC1(CO)CCC(Oc2nc3nc(-c4ccc(-c5ccccc5)cc4)c(Cl)cc3[nH]2)CC1] | 448.35 |

SCHEME 6

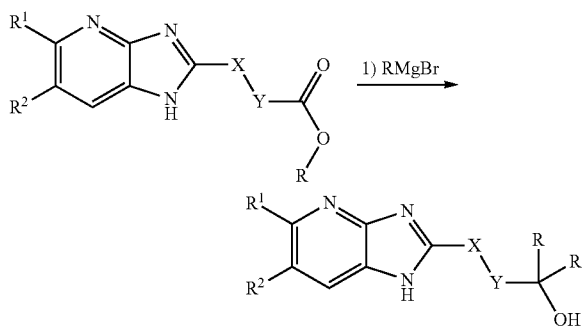

EXAMPLE 130

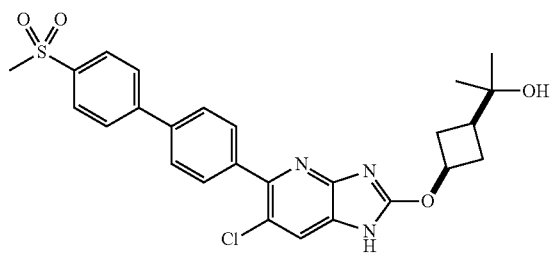

2-[cis-3-({6-chloro-5-[4'-(methylsulfonyl)biphenyl-4-yl]-1H-imidazo[4,5-b]pyridin-2-yl}oxy)cyclobutyl]propan-2-ol. To a solution of ethyl cis-3-({6-chloro-5-[4'-(methylsulfonyl)-biphenyl-4-yl]-1H-imidazo[4,5-b]pyridin-2-yl}oxy)cyclobutanecarboxylate (precursor to example 110, 19 mg, 0.036 mmol) in 0.5 mL anhydrous THF at 0° C. was added 100 μL of MeMgBr solution (3.0 M in THF, 0.3 mmol). The resulting clear solution was stirred at 0° C. for 46 min, and then quenched by the addition of saturated aqueous ammonium chloride solution. The mixture was then partitioned between EtOAc and water. The aqueous portion was back-extracted once with EtOAc. The combined organic extracts were further washed once with saturated aqueous ammonium chloride solution, once with brine, dried over $Na_2SO_4$, filtered, and concentrated. The resulting crude material was chromatographed on a Biotage™ 10 g SNAP cartridge, with a linear gradient of 0-20% of EtOAc in hexanes. The desired fractions were combined to provide the desired product as a white foam. LC-MS: calculated for C26H26ClN3O4S=511.13, observed m/e: 512.2 (M+H)+ (Rt 1.97/4 min). $^1$H NMR (500 MHz, CDCl$_3$): δ 11.21 (s, 1 H), 8.04 (d, J=8.0 Hz, 2 H); 7.92 (s, 1 H); 7.87-7.80 (m, 4 H); 7.71 (d, J=7.9 Hz, 2 H); 5.20 (s, 1 H); 3.12 (s, 3 H); 2.46 (s, 2 H); 2.11 (s, 2 H); 1.94 (m, 1 H); 1.11 (s, 6 H).

TABLE 6

Compounds prepared according to the methods in Example 130.

| Example Number | Structure | HPLC-mass spectrum m/e |
|---|---|---|
| 131 | 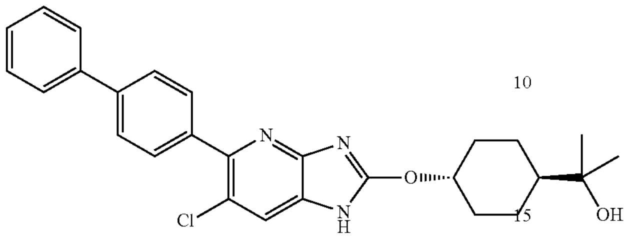 [SMILES: CC(C)(O)[C@H]1CC[C@H](Oc2nc3nc(-c4ccc(-c5ccccc5)cc4)c(Cl)cc3[nH]2)CC1] | 462.21 |
| 132 | 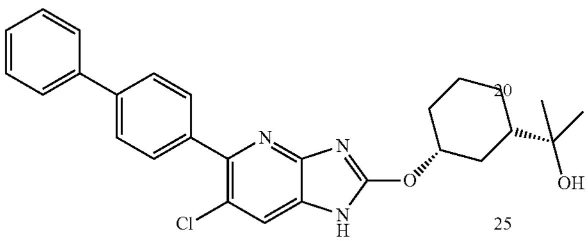 | 462.32 |
| 133 | 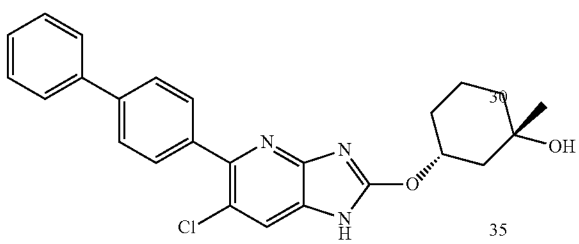 [SMILES: C[C@]1(O)CCC[C@@H](Oc2nc3nc(-c4ccc(-c5ccccc5)cc4)c(Cl)cc3[nH]2)C1] | 434.31 |
| 134 | 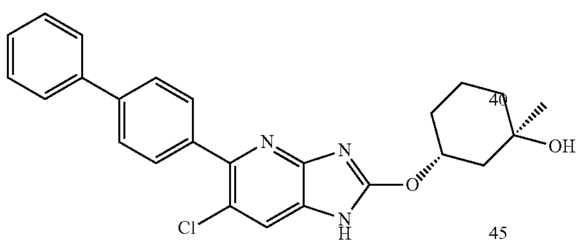 [SMILES: C[C@@]1(O)CCC[C@@H](Oc2nc3nc(-c4ccc(-c5ccccc5)cc4)c(Cl)cc3[nH]2)C1] | 434.33 |
| 135 | 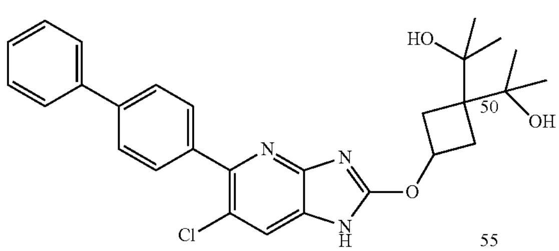 [SMILES: CC(C)(O)C1(C(C)(C)O)CC(Oc2nc3nc(-c4ccc(-c5ccccc5)cc4)c(Cl)cc3[nH]2)C1] | 492.31 |
| 136 | 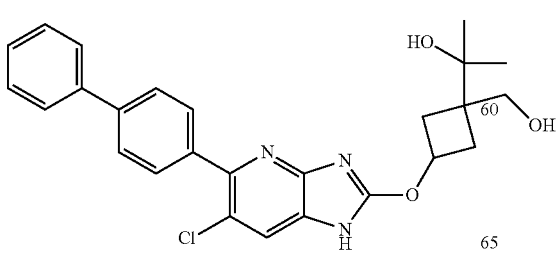 [SMILES: CC(C)(O)C1(CO)CC(Oc2nc3nc(-c4ccc(-c5ccccc5)cc4)c(Cl)cc3[nH]2)C1] | 464.42 |

SCHEME 7

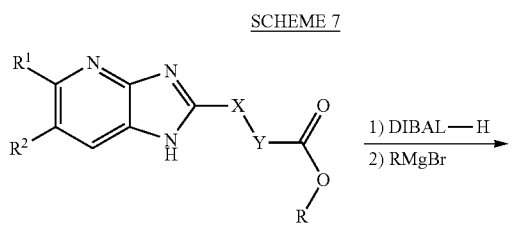

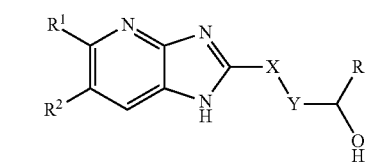

EXAMPLE 137

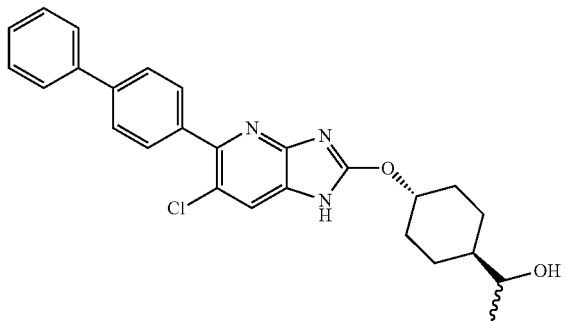 [SMILES: CC(O)[C@H]1CC[C@H](Oc2nc3nc(-c4ccc(-c5ccccc5)cc4)c(Cl)cc3[nH]2)CC1]

Step A: trans-4-{[5-(biphenyl-4-yl)-6-chloro-1H imidazo[4,5-b]pyridin-2-yl]-oxy}cyclohexanecarbaldehyde. To a solution of the ester precursor to Example 29 (200 mg, 0.420 mmol) in THF (10 mL) under $N_2$ at −78° C. was added DIBAL-H in toluene (0.364 ml, 0.546 mmol). The mixture was stirred at −78° C. for 2 hours, then additional DIBAL-H (0.840 ml, 1.261 mmol) was added. The reaction was stirred overnight (from −78° C. to −20° C.), and then quenched by the addition of a few drops of saturated $NH_4Cl$ at −78° C. Precipitate was formed and removed by filtration through Celite™. The filtrate was concentrated under reduced pressure, the resulting residue was purified by column chromatography on silica gel Biotage 25S, eluting with EtOAc/isohexane (gradient from 20% to 65%) to give the title compound as a white solid. LC-MS: calculated for $C_{25}H_{22}ClN_3O_2$ 431.914, observed m/e: 432.14 $(M+H)^+$ (Rt 3.54/5.5 min).

Step B: 1-(trans-4-{[5-(biphenyl-4-yl)-6-chloro-1H imidazo[4,5-b]pyridin-2-yl]-oxy}cyclohexyl)ethanol. To a solution of the product from step A (70 mg, 0.162 mmol) in THF (10 mL) under $N_2$ at 0° C. was added methylmagnesium bromide in ether (0.108 ml, 0.324 mmol). The mixture was stirred at 0° C. for 15 min and then for 2 hours at room temperature. The reaction was quenched by the addition of a few drops of saturated $NH_4Cl$ at 0° C. Precipitate was formed and removed by filtration through Celite™. The filtrate was concentrated under reduced pressure, and the resulting residue was purified by preparative TLC, eluting with EtOAc/isohexane (6:4) to give the title compound as 1:1 mixture of two isomers. LC-MS: calculated for $C_{26}H_{26}ClN_3O_2$ 447.957, observed m/e: 448.21 $(M+H)^+$ (Rt 3.59/5.5 min). $^1$H NMR δ (ppm) ($CD_3OD$): 7.78 (1H, s), 7.68-7.75 (6H, m), 7.46 (2H, t, J=7.5 Hz), 7.36 (1H, t, J=7.5 Hz), 4.96 (1H, m), 3.54 (1H, qn, J=6.0 Hz), 2.05 (1 H, m), 1.86 (1 H, m), 1.55 (2 H, m), 1.21-1.40 (3 H, m), 1.17 (3 H, d, J=6 Hz).

TABLE 7

Compound prepared according to the method in Example 137.

| Example Number | Structure | HPLC-mass spectrum m/e |
|---|---|---|
| 138 | ![structure] | 448.21 |

SCHEME 8

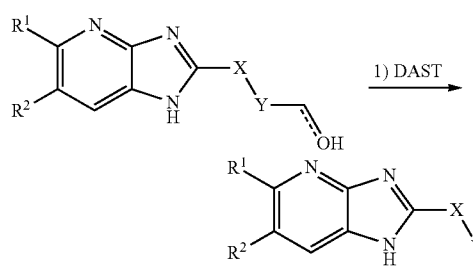

EXAMPLE 139

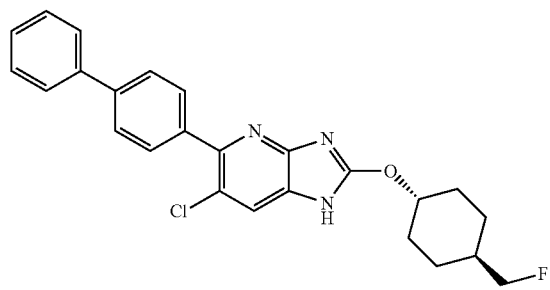 [SMILES: FC[C@H]1CC[C@H](Oc2nc3nc(-c4ccc(-c5ccccc5)cc4)c(Cl)cc3[nH]2)CC1]

Step A: 5-(biphenyl-4-yl)-6-chloro-2-{[trans-4-(fluoromethyl)cyclohexyl]oxy}-1H imidazo[4,5-b]pyridine. To a stirred solution of the alcohol (55.6 mg, 0.128 mmol) in $CH_2Cl_2$ (10 ml) at −78° C. was added DAST (0.085 ml, 0.641 mmol), and the mixture was allowed to stir at room temperature for 2 hours. The crude product precipitated from solution and was isolated by filtration. The crude product was purified by column chromatography eluting with EtOAC/Hexanes (1/1) to give the title compound as a white solid. LC-MS: calculated for $C_{25}H_{23}ClFN_3O$ 435.921, observed m/e: 436.15 $(M+H)^+$ (Rt 3.86/5.5 min). $^1H$ NMR δ (ppm) ($CD_3OD$): 7.78 (1H, s), 7.67-7.77 (6H, m), 7.46 (2H, t, J=7.5 Hz), 7.36 (1H, t, J=7.5 Hz), 4.99 (1H, m), 4.33 (1H, d, 6.0 Hz), 4.23 (1H, d, 6.0 Hz), 2.35 (2 H, m), 1.93 (2 H, m), 1.58 (2 H, m), 1.21-1.42 (3 H, m).

SCHEME 9

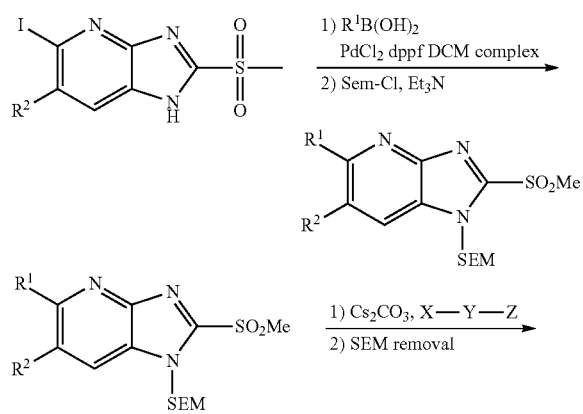

-continued

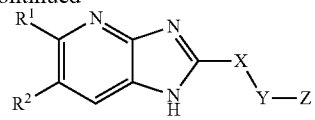

EXAMPLE 140

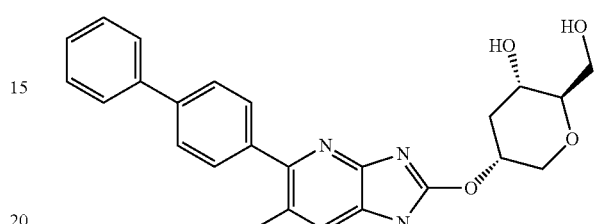

(2R,3S,5R)-5-[[6-chloro-5-(4-phenylphenyl)-1H-imidazo[4,5-b]pyridin-2-yl]oxy]-2-(hydroxymethyl)tetrahydropyran-3-ol Step A: 2-[[6-chloro-2-methylsulfonyl-5-(4- phenylphenyl)imidazo[4,5-b]pyridin-1-yl]methoxy]ethyl-trimethyl-silane To a 0° C. solution of intermediate 6 (4 g, 10.42 mmol) in THF (21 mL) was added triethylamine (1.89 mL, 13.5 mmol) and SEM-Cl (2.03 mL, 11.4 mmol). The reaction was warmed to rt and stirred 15 min, then diluted with EtOAc and water. The aqueous layer was extracted with EtOAc (×2) and the combined extracts were washed with brine, dried over $Na_2SO_4$, filtered, and concentrated. The resulting crude material was purified by column chromatography using a Biotage™ 100 g column eluted with a 5% to 50% EtOAc/Hexane gradient. The fractions containing product were collected and concentrated in vacuo to provide the desired product as a white solid. LC-MS: calculated for $C_{25}H_{28}ClN_3O_3SSi$ 513.13, observed m/e: 514.16 $(M+H)^+$; (Rt 1.4/2.0 min).

Step B: 2-[[2-[[(4aR,7R,8aS)-2-phenyl-4,4a6,7,8,8a-hexahydropyrano[3,2-d][1,3]dioxin-7-yl]oxy]-6-chloro-5-(4-phenylphenyl)imidazo[4,5-b]pyridin-1-yl]methoxy]ethyl-trimethyl-silane 1,5-Anhydro-4,6-O-benzylidene-3-deoxy-D-glucitol (266 mg, 1.125 mmol, Carbosynth, CAS Number: 152613-20-2), 2-[[6-chloro-2-methylsulfonyl-5-(4-phenylphenyl)imidazo[4,5-b]pyridin-1-yl]methoxy]ethyl-trimethyl-silane from step A (386 mg, 0.75 mmol), and cesium carbonate (489 mg, 1.5 mmol) were dissolved in DMF (1.5 mL). The reaction mixture was stirred for 3 h at rt, then diluted with water and EtOAc. The aqueous layer was separated, extracted with EtOAc (×1) and the combined organic layers were washed with saturated $NaHCO_3$ and brine, dried over $Na_2SO_4$, filtered and concentrated. The resulting crude material was purified by column chromatography using a Biotage™ 25 g column eluted with a 20% to 80% EtOAc:Hexane ramp. The fractions containing product were collected and concentrated in vacuo to provide the desired product as a white foam. LC-MS: calculated for $C_{37}H_{40}ClN_3O_5$ Si 669.24, observed m/e: 670.34 $(M+H)^+$; (Rt 1.4/2.0 min).

Step C: (2R,3S,5R)-5-[[6-chloro-5-(4-phenylphenyl)-1H-imidazo[4,5-b]pyridin-2-yl]oxy]-2-(hydroxymethyl)tetrahydropyran-3-ol 2-[[2-[[(4aR,7R,8aS)-2-phenyl-4,4-a,6,7,8,8a-hexahydropyrano[3,2-d][,3]dioxin-7-yl]oxy]-6-chloro-5-(4-phenylphenyl)imidazo[4,5-b]pyridin-1-yl]methoxy]ethyl-trimethyl-silane from step B (190 mg, 0.283 mmol) was dissolved in 4M HCl in dioxane (4 mL, 16 mmol). The reaction was stirred 3 h at rt and additional 4M HCl in dioxane (2 mL, 8 mmol) was added. The reaction was stirred an additional hour, then diluted with EtOAc and neutralized with 3 M NaOH and saturated NaHCO$_3$. The aqueous layer was separated, extracted with EtOAc (×2), and the combined extracts were washed with brine, dried over Na$_2$SO$_4$, filtered, and concentrated. The resulting crude material was purified by column chromatography using a Biotage™ 25 g column eluted with 10% to 100% EtOAc/Hexane, then 0% to 5% MeOH/CH$_2$Cl$_2$. The fractions containing the desired product were collected and concentrated in vacuo. The resulting foam was freeze dried from MeCN/water to provide the title compound as a white solid. LC-MS: calculated for C$_{24}$H$_{22}$ClN$_3$O$_4$ 451.13, observed m/e: 452.13 (M+H); (Rt 2.9/5.5 min); $^1$H NMR δ (ppm) (CD$_3$OD): 7.82 (S, 1H), 7.74-7.68 (m, 6H), 7.46 (t, J=7.5 Hz, 2H), 7.36 (t, J=7.5 Hz, 1H), 5.12 (septet, J=5.5 Hz, 1H), 4.34 (ddd, J=10.5, 5.0, 1.5 Hz, 1H), 3.88 (dd, J=12.0, 2.0 Hz, 1H), 3.67-3.59 (m, 2H), 3.37 (t, J=10 Hz, 1H), 3.18-3.15 (m, 1H), 2.76-2.74 (m, 1H), 1.69 (q, J=11.0 Hz, 1H).

TABLE 8

Compound prepared according to the methods in Example 140.

| Example Number | Structure | HPLC-mass spectrum m/e |
|---|---|---|
| 141 | 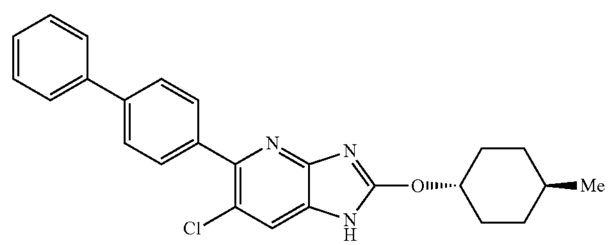 [SMILES: C[C@H]1CC[C@H](Oc2nc3nc(-c4ccc(-c5ccccc5)cc4)c(Cl)cc3[nH]2)CC1] | 418.20 |
| 142 | 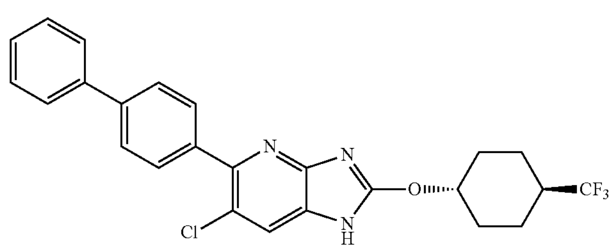 [SMILES: FC(F)(F)[C@H]1CC[C@H](Oc2nc3nc(-c4ccc(-c5ccccc5)cc4)c(Cl)cc3[nH]2)CC1] | 472.17 |
| 143 | 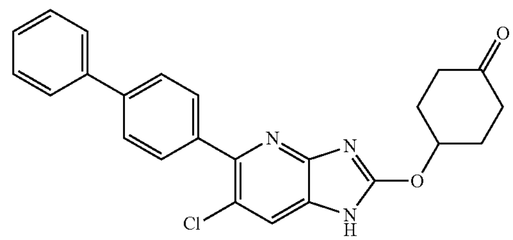 [SMILES: O=C1CCC(Oc2nc3nc(-c4ccc(-c5ccccc5)cc4)c(Cl)cc3[nH]2)CC1] | 418.1 |
| 144 | 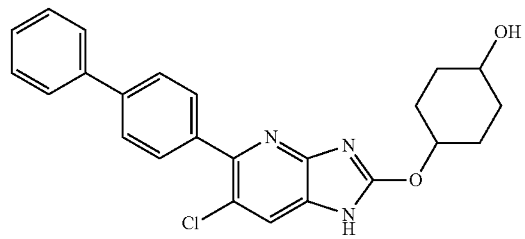 [SMILES: OC1CCC(Oc2nc3nc(-c4ccc(-c5ccccc5)cc4)c(Cl)cc3[nH]2)CC1] | 420.2 |

TABLE 8-continued

Compound prepared according to the methods in Example 140.

| Example Number | Structure | HPLC-mass spectrum m/e |
|---|---|---|
| 145 | 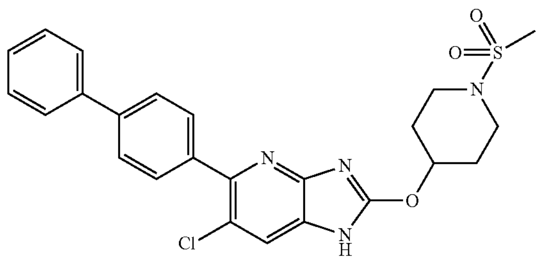 [SMILES: CS(=O)(=O)N1CCC(Oc2nc3nc(-c4ccc(-c5ccccc5)cc4)c(Cl)cc3[nH]2)CC1] | 483.1 |
| 146 | 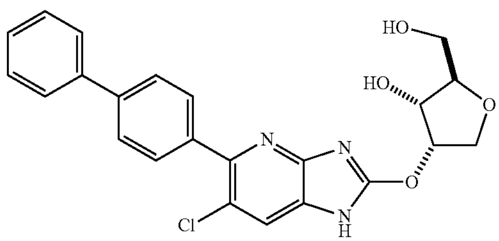 | 438.1 |
| 147 | 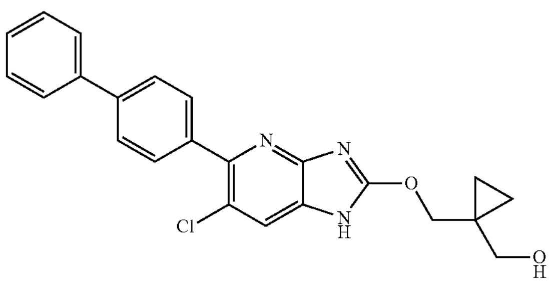 [SMILES: OCC1(COc2nc3nc(-c4ccc(-c5ccccc5)cc4)c(Cl)cc3[nH]2)CC1] | 406.18 |
| 148 | 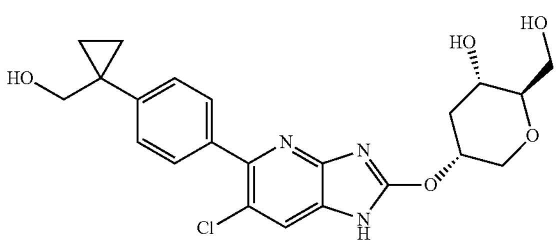 [SMILES: OC[C@H]1OC[C@H](Oc2nc3nc(-c4ccc(C5(CO)CC5)cc4)c(Cl)cc3[nH]2)C[C@@H]1O] | 446.14 |
| 149 | 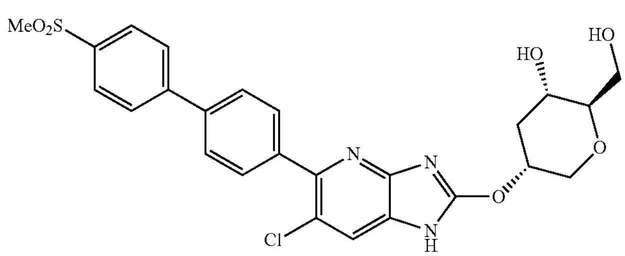 [SMILES: CS(=O)(=O)c1ccc(-c2ccc(-c3nc4nc(O[C@H]5CO[C@H](CO)[C@@H](O)C5)[nH]c4cc3Cl)cc2)cc1] | 530.13 |
| 150 | 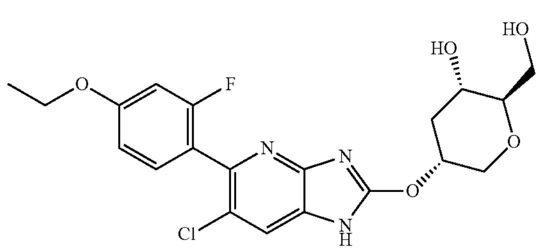 [SMILES: CCOc1ccc(-c2nc3nc(O[C@H]4CO[C@H](CO)[C@@H](O)C4)[nH]c3cc2Cl)c(F)c1] | 438.07 |

TABLE 8-continued

Compound prepared according to the methods in Example 140.

| Example Number | Structure | HPLC-mass spectrum m/e |
|---|---|---|
| 151 | 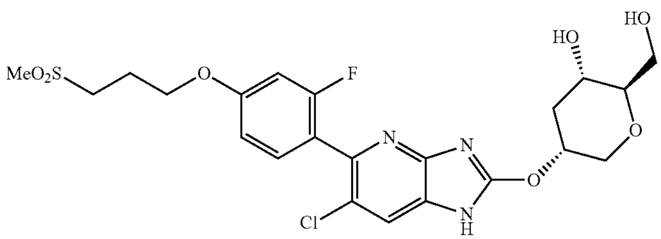 [SMILES: CS(=O)(=O)CCCOc1ccc(-c2nc3nc(O[C@H]4CO[C@H](CO)[C@@H](O)C4)[nH]c3cc2Cl)c(F)c1] | 530.20 |
| 152 | 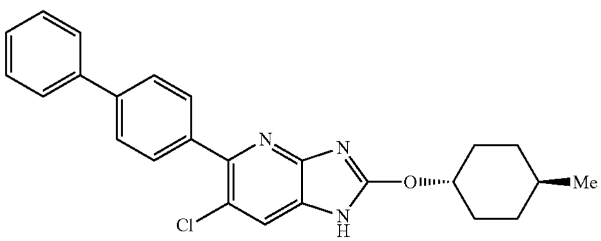 [SMILES: C[C@H]1CC[C@H](Oc2nc3nc(-c4ccc(-c5ccccc5)cc4)c(Cl)cc3[nH]2)CC1] | 418.20 |
| 153 | 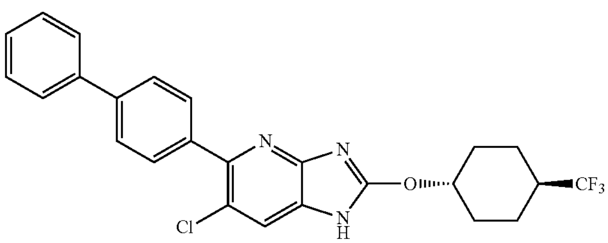 [SMILES: FC(F)(F)[C@H]1CC[C@H](Oc2nc3nc(-c4ccc(-c5ccccc5)cc4)c(Cl)cc3[nH]2)CC1] | 472.17 |
| 154 | 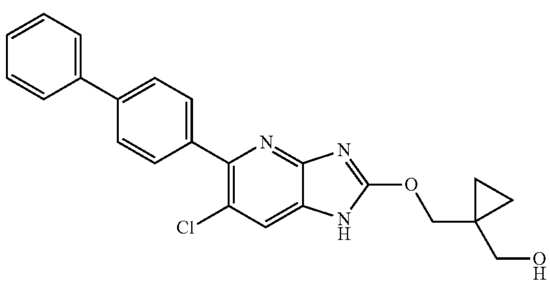 [SMILES: OCC1(COc2nc3nc(-c4ccc(-c5ccccc5)cc4)c(Cl)cc3[nH]2)CC1] | 406.18 |
| 155 | 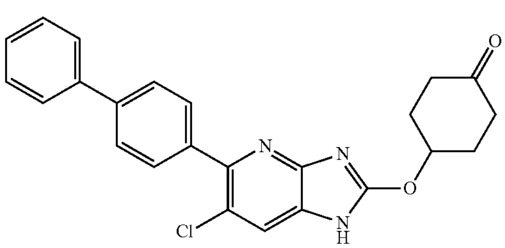 [SMILES: O=C1CCC(Oc2nc3nc(-c4ccc(-c5ccccc5)cc4)c(Cl)cc3[nH]2)CC1] | 418.1 |
| 156 | 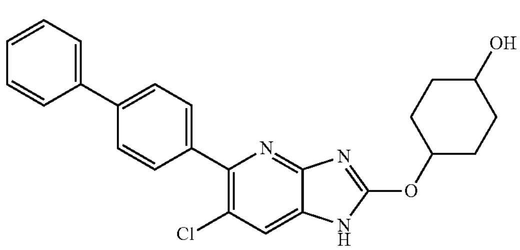 [SMILES: OC1CCC(Oc2nc3nc(-c4ccc(-c5ccccc5)cc4)c(Cl)cc3[nH]2)CC1] | 420.2 |

TABLE 8-continued

Compound prepared according to the methods in Example 140.

| Example Number | Structure | HPLC-mass spectrum m/e |
|---|---|---|
| 157 | ![structure 157] | 483.1 |
| 158 | ![structure 158] | 438.1 |

SCHEME 10

EXAMPLE 159

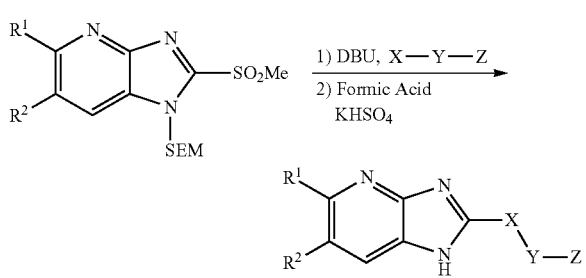

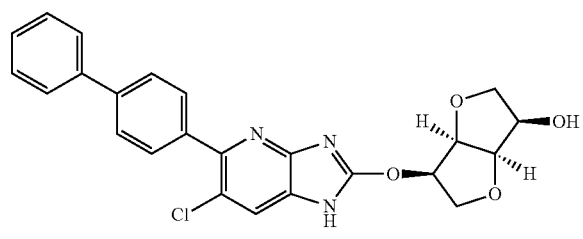 [SMILES: O[C@@H]1CO[C@H]2[C@@H]1OC[C@H]2Oc1nc2nc(-c3ccc(-c4ccccc4)cc3)c(Cl)cc2[nH]1]

1,4:3,6-dianhydro-2-O-[5-(biphenyl-4-yl)-6-chloro-1H-imidazo[4,5-b]pyridin-2-yl]-D-mannitol Step A: Mixture of 1,4:3,6-dianhydro-2-O-[5-(biphenyl-4-yl)-6-chloro-1-{[2-(trimethylsily)ethoxy]methyl}-1H-imidazo[4,5-b]pyridin-2-yl]-5-O-[tert-butyl(dimethyl)silyl]-D-mannitol and 1,4:3,6-dianhydro-2-O-[5-(biphenyl-4-yl)-6-chloro-1-{[2-(trimethlsilyl)ethoxy]methyl}-1H-imidazo[4,5-b]pyridin-2-yl]-D-mannitol A mixture of 2-[[6-chloro-2-methysulfonyl-5-(4-phenylphenyl(4-phenylphenyl)imidazo[4,5-b]pyridin-1-yl]methoxy]ethyl-trimethyl-silane (from step A in Example 147, 2023 mg, 3.93 mmol), 1,4:3,6-dianhydro-2-O-[tert-butyl(dimethyl)silyl]-D-mannitol (2049 mg, 7.87 mmol, from WuXi PharmaTech Co., Ltd.) and DBU (1.186 mL, 7.87 mmol) in DMA (30 mL) was stirred at r.t. overnight. Then the crude mixture was extracted with EtOAc and washed with water. The organic layer was dried over anhydrous sodium sulfate and concentrated under reduced pressure. The resulting residue was purified by column chromatography on silica gel Biotage™ 40M, eluting with a 5% to 100% EtOAc:Hexane ramp. The fractions containing product were collected and concentrated in vacuo to provide the desired products as white solid. LC-MS: calculated for $C_{36}H_{48}ClN_3O_5Si_2$ 693.28, observed m/e: 694.05 (M+H)$^+$; (Rt 3.17/4.0 min) and calculated for $C_{30}H_{34}ClN_3O_5Si$ 579.20, observed m/e: 579.97 (M+H)$^+$; (Rt 2.59/4.0 min), Step B: 1,4:3,6-dianhydro-2-O-[5-(biphenyl-4-yl)-6-chloro-1H-imidazo[4,5-b]pyridin-2-yl]-D-mannitol The product from step A (2160 mg, 1.695 mmol) was dissolved in formic acid (27 mL), and saturated aqueous potassium hydrogen sulfate (3 mL, 1.695 mmol) was added. The reaction was stirred at room temperature overnight, then cooled to 0° C., and basified to pH=12 with NaOH (50/50% by weight). The mixture was diluted with THF (10 mL) and stirred at room temperature for 45 min. Then resulting mixture was acidified to pH=7 with 2N HCl, and extracted with EtOAc. The combined organic layers were washed with water twice, once with brine, then dried over anhydrous sodium sulfate, filtered and concentrated to give the crude product. The crude product was purified by column chromatography on silica gel Biotage™ 40M, eluting with $CH_2Cl_2/EtOH/NH_4$=95/4/1 (gradient from 5% to 9%) to give crude product, which was recrystallized from $CH_2Cl_2$/MeOH to give the title compound as a white solid. LC-MS: calculated for $C_{24}H_{20}ClN_3O_4$ 449.11, observed m/e: 449.96 (M+H); (Rt 3.2/5.5 min); $^1$H NMR δ (ppm) (DMSO-$d_6$): 7.91 (S, 1H), 7.70-7.80 (m, 6H), 7.48 (t, J=7.5 Hz, 2H), 7.38 (t, J=7.5 Hz, 1H), 5.47 (qt, J=6.0 Hz, 1H), 5.05-4.90 (m, br, 1H), 4.82 (t, J=5.0 Hz, 1H), 4.35 (t, J=5.0 Hz, 1H), 4.20-4.00 (m, 2H), 3.90 (m, 1H), 3.77 (t, J=7.5 Hz, 1H), 3.42 (t, J=8.5z, 1H).

INTERMEDIATE 7

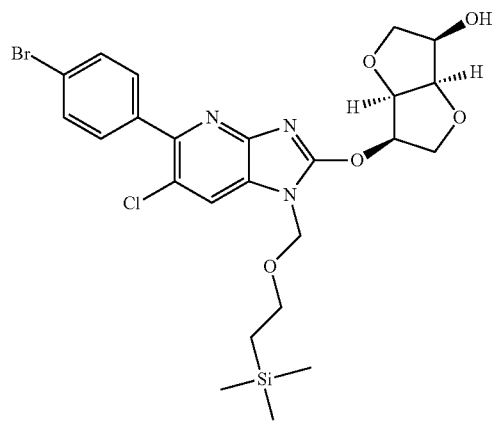

TABLE 9

Compound prepared according to the methods in scheme 10 and the procedure of Example 159.

| Example Number | Structure | HPLC-mass spectrum m/e |
|---|---|---|
| 160 | 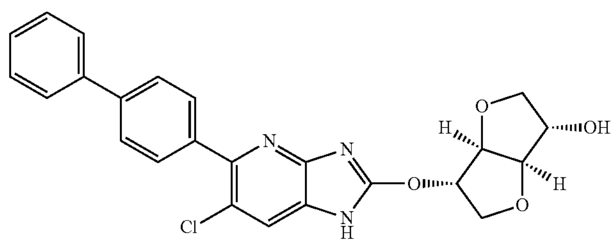 [SMILES: O[C@H]1CO[C@H]2[C@@H]1OC[C@@H]2Oc1nc2nc(-c3ccc(-c4ccccc4)cc3)c(Cl)cc2[nH]1] | 449.89 (M + 1) |
| 161 | 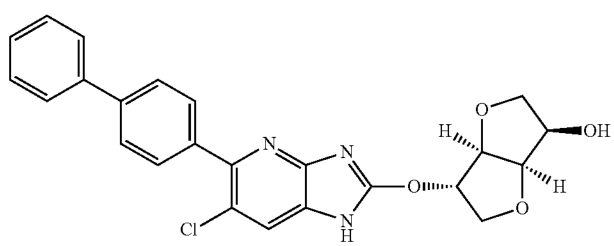 [SMILES: O[C@@H]1CO[C@H]2[C@@H]1OC[C@@H]2Oc1nc2nc(-c3ccc(-c4ccccc4)cc3)c(Cl)cc2[nH]1] | 449.89 (M + 1) |
| 162 | 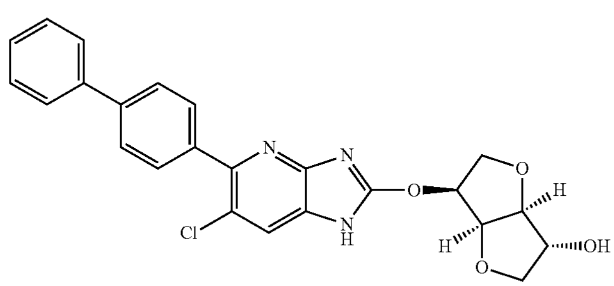 [SMILES: O[C@@H]1CO[C@@H]2[C@H]1OC[C@@H]2Oc1nc2nc(-c3ccc(-c4ccccc4)cc3)c(Cl)cc2[nH]1] | 449.89 (M + 1) |

(3R,3aR,6R,6aR)-6-[5-(4-bromophenyl)-6-chloro-1-(2-trimethylsilylethoxymethyl)imidazo[4,5-b]pyridin-2-yl]oxy-2,3,3a,5,6,6a-hexahdrofuro[3,2-b]furan-3-ol Step A 5-(4-bromophenyl)-6-chloro-2-(methylsulfonyl)-1H-imidazo[4,5-b]pyridine PalladiumTetrakis (1.63 g, 1.411 mmol) was added to a stirred hazy solution of intermediate 1 (10.08 g, 28.2 mmol), 4-bromophenylboronic acid (6.23 g, 31.0 mmol), and potassium phosphate (18.44 g, 87 mmol) in dioxane (150 mL) and water (30 mL). The reaction mixture was degassed (3×) and placed under nitrogen before being heated to 100° C. After 17 hours, the reaction mixture was cooled to room temperature before being evaporated under reduced pressure. The resulting residue was stripped with toluene (2×60 mL) to afford the product as a brown/white solid, which was used in the next step without further purification. LC-MS: calculated for $C_{13}H_9BrClN_3O_2S$ 384.93, 386.93 observed m/e: 385.81, 387.84 (M+H)(Rt 1.15/2 min).

Step B 2-[[5-(4-bromophenyl)-6-chloro-2-methylsulfonyl-imidazo[4,5-b]pyridin-1-yl]methoxy]-trimethyl-silane.

N,N-diisopropylethylamine (15 mL, 86 mmol) was added to a stirred suspension of the unpurified 5-(4-bromophenyl)-6-chloro-2-(methylsulfonyl)-1H-imidazo[4,5-b]pyridine from the previous step in THF (150 mL). The reaction mixture was cooled to 0° C. in an ice bath prior to the slow addition of SEM-Cl (10 mL, 56.4 mmol) over 9 minutes. Ten minutes after the addition was complete, the reaction mixture was removed from the ice bath and allowed to warm to room temperature. After 16 hours, the reaction mixture was partitioned following the addition of water (200 mL). The aqueous layer was extracted with EtOAc (3×200 mL). The organic layers were combined, washed with brine (1×100 mL), dried over $Na_2SO_4$, filtered, and evaporated under reduced pressure to give a yellow/brown solid. Flash chromatography of the solid utilizing two 165 g silica RediSep R® columns and employing a 0-30% EtOAc/hexane gradient with a 30% EtOAc/hexane hold afforded the desired product as a yellow solid. LC-MS: calculated for $C_{19}H_{23}BrClN_3O_3SSi$ 515.01, 517.01 observed m/e: 515.85, 517.86 (M+H)$^+$ (Rt 1.33/2 min).

Step C (3R,3aR,6R,6aR)-6-[5-(4-bromophenyl)-6-chloro-(2-trimethylsilylethoxymethyl)imidazo[4,5-b]pyridin-2-yl]oxy-2,3,3a,5,6,6a-hexahydrofuro[3,2-b]furan-3-ol. DBU (4.2 mL, 27.9 mmol) was added to a stirred solution of isomannide (4.11 g, 28.1 mmol) in DMF (60 mL). The reaction mixture was a yellow solution that was stirred at room temperature. A suspension of 2-[[5-(4-bromophenyl)-6-chloro-2-methylsulfonyl-imidazo[4,5-b]pyridin-1-yl]methoxy]ethyl-trimethyl-silane (4.78 g, 9.25 mmol) in DMF (34 mL) was added dropwise to the reaction mixture over 54 minutes. After 1.5 hours, the reaction mixture was partitioned between EtOAc (500 mL) and water (200 mL). The organic layer was washed with water (4×100 mL) and brine (1×100 mL), dried over $Na_2SO_4$, filtered, and evaporated under reduced pressure to give a yellow foam. Flash chromatography of the foam utilizing a 120 g silica RediSep R$_f$® column and employing a 0-70% EtOAc/hexane gradient with a 70% EtOAc/hexane hold afforded the title compound as a white foam. LC-MS: calculated for $C_{24}H_{29}BrClN_3O_5Si$ 581.07, 583.07 observed m/e: 582.20, 584.23 (M+H)$^+$ (Rt 1.32/2 min).

INTERMEDIATE 8

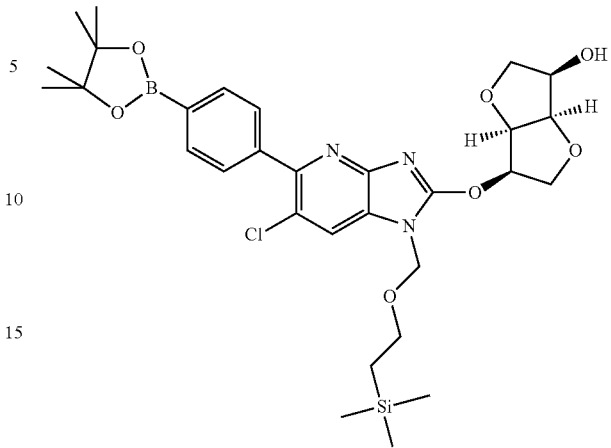

(3R,3aR,6R,6aR)-6-[6-chloro-5-[4-(4,4,5,5-tetramethyl-1,3,2-dioxaborolan-2-yl)phenyl]-1-(2-trimethylsilylylethoxymethyl)imidazo[4,5-b]pyridin-2-yl]oxy-2,3,3a,5,6,6a-hexahydrofuro[3,2-b]furan-3-ol 1,1'-bis(diphenylphosphino)ferrocene-palladium(1) dichloride dichloromethane complex (0.5137 g, 0.629 mmol) was added to a stirred suspension of intermediate 7 (3.1823 g, 5.46 mmol), bis(pinacolato)diboron (4.09 g, 16.11 mmol), and potassium acetate (2.79 g, 28.4 mmol) in dioxane (50 mL). The reaction mixture was degassed (3×) and placed under nitrogen before being heated to 80° C. After 2 hours, the reaction mixture was cooled to room temperature before being partitioned between EtOAc (200 mL), water (200 mL), and enough brine to break an emulsion. The aqueous layer was extracted with EtOAc (3×100 mL). The organic layers were combined, washed with brine (1×100 mL), dried over $Na_2SO_4$, filtered, and evaporated under reduced pressure to give a dark brown residue. Flash chromatography of the residue utilizing a 120 g silica RediSep R$_f$® column and employing a 0-70% EtOAc/hexane gradient with a 70% EtOAc/hexane hold afforded the title compound as a white foam. LC-MS: calculated for $C_{30}H_{41}BClN_3O_7Si$ 629.25 observed m/e: 630.46 (M+H)$^+$ (Rt 1.34/2 min).

INTERMEDIATE 9

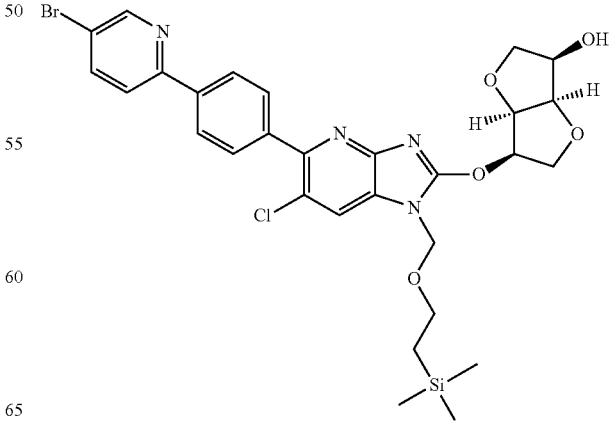

(3R,3aR,6R,6aR)-6-[5-[4-(5-bromo-2-pyridyl)phenyl]-6-chloro-1-(2-trimethlsilylethoxymethyl)imidazo[4,5-b]pyridin-2-yl]oxy-2,3,3a,5,6,6a-hexahydrofuro[3,2-b]furan-3-ol PalladiumTetrakis (189.5 mg, 0.164 mmol) was added to a hazy stirred solution of intermediate 8 (0.98 g, 1.556 mmol), 2,5-dibromopyridine (375.5 mg, 1.585 mmol), and sodium carbonate (669.9 mg, 6.32 mmol) in 1,4-dioxane (80 mL) and water (20 mL). The reaction mixture was degassed (3×) and placed under nitrogen before being heated to 80° C. After 2 hours, the reaction mixture was cooled to room temperature before being partitioned between EtOAc (150 mL) and water (150 mL). The aqueous layer was extracted with EtOAc (3×75 mL). The organic layers were combined, washed with brine (1×100 mL), dried over $Na_2SO_4$, filtered, and evaporated under reduced pressure to give an amber foam. Flash chromatography of the foam utilizing an 80 g silica RediSep $R_f$® column and employing a 0-80% EtOAc/hexane gradient with a 80% EtOAc/hexane hold afforded the title compound as a white solid. LC-MS: calculated for $C_{29}H_{32}BrClN_4O_5Si$ 658.1, 660.1 observed m/e: 659.36, 661.33 $(M+H)^+$ (Rt 1.33/2 min).

INTERMEDIATE 10

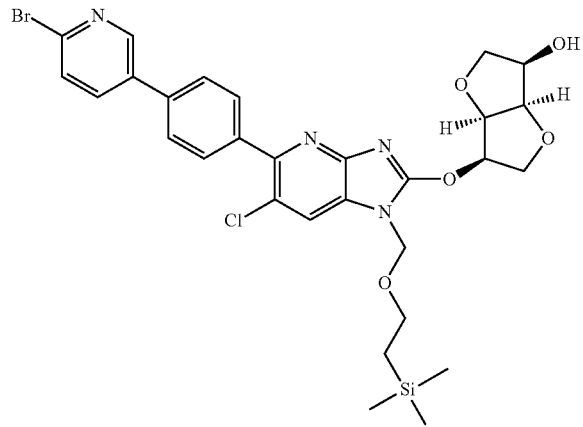 [SMILES: C[Si](C)(C)CCOCn1c(O[C@@H]2CO[C@H]3[C@@H]2OC[C@H]3O)nc2nc(-c3ccc(-c4ccc(Br)nc4)cc3)c(Cl)cc21]

(3R,3aR,6R,6aR)-6-[5-[4-(6-bromo-3-pyridyl)phenyl]-6-chloro-1-(2-trimethylsilylethoxymethyl)imidazo[4,5-b]pyridin-2-yl]oxy-2,3,3a,5,6,6a-hexahdrofuro[3,2-b]furan-3-ol
PalladiumTetrakis (134.9 mg, 0.117 mmol) was added to a stirred hazy solution of intermediate 8 (625.8 mg, 0.993 mmol), 2-bromo-5-iodopyridine (313.1 mg, 1.103 mmol), and potassium phosphate (631.3 mg, 2.97 mmol) in 1,4-dioxane (8 mL) and water (2 mL). The reaction mixture was degassed (3×) and placed under nitrogen before being heated to 80° C. After 7.5 hours, the reaction mixture was cooled to room temperature before being partitioned between EtOAc (150 mL) and water (150 mL). The aqueous layer was extracted with EtOAc (3×75 mL). The organic layers were combined, washed with brine (1×100 mL), dried over $Na_2SO_4$, filtered, and evaporated under reduced pressure to give an amber foam. Flash chromatography of the foam utilizing a 40 g silica RediSep $R_f$® column and employing a 0-80% EtOAc/hexane gradient with a 80% EtOAc/hexane hold afforded the title compound as an off-white solid following lyophilization from ethanol and benzene. LC-MS: calculated for $C_{29}H_{32}BrClN_4O_5Si$ 658.1, 660.1 observed m/e: 659.30, 661.33 $(M+H)^+$ (Rt 1.31/2 min).

INTERMEDIATE 11

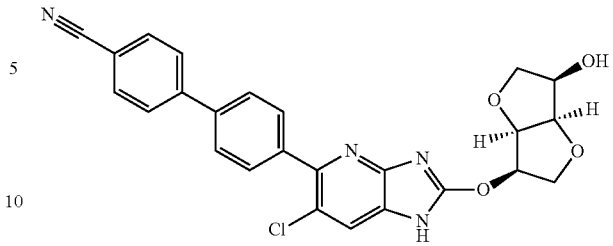

4-[4-[2-[[(3R,3aR,6R6aR)-3-hydroxy-2,3,3a,5,6,6a-hexahdrofuro[3,2-b]furan-6-yl]oxy]-6-chloro-1H-imidazo[4,5-b]pyridin-5-yl]phenyl]benzonitrile Step A 4-[4-[2-[[(3R,3aR6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]benzonitrile. LiOH (0.22 mL, 0.660 mmol) and 1,1'-bis(diphenylphosphino)-ferrocene-palladium(II)dichloride dichloromethane complex (24.1 mg, 0.030 mmol) were added to a stirred solution of intermediate 7 (153.1 mg, 0.263 mmol) and 4-(4,4,5,5-tetramethyl-1,3,2-dioxaborolan-2-yl)benzonitrile (126.4 mg, 0.552 mmol) in 1,4-dioxane (2.1 mL) and water (0.31 mL). The reaction mixture was degassed (3×) and placed under nitrogen before being heated to 80° C. After 16 hours, the reaction mixture was cooled to room temperature before being partitioned between EtOAc (40 mL) and water (40 mL). The aqueous layer was extracted with EtOAc (2×20 mL). The organic layers were combined, washed with brine (1×20 mL), dried over $Na_2SO_4$, filtered, and evaporated under reduced pressure to give a brown residue. This material was purified by flash chromatography utilizing a 4 g silica RediSep $R_f$® column and the following conditions: a 0-60% EtOAc/hexane gradient, a 60% EtOAc/hexane hold, a 60%-70% EtOAc/hexane gradient, and a 70% EtOAc/hexane hold. The desired fractions were combined, evaporated under reduced pressure, and lyophilized from ethanol and benzene to give the desired compound as a yellow solid. LC-MS: calculated for: $C_{31}H_{33}ClN_4O_5Si$ 604.19 observed m/e: 605.21 $(M+H)^+$ (Rt 1.31/2 min).

Step B 4-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]benzonitrile. A mixture of 4-[4-[2-[[(3R,3aR,6R,6aR)-3-hydroxy-2,3,3a,5,6,6a-hexahydrofuro[3,2-b]furan-6-yl]oxy]-6-chloro-(2-trimethylsilylethoxymethyl)imidazo[4,5-b]pyridin-5-yl]phenyl]benzonitrile (49.4 mg, 0.082 mmol), formic acid (1.0 mL, 26.1 mmol), and saturated aqueous $KHSO_4$ (0.06 mL) was heated to 40° C. with stirring. After 6.5 hours, the reaction mixture was cooled to room temperature and placed in the refrigerator overnight, and then cooled to 0° C. in an ice bath. The pH was adjusted to pH 14 through the addition of 5 N NaOH (5.2 mL, 26 mmol). THF (2 mL) was added to the reaction mixture, which was removed from the ice bath and allowed to warm to room temperature. After stirring for 45 minutes at room temperature, the pH was adjusted to 7 through the addition of 2 N HCl. The reaction mixture was partitioned between EtOAc (30 mL) and water (30 mL). The aqueous layer was extracted with EtOAc (2×20 mL). The organic layers were combined, washed with brine (1×20 mL), dried over $Na_2SO_4$, filtered, and evaporated under reduced pressure to give a pale yellow solid. Purification by HPLC reverse phase (C-18), using a 30×150 mm Sunfire™ column and eluting with a 20%-100% acetonitrile/water+0.05% TFA gradient followed by a 100% acetonitrile+0.05% TFA flush afforded the title compound as a white solid following lyophilization from ethanol and benzene. LC-MS: calculated for: $C_{25}H_{19}ClN_4O_4$ 474.11 observed m/e: 475.12 (M+H)⁺ (Rt 1.15/2 min).

INTERMEDIATE 12

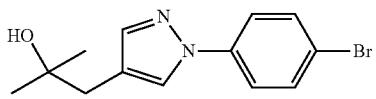 [SMILES: CC(C)(O)Cc1cnn(-c2ccc(Br)cc2)c1]

1-(1-(4-bromophenyl)-1H-pyrazol-4-yl)-2-methyl-propan-2-ol

Step A methyl 2-(1H-pyrazol-4-yl)acetate. 2-(1H-pyrazol-4-yl)acetic acid (970 mg, 7.69 mmol) was placed under nitrogen in anhydrous methanol (80 mL). The mixture was sonicated until solid completely dissolved. To this solution was added dropwise over 30 minutes a 2.0M solution of trimethylsilyldiazomethane in hexanes (3.85 mL, 7.69 mmol). A small excess of trimethylsilyldiazomethane was added until the yellow color persisted. The mixture was allowed to stir for 20 minutes at room temperature, and then concentrated under reduced pressure. The resulting orange oil was chromatographed using a Biotage 25 g silica gel cartridge eluted with 0-5% methanol in dichloromethane over 10 column volumes with a 10 column volume hold at 5% methanol. The product fractions were combined and concentrated under reduced pressure to afford the desired compound as a clear, colorless oil. ¹H NMR δ (ppm) (CDC₃): 7.54 (2H, s), 3.70 (3H, s), 3.55 (2H, s).

Step B 2-methyl-1-(1H-pyrazol-4-yl)propan-2-ol. Methyl 2-(1H-pyrazol-4-yl)acetate (700 mg, 4.99 mmol) was placed under nitrogen in anhydrous THF (100 mL). The mixture was cooled to 0° C. and a 3.0M solution of MeMgBr (15.38 mL, 46.10 mmol) was added dropwise over 5 minutes. The mixture was allowed to warm to room temperature. After 16 hours the mixture was poured into saturated aqueous sodium bicarbonate (100 mL). The mixture was extracted with EtOAc (4×100 mL). The combined organic layers were washed with brine (100 mL), dried over sodium sulfate, and concentrated under reduced pressure. The resulting orange oil was chromatographed using a Biotage 25 g silica gel cartridge eluted with 0-10% methanol in dichloromethane over 15 column volumes with a 5 column volume hold at 10% methanol. The product fractions were combined and concentrated under reduced pressure to provide the desired product as a white solid. ¹H NMR δ (ppm) (CDCl₃): 7.40 (2H, s), 2.63 (2H, s), 1.21 (6H, s).

Step C 1-(1-(4-bromophenyl)-1H-pyrazol-4-yl-2-methyl-propan-2-ol. 2-methyl-1-(1H-pyrazol-4-yl)propan-2-ol (21 mg, 0.15 mmol), copper (II) acetate (27 mg, 0.15 mmol), and 4-bromophenylboronic acid (30 mg, 0.15 mmol) were placed under nitrogen in 1,2-dichloroethane (1 mL). Added 4 A molecular sieves (~20 mg) and pyridine (36 uL, 36 mg, 0.45 mmol). The mixture was stirred at 50° C. for 9 hours while open to the atmosphere. The mixture was allowed to cool to room temperature, filtered through Celite™, rinsed with methanol, and concentrated under reduced pressure. The resulting orange oil was chromatographed using a Biotage 50 g (2×25 g in series) silica gel cartridge eluted with 0-5% methanol in dichloromethane over 30 column volumes. The desired product fractions were combined and concentrated under reduced pressure to provide a colorless oil (25 mg, 54%). LC-MS: calculated for $C_{13}H_{15}BrN_2O$; 295.17 observed m/e: 296.87 (M+H)⁺ (Rt 1.75/4 min). ¹H NMR δ (ppm) (CDCl₃): 7.77 (1H, s), 7.58 (1H, s), 7.55 (4H, s), 2.67 (2H, s), 1.26 (6H, s).

EXAMPLE 163

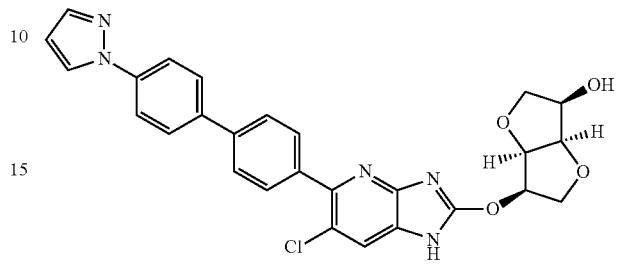

(3R,3aR,6R,6aR)-6-[[6-chloro-5-[4-(4-pyrazol-1-ylphenyl)phenyl]-1H-imidazo[4,5-b]pyridin-2-yl]oxy]-2,3,3a,5,6,6a-hexahydrofuro[3,2-b]furan-3-ol Step A (3R,3aR,6R,6aR-6-[6-chloro-5-[4-(4-pyrazol-1-ylphenyl)phenyl]-1-(2-trimethylsilylethoxymethyl)imidazo[4,5-b]pyridin-2-yl]oxy-2,3,3a,5,6,6a-hexahydrofuro[3,2-b]furan-3-ol. (4-pyrazol-1-ylphenyl)boronic acid (127 mg, 0.675 mmol), 1,1'-bis(diphenylphosphino)ferrocene-palladium(II)dichloride dichloromethane complex (45.9 mg, 0.056 mmol), and LiOH (0.469 mL, 1.407 mmol) were added to a stirred mixture of intermediate 7 (328 mg, 0.563 mmol) in 1,4-dioxane (3 mL) and water (0.8 mL). The reaction mixture was placed under nitrogen before being heated 90° C. After 2 hours, the reaction mixture was cooled to room temperature before being partitioned between EtOAc (50 mL) and saturated aqueous ammonium chloride (50 mL). The aqueous layers were extracted with EtOAc (2×50 mL). The organic layers were combined, washed with brine (1×50 mL), dried over Na₂SO₄, filtered, and evaporated under reduced pressure. Flash chromatography of the resulting residue utilizing a silica gel Biotage™ 25S column and employing a 0-80% EtOAc/hexane gradient afforded the desired compound as a light yellow solid. LC-MS: calculated for $C_{33}H_{36}CN_5O_5Si$ 645.22 observed m/e: 646.48 (M+H)⁺ (Rt 1.32/2 min).

Step B (3R,3aR,6R,6aR)-6-[[6-chloro-5-[4-(4-pyrazol-1-ylphenyl)phenyl]-1H-imidazo[4,5-b]pyridin-2-yl]oxy]-2,3,3a,5,6,6a-hexahydrofuro[3,2-b]furan-3-ol. Combined formic acid (3 mL, 78 mmol), saturated aqueous KHSO₄ (0.33 mL, 0.289 mmol), and (3R,3aR,6R,6aR)-6-[6-chloro-5-[4-(4-pyrazol-1-ylphenyl)phenyl]-1-(2-trimethylsilylethoxymethyl)imidazo-[4,5-b]pyridin-2-yl]oxy-2,3,3a,5,6,6a-hexahydrofuro[3,2-b]furan-3-ol (187 mg, 0.289 mmol). The reaction mixture was stirred at 60° C. overnight. The reaction mixture was cooled to 0° C. in an ice bath. The pH of the reaction mixture was adjusted to >11 by the addition of NaOH (3120 mg, 78 mmol) in water (5 mL). THF (5 mL) was added to the reaction mixture, then the reaction was removed from the ice bath and allowed to warm to room temperature. After 30 minutes, the pH of the reaction mixture was adjusted to 6 through the addition of concentrated HCl. The reaction mixture was partitioned between EtOAc (100 mL) and water (50 mL). The aqueous layer was extracted with EtOAc (2×100 mL). The organic layers were combined, washed with brine (1×50 mL), dried over Na₂SO₄, filtered and evaporated under reduced pressure. The resulting residue was purified by preparative HPLC reverse phase (C-18), using a 19×100 mm Sunfire™ column and eluting with a 10%-90% acetonitrile/water+0.05% TFA gradient followed by a 90% acetonitrile/water+0.05% TFA flush. The desired fractions were combined, evaporated under reduced pressure, and lyophilized from acetonitrile and water to give the title compound as a white solid. LC-MS: calculated for $C_{27}H_{22}ClN_5O_4$ 515.14 observed m/e: 515.92 (M+H)+(Rt 1.16/2 min); $^1$H NMR δ (ppm) (CD$_3$OD): 8.30 (d, J=2.5 Hz, 1H), 7.87 (m, 4H), 7.85 (s, 1H), 7.79 (m, 4H), 7.77 (d, J=1.5 Hz, 1H), 6.58 (t, J=2 Hz, 1H), 5.56 (qt, J=5 Hz, 11H), 4.99 (t, J=5.3 Hz, 1H), 4.49 (t, J=5.3 Hz, 1H), 4.28-4.31 (m, 1H), 4.19 (dd, J=5.5 Hz, 10.5 Hz, 1H), 4.12 (dd, J=4.5 Hz, 10 Hz, 1H), 3.92 (t, J=7.5 Hz, 1H), 3.62 (t, J=8.8 Hz, 1H).

(3R,3aR,6R,6aR)-6-[6-chloro-5-[4-[4-(1-methylimidazol-2-yl)phenyl]phenyl]-1H-imidazo[4,5-b]pyridin-2-yl]oxy]-2,3,3a,5,6,6a-hexahydrofuro[3,2-b]furan-3-ol Step A (3R,3aR,6R,6aR)-6-[[5-(4-bromophenyl)-6-chloro-1H-imidazo[4,5-b]pyridin-2-yl]oxy]-2,3,3a,5,6,6a-hexahydrofuro[3,2-b]furan-3-ol. A mixture of formic acid (4.5 mL, 117 mmol), saturated aqueous KHSO$_4$ (0.5 mL, 0.940 mmol), and intermediate 7 (548 mg, 0.940 mmol) was heated at 60° C. overnight. The reaction mixture was cooled to 0° C. in an ice bath. The pH of the reaction mixture was adjusted to >pH 11 through the addition of NaOH (4680 mg, 117 mmol) in water (10 mL). THF (10 mL) was added to the

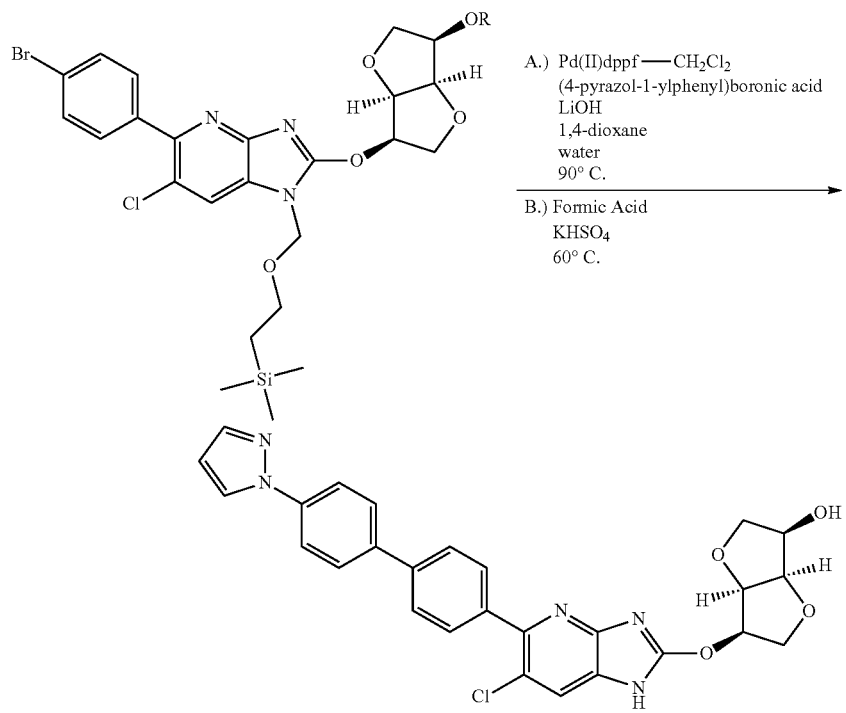

The isomannide alcohol starting material was either unprotected (R=H) or TBS protected (R=OTBS) during the 1,1'-bis(diphenylphosphino)ferrocene-palladium(II)-dichloride dichloromethane complex coupling reaction used to prepare Example 163, as shown above. The TBS group was observed to substantially deblock during the reaction giving the unprotected alcohol.

EXAMPLE 164

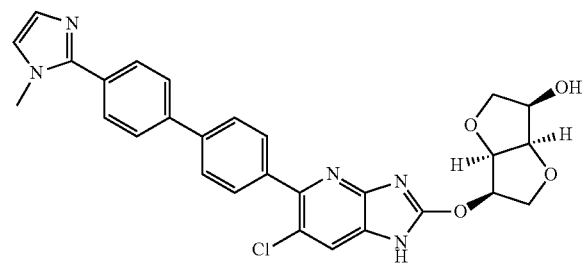 [SMILES: Cn1ccnc1-c1ccc(-c2ccc(-c3nc4nc(O[C@@H]5CO[C@H]6[C@@H]5OC[C@H]6O)[nH]c4cc3Cl)cc2)cc1]

reaction mixture, which was removed from the ice bath and allowed to warm to room temperature. After 30 minutes, the pH of the reaction mixture was adjusted to pH 6 through the addition of concentrated HCl. The reaction mixture was extracted with EtOAc (3×80 mL). The organic layers were combined, washed with brine (1×100 mL), dried over Na$_2$SO$_4$, filtered, and evaporated under reduced pressure. Flash chromatography of the resulting residue utilizing a silica gel Biotage™ 25M column and employing a 0-10% MeOH/DCM gradient afforded the desired product as a white solid. LC-MS: calculated for $C_{18}H_{15}BrClN_3O_4$ 450.99, 452.99 observed m/e: 452.00, 454.02 (M+H)+ (Rt 1.14/2 min).

Step B (3R,3aR,6R,6aR)-6-[[6-chloro-5-[4-[4-(1-methylimidazol-2-yl)phenyl]phenyl]-1H-imidazo[4,5-b]pyridin-2-yl]oxy]-2,3,3a,5,6,6a-hexahdrofuro[3,2-b]furan-3-ol. 1-methyl-2-[4-(4,4,5,5-tetramethyl-1,3,2-dioxaborolan-2-yl)phenyl]imidazole (26.4 mg, 0.093 mmol), 1,1'-bis(diphenylphosphino)ferrocene-palladium(II)dichloride dichloromethane complex (6.33 mg, 7.75 μmol), and LiOH (0.065 mL, 0.194 mmol) were added to a stirred mixture of (3R,3aR, 6R,6aR)-6-[[5-(4-bromophenyl)-6-chloro-1H-imidazo[4,5- b]pyridin-2-yl]oxy]-2,3,3a,5,6,6a-hexahydrofuro[3,2-b]furan-3-ol (35.1 mg, 0.078 mmol) in 1,4-dioxane (3 mL) and water (0.8 mL). The reaction mixture was placed under nitrogen and heated to 90° C. After 2 hours, the reaction mixture was cooled to room temperature before being partitioned between EtOAc (30 mL) and saturated NH$_4$Cl (30 mL). The aqueous layer was extracted with EtOAc (1× mL). The organic layers were combined, washed with brine (1×40 mL), dried over Na$_2$SO$_4$, filtered, and evaporated under reduced pressure. The resulting residue was purified by preparative thin layer chromatography using a 500 micron 20 cm×20 cm silica gel plate, which was developed using 10% MeOH/DCM. The material isolated from the plate was further purified by preparative HPLC reverse phase (C-18), using a 19×100 mm Sunfire™ column and eluting with a 10%-90% acetonitrile/water+0.05% TFA gradient, followed by a 90% acetonitrile/water+0.05% TFA flush. The desired fractions were combined, concentrated under reduced pressure and lyophilized from acetonitrile and water to afford the title compound as a white solid. LC-MS: calculated for $C_{28}H_{24}ClN_5O_4$ 529.15 observed m/e: 530.28 (M+H)$^+$ (Rt 1.00/2 min); $^1$H NMR δ (ppm) (CD$_3$OD): 8.04 (d, J=8 Hz, 2H), 7.81-7.88 (m, 7H), 7.69 (d, J=1.5 Hz, 1H), 7.66 (d, J=2.0 Hz, 1H), 5.55 (qt, J=5.5 Hz, 11H), 4.97 (t, J=5.3 Hz, 1H), 4.47 (t, J=5.0 Hz, 1H), 4.28-4.29 (m, 1H), 4.17 (dd, J=5.8 Hz, 10.3 Hz, 1H), 4.11 (dd, J=4.5 Hz, 10.0 Hz, 1H), 3.99 (s, 3H), 3.90 (t, J=7.5 Hz, 1H), 3.62 (t, J=8.5 Hz, 1H).

TABLE 10

The compounds in Table 10 were prepared according to the methods in Examples 163 and 164, starting with the appropriate starting materials.

| Example Number | Structure | HPLC-mass spectum m/e |
|---|---|---|
| 165 | 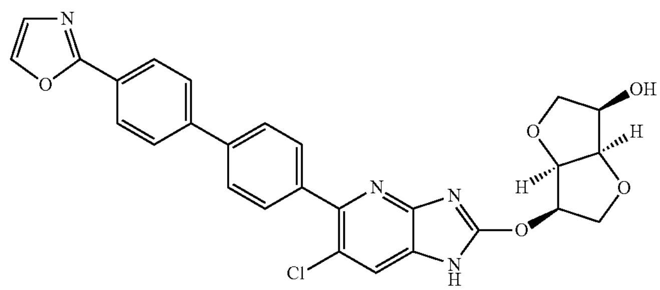 | 517.16 R = H* |
| 166 | 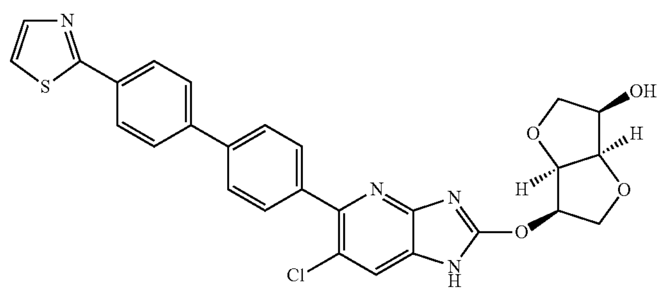 [SMILES: O[C@@H]1CO[C@H]2[C@@H]1OC[C@H]2Oc1nc2nc(-c3ccc(-c4ccc(-c5nccs5)cc4)cc3)c(Cl)cc2[nH]1] | 533.16 R = H* |
| 167 | 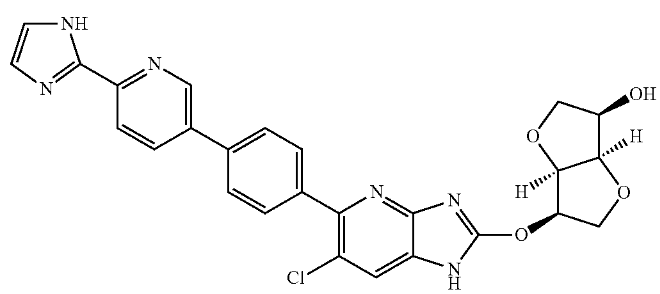 [SMILES: O[C@@H]1CO[C@H]2[C@@H]1OC[C@H]2Oc1nc2nc(-c3ccc(-c4ccc(-c5ncc[nH]5)nc4)cc3)c(Cl)cc2[nH]1] | 517.28 R = H* |
| 168 | 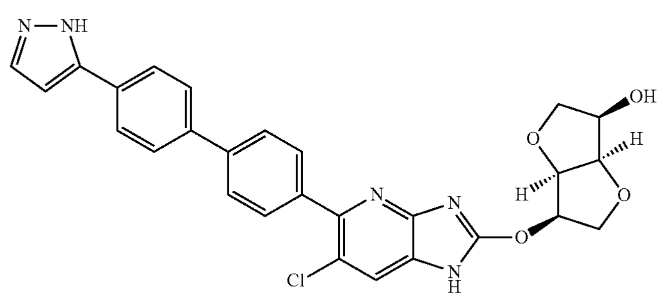 [SMILES: O[C@@H]1CO[C@H]2[C@@H]1OC[C@H]2Oc1nc2nc(-c3ccc(-c4ccc(-c5ccn[nH]5)cc4)cc3)c(Cl)cc2[nH]1] | 516.21 R = TBS* |

TABLE 10-continued

The compounds in Table 10 were prepared according to the methods in Examples 163 and 164, starting with the appropriate starting materials.

| Example Number | Structure | HPLC-mass spectum m/e |
|---|---|---|
| 169 | 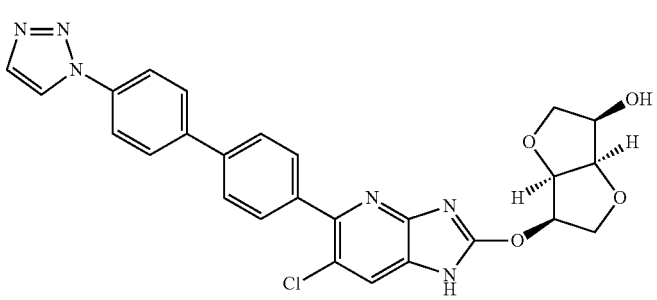 [SMILES: O[C@@H]1CO[C@H]2[C@@H]1OC[C@H]2Oc1nc2nc(-c3ccc(-c4ccc(-n5ccnn5)cc4)cc3)c(Cl)cc2[nH]1] | 517.20<br>R = TBS* |
| 170 | 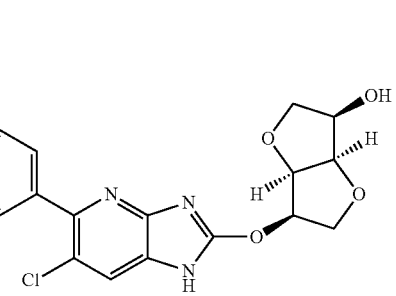 | 517.20<br>R = TBS* |

*The isomannide alcohol starting material was either unprotected (as —OH) or TBS protected (as —OTBS) during the 1,1'-bis(diphenylphosphino)ferrocene-palladium(II) dichloride dichloromethane complex coupling reaction used to prepare Examples 164-170 in Table 10. The TBS group was observed to substantially deblock during the reaction giving the unprotected alcohol (—OH). The use of TBS protection is noted in the mass spectrum entry of Examples 164-170 in Table 10.

The substituted dihydropyrrolo[3,4-c]pyrazole starting materials used in the coupling reactions of Examples 171-178 were prepared using procedures described in WO 2011/028455, and modifications of the procedures known to those skilled in the art. Example 173 uses a mixture of regioisomers 1-(cyclopropylmethyl)-5,6-dihydro-4H-pyrrolo[3,4-c]pyrazole and 2-(cyclopropylmethyl)-5,6-dihydro-4H-pyrrolo[3,4-c]pyrazole as the starting material. Example 177 is derived from starting material 2,4,5,6-tetrahydropyrrolo[3,4-c]pyrazole. Example 176 uses N-ethyl-5,6-dihydro-4H-pyrrolo[3,4-c]pyrazole-2-sulfonamide as the starting material; the sulfonamide of N-ethyl-5,6-dihydro-4H-pyrrolo[3,4-c]pyrazole-2-sulfonamide hydrolyzed under the reaction conditions to give Example 176.

EXAMPLE 171

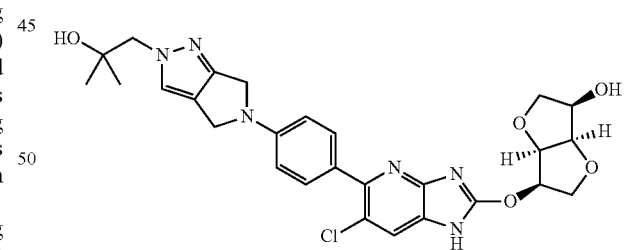

(3R,3aR,6R,6aR)-6-[[6-chloro-5-[4-[2-(2-hydroxy-2-methyl-propyl)-4,6-dihydropyrrolo[3,4-c]pyrazol-5-yl]phenyl]-1H-imidazo[4,5-b]pyridin-2-yl]oxy]-2,3,3a,5,6,6a-hexahydrofuro[3,2-b]furan-3-ol Step A (3R,3aR,6R,6aR)-6-[6-chloro-5-[4-[2-(2-hydroxy-2-methyl-propyl)-4,6-dihydropyrrolo[3,4-c]pyrazol-5-yl]phenyl]-1-(2-trimethysilylethoxymethyl)imidazo[4,5-b]pyridin-2-yl]oxy-2,3,3a,5,6,6a-hexahydrofuro[3,2-b]furan-3-ol. A mixture of tris(dibenzylideneacetone)dipalladium(0) (3.8 mg, 0.0041 mmol) and 1-phenyl-2-(di-tert-butylphosphino)-1H-pyrrole (3.0 mg, 0.010 mmol) in dioxane (0.2 mL) was stirred at room temperature under a nitrogen atmosphere for 30 minutes. A solution of 1-(5,6-dihydro-4H-pyrrolo[3,4-c]pyrazol-2-yl)-2-methyl-propan-2-ol; 2,2,2-trifluoroacetic acid (68.7 mg, 0.233 mmol), 2 M aqueous $K_3PO_4$ (0.2 mL, 0.4 mmol), and intermediate 7 (72.0 mg, 0.124 mmol) in dioxane (1.2 mL) was added to the above catalysts and the mixture was blanketed with nitrogen and placed in a 110° C. oil bath for 20 hours. The resulting mixture was added to ethyl acetate (30 mL) and water (20 mL), the organic layer was separated, washed with saturated aqueous sodium chloride (1×10 mL), dried with anhydrous magnesium sulphate, filtered and evaporated to an oil. The residue was dissolved in ethyl acetate and placed onto a preparative silica plate (1×1000 u) which was developed and the UV active band eluted with ethyl acetate to give an oil upon evaporation. LC-MS: calculated for $C_{33}H_{43}ClN_6O_6Si$ 682.27 observed m/e: 683.57 $(M+H)^+$ (Rt 1.25/2.0 min).

Step B (3R,3aR,6R,6aR-6-[[6-chloro-5-[4-[2-(2-hydroxy-2-methyl-propyl)-4,6-dihydropyrrolo[3,4-c]pyrazol-5-yl]phenyl]-1H-imidazo[4,5-b]pyridin-2-yl]oxy]-2,3,3a,5,6,6a-hexahydrofuro[3,2-b]furan-3-ol. A mixture of (3R,3aR,6R,6aR)-6-[6-chloro-5-[4-[2-(2-hydroxy-2-methyl-propyl)-4,6-dihydropyrrolo[3,4-c]pyrazol-5-yl]phenyl]-1-(2-trimethylsilylethoxymethyl)imidazo[4,5-b]pyridin-2-yl]oxy-2,3,3a,5,6,6a-hexahydrofuro[3,2-b]furan-3-ol (48.8 mg, 0.07 mmol), formic acid (1.5 mL), and saturated aqueous $KHSO_4$ (0.2 mL) was stirred at ambient temperature for 40 minutes and then placed in a refrigerator. After 18 hours, the reaction mixture was partitioned between EtOAc (50 mL) and saturated aqueous sodium bicarbonate (25 mL). The aqueous layer was extracted with EtOAc (2×20 mL). The organic layers were combined, washed with brine (1×10 mL), dried over $MgSO_4$, filtered, and evaporated under reduced pressure. The residue was dissolved in MeOH (1 mL) and 7 drops of 3 N aqueous NaOH were added over 15 minutes. The mixture was purified by HPLC reverse phase (C-18), using a 30×150 mm Sunfire™ column and eluting with a 20%-80% acetonitrile/water gradient to give the title compound as a light yellow solid following lyophilization. LC-MS: calculated for $C_{27}H_{29}ClN_6O_5$ 552.19 observed m/e: 553.44 $(M+H)^+$ (Rt 1.09/2.0 min); $^1H$ NMR δ (ppm) ($CD_3OD$): 7.96 (s, 1H), 7.62 (d, 1H), 7.52 (s, 1H), 6.81 (d, 1H), 5.59 (m, 1H), 4.98 (dd, 1H), 4.48 (dd, 1H), 4.30 (m, 1H), 4.16 (m, 2H), 4.14 (s, 2H), 3.91 (dd, 1H), 3.60 (dd, 1H) and 1.20 (s, 6H).

TABLE 11

The compounds in Table 11 were prepared according to the methods in Example 171, starting from the appropriate starting materials.

| Example Number | Structure | HPLC-mass spectrum m/e |
|---|---|---|
| 172 | 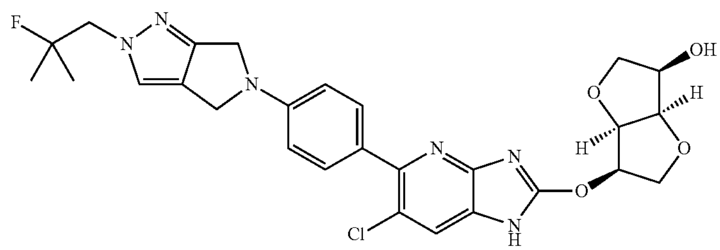 [SMILES: CC(C)(F)Cn1cc2c(n1)CN(c1ccc(-c3nc4nc(O[C@@H]5CO[C@H]6[C@@H]5OC[C@H]6O)[nH]c4cc3Cl)cc1)C2] | 555.08 |
| 173 | | 535.07 mixture of regioisomers |
| | | |

TABLE 11-continued

The compounds in Table 11 were prepared according to the methods in Example 171, starting from the appropriate starting materials.

| Example Number | Structure | HPLC-mass spectum m/e |
|---|---|---|
| 174 | 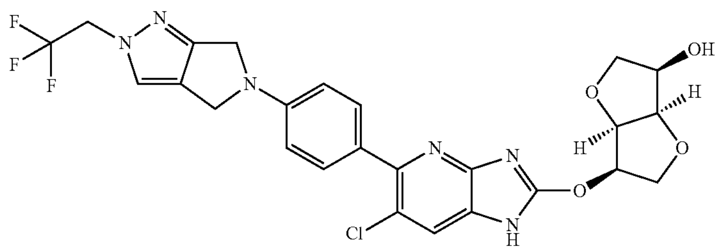 [SMILES: O[C@@H]1CO[C@H]2[C@@H]1OC[C@H]2Oc1nc2nc(-c3ccc(N4Cc5cn(CC(F)(F)F)nc5C4)cc3)c(Cl)cc2[nH]1] | 562.99 |
| 175 | 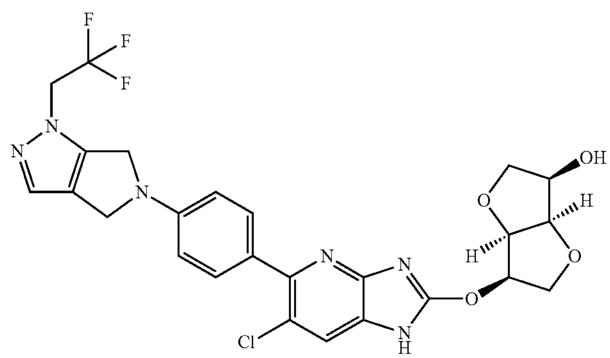 [SMILES: O[C@@H]1CO[C@H]2[C@@H]1OC[C@H]2Oc1nc2nc(-c3ccc(N4Cc5cnn(CC(F)(F)F)c5C4)cc3)c(Cl)cc2[nH]1] | 563.08 |
| 176 | 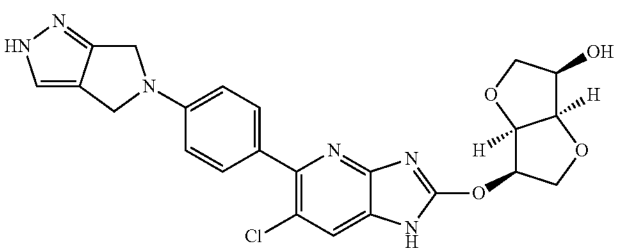 [SMILES: O[C@@H]1CO[C@H]2[C@@H]1OC[C@H]2Oc1nc2nc(-c3ccc(N4Cc5c[nH]nc5C4)cc3)c(Cl)cc2[nH]1] | 481.07 |
| 177 | 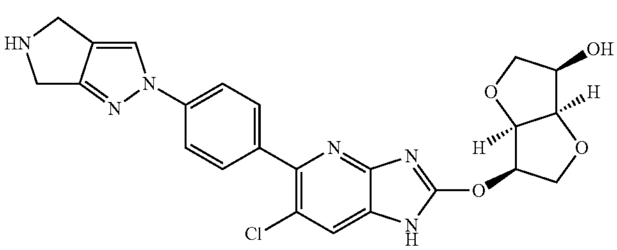 [SMILES: O[C@@H]1CO[C@H]2[C@@H]1OC[C@H]2Oc1nc2nc(-c3ccc(-n4cc5c(n4)CNC5)cc3)c(Cl)cc2[nH]1] | 480.92 |
| 178 | 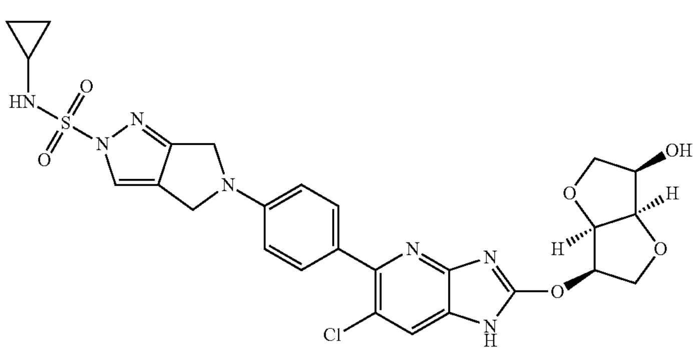 [SMILES: O=S(=O)(NC1CC1)n1cc2c(n1)CN(c1ccc(-c3nc4nc(O[C@@H]5CO[C@H]6[C@@H]5OC[C@H]6O)[nH]c4cc3Cl)cc1)C2] | 585.13 |

EXAMPLE 179

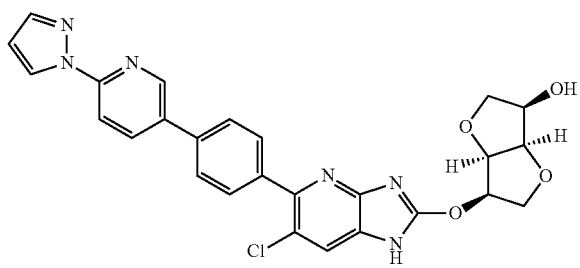

(3R,3aR,6R,6aR)-6-[[6-chloro-5-[4-(6-pyrazol-1-yl-3-pyridyl)phenyl]-1H-imidazo[4,5-b]pyridin-2-yl]oxy]-2,3,3a,5,6,6a-hexahydrofuro[3,2-b]furan-3-ol Step A (3R,3aR,6R,6aR)-6-[6-chloro-5-[4-(6-pyrazol-1-yl-3-pyridyl)phenyl]-1-(2-trimethlsilylethoxymethyl)imidazo[4,5-b]pyridin-2-yl]oxy-2,3,3a,5,6,6a-hexahydrofuro[3,2-b]furan-3-ol. 5-bromo-2-pyrazol-1-yl-pyridine (0.879 g, 3.92 mmol), 1,1'-bis(diphenylphosphino)ferrocene-palladium(II)dichloride dichloromethane complex (0.267 g, 0.327 mmol), and LiOH (2.72 mL, 8.17 mmol) were added to a stirred mixture of intermediate 8 (2.06 g, 3.27 mmol) in 1,4-dioxane (9 mL) and water (2.4 mL). The reaction mixture was placed under nitrogen, and then heated to 90° C. After 4 hours, the reaction mixture was cooled to room temperature before being partitioned between saturated aqueous ammonium chloride (200 mL) and EtOAc (150 mL). The aqueous layer was extracted with EtOAc (2×150 mL). The organic layers were combined, washed with brine (1×100 mL), dried over $Na_2SO_4$, filtered, and evaporated under reduced pressure. Flash chromatography of the resulting residue utilizing a silica gel Biotage™ 40M column and employing a 0-80% EtOAc/hexane gradient afforded the desired product as a light yellow solid. LC-MS: calculated for $C_{32}H_{35}ClN_6O_5Si$ 646.21 observed m/e: 647.53 (M+H)$^+$ (Rt 1.32/2 min).

Step B (3R,3aR,6R,6aR)-6-[[6-chloro-5-[4-(6-pyrazol-1-yl-3-pyridyl)phenyl]-1H-imidazo[4,5-b]pyridin-2-yl]oxy]-2,3,3a,5,6,6a-hexahydrofuro[3,2-b]furan-3-ol. A mixture of formic acid (6 mL, 156 mmol), saturated aqueous $KHSO_4$ (0.66 mL, 2.58 mmol), and (3R,3aR,6R,6aR)-6-[6-chloro-5-[4-(6-pyrazol-1-yl-3-pyridyl)phenyl]-1-(2-trimethylsilylethoxymethyl)imidazo[4,5-b]pyridin-2-yl]oxy-2,3,3a,5,6,6a-hexahydro-furo[3,2-b]furan-3-ol (1.67 g, 2.58 mmol) was stirred at 60° C. overnight, and then cooled to 0° C. in an ice bath. The pH of the reaction mixture was adjusted to pH>11 through the addition of NaOH (6.24 g, 156 mmol) in water (5 mL). THF (10 mL) was added to the reaction mixture, and the reaction was removed from the ice bath and allowed to warm to room temperature. After 30 minutes, the pH of the reaction mixture was adjusted to pH 6 through the addition of concentrated HCl. The biphasic mixture was separated. The organic layer and the resulting white precipitate were concentrated under reduced pressure, redissolved in DMSO, and filtered before being purified by preparative HPLC Reverse phase (C-18), using a 19×100 mm Sunfire™ column and eluting with a 10%-90% acetonitrile/water+0.05% TFA gradient followed by a 90% acetonitrile/water+0.05% TFA flush. The desired fractions were combined, and evaporated under reduced pressure. The resulting residue was washed with MeOH and lyophilized from acetonitrile and water to afford the title compound as a white solid. LC-MS: calculated for $C_{26}H_{21}ClN_6O_4$ 516.13 observed m/e: 517.22 (M+H)$^+$ (Rt 1.16/2 min); $^1$H NMR δ (ppm) (CD$_3$OD): 8.80 (d, J=2.5 Hz, 1H), 8.67 (d, J=2.0 Hz, 1H), 8.30 (dd, J=2.8 Hz, 8.5 Hz, 1H), 8.06 (d, J=9.0 Hz, 1H), 7.81-7.83 (m, 6H), 6.84 (t, J=2.3 Hz, 1H), 5.56 (qt, J=55 Hz, 1H), 4.99 (t, J=5.3 Hz, 1H), 4.49 (t, J=5.0 Hz, 1H), 4.28-4.32 (m, 1H), 4.19 (dd, J=6.0 Hz, 10 Hz, 1H), 4.13 (dd, J=4.8 Hz, 10.3 Hz, 1H), 3.92 (dd, J=7.0 Hz, J=8.0 Hz, 1H), 3.62 (t, J=8.5 Hz, 1H).

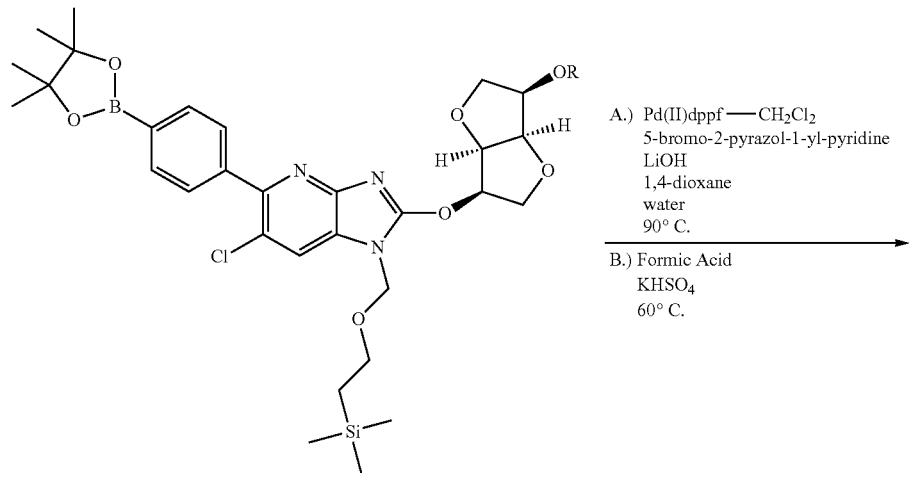

-continued

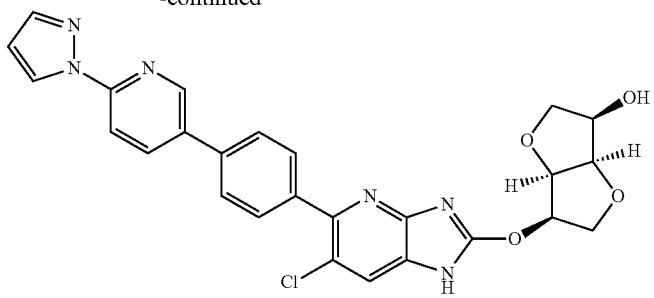

The isomannide alcohol was either unprotected (R=H) or TBS protected (R=TBS) during the coupling reaction used to prepare Example 179, as shown above. The TBS group was observed to substantially deblock during the reaction giving the unprotected alcohol (R=H).

EXAMPLE 180

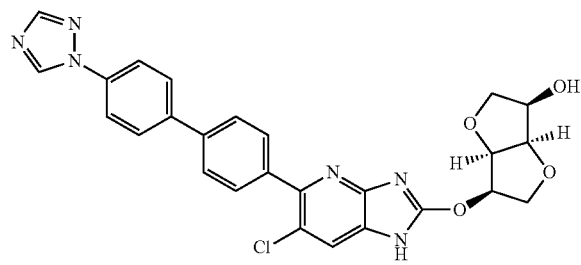 [SMILES: O[C@@H]1CO[C@H]2[C@@H]1OC[C@H]2Oc1nc2nc(-c3ccc(-c4ccc(-n5cncn5)cc4)cc3)c(Cl)cc2[nH]1]

(3R,3a,6R,6aR)-6-[[6-chloro-5-[4-[4-(1,2,4-triazol-1-yl)phenyl]phenyl]-1H-imidazo[4,5-b]pyridin-2-yl]oxy]-2,3,3a,5,6,6a-hexahdrofuro[3,2-b]furan-3-ol Step A (3R,3aR,6R,6aR)-6-[6-chloro-5-[4-[4-(1,2,4-triazol-1-yl)phenyl]phenyl]-1-(2-trimethylsilylethoxymethyl)imidazo[4,5-b]pyridin-2-yl]oxy-2,3,3a,5,6,6a-hexahdrofuro[3,2-b]furan-3-ol. 1-(4-bromophenyl)-1,2,4-triazole (0.557 g, 2.486 mmol), PalladiumTetrakis (0.383 g, 0.331 mmol), and potassium phosphate (1.407 g, 6.63 mmol) were added to a stirred mixture of intermediate 8 (1.044 g, 1.657 mmol) in dioxane (9 mL) and water (2.4 mL). The reaction mixture was placed under nitrogen before being heated to 90° C. After 4 hours, the reaction mixture was cooled to room temperature, and then partitioned between EtOAc (100 mL) and saturated aqueous ammonium chloride (100 mL). The aqueous layer was extracted with ethyl acetate (2×100 mL). The organic layers were combined, washed with brine (1×50 mL), dried over $Na_2SO_4$, filtered, and evaporated under reduced pressure. Flash chromatography of the resulting residue utilizing a silica gel Biotage™ 40M column and employing a 0-100% EtOAc/hexane gradient afforded the desired product as a light yellow solid. LC-MS: calculated for $C_{32}H_{35}ClN_6O_5Si$ 646.21 observed m/e: 647.01 (M+H)(Rt 1.26/2 min).

Step B (3R,3aR,6R,6aR)-6-[[6-chloro-5-[4-[4-(1,2,4-triazol-1-yl)phenyl]phenyl]-1H-imidazo[4,5-b]pyridin-2-yl]oxy]-2,3,3a,5,6,6a-hexahydrofuro[3,2-b]furan-3-ol. A mixture of formic acid (3 mL, 68.8 mmol), saturated aqueous $KHSO_4$ (0.33 mL, 1.777 mmol), and (3R,3aR,6R,6aR)-6-[6-chloro-5-[4-[4-(1,2,4-triazol-1-yl)phenyl]phenyl]-1-(2-trimethylsilylethoxymethyl)imidazo[4,5-b]pyridin-2-yl]oxy-2,3,3a,5,6,6a-hexahydrofuro[3,2-b]furan-3-ol (1.15 g, 1.777 mmol). The reaction mixture was stirred at 60° C. overnight, and then cooled to 0° C. in an ice bath. The pH of the reaction mixture was adjusted to pH>11 through the addition of NaOH (2.75 g, 68.8 mmol) in water (5 mL). THF (5 mL) was added to the reaction mixture, and the reaction was removed from the ice bath and allowed to warm to room temperature. After 30 minutes, the pH of the reaction mixture was adjusted to pH 6 through the addition of concentrated HCl. The biphasic mixture was separated. The organic layer and the resulting white precipitate that had formed were concentrated under reduced pressure, redissolved in DMSO, and filtered before being purified by preparative HPLC Reverse phase (C-18), using a 19×100 mm Sunfire™ column and eluting with a 10%-90% acetonitrile/water gradient+0.05% TFA followed by a 90% acetonitrile/water+0.05% TFA flush. The desired fractions were combined, and evaporated under reduced pressure. The resulting residue was washed with MeOH and lyophilized from acetonitrile and water to afford the title compound as a white solid. LC-MS: calculated for $C_{26}H_{21}ClN_6O_4$ 516.13 observed m/e: 516.85 (M+H)$^+$ (Rt 1.11/2 min); $^1$H NMR δ (ppm) (CD$_3$OD): 9.17 (s, 1H), 8.21 (s, 1H), 7.82-7.97 (m, 4H), 7.78-7.80 (m, 5H), 5.56 (qt, J=5.5 Hz, 1H), 4.98 (t, J=5.3 Hz, 1H), 4.49 (t, J=5 Hz, 11H), 4.28-4.32 (m, 1H), 4.19 (dd, J=6.0 Hz, 10.0 Hz, 1H), 4.12 (dd, J=5.0 Hz, 10.0 Hz, 1H), 3.92 (dd, J=7.0 Hz, 8.0 Hz, 1H), 3.62 (t, J=8.8 Hz, 1H).

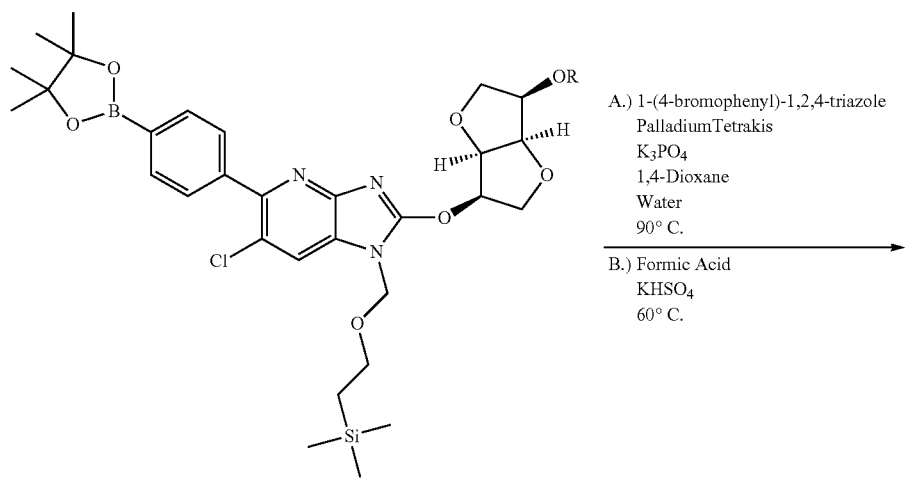

A.) 1-(4-bromophenyl)-1,2,4-triazole
PalladiumTetrakis
K₃PO₄
1,4-Dioxane
Water
90° C.

B.) Formic Acid
KHSO₄
60° C.

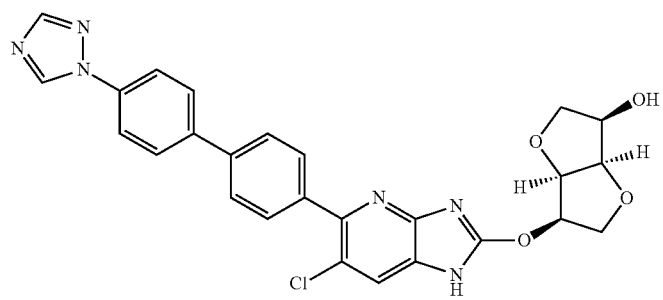

The isomannide alcohol starting material was either unprotected (R=H) or TBS protected (R=TBS) during the coupling reaction used to prepare Example 180, as shown above. The TBS group was observed to substantially deblock during the reaction giving the unprotected alcohol (R=H).

TABLE 12

The compounds in Table 12 were prepared according to the methods in Examples 179 and 180, starting from the appropriate starting materials.

| Example Number | Structure | HPLC-mass spectrum m/e |
|---|---|---|
| 181 | 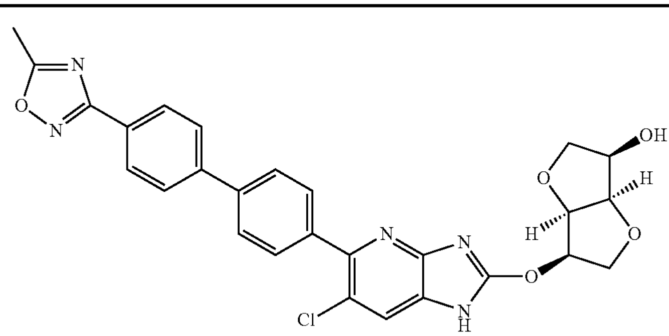 | 532.28 R = TBS* |

TABLE 12-continued

The compounds in Table 12 were prepared according to the methods in Examples 179 and 180, starting from the appropriate starting materials.

| Example Number | Structure | HPLC-mass spectum m/e |
|---|---|---|
| 182 | 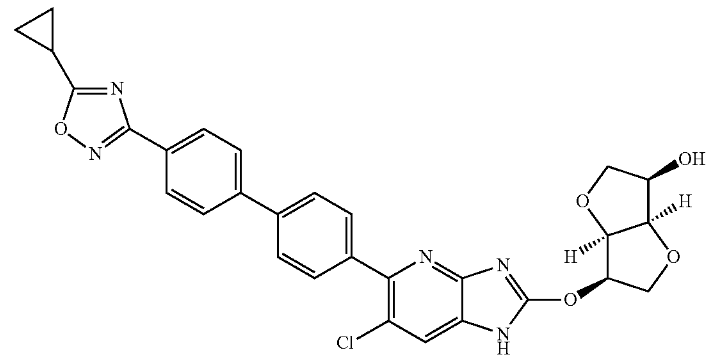 [SMILES: O[C@@H]1CO[C@H]2[C@@H]1OC[C@H]2Oc1nc2nc(-c3ccc(-c4ccc(-c5noc(C6CC6)n5)cc4)cc3)c(Cl)cc2[nH]1] | 558.36<br>R = H* |
| 183 | 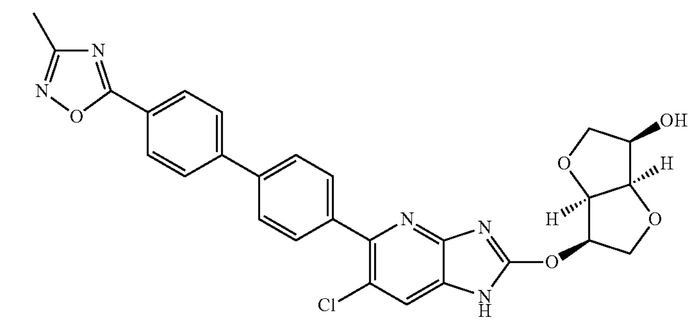 [SMILES: Cc1noc(-c2ccc(-c3ccc(-c4nc5nc(O[C@@H]6CO[C@H]7[C@@H]6OC[C@H]7O)[nH]c5cc4Cl)cc3)cc2)n1] | 532.29<br>R = H* |
| 184 | 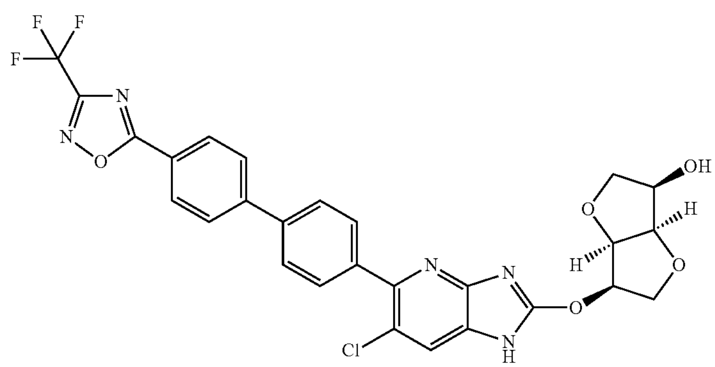 [SMILES: O[C@@H]1CO[C@H]2[C@@H]1OC[C@H]2Oc1nc2nc(-c3ccc(-c4ccc(-c5nc(C(F)(F)F)no5)cc4)cc3)c(Cl)cc2[nH]1] | 586.32<br>R = H* |
| 185 | 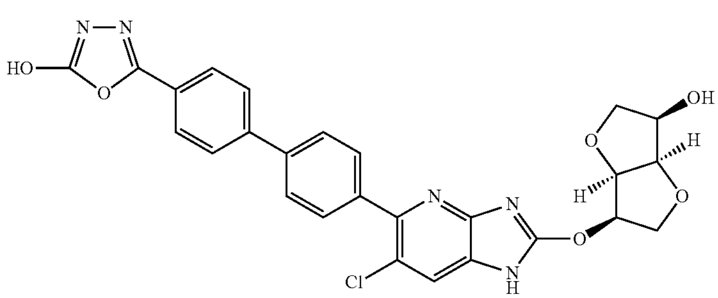 [SMILES: Oc1nnc(-c2ccc(-c3ccc(-c4nc5nc(O[C@@H]6CO[C@H]7[C@@H]6OC[C@H]7O)[nH]c5cc4Cl)cc3)cc2)o1] | 534.34<br>R = H* |

TABLE 12-continued

The compounds in Table 12 were prepared according to the methods in Examples 179 and 180, starting from the appropriate starting materials.

| Example Number | Structure | HPLC-mass spectum m/e |
|---|---|---|
| 186 | 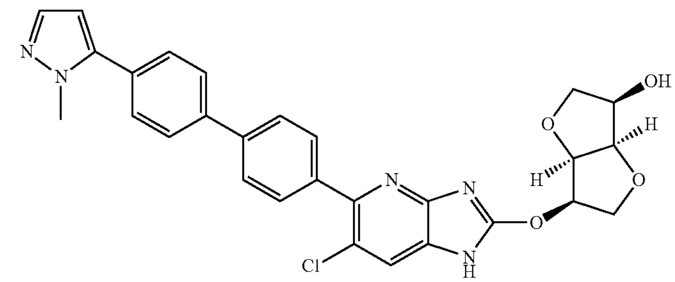 [SMILES: Cn1nccc1-c1ccc(-c2ccc(-c3nc4nc(O[C@@H]5CO[C@H]6[C@@H]5OC[C@H]6O)[nH]c4cc3Cl)cc2)cc1] | 529.97 R = H* |
| 187 | 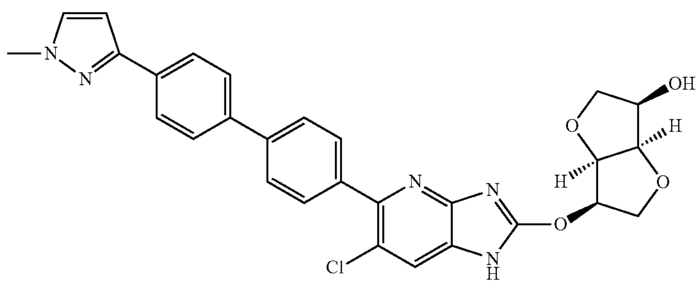 [SMILES: Cn1ccc(-c2ccc(-c3ccc(-c4nc5nc(O[C@@H]6CO[C@H]7[C@@H]6OC[C@H]7O)[nH]c5cc4Cl)cc3)cc2)n1] | 529.96 R = H* |
| 188 | 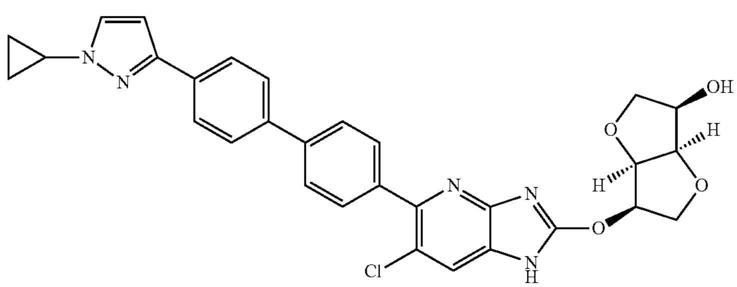 [SMILES: O[C@@H]1CO[C@H]2[C@@H]1OC[C@H]2Oc1nc2nc(-c3ccc(-c4ccc(-c5ccn(C6CC6)n5)cc4)cc3)c(Cl)cc2[nH]1] | 556.43 R = H* |
| 189 | 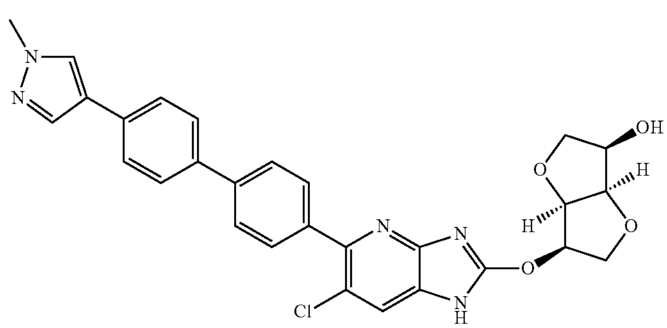 [SMILES: Cn1cc(-c2ccc(-c3ccc(-c4nc5nc(O[C@@H]6CO[C@H]7[C@@H]6OC[C@H]7O)[nH]c5cc4Cl)cc3)cc2)cn1] | 530.29 R = H* |
| 190 | 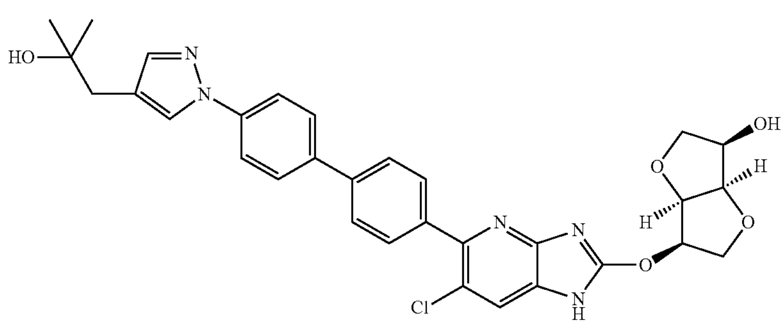 [SMILES: CC(C)(O)Cc1cnn(-c2ccc(-c3ccc(-c4nc5nc(O[C@@H]6CO[C@H]7[C@@H]6OC[C@H]7O)[nH]c5cc4Cl)cc3)cc2)c1] | 587.97 R = H* |

TABLE 12-continued

The compounds in Table 12 were prepared according to the methods in Examples 179 and 180, starting from the appropriate starting materials.

| Example Number | Structure | HPLC-mass spectum m/e |
|---|---|---|
| 191 | 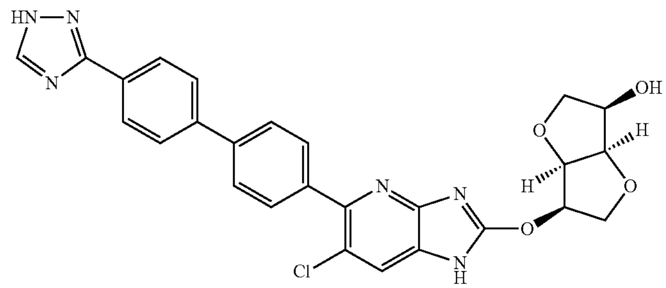 [SMILES: O[C@@H]1CO[C@H]2[C@@H]1OC[C@H]2Oc1nc2nc(-c3ccc(-c4ccc(-c5nc[nH]n5)cc4)cc3)c(Cl)cc2[nH]1] | 517.27<br>R = H* |
| 192 | 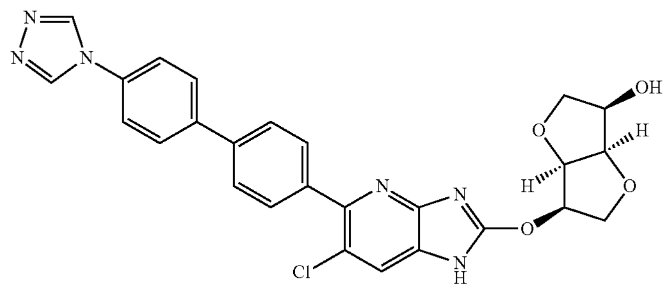 [SMILES: O[C@@H]1CO[C@H]2[C@@H]1OC[C@H]2Oc1nc2nc(-c3ccc(-c4ccc(-n5cnnc5)cc4)cc3)c(Cl)cc2[nH]1] | 517.34<br>R = TBS* |
| 193 | 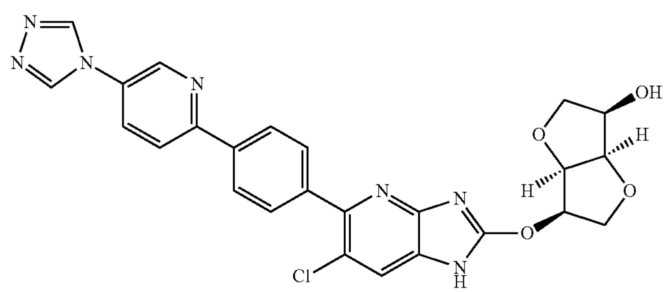 [SMILES: O[C@@H]1CO[C@H]2[C@@H]1OC[C@H]2Oc1nc2nc(-c3ccc(-c4ccc(-n5cnnc5)cn4)cc3)c(Cl)cc2[nH]1] | 518.26<br>R = TBS* |
| 194 | 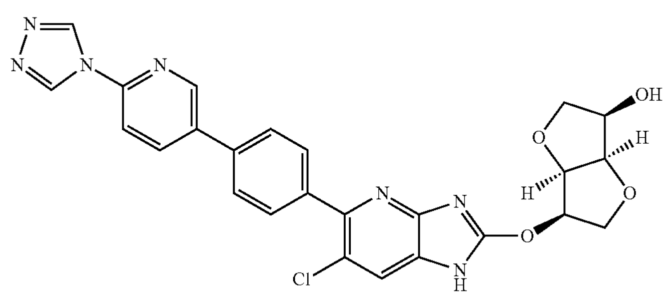 [SMILES: O[C@@H]1CO[C@H]2[C@@H]1OC[C@H]2Oc1nc2nc(-c3ccc(-c4ccc(-n5cnnc5)nc4)cc3)c(Cl)cc2[nH]1] | 518.41<br>R = H* |
| 195 | 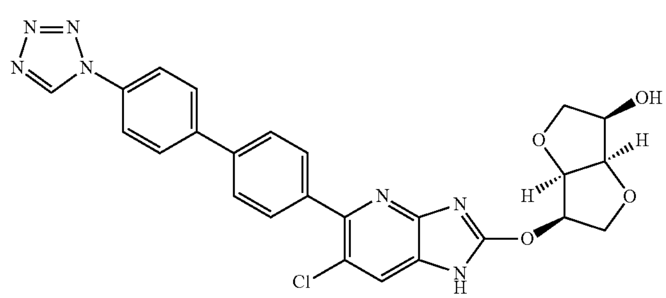 [SMILES: O[C@@H]1CO[C@H]2[C@@H]1OC[C@H]2Oc1nc2nc(-c3ccc(-c4ccc(-n5cnnn5)cc4)cc3)c(Cl)cc2[nH]1] | 517.99<br>R = H* |

TABLE 12-continued

The compounds in Table 12 were prepared according to the methods in Examples 179 and 180, starting from the appropriate starting materials.

| Example Number | Structure | HPLC-mass spectum m/e |
|---|---|---|
| 196 | (structure shown) | 518.98<br>R = H* |
| 197 | (structure shown) | 519.35<br>R = H* |

*The isomannide alcohol starting material was either unprotected (as —OH) or TBS protected (as —OTBS) during the coupling reaction used to prepare Examples 181-197 in Table 12. The TBS group was observed to substantially deblock during the reaction giving the unprotected alcohol (—OH). The use of TBS protection is noted in the mass spectrum entry of Examples 181-197 in Table 12.

EXAMPLE 198

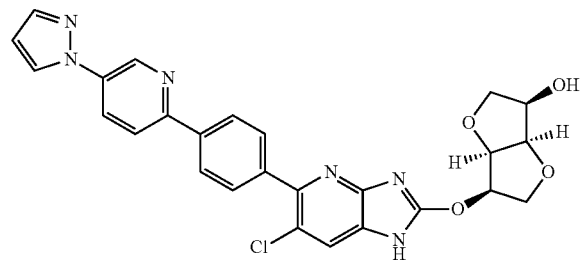 [SMILES: O[C@@H]1CO[C@H]2[C@@H]1OC[C@H]2Oc1nc2nc(-c3ccc(-c4ccc(-n5cccn5)cn4)cc3)c(Cl)cc2[nH]1]

(3R,3aR,6R,6aR)-6-[[6-chloro-5-[4-(5-pyrazol-1-yl-2-pyridyl)phenyl]-1H-imidazo[4,5-b]pyridin-2-yl]oxy]-2,3,3a,5,6,6a-hexahydrofuro[3,2-b]furan-3-ol Step A (3R,3aR,6R,6aR)-6-[6-chloro-5-[4-(5-pyrazol-1-yl-2-pyridyl)phenyl-1-(2-trimethylsilylethoxymethyl)imidazo[4,5-b]pyridin-2-yl]oxy-2,3,3a,5,6,6a-hexahydrofuro[3,2-b]furan-3-ol. A mixture of intermediate 9 (81.0 mg, 0.123 mmol), pyrazole (11.2 mg, 0.165 mmol), potassium phosphate (76.1 mg, 0.359 mmol), and copper(I) iodide (5.0 mg, 0.026 mmol) was evacuated and backfilled with nitrogen (3×). Trans-(1R,2R)—N,N'-bismethyl-1,2-cyclohexanediamine (10 µl, 0.063 mmol) and DMF (0.25 mL) were added, and the suspension was heated to 110° C. with stirring. After 24 hours, the reaction mixture was cooled to room temperature, and then filtered through a pad of Celite™, and rinsed with EtOAc (75 mL). The filtrate was washed with water (3×30 mL) and brine (1×20 mL), dried over Na$_2$SO$_4$, filtered, and evaporated under reduced pressure to give an amber residue. Preparative thin layer chromatography of the residue using two 500 micron 20 cm×20 cm silica gel plates, which were developed using 80% EtOAc/Hexanes afforded the desired product as a colorless residue. LC-MS: calculated for C$_{32}$H$_{35}$ClN$_6$O$_5$S±646.21 observed m/e: 647.45 (M+H)$^+$ (Rt 1.27/2 min).

Step B (3R,3aR,6R6aR)-6-[[6-chloro-5-[4-(5-pyrazol-1-yl-2-pyridyl)phenyl]-1H-imidazo[4,5-b]pyridin-2-yl]oxy]-2,3,3a,5,6,6a-hexahdrofuro[3,2-b]furan-3-ol. A mixture of (3R,3aR,6R,6aR)-6-[6-chloro-5-[4-(5-pyrazol-1-yl-2-pyridyl)phenyl]-1-(2-trimethylsilylethoxymethyl)imidazo[4,5-b]pyridin-2-yl]oxy-2,3,3a,5,6,6a-hexahydrofuro[3,2-b]furan-3-ol (32.7 mg, 0.051 mmol), formic acid (1.0 mL, 26.1 mmol), and saturated aqueous KHSO$_4$ (0.05 mL) was heated to 40° C. with stirring. After 16.5 hours, the reaction mixture was cooled to room temperature, and then cooled to 0° C. in an ice bath. The pH of the reaction mixture was adjusted to pH 14 through the addition of 5 N NaOH (5.8 mL, 29 mmol). THF (2 mL) was added to the reaction mixture, which was removed from the ice bath and allowed to warm to room temperature. After 1.5 hours, the pH of the reaction mixture was adjusted to pH 6 through the addition of 2 N HCl. The reaction mixture was partitioned between EtOAc (30 mL) and water (30 mL). The aqueous layer was extracted with EtOAc (2×20 mL). The organic layers were combined, washed with brine (1×20 mL), dried over Na$_2$SO$_4$, filtered, and evaporated under reduced pressure to give a white residue. Purification of the residue by HPLC reverse phase (C-18), using a 30×150 mm Sunfire™ column and eluting with a 20%-70% acetonitrile/water+0.05% TFA gradient, followed by a 70% acetonitrile/water+0.05% TFA flush solid followed by lyophilization from ethanol and benzene afforded the title compound as a white. LC-MS: calculated for C$_{26}$H$_{21}$ClN$_6$O$_4$ 517.13 observed m/e: 517.35 (M+H)$^+$ (Rt 1.11/2 min); $^1$H NMR δ

(ppm) (CD$_3$OD): 9.21 (d, J=2.6 Hz, 1H), 8.52 (dd, J=2.6 Hz, 8.6 Hz, 1H), 8.47 (d, J=2.6 Hz, 1H), 8.24 (d, J=8.7 Hz, 1H), 8.19 (d, J=8.4 Hz, 2H), 8.04 (s, 1H), 7.89 (d, J=8.3 Hz, 2H), 7.87 (d, J=1.8 Hz, 1H), 6.66 (t, J=2.2 Hz, 1H), 5.61 (qt, J=5.2 Hz, 1H), 4.99 (t, J=5.2 Hz, 1H), 4.48 (t, J3=5.1Hz, 1H), 4.28-4.32 (m, 1H), 4.18 (d, J=5.1Hz, 2H), 3.91 (dd, J=6.8 Hz, 8.2 Hz, 1H), 3.61 (t, J=8.6, 1H).
TABLE 13
The compounds in Table 13 were prepared according to the methods in Example 198, starting from the appropriate starting materials.
| Example Number | Structure | HPLC-mass spectum m/e |
|---|---|---|
| 199 | 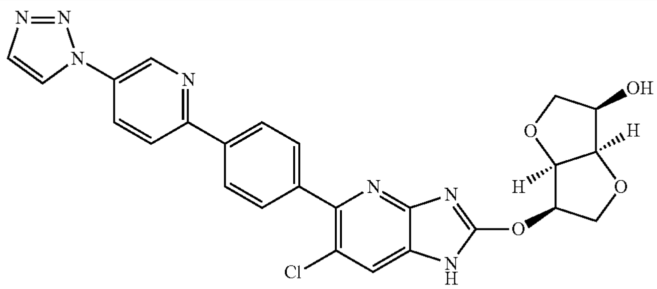 [SMILES: O[C@@H]1CO[C@H]2[C@@H]1OC[C@H]2Oc1nc2nc(-c3ccc(-c4ccc(-n5ccnn5)cn4)cc3)c(Cl)cc2[nH]1] | 518.36 |
| 200 | 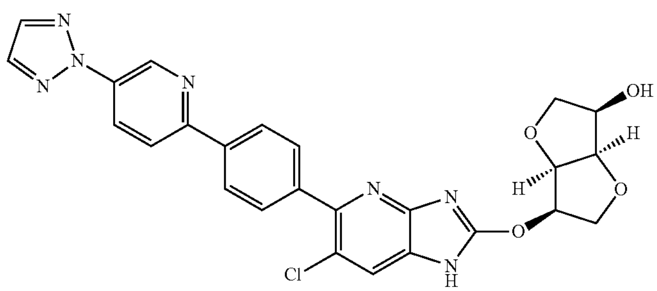 [SMILES: O[C@@H]1CO[C@H]2[C@@H]1OC[C@H]2Oc1nc2nc(-c3ccc(-c4ccc(-n5nccn5)cn4)cc3)c(Cl)cc2[nH]1] | 518.36 |
| 201 | 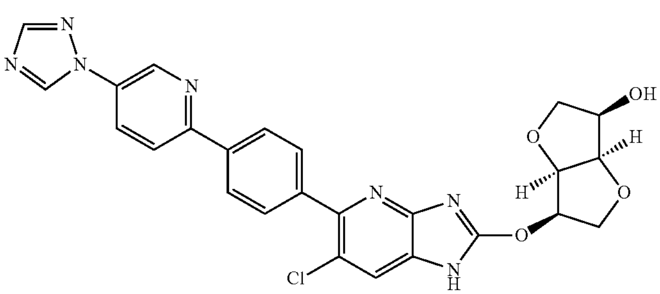 [SMILES: O[C@@H]1CO[C@H]2[C@@H]1OC[C@H]2Oc1nc2nc(-c3ccc(-c4ccc(-n5cncn5)cn4)cc3)c(Cl)cc2[nH]1] | 518.32 |
EXAMPLE 202
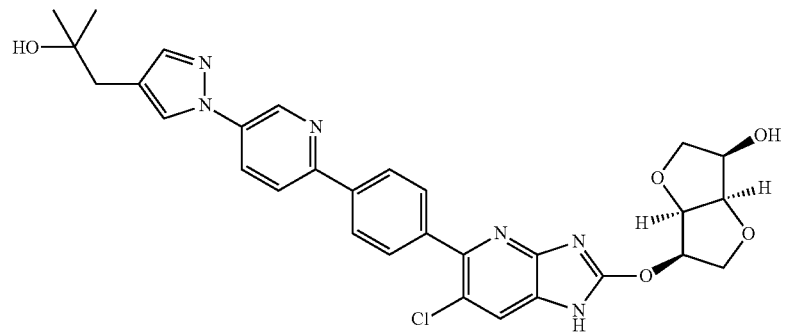 [SMILES: CC(C)(O)Cc1cnn(-c2ccc(-c3ccc(-c4nc5nc(O[C@@H]6CO[C@H]7[C@@H]6OC[C@H]7O)[nH]c5cc4Cl)cc3)nc2)c1]

(3R,3aR,6R,6aR)-6-[[6-chloro-5-[4-[5-[4-(2-hydroxy-2-methyl-propyl)pyrazol-1-yl]-2-pyridyl]phenyl]-1H-imidazo[4,5-b]pyridin-2-yl]oxy]-2,3,3a,5,6,6a-hexahydrofuro[3,2-b]furan-3-ol Step A 2-[1-[6-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]-3-pyridyl]pyrazol-4-yl]acetic acid. To a mixture of intermediate 9 (196.6 mg, 0.298 mmol), methyl 2-(1H-pyrazol-4-yl)acetate (87.2 mg, 0.622 mmol), potassium phosphate (191.9 mg, 0.904 mmol), and copper(I) iodide (11.9 mg, 0.062 mmol) in an 8 mL vial was added trans-(1R,2R)—N,N'-bismethyl-1,2-cyclohexanediamine (20.0 μl, 0.127 mmol) and DMF (0.6 mL). The resulting suspension was heated to 110° C. After 24 hours, the reaction mixture was cooled to room temperature before being partitioned between EtOAc (50 mL) and 2 NHCl (50 mL). The biphasic mixture was filtered and the solids were collected. The biphasic filtrate was partitioned, while the solids were washed with EtOAc (2×30 mL). Each of these EtOAc washes was used to extract the aqueous layer. The organic layers were combined, washed with brine (1×30 mL), dried over $Na_2SO_4$, filtered, and evaporated under reduced pressure to give a yellow residue. The residue was dissolved in EtOAc (50 mL) and water (20 mL). The biphasic mixture was partitioned and the aqueous layer was extracted with EtOAc (1×50 mL). The organic layers were combined, washed with brine (1×20 mL), dried over $MgSO_4$, filtered, and evaporated under reduced pressure to give a yellow residue. The filtered solids were washed with MeOH (30 mL), which was combined with the residue from the workup and evaporated under reduced pressure to give a yellow residue. Purification of the residue by HPLC reverse phase (C-18), using a 30×150 mm Sunfire™ column and eluting with a 20%-100% acetonitrile/water+0.05% TFA gradient followed by a 100% acetonitrile+0.05% TFA flush afforded the desired compound as a yellow residue. LC-MS: calculated for $C_{34}H_{37}ClN_6O_7Si$ 704.22 observed m/e: 705.32 (M+H)$^+$ (Rt 1.20/2 min).

Step B methyl 2-[1-[6-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]-3-pyridyl]pyrazol-4-yl]acetate. TMS-Diazomethane (2 M in hexanes, 0.15 mL, 0.300 mmol) was added to a stirred solution of 2-[1-[6-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)-imidazo[4,5-b]pyridin-5-yl]phenyl]-3-pyridyl]pyrazol-4-yl] acetic acid (27.3 mg, 0.039 mmol) in MeOH (0.5 mL) and DCM (0.5 mL). The reaction mixture was stirred at room temperature. After 3.5 hours, the reaction mixture was evaporated under reduced pressure to give the desired compound as a yellow residue. This material was used in the next step without further purification. LC-MS: calculated for $C_{35}H_{39}ClN_6O_7Si$ 718.23 observed m/e: 719.31 (M+H)$^+$ (Rt 1.26/2 min).

Step C (3R,3aR,6R,6aR)-6-[6-chloro-5-[4-[5-[4-(2-hydroxy-2-methyl-propyl)pyrazol-1-yl]-2-pyridyl]phenyl]-1-(2-trimethlsilylethoxymethyl)imidazo[4,5-b]pyridin-2-yl]oxy-2,3,3a,5,6,6a-hexahydrofuro[3,2-b]furan-3-ol.
Methylmagnesium bromide (0.2 mL, 0.600 mmol) was added to a stirred solution of methyl 2-[1-[6-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]-3-pyridyl]pyrazol-4-yl] acetate from Step B in THF (1 mL). The reaction mixture was stirred at room temperature. After 2.5 hours, the reaction mixture was partitioned between EtOAc (40 mL) and saturated aqueous $NH_4Cl$ (40 mL). The aqueous layer was extracted with EtOAc (2×20 mL). The organic layers were combined, washed with brine (1× mL), dried over $Na_2SO_4$, filtered, and evaporated under reduced pressure to give a yellow residue. Purification of the residue by HPLC reverse phase (C-18), using a 30×150 mm Sunfire™ column and eluting with a 20%-100% acetonitrile/water+0.05% TFA gradient followed by a 100% acetonitrile+0.05% TFA flush afforded the desired compound as a yellow residue. LC-MS: calculated for $C_{36}H_{43}ClN_6O_6S\pm 718.27$ observed m/e: 719.52 (M+H)$^+$ (Rt 1.23/2 min).

Step D (3R,3aR6R,6aR)-6-[[6-chloro-5-[4-[5-[4-(2-hydroxy-2-methyl-propyl)pyrazol-1-yl]-2-pyridyl]phenyl]-1H-imidazo[4,5-b]pyridin-2-yl]oxy]-2,3,3a,5,6,6a-hexahydrofuro[3,2-b]furan-3-ol. A mixture of (3R,3aR,6R,6aR)-6-[6-chloro-5-[4-[5-[4-(2-hydroxy-2-methyl-propyl)pyrazol-1-yl]-2-pyridyl]phenyl]-1-(2-trimethylsilylethoxy-methyl)imidazo[4,5-b]pyridin-2-yl]oxy-2,3,3a,5,6,6a-hexahydrofuro[3,2-b]furan-3-ol (10.1 mg, 0.014 mmol), formic acid (1.0 mL, 26.1 mmol), and saturated aqueous $KHSO_4$ (0.05 mL) was heated to 40° C. with stirring. After 16 hours, the reaction mixture was cooled to room temperature before being cooled to 0° C. in an ice bath. The pH of the reaction mixture was adjusted to pH 14 through the addition of 5 N NaOH (5.8 mL, 29.0 mmol). THF (2 mL) was added to the reaction mixture, and the reaction was removed from the ice bath and allowed to warm to room temperature. After 30 minutes, the pH of the reaction mixture was adjusted to pH 7 through the addition of 2 N HCl. The reaction mixture was partitioned between EtOAc (30 mL) and water (20 mL). The aqueous layer was extracted with EtOAc (2×20 mL). The organic layers were combined, washed with brine (1× mL), dried over $MgSO_4$, filtered, and evaporated under reduced pressure to give a white residue. This material was dissolved in DMSO/MeOH, and purified by HPLC reverse phase (C-18), using a 30×150 mm Sunfire™ column and eluting with a 20%-100% acetonitrile/water+0.05% TFA gradient followed by a 100% acetonitrile+0.05% TFA flush. The desired fractions were combined, evaporated under reduced pressure, and lyophilized from ethanol and benzene to afford the title compound as a pale yellow solid. LC-MS: calculated for $C_{30}H_{29}ClN_6O_5$ 589.19 observed m/e: 589.28 (M+H)$^+$ (Rt 1.10/2 min); $^1$H NMR δ (ppm) (CD$_3$OD): 9.15 (d, J=2.5 Hz, 1H), 8.46 (dd, J=2.7 Hz, 8.9 Hz, 1H), 8.26 (s, 1H), 8.19 (d, J=8.7 Hz, 1H), 8.14 (d, J=8.4 Hz, 2H), 7.97 (s, 1H), 7.86 (d, J=8.4 Hz, 1H), 7.73 (s, 1H), 5.58 (qt, J=5.2 Hz, 1H), 4.98 (t, J=5.2 Hz, 11H), 4.47 (t, J=5.0 Hz, 1H), 4.27-4.31 (m, 1H), 4.17 (dd, J=5.4 Hz, 10.2 Hz, 1H), 4.14 (dd, J=4.7 Hz, 10.2 Hz, 1H), 3.91 (m, 1H), 3.60 (t, J=8.6 Hz, 1H), 2.73 (s, 2H), 1.25 (s, 6H).

EXAMPLE 203

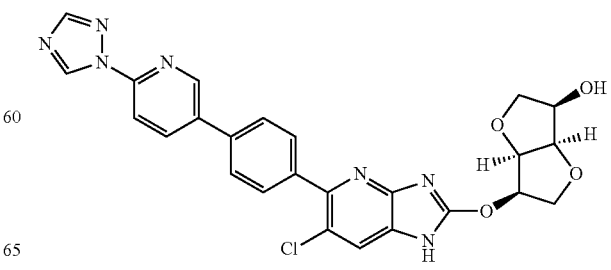

(3R,3aR,6R,6aR-6-[[6-chloro-5-[4-[6-(1,2,4-triazol-1-yl)-3-pyridyl]phenyl-1H-imidazo[4,5-b]pyridin-2-yl]oxy]-2,3,3a,6,6a-hexahydrofuro3,2-b]furan-3-ol Step A (3R,3aR,6R,6aR)-6-[6-chloro-5-[4-[6-(1,2,4-triazol-1-yl)-3-pyridyl]phenyl]-1-(2-trimethylsilylethoxymethyl)imidazo[4,5-b]pyridin-2-yl]oxy-2,3,3a,5,6,6a-hexahydrofuro[3,2-b]furan-3-ol. To a mixture of intermediate 10 (89.7 mg, 0.136 mmol), 1,2,4-triazole (11.5 mg, 0.167 mmol), copper(I) iodide (5.4 mg, 0.028 mmol), and potassium phosphate (71.8 mg, 0.338 mmol) under nitrogen was added trans-(1R,2R)—N,N'-bismethyl-1,2-cyclohexanediamine (10 μl, 0.063 mmol) and DMF (0.27 mL). The resulting suspension was heated to 110° C. with stirring. After 25 hours, the reaction mixture was cooled to room temperature and then filtered through a pad of Celite™, and rinsed with EtOAc (75 mL). The filtrate was washed with water (3×20 mL) and brine (1×20 mL), dried over $Na_2SO_4$, filtered, and evaporated under reduced pressure to give a pale yellow residue. The residue was purified by preparative thin layer chromatography using a 500 micron 20 cm×20 cm silica gel plate, which was developed using 85% EtOAc/Hexanes to give a colorless residue. The residue was further purified by HPLC reverse phase (C-18), using a 30×150 mm Sunfire™ column and eluting with a 20%-100% acetonitrile/water+0.05% TFA gradient, followed by a 100% acetonitrile+0.05% TFA flush to give the desired compound as a colorless residue. LC-MS: calculated for $C_{31}H_{34}ClN_7O_5Si$ 647.21 observed m/e: 648.45 $(M+H)^+$ (Rt 1.27/2 min).

Step B (3R,3aR,6R,6aR)-6-[[6-chloro-5-[4-[6-(1,2,4-triazol-1-yl)-3-pyridyl]phenyl-1H-imidazo[4,5-b]pyridin-2-yl]oxy]-2,3,3a,5,6,6a-hexahydrofuro[3,2-b]furan-3-ol A mixture of (3R,3aR,6R,6aR)-6-[6-chloro-5-[4-[6-(1,2,4-triazol-1-yl)-3-pyridyl]phenyl]-1-(2-trimethylsilylethoxymethyl)imidazo[4,5-b]pyridin-2-yl]oxy-2,3,3a,5,6,6a-hexahydrofuro[3,2-b]furan-3-ol (29.2 mg, 0.045 mmol), formic acid (1.0 mL, 26.1 mmol), and saturated aqueous $KHSO_4$ (0.05 mL) was heated to 40° C. After 15 hours, the reaction mixture was cooled to room temperature before being cooled to 0° C. in an ice bath. The pH of the reaction mixture was adjusted to pH 14 through the addition of 5 N NaOH (5.8 mL, 29.0 mmol). THF (2 mL) was added to the reaction mixture, and the reaction was removed from the ice bath and allowed to warm to room temperature. After 30 minutes, the pH of the reaction mixture was adjusted to pH 6 through the addition of 2 N HCl. The reaction mixture was partitioned between EtOAc (40 mL) and water (30 mL). The aqueous layer was extracted with EtOAc (2×20 mL). The organic layers were combined, washed with brine (1×20 mL), dried over $Na_2SO_4$, filtered, and evaporated under reduced pressure to give a white residue. Purification of the residue by HPLC reverse phase (C-18), using a 30×150 mm Sunfire™ column and eluting with a 20%-80% acetonitrile/water+ 0.05% TFA gradient, followed by a 80% acetonitrile/water+ 0.05% TFA flush and followed by lyophilization from ethanol and benzene afforded the title compound as an off-white solid. LC-MS: calculated for $C_{25}H_{20}ClN_7O_4$ 517.13 observed m/e: 517.30 $(M+H)^+$ (Rt 1.10/2 min); $^1H$ NMR δ (ppm) ($CD_3OD$): 9.42 (s, 1H), 8.89 (d, J=2.2 Hz, 1H), 8.39 (dd, J=2.4 Hz, 8.6 Hz, 1H), 8.25 (s, 1H), 8.07 (d, J=8.5 Hz, 1H), 7.97 (s, 1H), 7.86 (m, 4H), 5.59 (qt, J=5.2 Hz, 1H), 4.99 (t, J=5.2 Hz, 1H), 4.48 (t, J=5.0 Hz, 1H), 4.28-4.32 (m, 1H), 4.14-4.20 (m, 2H), 3.92 (dd, J=6.8 Hz, 8.2 Hz, 1H), 3.61 (t, J=8.7 Hz, 1H).

TABLE 14

The compounds in Table 14 were prepared according to the methods in Example 203, starting from the appropriate starting materials.

| Example Number | Structure | HPLC-mass spectrum m/e |
| --- | --- | --- |
| 204 | 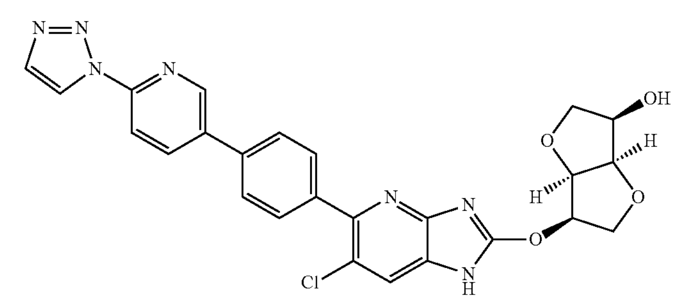 [SMILES: O[C@@H]1CO[C@H]2[C@@H]1OC[C@H]2Oc1nc2nc(-c3ccc(-c4ccc(-n5ccnn5)nc4)cc3)c(Cl)cc2[nH]1] | 518.36 |
| 205 | 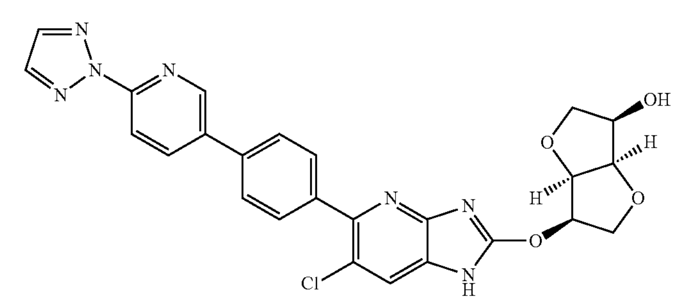 [SMILES: O[C@@H]1CO[C@H]2[C@@H]1OC[C@H]2Oc1nc2nc(-c3ccc(-c4ccc(-n5nccn5)nc4)cc3)c(Cl)cc2[nH]1] | 518.36 |

EXAMPLE 206

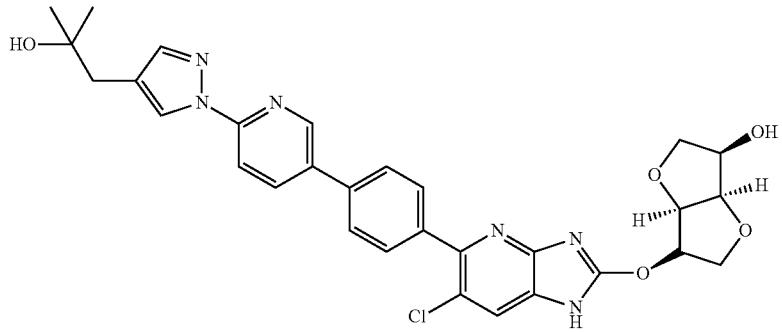

(3R,3aR6R6aR)-6-[[6-chloro-5-[4-[6-[4-(2-hydroxy-2-methyl-propyl)pyrazol-1-yl]-3-pyridyl]phenyl]-1H-imidazo[4,5-b]pyridin-2-yl]oxy]-2,3,3a,5,6,6a-hexahydrofuro[3,2-b]furan-3-ol Step A 2-[1-[5-[4-[2-[[(3R,3aR6R6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]yl]pyridin-5-yl]phenyl]-2-pyridyl]pyrazol-4-yl]acetic acid. To a mixture of methyl 2-(1H-pyrazol-4-yl)acetate (36.9 mg, 0.263 mmol), intermediate 10 (147.3 mg, 0.223 mmol), potassium phosphate (152.9 mg, 0.720 mmol), and copper(I) iodide (8.8 mg, 0.046 mmol) under nitrogen was added trans-(1R,2R)—N,N'-bismethyl-1,2-cyclohexanediamine (15 µl, 0.095 mmol) and DMF (0.45 mL). The resulting suspension was heated to 110° C. with stirring. After 24 hours, the reaction mixture was cooled to room temperature before being partitioned between EtOAc (100 mL) and 2 N HCl (30 mL). The biphasic mixture was filtered through a pad of Celite™. The solid from the top of the Celite™ pad was dissolved in DMA and combined with the biphasic filtrate. The resulting solid was collected by filtration of the aqueous layer. The organic layer was washed with water (3× mL) and brine (1×30 mL). The organic layer was dried over $Na_2SO_4$, filtered, and evaporated under reduced pressure to give a pale yellow residue. The solid collected from the filtration of the aqueous layer and the residue from the organic layer were dissolved in DMSO and MeOH and purified by preparative HPLC Reverse phase (C-18), using a 30×150 mm Sunfire™ column and eluting with a 20%-100% acetonitrile/water+0.05% TFA gradient followed by a 100% acetonitrile+0.05% TFA flush. The desired fractions were combined and evaporated under reduced pressure to give the title compound as a yellow residue. LC-MS: calculated for $C_{34}H_{37}ClN_6O_7Si$ 704.22 observed m/e: 705.13 $(M+H)^+$ (Rt 1.24/2 min).

Step B methyl 2-[1-[5-[4-[2-[[(3,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]-2-pyridyl]pyrazol-4-yl]acetate. TMS-Diazomethane (2 M in hexanes, 0.06 mL, 0.120 mmol) was added to a stirred suspension of the 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)-imidazo[4,5-b]pyridin-5-yl]phenyl]-2-pyridyl]pyrazol-4-yl]acetic acid (60.4 mg, 0.086 mmol) in MeOH (1 mL). DCM (0.6 mL) was added to the reaction mixture to give a yellow solution. Additional TMS-Diazomethane (2 M in hexanes, 0.04 mL, 0.080 mmol) was added to the reaction mixture. After 1 hour, the reaction mixture was evaporated under reduced pressure to give a yellow residue. The residue was purified by preparative thin layer chromatography using two 500 micron 20 cm×20 cm silica gel plates, which were developed using 75% EtOAc/hexanes to afford the title compound as a colorless residue. LC-MS: calculated for $C_{35}H_{39}ClN_6O_7S±718.23$ observed m/e: 719.03 $(M+H)^+$ (Rt 1.29/2 min).

Step C 2-[1-[5-[4-[2-[[(3R,3aR6R6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]-2-pyridyl]pyrazol-4-yl]acetic acid. A mixture of methyl 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilyl-ethoxymethyl)imidazo[4,5-b]pyridin-5-yl]phenyl]-2-pyridyl]pyrazol-4-yl]acetate (28.5 mg, 0.040 mmol), formic acid (1.0 mL, 26.1 mmol), and saturated aqueous $KHSO_4$ (0.05 mL) was heated to 40° C. with stirring. After 16 hours, the reaction mixture was cooled to room temperature before being partitioned between EtOAc (40 mL) and saturated aqueous $NaHCO_3$ (40 mL). A white precipitate formed during the partition. The aqueous layer was extracted with EtOAc (2×20 mL). The organic layers were combined and washed with brine (1×20 mL). 2N HCl (20 mL) was added to the brine layer, dissolving the white precipitate. The brine/2N HCl layer was repartitioned with the combined organic layers. The aqueous layers were combined and the pH was adjusted to ~pH 3 through the addition of 2 N HCl. The combined aqueous layers were extracted with EtOAc (3×20 mL). The combined EtOAc extracts were washed with brine (1×20 mL) before being combined with the original organic layers. The combined organic layers were dried over $Na_2SO_4$, filtered, and evaporated under reduced pressure to give a mixture of: 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]-2-pyridyl]pyrazol-4-yl]acetic acid and methyl 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]-2-pyridyl]pyrazol-4-yl]acetate as a pale yellow residue. This residue was used in the next step without further purification. LC-MS: calculated for $C_{28}H_{23}ClN_6O_6$ 574.14 observed m/e: 574.90 $(M+H)^+$ (Rt 1.11/2 min).

Step D methyl 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-phenyl]-2-pyridyl]pyrazol-4-yl]acetate. TMS-Diazomethane (2 M in hexanes, 25 µl, 0.050 mmol) was added to a stirred hazy solution of the mixture of 2-[1-[5-[4-[2-[[(3R,3aR,6R,6aR)-3-hydroxy-2,3,3a,5,6,6a-hexahydrofuro[3,2-b]furan-6-yl]oxy]-6-chloro- 1H-imidazo[4,5-b]pyridin-5-yl]phenyl]-2-pyridyl]pyrazol-4-yl]acetic acid and methyl 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]-2-pyridyl]pyrazol-4-yl]acetate (23.1 mg) from Step C in MeOH (0.7 mL) and DCM (0.7 mL). Additional MeOH (0.5 mL), DCM (0.7 mL) and TMS-Diazomethane (20 μl, 0.040 mmol) were added to the reaction mixture, and the reaction mixture was stirred at room temperature. After 50 minutes, additional TMS-Diazomethane (20 μl, 0.040 mmol) was added to the reaction mixture. After 35 minutes, the reaction mixture was evaporated under reduced pressure to give the title compound as a white solid, which was used in the next step without further purification. LC-MS: calculated for $C_{29}H_{25}ClN_6O_6$ 588.15 observed m/e: 588.95 (M+H)$^+$ (Rt 1.15/2 min).

Step E (3R,3aR,6R,6aR)-6-[[6-chloro-5-[4-[6-[4-(2-hydroxy-2-methyl-propyl)pyrazol-1-yl]-3-pyridyl]phenyl]-1H-imidazo[4,5-b]pyridin-2-yl]oxy]-2,3,3a,5,6,6a-hexahydrofuro[3,2-b]furan-3-ol. Methylmagnesium bromide (0.13 mL, 0.390 mmol) was added dropwise to a stirred solution of methyl 2-[1-[5-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]-2-pyridyl]pyrazol-4-yl]acetate from Step D in THF (1 mL). The reaction mixture was stirred at room temperature. After 1 hour, additional methylmagnesium bromide (0.05 mL, 0.15 mmol) was added to the reaction mixture. One hour later, the reaction mixture was partitioned between EtOAc (40 mL) and saturated aqueous NH$_4$Cl (40 mL). The aqueous layer was extracted with EtOAc (2×20 mL). The organic layers were combined, washed with brine (1×20 mL), dried over Na$_2$SO$_4$, filtered, and evaporated under reduced pressure to give a pale yellow residue. Purification by HPLC reverse phase (C-18), using a 30×150 mm Sunfire™ column and eluting with a 20%-100% acetonitrile/water+0.05% TFA gradient followed by a 100% acetonitrile+0.05% TFA flush and followed by lyophilization from ethanol and benzene afforded the title compound as a white solid. LC-MS: calculated for $C_{30}H_{29}ClN_6O$ 588.19 observed m/e: 588.95 (M+H)$^+$ (Rt 1.13/2 min); $^1$H NMR δ (ppm) (CD$_3$OD): 8.78 (broad s, 1H), 8.50 (broad s, 1H), 8.28 (dd, J=2.0 Hz, 8.6 Hz, 1H), 8.02 (broad d, J=8.6 Hz, 1H), 7.93 (s, 1H), 7.81-7.85 (m, 4H), 7.69 (broad s, 1H), 5.58 (qt, J=5.3 Hz, 1H), 4.99 (t, J=5.2 Hz, 1H), 4.48 (t, J=5.0 Hz, 1H), 4.28-4.32 (m, 1H), 4.18 (dd, J=5.6 Hz, 10.3 Hz, 1H), 4.14 (dd, J=4.7 Hz, 10.2 Hz, 1H), 3.92 (dd, J=6.9 Hz, 8.3 Hz, 1H), 3.61 (t, J=8.6 Hz, 1H), 2.73 (s, 2H), 1.25 (s, 6H).

EXAMPLE 207

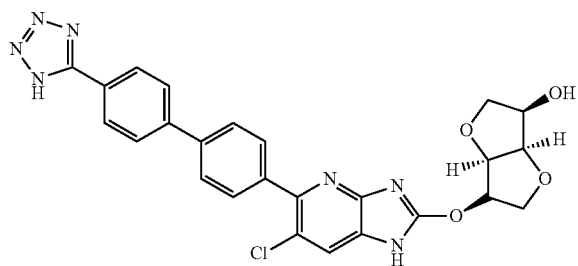

(3R,3aR,6R,6R)-6-[[6-chloro-5-[4-[4-(1H-tetrazol-5-yl)phenyl]phenyl]-1H-imidazo[4,5-b]pyridin-2-yl]oxy]-2,3,3a,5,6,6a-hexahydrofuro[3,2-b]furan-3-ol A mixture of intermediate 11 (27.9 mg, 0.059 mmol), azidotrimethyltin (153.5 mg, 0.746 mmol), and toluene (1 mL) was heated to 110° C. with stirring. After 16 hours, the reaction mixture was cooled to room temperature. The reaction mixture was purified by preparative thin layer chromatography using two 1000 micron 20 cm×20 cm silica gel plates, which were developed using 90:9:1 DCM/MeOH/acetic acid to give a white solid. The product was purified again by preparative thin layer chromatography using a 500 micron 20 cm×20 cm silica gel plate, which was developed twice using 90:9:1 DCM/MeOH/acetic acid to give a white solid. This material was further purified by HPLC reverse phase (C-18), using a 30×150 mm Sunfire™ column and eluting with a 20%-100% acetonitrile/water+0.05% TFA gradient followed by a 100% acetonitrile+0.05% TFA flush. The desired fractions were combined, evaporated under reduced pressure, and lyophilized from ethanol and benzene to give the title compound as a white solid. LC-MS: calculated for: $C_{25}H_{20}ClN_7O_4$ 517.13 observed m/e: 518.20 (M+H)$^+$ (Rt 1.08/2 min); $^1$H NMR δ (ppm) (CD$_3$OD): 8.14 (d, J=8.3 Hz, 2H), 7.95 (d, J=8.3 Hz, 2H), 7.87 (s, 1H), 7.79-7.84 (m, 4H), 5.56 (qt, J=5.3 Hz, 1H), 4.97 (t, J=5.2 Hz, 1H), 4.47 (t, J=5.0 Hz, 1H), 4.26-4.30 (m, 1H), 4.17 (dd, J=5.7 Hz, 10.1Hz, 1H), 4.12 (dd, J=4.8 Hz, 10.3 Hz, 1H), 3.90 (dd, J=7.0 Hz, 8.3 Hz, 1H), 3.60 (t, J=8.6 Hz, 1H).

EXAMPLE 208

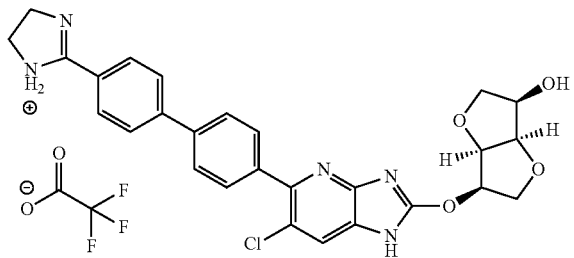 [SMILES: O[C@@H]1CO[C@H]2[C@@H]1OC[C@H]2Oc1nc2nc(-c3ccc(-c4ccc(C5=NCC[NH2+]5)cc4)cc3)c(Cl)cc2[nH]1 ; O=C([O-])C(F)(F)F]

(3R,3aR,6R,6aR)-6-[[6-chloro-5-[4-[4-(2,5-dihydro-1H-imidazol-2-yl)phenyl]phenyl]-1H-imidazo[4,5-b]pyridin-2-yl]oxy]-2,3,3a,5,6,6a-hexahydrofuro[3,2-b]furan-3-ol A mixture of intermediate 11 (28.4 mg, 0.060 mmol), ethylenediamine (0.5 mL, 7.46 mmol), and carbon disulfide (6 μl, 0.100 mmol) was heated to 50° C. with stirring. After 18 hours, the reaction mixture was cooled to room temperature before being evaporated under reduced pressure to give a yellow solid. Purification of the solid by HPLC reverse phase (C-18), using a 30×150 mm Sunfire™ column and eluting with a 20%-100% acetonitrile/water+0.05% TFA gradient followed by a 100% acetonitrile+0.05% TFA flush and followed by lyophilization from ethanol and benzene afforded the title compound as a white solid. LC-MS: calculated for: $C_{27}H_{24}ClN_5O_4$ 517.15 observed m/e: 518.14 (M+H)$^+$ (Rt 0.98/2 min); $^1$H NMR δ (ppm) (CD$_3$OD): 7.96-8.01 (m, 4H), 7.81-7.85 (m, 5H), 5.55 (qt, J=5.4 Hz, 1H), 4.97 (t, J=5.2 Hz, 1H), 4.47 (t, J=5.0 Hz, 1H), 4.26-4.30 (m, 1H), 4.09-4.19 (m, 6H), 3.90 (t, J=7.0 Hz, 1H), 3.60 (t, J=8.6 Hz, 1H).

TABLE 15

The compounds in Table 15 were prepared according to the methods in Example 208, starting from the appropriate starting materials.

| Example Number | Structure | HPLC-mass spectum m/e |
|---|---|---|
| 209 | 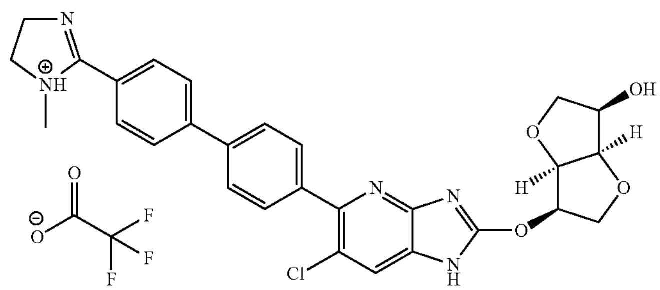 [SMILES: C[NH+]1CCN=C1c1ccc(-c2ccc(-c3nc4nc(O[C@@H]5CO[C@H]6[C@@H]5OC[C@H]6O)[nH]c4cc3Cl)cc2)cc1 ; O=C([O-])C(F)(F)F] | 532.22 |
| 210 | 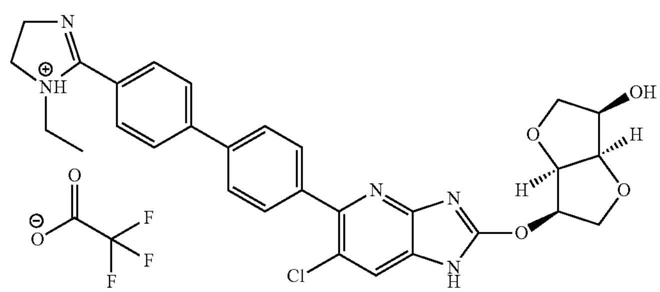 [SMILES: CC[NH+]1CCN=C1c1ccc(-c2ccc(-c3nc4nc(O[C@@H]5CO[C@H]6[C@@H]5OC[C@H]6O)[nH]c4cc3Cl)cc2)cc1 ; O=C([O-])C(F)(F)F] | 546.26 |
| 211 | 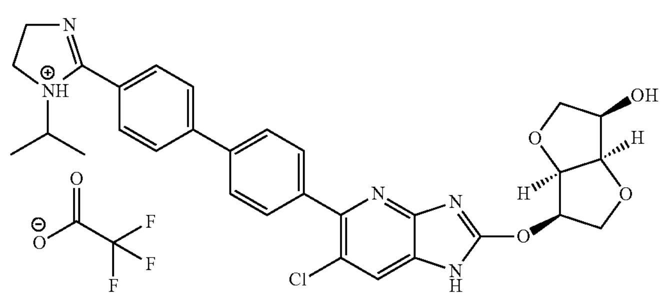 [SMILES: CC(C)[NH+]1CCN=C1c1ccc(-c2ccc(-c3nc4nc(O[C@@H]5CO[C@H]6[C@@H]5OC[C@H]6O)[nH]c4cc3Cl)cc2)cc1 ; O=C([O-])C(F)(F)F] | 560.31 |
| 212 | 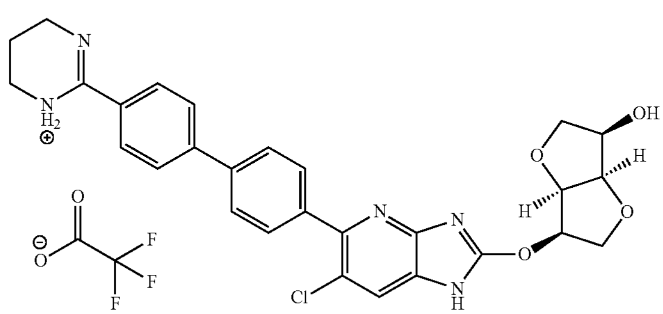 [SMILES: O[C@@H]1CO[C@H]2[C@@H]1OC[C@H]2Oc1nc2nc(-c3ccc(-c4ccc(C5=NCCC[NH2+]5)cc4)cc3)c(Cl)cc2[nH]1 ; O=C([O-])C(F)(F)F] | 532.20 |

EXAMPLE 213

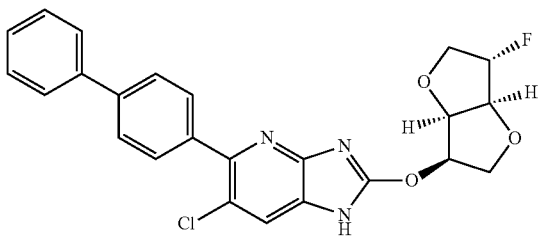 [SMILES: F[C@H]1CO[C@H]2[C@@H]1OC[C@H]2Oc1nc2nc(-c3ccc(-c4ccccc4)cc3)c(Cl)cc2[nH]1]

2-[[(3R,3aR,6S,6aS -6-fluoro-2,3,3a,5,6,6a-hexahydrofurofuro[3,2-b]furan-3-yl]oxy]-6-chloro-5-(4-phenylphenyl)-1H-imidazo[4,5-b]pyridine Step A 2-[[2-[[(3R,3aR,6S,6aS)-6-fluoro-2,3,3a,5,6,6a-hexahydrofuro[3,2-b]furan-3-yl]oxy]-6-chloro-5-(4-phenylphenyl)imidazo[4,5-b]pyridin-1-yl]methoxy]ethyl-trimethyl-silane. A stirred solution of the intermediate from Example 159 Step A (85.8 mg, 0.148 mmol) in DCM (1.5 mL) (in a 20 mL plastic vial) was cooled to 0° C. in an ice bath. DAST (0.12 mL, 0.908 mmol) was added to the reaction mixture dropwise. After 10 minutes, the reaction mixture was removed from the ice bath and allowed to warm to room temperature. After 21.5 hours, the reaction mixture was cooled to 0° C. in an ice bath prior to the slow addition of saturated aqueous $NaHCO_3$ (30 mL). The resulting biphasic suspension was extracted with EtOAc (3×30 mL). The organic layers were combined, dried over $Na_2SO_4$, filtered, and evaporated under reduced pressure to give an amber residue. Flash chromatography of the residue utilizing a 4 g silica RediSep R$^f$® column and employing a 0-50% EtOAc/hexane gradient with a 50% EtOAc/hexane hold afforded the desired compound as a colorless residue. LC-MS: calculated for: $C_{30}H_{33}ClFN_3O_4S$ 581.19 observed m/e: 582.21 $(M+H)^+$ (Rt 1.41/2 min).

Step B 2-[[(3R,3aR,6,6aS)-6-fluoro-2,3,3a-5,6,6a-hexahydrofuro[3,2-b]furan-3-yl]oxy]-6-chloro-5-(4-phenylphenyl)-1H-imidazo[4,5-b]pyridine. A mixture of 2-[[2-[[(3R,3aR,6S,6aS)-6-fluoro-2,3,3a,5,6,6a-hexahydrofuro[3,2-b]furan-3-yl]oxy]-6-chloro-5-(4-phenylphenyl)imidazo[4,5-b]pyridin-1-yl]methoxy]ethyl-trimethyl-silane (23.2 mg, 0.040 mmol), formic acid (1.0 mL, 26.1 mmol), and saturated aqueous $KHSO_4$ (0.05 mL) was heated to 40° C. with stirring. After 4 hours, the reaction mixture was cooled to room temperature before being concentrated under reduced pressure. The concentrated reaction mixture was partitioned between EtOAc (20 mL) and saturated aqueous $NaHCO_3$ (20 mL). The aqueous layer was extracted with EtOAc (2×20 mL). The organic layers were combined, dried over $Na_2SO_4$, filtered, and evaporated under reduced pressure to give a colorless residue. Purification of the residue by HPLC reverse phase (C-18), using a 30×150 mm Sunfire™ column and eluting with a 20%-100% acetonitrile/water+0.05% TFA gradient followed by a 100% acetonitrile+0.05% TFA flush and followed by lyophilization from ethanol and benzene afforded the title compound as a white solid. LC-MS: calculated for: $C_{24}H_{19}ClFN_3O_3$ 451.11 observed m/e: 452.14 $(M+H)^+$ (Rt 1.23/2 min); $^1$H NMR δ (ppm) ($CD_3OD$): 7.86 (s, 1H), 7.71-7.75 (m, 4H), 7.69 (d, J=7.3 Hz, 2H), 7.46 (t, J=7.7 Hz, 2H), 7.36 (t, J=7.4 Hz, 1H), 5.59 (qt, J=4.8 Hz, 1H), 5.13 (dd, J=2.4 Hz, 50.4 Hz, 1H), 5.13 (t, J=5.3 Hz, 1H), 4.67 (dd, J=5.0 Hz, 11.4 Hz, 1H), 4.11 (t, J=11.5 Hz, 1H), 4.03-4.08 (m, 2H), 3.97 (ddd, J=2.5 Hz, 11.3 Hz, 41.1, 1H).

INTERMEDIATE 13

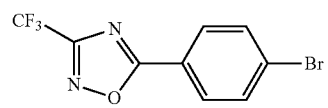

5-(4-bromophenyl)-3-(trifluoromethyl)-1,2,4-oxadiazole Carbonyldiimidazole (202 mg, 1.244 mmol) was added to a solution of 4-bromobenzoic acid (208.4 mg, 1.037 mmol) in anhydrous methylene chloride (2 mL). Then 2,2,2-trifluoro-N'-hydroxy-acetamidine (173 mg, 1.348 mmol) was added and the mixture was stirred for 1 hour at room temperature. The mixture was evaporated and the resulting residue was dissolved in toluene (2 mL) and heated in a 100 degree oil bath for 18 hours. The solution was evaporated and the reside was purified on a silica gel Biotage 25S, eluting with EtOAc/isohexane (0-5% EtOAc in hexane) to give the title compound as a light yellow oil. $^1$H NMR δ (ppm) ($CDCl_3$): 8.08 (d, 2H) and 7.76 (d, 2H).

INTERMEDIATE 14

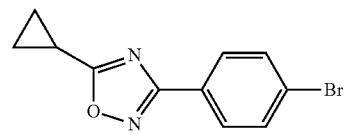 [SMILES: Brc1ccc(-c2noc(C3CC3)n2)cc1]

3-(4-bromophenyl)-5-cyclopropyl-1,2,4-oxadiazole Triethylamine (0.204 mL, 1.463 mmol) and cyclopropanecarbonyl chloride (0.089 mL, 0.976 mmol) were added to a stirred mixture of 4-bromo-N'-hydroxy-benzamidine (104.9 mg, 0.488 mmol) in methylene chloride (2 mL) and the mixture was stirred at room temperature for 30 min. The mixture was evaporated, dissolved in toluene and re-evaporated. The resulting residue was dissolved in toluene (3 mL) and heated in a 110° C. oil bath for 18 hours. Evaporation and purification of the resulting mixture by preparative TLC gave the title compound. LC-MS: calculated for: $C_{11}H_9BrN_2O$ 263.99 observed m/e: 265.18/267.18 $(M+H)^+$ (Rt 1.25/2 min).

INTERMEDIATE 15

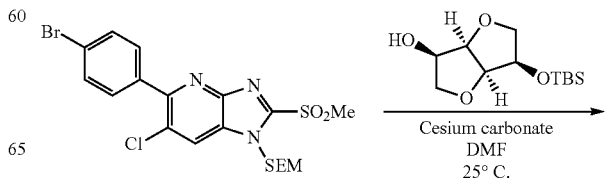

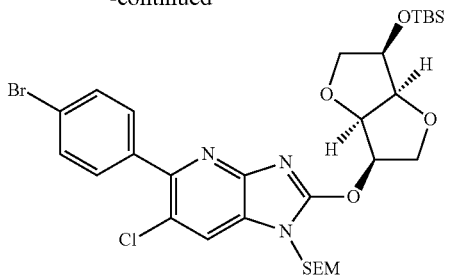

5-(4-bromophenyl)-2-(((3R,3aR,6R,6aS)-6-((tert-butyldimethylsilyl)oxy)hexa-hydrofuro[3,2-b furan-3-yl)oxy)-6-chloro-1-((2-(trimethylsilyl)ethoxy)methyl)-1H-imidazol-4,5-b]pyridine. 5-(4-bromophenyl)-6-chloro-2-(methylsulfonyl)-1-((2-(trimethylsilyl)ethoxy)methyl)-1H-imidazo[4,5-b]pyridine (2.00 g, 3.87 mmol) and (3R,3aR,6R,6aS)-6-((tert-butyldimethylsilyl)oxy)hexahydrofuro[3,2-b]furan-3-ol (2.02 g, 7.74 mmol) were placed under nitrogen in anhydrous DMF (15 mL). Then cesium carbonate (3.78 g, 11.61 mmol) was added and the mixture was allowed to stir at room temperature for 2 hours. Then the mixture was poured into water (200 mL) and extracted with ethyl acetate (2×150 mL). The combined organic layers were washed with brine (100 mL), dried over sodium sulfate, and concentrated under reduced pressure to afford a dark oil. The oil was chromatographed using a Biotage 100 g silica gel cartridge eluted with 0-75% ethyl acetate in a 1:1 mixture of dichloromethane/hexane. The desired product fractions were combined and concentrated under reduced pressure to afford the title compound as an off-white solid. LC-MS: calculated for $C_{30}H_{43}BrClN_3O_5Si_2$ 697.21 observed m/e: 698.17 $(M+H)^+$ (Rt 3.19/4 min).

INTERMEDIATE 16

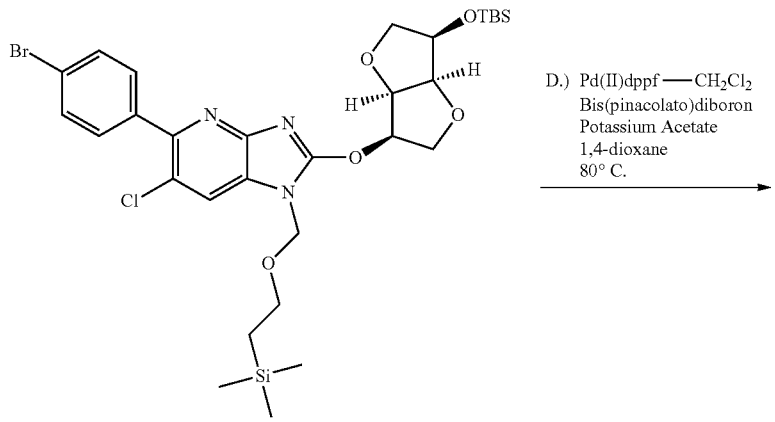

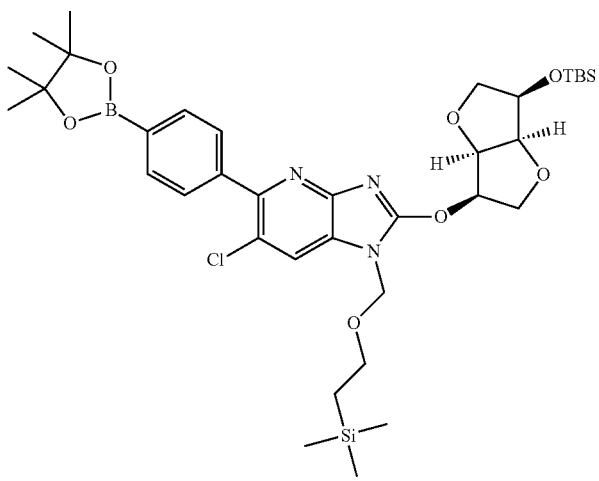

Bis(pinacolato)diboron (1.573 g, 6.20 mmol), 1,1'-bis(diphenylphosphino)ferrocene-palladium(II)dichloride dichloromethane complex (0.337 g, 0.413 mmol) and potassium acetate (1.014 g, 10.33 mmol) were added to a stirred solution of [(3R,3aR,6R,6aS)-3-[5-(4-bromophenyl)-6-chloro-1-(2-trimethylsilylethoxymethyl)imidazo[4,5-b]pyridin-2-yl]oxy-2,3,3a,5,6,6a-hexahydrofuro[3,2-b]furan-6-yl]oxy-tert-butyl-dimethyl-silane (intermediate 15, 1.44 g, 2.065 mmol) in DMF (15 mL). The mixture was heated in a 80° C. oil bath for 18 hours, and after cooling to room temperature, was diluted with EtOAc (100 mL), filtered through Celite™, and the filter pad was washed with ethyl acetate (100 mL). The combined organic layer was washed with brine (100 mL), dried with $Na_2SO_4$, filtered and evaporated under reduced pressure. The resulting residue was purified by column chromatography on silica gel Biotage 40M, eluting with EtOAc/isohexane (0-30% EtOAc in hexane) to give the title compound as a light yellow solid. LC-MS: calculated for: $C_{36}H_{55}BClN_3O_7Si_2$ 743.34 observed m/e: 744.52 $(M+H)^+$ (Rt 1.53/2 min)

INTERMEDIATE 17

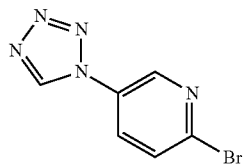

2-bromo-5-(tetrazol-1-yl)pyridine. Sodium azide (241.6 mg, 3.72 mmol) and triethyl orthoformate (1.0 mL, 6.01 mmol) were added to a stirred solution of 5-amino-2-bromopyridine (511.8 mg, 2.96 mmol) in acetic acid (3 mL, 52.4 mmol), and the reaction mixture was heated to 80° C. After 7 hours, the reaction mixture was cooled to room temperature before being evaporated under reduced pressure. The resulting red/brown solid was partitioned between EtOAc (50 mL) and water (50 mL). The aqueous layer was extracted with EtOAc (2×50 mL). The organic layers were combined, washed with 1 N HCl (2×50 mL), saturated aqueous $NaHCO_3$ (1×50 mL), and brine (1×50 mL), dried over $Na_2SO_4$, filtered, and evaporated under reduced pressure to give an amber solid. Flash chromatography of the solid utilizing an 40 g silica RediSep R$_f$® column and employing a 0-2% MeOH/DCM gradient with a 2% MeOH/DCM hold afforded the title compound as a light yellow solid. LC-MS: calculated for $C_6H_4BrN_5$ 224.97, 226.96 observed m/e: 226.22, 228.21 $(M+H)^+$ (Rt 0.42/2 min).

INTERMEDIATE 18

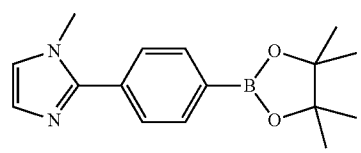 [SMILES: Cn1ccnc1-c1ccc(B2OC(C)(C)C(C)(C)O2)cc1]

1-methyl-2-[4-(4,4,5,5-tetramethyl-1,3,2-dioxaborolan-2-yl)phenyl]imidazole. A solution of 2-(4-bromophenyl)-1-methyl-1H-imidazole (71.1 g, 300 mmol, 1 equiv) in DMSO (660 mL), 4,4,5,5-tetramethyl-2-(4,4,5,5-tetramethyl-1,3,2-dioxaborolan-2-yl)-1,3,2-dioxaborolane (83.8 g, 329.92 mmol, 1.1 equiv), dppfPdCl$_2$ (6.6 g, 9.03 mmol, 0.03 equiv) and KOAc (88.2 g, 900 mmol, 3 equiv) was stirred overnight at 85° C. in an oil bath. The reaction mixture was cooled and then quenched by the addition of 1200 mL of water. The resulting solution was extracted with 2×500 mL of dichloromethane. The organic layers were combined, dried over anhydrous magnesium sulfate and concentrated under vacuum. The resulting residue was applied onto a silica gel column and eluted with ethyl acetate/petroleum ether (1:5-1:2) to afford the title compound as a gray powder. LC-MS: calculated for $C_{16}H_{21}BN_2O_2$ 284.17 observed m/e: 285 $(M+H)^+$; $^1$H NMR δ (ppm) (CDCl$_3$): 7.89 (2H, d, J=8.0 Hz), 7.65 (2H, d, J=8.0 Hz), 7.14 (1H, d, J=1.2 Hz), 6.97 (1H, d, J=1.2 Hz), 3.76 (3H, s), 1.36 (12H, s).

INTERMEDIATE 19

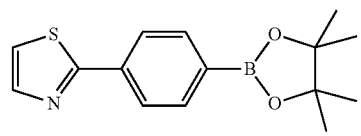 [SMILES: CC1(C)OB(c2ccc(-c3nccs3)cc2)OC1(C)C]

Intermediate 19 may be prepared from 2-(4-bromophenyl)thiazole according to the procedure described in Intermediate 18.

INTERMEDIATE 20

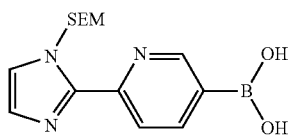 [SMILES: C[Si](C)(C)CCOCn1ccnc1-c1ccc(B(O)O)cn1]

Intermediate 20 may be prepared by reacting [6-(1H-imidazol-2-yl)-3-pyridyl]boronic acid with SEMCl.

INTERMEDIATE 21

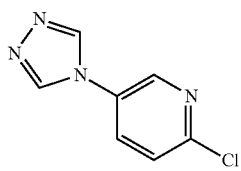 [SMILES: Clc1ccc(-n2cnnc2)cn1]

Intermediate 21 may be prepared by reacting N,N'-bis(dimethylaminomethylene)-hydrazine with 6-chloropyridin-3-amine.

INTERMEDIATE 22

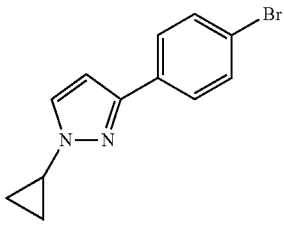 [SMILES: Brc1ccc(-c2ccn(C3CC3)n2)cc1]

3-(4-bromophenyl)-1-cyclopropyl-pyrazole. A solution of 3-(4-bromophenyl)-1H-pyrazole (302 g, 1.35 mol), cyclopropylboronic acid (233 g, 2.71 mol), copper(II) acetate (246 g, 1.35 mol), 4-(dimethylamino)pyridine (662 g, 5.42 mol), cesium carbonate (1103 g, 3.39 mol), and 1,4-dioxane (8 L) was stirred at 90° C. for 36 h. The reaction mixture was cooled to room temperature before being filtered through Celite™, which was washed with EtOAc (4 L). The filtrate was acidified to pH 5 with 2 N HCl. The aqueous layer was extracted with EtOAc (12 L). The organic layers were combined, washed with brine, dried over MgSO$_4$, filtered, and evaporated under reduced pressure. The resulting residue was purified on an ISCO 1500 g column eluting with a 0-20% EtOAc/Heptane gradient to afford the title compound. LC-MS: calculated for $C_{12}H_{11}BrN_2$ 262.01, 264.01, observed m/e: 263.04, 265.06 (M+H)$^+$ (Rt 1.19/2 min).

EXAMPLE 214

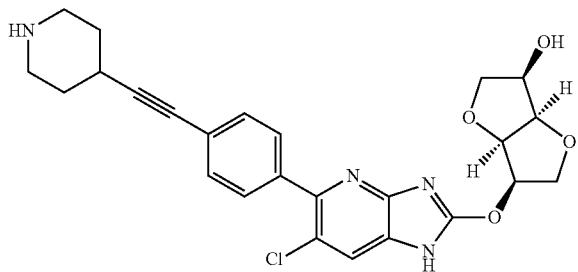 [SMILES: O[C@@H]1CO[C@H]2[C@@H]1OC[C@H]2Oc1nc2nc(-c3ccc(C#CC4CCNCC4)cc3)c(Cl)cc2[nH]1]

(3R,3aR6R,6aR)-6-((6-chloro-5-(4-(piperidin-4-ylethynyl)phenyl-1H-imidazo[4,5-b]pyridin-2-yl)oxy)hexahydrofuro[3,2-b]furan-3-ol Step A: tert-butyl 4-((4-(2-(((3R,3aR,6R,6aS)-6-((tert-butyldimethylsilyl)oxy)hexa-hydrofuro[3,2-b]furan-3-yl)oxy)-6-chloro-1-((2-(trimethylsilylethox)methyl)-1H-imidazo[4,5-b]pyridin-5-yl)phenyl)ethynyl)piperidine-1-carboxylate 5-(4-bromophenyl)-2-(((3R,3aR,6R,6aS)-6-((tert-butyldimethylsilyl)oxy)hexa-hydro-furo[3,2-b]furan-3-yl)oxy)-6-chloro-1-((2-(trimethylsilyl)ethoxy)methyl)-1H-imidazo-[4,5-b]pyridine (intermediate 15, 63 mg, 0.090 mmol), tert-butyl 4-ethynyl-piperidine-1-carboxylate (23 mg, 0.108 mmol), bis(triphenylphospine)palladium(II)dichloride (10 mg, 0.014 mmol), and copper(I) iodide (1.4 mg, 0.007 mmol) were placed under nitrogen in anhydrous triethylamine (0.5 mL). While cooling the mixture in a dry-ice/acetone bath, a hard vacuum was applied and nitrogen was subsequently introduced (3×). The mixture was removed from the ice-bath, sealed with a teflon cap, and heated to 50° C. for 24 hours. After cooling to room temperature, the mixture was filtered through Celite™, and rinsed with ethyl acetate until the filtrate was colorless. The filtrate was then concentrated under reduced pressure to provide an orange oil, which was used directly in the next step without further purification. LC-MS: calculated for $C_{42}H_{61}ClN_4O_7Si_2$ 824.38 observed m/e: 825.45 (M+H)$^+$ (Rt 3.34/4 min).

Step B: (3R,3aR,6R,6aR)-6-((6-chloro-5-(4-(piperidin-4-ylethynyl)phenyl)-1H-imidazo[4,5-b]pyridin-2-yl)oxy) hexahydrofuro[3,2-b]furan-3-ol Unpurified tert-butyl 4-((4-(2-(((3R,3aR,6R,6aS)-6-((tert-butyldimethylsilyl)oxy)-hexahydrofuro[3,2-b]furan-3-yl)oxy)-6-chloro-1-((2-(trimethylsilyl)ethoxy)methyl)-1H-imidazo[4,5-b]pyridin-5-yl)phenyl)ethynyl)piperidine-1-carboxylate (0.090 theoretical mol) from Step A was placed under nitrogen in formic acid (1.0 mL). A saturated aqueous solution of potassium hydrogen sulfate (0.2 mL) was added and the mixture was allowed to stir at 50° C. for 4 hours. The mixture was allowed to cool to room temperature. Then the mixture was diluted with methanol (5 mL), cooled to 5° C. in an ice bath, and basified to pH 14 using an aqueous solution of 6N NaOH. The mixture was stirred at pH 14 for 10 minutes, then concentrated aqueous HCl was added dropwise until the pH was pH 7. The mixture was poured into saturated aqueous sodium bicarbonate (40 mL) and extracted with ethyl acetate (2×70 mL). The combined organic layers were concentrated under reduced pressure. The resultant yellow solid was dissolved in DMSO and chromatographed using a Gilson reverse phase preparatory HPLC eluted with 0-60% acetonitrile in water (0.1% TFA) over 10 minutes. The desired product fractions were combined, frozen at −78° C., and lyophilized to dryness to provide a yellow solid. LC-MS: calculated for $C_{25}H_{25}ClN_4O_4$ 480.16 observed m/e: 481.14 (M+H)$^+$ (Rt 1.43/4 min). $^1$H NMR δ (ppm) (CD$_3$OD): 7.80 (1H, s), 7.62 (2H, d, J=8.5 Hz), 7.49 (2H, d, J=8.5 Hz), 5.53 (1H, m), 4.95 (1H, t, J=5.5 Hz), 4.46 (1H, t, J=5.0 Hz), 4.27 (1H, m), 4.15 (1H, dd, J=9.5, 6.0 Hz), 4.09 (1H, dd, J=10.0, 4.9 Hz), 3.88 (1H, dd, J=8.0, 7.0 Hz), 3.58 (1H, t, J=8.5 Hz), 3.42 (2H, m), 3.18 (2H, m), 3.09 (1H, m), 2.17 (2H, m), 1.96 (2H, m)

Alternatively, (3R,3aR,6R,6aR)-6-((6-chloro-5-(4-(piperidin-4-ylethynyl)phenyl)-1H-imidazo[4,5-b]pyridin-2-yl)oxy)hexahydrofuro[3,2-b]furan-3-ol may be prepared according to the following procedure:

Step A: (3R,3aR,6R,6aR)-6-((5-(4-bromophenyl)-6-chloro-1H-imidazo[4,5-b]pyridin-2-yl)oxy)hexahydrofuro[3,2-b]furan-3-ol (3R,3aR,6R,6aR)-6-((5-(4-bromophenyl)-6-chloro-1-((2-(trimethylsilyl)ethoxy)methyl)-1H-imidazo[4,5-b]pyridin-2-yl)oxy)hexahydrofuro[3,2-b]furan-3-ol (intermediate 7, 527 mg, 0.904 mmol) was placed under nitrogen in formic acid (2.5 mL). A saturated aqueous solution of potassium hydrogen sulfate (0.4 mL) was added and the resulting mixture was allowed to stir at 50° C. for 9 hours. The mixture was cooled and added slowly to saturated aqueous sodium bicarbonate (200 mL). The mixture was extracted with ethyl acetate (2×150 mL) and concentrated under reduced pressure. The resulting white solid was dissolved in methanol (5 mL) and basified with 3N aqueous sodium hydroxide (2 mL). The mixture was stirred at room temperature for 10 minutes, then neutralized with 1N aqueous hydrochloric acid (6 mL). The mixture was poured into saturated aqueous sodium bicarbonate (25 mL) and extracted with ethyl acetate (2×50 mL). The combined organic layers were dried over sodium sulfate and concentrated under reduced pressure. The resulting white solid was chromatographed using a Biotage 25 g silica gel cartridge eluted with 0-5% methanol in dichloromethane over 20 minutes. The product fractions were combined, concentrated under reduced pressure, and dried under high vacuum to obtain a white solid. LC-MS: calculated for $C_{18}H_{15}BrClN_3O_4$ 452.69 observed m/e: 454.02 (M+H)$^+$ (Rt 1.84/4 min).

Step B: (3R,3aR,6R6aR)-6-((6-chloro-5-(4-(piperidin-4-ylethynyl)phenyl)-1H-imidazo[4,5-b]pyridin-2-yl)oxy)hexahydrofuro[3,2-b]furan-3-ol. 3R,3aR,6R,6aR)-6-((5-(4-bromophenyl)-6-chloro-1H-imidazo[4,5-b]pyridin-2-yl)oxy)hexahydrofuro[3,2-b]furan-3-ol (25 mg, 0.055 mmol), 4-ethynylpiperidine (10.5 mg, 0.072 mmol), copper (I) iodide (2.1 mg, 0.011 mmol), chloro(tri-tert-butyl)-2-[-(2'amino-1,1'-biphenyl)]palladium (II) (5.7 mg, 0.011 mmol, prepared by a procedure analogous to procedures described in J. AM. CHEM. SOC. 2010, 132, 14073-14075), and cesium carbonate (54.0 mg, 0.166 mmol) were placed under nitrogen in dry, degassed toluene (138 µl) and dimethylacetamide (138 µl). The mixture was stirred at 50° C. for 2 hours. The resulting residue was diluted with dimethylformamide (0.7 mL), then filtered through a filter disc (0.45 micron). The material was purified by reverse phase HPLC purification using 0-100% acetonitrile in water over 10 minutes. The desired product fraction was concentrated under reduced pressure to afford the title compound as an off-white solid. LC-MS: calculated for $C_{25}H_{25}ClN_4O_4$ 480.16 observed m/e: 481.14 (M+H)$^+$ (Rt 1.43/4 min). $^1$H NMR δ (ppm) (CD$_3$OD): 7.80 (1H, s), 7.62 (2H, d, J=8.5 Hz), 7.49 (2H, d, J=8.5 Hz), 5.53 (1H, m), 4.95 (1H, t, J=5.5 Hz), 4.46 (1H, t, J=5.0 Hz), 4.27 (1H, m), 4.15 (1H, dd, J=9.5, 6.0 Hz), 4.09 (1H, dd, J=10.0, 4.9 Hz), 3.88 (1H, dd, J=8.0, 7.0 Hz), 3.58 (1H, t, J=8.5 Hz), 3.42 (2H, m), 3.18 (2H, m), 3.09 (1H, m), 2.17 (2H, m), 1.96 (2H, m)

TABLE 16

The compounds in Table 16 were prepared according to the methods described in Example 214, starting from the appropriate starting materials.

| Example Number | Structure | HPLC-mass spectrum m/e |
|---|---|---|
| 215 | [structure] | 466.12 |
| 216 | [structure] | 480.12 |
| 217 | [structure] | 497.18 |
| 218 | [structure] | 480.19 |

TABLE 16-continued

The compounds in Table 16 were prepared according to the methods described in Example 214, starting from the appropriate starting materials.

| Example Number | Structure | HPLC-mass spectrum m/e |
|---|---|---|
| 219 | 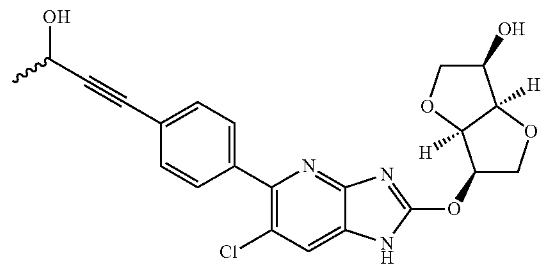 [SMILES: CC(O)C#Cc1ccc(-c2nc3nc(O[C@@H]4CO[C@H]5[C@@H]4OC[C@H]5O)[nH]c3cc2Cl)cc1] | 442.15 |
| 220 | 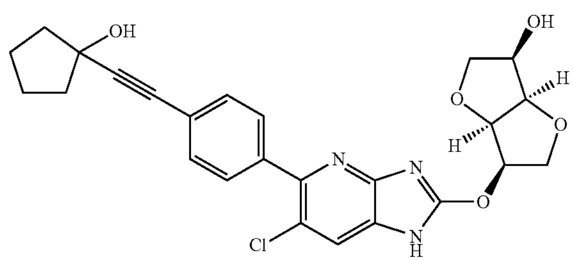 [SMILES: O[C@@H]1CO[C@H]2[C@@H]1OC[C@H]2Oc1nc2nc(-c3ccc(C#CC4(O)CCCC4)cc3)c(Cl)cc2[nH]1] | 482.18 |
| 221 | 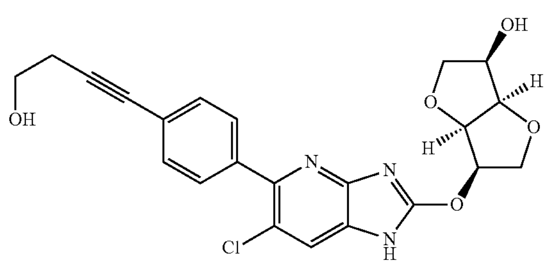 [SMILES: OCCC#Cc1ccc(-c2nc3nc(O[C@@H]4CO[C@H]5[C@@H]4OC[C@H]5O)[nH]c3cc2Cl)cc1] | 442.15 |
| 222 | 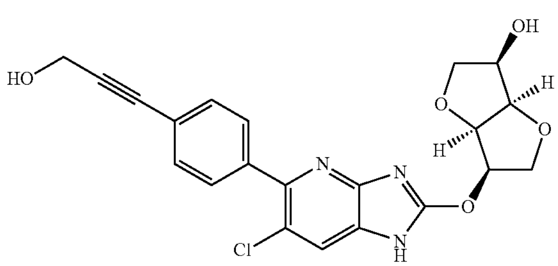 [SMILES: OCC#Cc1ccc(-c2nc3nc(O[C@@H]4CO[C@H]5[C@@H]4OC[C@H]5O)[nH]c3cc2Cl)cc1] | 428.13 |
| 223 | 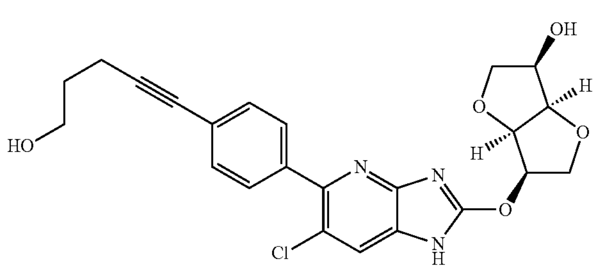 [SMILES: OCCCC#Cc1ccc(-c2nc3nc(O[C@@H]4CO[C@H]5[C@@H]4OC[C@H]5O)[nH]c3cc2Cl)cc1] | 456.15 |

TABLE 16-continued

The compounds in Table 16 were prepared according to the methods described in Example 214, starting from the appropriate starting materials.

| Example Number | Structure | HPLC-mass spectrum m/e |
|---|---|---|
| 224 | 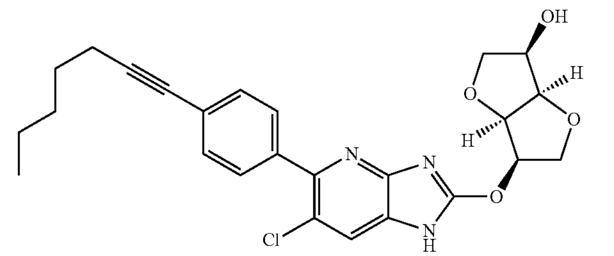 [SMILES: CCCCCC#Cc1ccc(-c2nc3nc(O[C@@H]4CO[C@H]5[C@@H]4OC[C@H]5O)[nH]c3cc2Cl)cc1] | 468.20 |
| 225 | 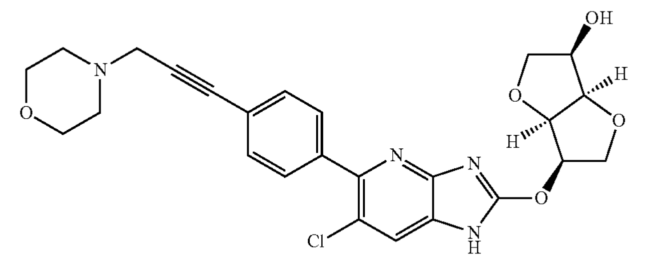 [SMILES: O[C@@H]1CO[C@H]2[C@@H]1OC[C@H]2Oc1nc2nc(-c3ccc(C#CCN4CCOCC4)cc3)c(Cl)cc2[nH]1] | 497.18 |
| 226 | 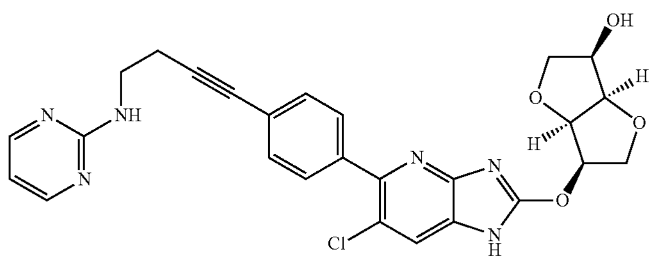 [SMILES: O[C@@H]1CO[C@H]2[C@@H]1OC[C@H]2Oc1nc2nc(-c3ccc(C#CCCNc4ncccn4)cc3)c(Cl)cc2[nH]1] | 519.17 |
| 227 | 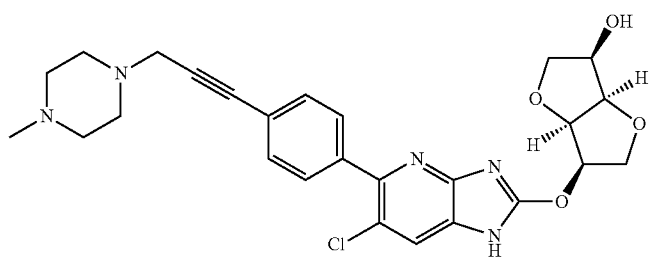 [SMILES: CN1CCN(CC#Cc2ccc(-c3nc4nc(O[C@@H]5CO[C@H]6[C@@H]5OC[C@H]6O)[nH]c4cc3Cl)cc2)CC1] | 510.20 |
| 228 | 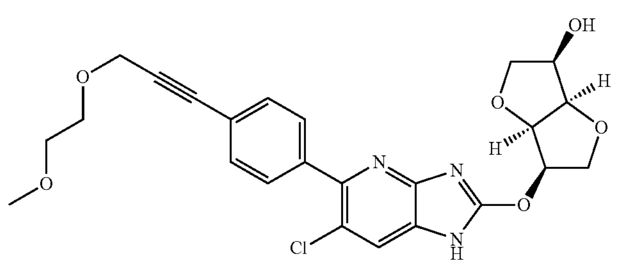 [SMILES: COCCOCC#Cc1ccc(-c2nc3nc(O[C@@H]4CO[C@H]5[C@@H]4OC[C@H]5O)[nH]c3cc2Cl)cc1] | 486.15 |

TABLE 16-continued

The compounds in Table 16 were prepared according to the methods described in Example 214, starting from the appropriate starting materials.

| Example Number | Structure | HPLC-mass spectrum m/e |
|---|---|---|
| 229 | (structure) | 455.13 |

BIOLOGICAL EXAMPLE 1

AMPKSAMSF (In Vitro AMPK Activation Assay)

The recombinant human AMPK complex 1 (containing α1β1γ1) was obtained from baculovirus expression system. Recombinant viruses were generated by cotransfection of AMPK/pBacPak9 clones with Baculogold baculovirus DNA (Pharmingen) in *spodoptera frugiperda* 21 cells according to the manufacturer's instructions. Each round of virus amplification was performed for 5 days in Grace's medium containing 10% serum. Virus that had been subjected to three rounds of amplification was used for all protein production procedures. To express the AMPK complex, sf21 cells were adapted to serum free medium (SF900 II, Invitrogen) by sequential dilution from serum containing stocks into SF900II medium and maintained in shaker flasks at 90 rpm at 27° C. The recombinant AMPK enzyme complex was produced by triple infection, one recombinant virus for each of the subunits, in sf21 cells under serum free conditions. Cells were infected in log phase, $1 \times 10^6$ cells/ml, at a multiplicity of infection of ~5. Cells were harvested by centrifugation at 10,000×g for 15 minutes after 72 hours of infection with viruses. The insect cell pellet from 2 liters of culture was resuspended in 50 ml lysis buffer (20 mM Tris-HCl, 50 mM NaCl, 50 mM NaF, 30 mM Na PPi, 0.25 M sucrose, 10 mM ZnCl₂, 2 mM DTT, 0.4 mg/ml digitonin) and subjected to two cycles of freeze-thaw lysis in a dry-ice ethanol bath. Insoluble material was removed by centrifugation at 10,000×g and the supernatant was fractionated with use of polyethylene glycol (PEG). The protein fraction precipitating between 2.5 and 6% PEG was used for further purification using a Blue-Sepharose step (Zhou et al, J. Clin. Invest. 108, 1167-1174, 2001).

The in vitro AMPK activation assay is performed in a volume of 30 μl in a 384-well plate. Enzyme reactions were assembled in the microtiter plate by adding 15 μl of 2× enzyme in assay buffer (20 mM HEPES, pH 7.3, 5 mM MgCl₂, 3 mM DTT, 0.01% Brij 35 and CamK Kinase, to activate AMPK) to wells which contained either DMSO or compound. The reaction was initiated with the addition of 15 μl 2× substrate mixture containing 200 μM ATP, and 3.0 μM fluorescently labeled SAMS (5-FAM-HMRSAMS-GLHLVKRR-COOH) in assay buffer. After 45-minute incubation at 25° C., the reaction was stopped by the addition of 70 μl stop buffer (100 mM HEPES, pH 7.3, 40 mM EDTA, 0.015% Brij 35). Phosphorylated 5-FAM SAMS product is assessed using a Caliper EZ Reader LabChip microfluidics reader. Product conversion is determined by calculating the peak heights of the substrate and product and reporting the product/(product+substrate) peak ratio. The 10-point titration data were expressed as % maximum AMP activation. The results were plotted using 4 parameter fit and the inflection point reflecting 50% of the maximum activation was reported as the $EC_{50}$. The % maximum AMP activation for selected compounds is provided in the table below.

The compounds of present invention, including the compounds of Examples 1-229, were tested in the in vitro AMPK activation assay using recombinant human AMPK complex 1 (containing α1β1γ1) and found to have greater than 50% maximum AMP activation of human AMPK complex 1 (containing α1β1γ1), and $EC_{50}$ values of less than micromolar. Preferred compounds of the present invention were found to have $EC_{50}$ values of less than 0.1 micromolar in the in vitro AMPK activation assay using recombinant human AMPK complex 1.

| Maximum AMP Activation for Selected Compounds | | |
|---|---|---|
| Example No. | % Maximum AMP Activation of human AMPK Complex 1 | $EC_{50}$ (nM) |
| 3 | 681% | 1 |
| 29 | 798% | 7 |
| 30 | 852% | 24 |
| 79 | 661% | 5 |
| 111 | 813% | 28 |
| 130 | 440% | 47 |
| 140 | 668% | 38 |
| 159 | 373% | 4 |
| 163 | 362% | 0.3 |
| 171 | 252% | 1 |
| 172 | 249% | 2 |
| 177 | 368% | 18 |
| 178 | 223% | 1 |
| 179 | 292% | 0.9 |
| 180 | 350% | 0.3 |
| 190 | 374% | 1 |
| 202 | 372% | 1 |
| 207 | 289% | 0.5 |
| 214 | 386% | 6 |

BIOLOGICAL EXAMPLE 2

Phosphoroylation of Acetyl CoA Carboxylase by AMPK Activators in db/+ Mice:

To assess the potential for AMPK activators to increase the phosphorylation of Acetyl COA Carboxylase (ACC) in liver and skeletal muscle, db/+ mice were dosed with AMPK activators at either 2 or 7 h prior to evaluation where phosphorylated ACC (p-ACC)/total ACC levels were compared in the tissues of vehicle and compound treated mice. Briefly, mice were anesthetized using gas anesthesia with 1-4% isoflurane administered to effect via nose cone. Once anesthetized, samples of liver and skeletal muscle (gastrocnemius) are removed, snap frozen in liquid nitrogen, and homogenized. Homogenates are analyzed for protein concentration and equal amounts of protein are assayed for total and phosphorylated ACC (p-ACC) levels using Meso Scale Discovery's Multi-array assay kit. MSD assay plates contain an electrode surface that is coated with streptavidin. Protein sample binds to streptavidin. The primary ACC or p-ACC specific antibody binds to protein and a secondary antibody labeled with MSD SULFO-TAG then binds to the primary antibody. The electrode surface of the MSD plate responds to an electrical stimulus and causes the SULFO-TAG labels bound to ACC and p-ACC to emit a light signal in proportion to the amount of p-ACC or total ACC present. The ratio of p-ACC/total ACC levels are determined for each sample and the ratio of p-ACC/total ACC levels for mice treated with AMPK activators is significantly elevated compared to the ratio of those treated with the vehicle control (significant elevations are described as differences where $p<0.05$).

BIOLOGICAL EXAMPLE 3

Inhibition of Fatty Acid Synthesis (FAS) by AMPK activators in db/+ Mice:

To determine the effect of AMPK activators on Fatty Acid Synthesis (FAS) in the liver, the effect of oral pre-dosing of compounds on the amount of $^3H$ incorporated into hepatic triglyceride is determined as described by Sakurai T, Miyazawa S, Shindo Y, and T. Hashimoto (Biochim Biophys Acta. 1974 Sep. 19; 360 (3):275-88). Briefly, mice (db/+, Jackson Laboratory, Maine) are orally dosed with AMPK activators at time=−8 h. Then at time=−1 h, mice are injected with 0.5 ml of 0.15 M NaCl containing 0.2 mCi of $^3H$ water per 100 g of body weight. At time 0, mice are sacrificed via cervical dislocation and livers are harvested for FAS analysis. To analyze livers for FAS, samples of liver are heated at 90° C. for 5 hours in a 4 M KOH/50% ethanol solution. Then the alkaline hydrolysate of liver is extracted with hexane and acidified to a pH<2 with 10 M $H_2SO_4$. The fatty acids of liver are then extracted from acidified hydrolysate with additional hexane, dried down with a stream of warm air, then re-suspended in scintillation fluid, and counted on a beta counter. The amount of fatty acids synthesized per gram of liver is calculated based on the amount of $^3H$ incorporated into hepatic triglyceride. The amount of $^3H$ radiolabelled fatty acids synthesized in mice with treated with an AMPK activator is significantly less than the amount of $^3H$ radiolabelled fatty acids synthesized in the control mice.

BIOLOGICAL EXAMPLE 4

In Vivo Study for Therapy with an AMPK Activator in Mice (Glucose Tolerance Test):

DIO mice are treated simultaneously with an effective dose of an AMPK-activated protein kinase activator.

Materials and Methods: Male C57BL/6NT mice (Taconic, 16-18 weeks old at the beginning of the drug administration) are used. Mice are given water and high fat diet D12492 (Research Diet Inc.) ad libitum. They are kept in an animal room which is maintained at 23±2 C temperature, 55±15% relative humidity and on a 12-hr light-dark cycle (7:00-19:00) during a quarantine and acclimatization period of 1 week. Animals are then administered vehicle (5 ml/kg of 0.5% methylcellulose in distilled water) by oral gavage twice-daily at 9 AM and 5 PM. After 9 days, stable body weight is observed. The following day (day −1), the mice are fasted for 4 hours and tail bled to determine the glucose and insulin levels. Animals are sorted into groups based on plasma glucose, insulin levels and body weight (n=8). The body weight and food in the hopper are recorded on day 0 before compound dosing is initiated. One of the groups is orally administered vehicle while the second group is administered an AMPK-activated protein kinase activator of the present invention at a dose of 30 mg/kg (5 ml/kg) twice-daily for 12 days by gavage. Body weight and food intake are measured every other day. On day 5, the animals are fasted 4 hours for measuring plasma glucose and insulin levels after morning dosing. At day 12, body weight and food intake are measured and animals receive their last morning dose. Mice again are fasted 4 hours, blood is collected at a set time point (t=0 min), and then challenged with dextrose orally (2 g/kg) Plasma glucose and insulin levels are determined from tail bleeds taken at 20 and 90 minutes after dextrose challenge. The plasma glucose and insulin excursion profile from t=0 to t=90 min is used to integrate an area under the curve (AUC) for each treatment. Percent inhibition values for each treatment are generated from the AUC data normalized to the C57BL/6NT mice feed with D7012. Preferred compounds of the present invention significantly reduce day 12 glucose and/or insulin AUC during the Oral Glucose Tolerance Test after an oral dose in the range of 0.1 to 100 mg/kg.

BIOLOGICAL EXAMPLE 5

Acute Food Intake Studies in Diet Induced Obese (DIO) Mice: General Procedure

Adult DIO mice are used in these studies. After at least 2 days of acclimation to the vivarium conditions (controlled humidity and temperature, lights on for 12 hours out of 24 hours) food (D12492 (Research Diet Inc.) is removed from rodent cages. An AMPK activator of the present invention or the vehicle is administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the AMPK activator is compared to the effect of the vehicle. The food intake of mice treated with an AMPK activator is significantly less than the food intake of control mice.

BIOLOGICAL EXAMPLE 6

Chronic Weight Reduction Studies in Diet Induced Obese (DIO) Mice: General Procedure Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

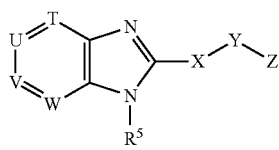

or a pharmaceutically acceptable salt thereof, wherein:
T is N;
U is $CR^1$;
V is $CR^2$;
W is $CR^4$;
X is selected from:
  (1) —O—, and
  (2) —O—$CH_2$—;
Y is selected from:
  (1) $C_{3-10}$cycloalkyl,
  (2) $C_{3-10}$cycloalkenyl,
  (3) $C_{2-10}$cycloheteroalkyl,
  (4) $C_{2-10}$cycloheteroalkenyl,
  (5) aryl, and
  (6) heteroaryl,
wherein cycloalkyl, cycloalkenyl, cycloheteroalkyl, cycloheteroalkenyl, aryl and heteroaryl are unsubstituted or substituted with 1, 2, 3 or 4 substituents selected from $R^b$;
Z is selected from:
  (1) oxo,
  (2) —$CF_3$,
  (3) —$C_{1-6}$alkyl,
  (4) —$(CH_2)_t$-halogen,
  (5) —$(CH_2)_nCO_2H$,
  (6) —$(CH_2)_nOH$, and
  (7) —$(CH_2)_nSO_2C_{1-6}$alkyl, wherein each $CH_2$ is unsubstituted or substituted with 1 or 2 substituents selected from $C_{1-6}$alkyl, —OH and —$NH_2$, and wherein each alkyl is unsubstituted or substituted with 1, 2, 3 or 4 substituents selected from $R^c$;
each $R^1$ and $R^2$ is independently selected from:
  (1) hydrogen,
  (2) halogen,
  (3) CN,
  (4) $CF_3$,
  (5) —$C_{1-6}$alkyl,
  (6) —$C_{2-6}$alkenyl,
  (7) —$C_{2-6}$alkynyl,
  (8) —$(CH_2)_pC_{3-10}$cycloalkyl,
  (9) —$(CH_2)_pC_{3-7}$cycloalkyl-aryl,
  (10) —$(CH_2)_pC_{3-7}$cycloalkyl-heteroaryl,
  (11) —$(CH_2)_pC_{4-10}$cycloalkenyl,
  (12) —$(CH_2)_pC_{4-7}$cycloalkenyl-aryl,
  (13) —$(CH_2)_pC_{4-7}$cycloalkenyl-heteroaryl,
  (14) —$(CH_2)_pC_{2-10}$cycloheteroalkyl,
  (15) —$(CH_2)_pC_{2-10}$cycloheteroalkenyl,
  (16) —$(CH_2)_p$aryl,
  (17) —$(CH_2)_p$aryl-$C_{1-8}$alkyl,
  (18) —$(CH_2)_p$aryl-$C_{2-8}$alkenyl,
  (19) —$(CH_2)_p$aryl-$C_{2-8}$alkynyl-$C_{1-8}$alkyl,
  (20) —$(CH_2)_p$aryl-$C_{2-8}$alkynyl-$C_{3-7}$cycloalkyl,
  (21) —$(CH_2)_p$aryl-$C_{2-8}$alkynyl-$C_{3-7}$cycloalkenyl,
  (22) —$(CH_2)_p$aryl-$C_{2-8}$alkynyl-$C_{2-10}$cycloheteroalkyl,
  (23) —$(CH_2)_p$aryl-$C_{2-8}$alkynyl-$C_{2-10}$cycloheteroalkenyl,
  (24) —$(CH_2)_p$aryl-$C_{2-8}$alkynyl-aryl,
  (25) —$(CH_2)_p$aryl-$C_{2-8}$alkynyl-heteroaryl,
  (26) —$(CH_2)_p$aryl-$C_{3-7}$cycloalkyl,
  (27) —$(CH_2)_p$aryl-$C_{2-10}$cycloheteroalkyl,
  (28) —$(CH_2)_p$aryl-$C_{2-10}$cycloheteroalkenyl,
  (29) —$(CH_2)_p$aryl-aryl,
  (30) —$(CH_2)_p$aryl-heteroaryl,
  (31) —$(CH_2)_p$heteroaryl,
  (32) —$C_{2-6}$alkenyl-alkyl,
  (33) —$C_{2-6}$alkenyl-aryl,
  (34) —$C_{2-6}$alkenyl-heteroaryl,
  (35) —$C_{2-6}$alkenyl-$C_{3-7}$cycloalkyl,
  (36) —$C_{2-6}$alkenyl-$C_{3-7}$cycloalkenyl,
  (37) —$C_{2-6}$alkenyl-$C_{2-7}$cycloheteroalkyl,
  (38) —$C_{2-6}$alkenyl-$C_{2-7}$cycloheteroalkenyl,
  (39) —$C_{2-6}$alkynyl-$(CH_2)_{1-3}$—O-aryl,
  (40) —$C_{2-6}$alkynyl-alkyl,
  (41) —$C_{2-6}$alkynyl-aryl,
  (42) —$C_{2-6}$alkynyl-heteroaryl,
  (43) —$C_{2-6}$alkynyl-$C_{3-7}$cycloalkyl,
  (44) —$C_{2-6}$alkynyl-$C_{3-7}$cycloalkenyl,
  (45) —$C_{2-6}$alkynyl-$C_{2-7}$cycloheteroalkyl,
  (46) —$C_{2-6}$alkynyl-$C_{2-7}$cycloheteroalkenyl, and
  (47) —$C(O)NH$—$(CH_2)_{0-3}$phenyl,
wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$,
provided that at least one of and only one of $R^1$ and $R^2$ is selected from the group consisting of:
hydrogen, halogen, —CN, —$CF_3$, —$C_{1-6}$alkyl, —$C_{2-6}$alkenyl and —$C_{2-6}$alkynyl;

each R$^4$ is independently selected from:
(1) hydrogen,
(2) halogen,
(3) —C$_{1-6}$ alkyl,
(4) —C$_{2-6}$ alkenyl,
(5) —C$_{2-6}$ alkynyl,
(6) —CN,
(7) —CF$_3$,
(8) —OH,
(9) —OC$_{1-6}$alkyl,
(10) —NH$_2$,
(11) —NHC$_{1-6}$alkyl,
(12) —N(C$_{1-6}$alkyl)$_2$,
(13) —SC$_{1-6}$alkyl,
(14) —SOC$_{1-6}$alkyl,
(15) —SO$_2$C$_{1-6}$alkyl,
(16) —NHSO$_2$C$_{1-6}$alkyl,
(17) —NHC(O)C$_{1-6}$alkyl,
(18) —SO$_2$NHC$_{1-6}$alkyl, and
(19) —C(O)NHC$_{1-6}$alkyl;
R$^5$ is selected from:
(1) hydrogen,
(2) —C$_{1-6}$alkyl,
(3) —CH$_2$CO$_2$H, and
(4) —CH$_2$CO$_2$C$_{1-6}$alkyl;
each R$^a$ is independently selected from the group consisting of:
(1) —(CH$_2$)$_m$-halogen,
(2) oxo,
(3) —(CH$_2$)$_m$OH,
(4) —(CH$_2$)$_m$N(Rj)$_2$,
(5) —(CH$_2$)$_m$NO$_2$,
(6) —(CH$_2$)$_m$CN,
(7) —C$_{1-6}$alkyl,
(8) —(CH$_2$)$_m$CF$_3$,
(9) —(CH$_2$)$_m$OCF$_3$,
(10) —O—(CH$_2$)$_m$—OC$_{1-6}$alkyl,
(11) —(CH$_2$)$_m$C(O)N(Rj)$_2$,
(12) —(CH$_2$)$_m$C(=N—OH)N(Rj)$_2$,
(13) —(CH$_2$)$_m$OC$_{1-6}$alkyl,
(14) —(CH$_2$)$_m$O—(CH$_2$)$_m$—C$_{3-7}$cycloalkyl,
(15) —(CH$_2$)$_m$O—(CH$_2$)$_m$—C$_{2-7}$cycloheteroalkyl,
(16) —(CH$_2$)$_m$O—(CH$_2$)$_m$-aryl,
(17) —(CH$_2$)$_m$O—(CH$_2$)$_m$-heterolaryl,
(18) —(CH$_2$)$_m$SC$_{1-6}$alkyl,
(19) —(CH$_2$)$_m$S(O)C$_{1-6}$alkyl,
(20) —(CH$_2$)$_m$SO$_2$C$_{1-6}$alkyl,
(21) —(CH$_2$)$_m$SO$_2$C$_{3-7}$cycloalkyl,
(22) —(CH$_2$)$_m$SO$_2$C$_{2-7}$cycloheteroalkyl,
(23) —(CH$_2$)$_m$SO$_2$-aryl,
(24) —(CH$_2$)$_m$SO$_2$-heteroaryl,
(25) —(CH$_2$)$_m$SO$_2$NHC$_{1-6}$alkyl,
(26) —(CH$_2$)$_m$SO$_2$NHC$_{3-7}$cycloalkyl,
(27) —(CH$_2$)$_m$SO$_2$NHC$_{2-7}$cycloheteroalkyl,
(28) —(CH$_2$)$_m$SO$_2$NH-aryl,
(29) —(CH$_2$)$_m$SO$_2$NH-heteroaryl,
(30) —(CH$_2$)$_m$NHSO$_2$—C$_{1-6}$alkyl,
(31) —(CH$_2$)$_m$NHSO$_2$—C$_{3-7}$cycloalkyl,
(32) —(CH$_2$)$_m$NHSO$_2$—C$_{2-7}$cycloheteroalkyl,
(33) —(CH$_2$)$_m$NHSO$_2$-aryl,
(34) —(CH$_2$)$_m$NHSO$_2$NH-heteroaryl,
(35) —(CH$_2$)$_m$N(R$^j$)—C$_{1-6}$alkyl,
(36) —(CH$_2$)$_m$N(R$^j$)—C$_{3-7}$cycloalkyl,
(37) —(CH$_2$)$_m$N(R$^j$)—C$_{2-7}$cycloheteroalkyl,
(38) —(CH$_2$)$_m$N(R$^j$)—C$_{2-7}$cycloheteroalkenyl,
(39) —(CH$_2$)$_m$N(R$^j$)-aryl,
(40) —(CH$_2$)$_m$N(R$^j$)-heteroaryl,
(41) —(CH$_2$)$_m$C(O)R$^f$,
(42) —(CH$_2$)$_m$C(O)N(R$^j$)$_2$,
(43) —(CH$_2$)$_m$N(Rj)C(O)N(R$^j$)$_2$,
(44) —(CH$_2$)$_m$CO$_2$H,
(45) —(CH$_2$)$_m$OCOH,
(46) —(CH$_2$)$_m$CO$_2$R$^f$,
(47) —(CH2)$_m$OCOR$^f$,
(48) —(CH2)$_m$C$_{3-7}$cycloalkyl,
(49) —(CH2)$_m$C$_{3-7}$cycloalkenyl,
(50) —(CH2)$_m$C$_{2-6}$cycloheteroalkyl,
(51) —(CH2)$_m$C$_{2-6}$cycloheteroalkenyl,
(52) —(CH2)$_m$aryl, and
(53) —(CH2)$_m$heteroaryl,
wherein each CH2 is unsubstituted or substituted with 1 or 2 substituents selected from: oxo, —(CH$_2$)$_{t-3}$OH, —CN, —NH$_2$, —NH(C$_{1-6}$alkyl), —N(C$_{1-6}$alkyl)$_2$, —C$_{1-6}$alkyl (CH$_3$), OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, OC$_{1-6}$alkyl, halogen, —CH$_2$F, —CHF$_2$, —CF$_3$, —CO$_2$H, —CO$_2$C$_{1-6}$alkyl, -SO$_2$C$_{1-6}$ alkyl, —C$_{3-7}$cycloalkyl, phenyl, CH$_2$phenyl, heteroaryl and CH$_2$heteroaryl;
each R$^b$ is independently selected from:
(1) hydrogen,
(2) —C$_{1-6}$alkyl,
(3) —C$_{3-6}$cycloalkyl,
(4) —C$_{3-6}$cycloalkenyl,
(5) —C$_{2-6}$cycloheteroalkyl,
(6) —C$_{2-6}$cycloheteroalkenyl,
(7) aryl,
(8) heteroaryl,
(9) —(CH$_2$)t-halogen,
(10) —(CH$_2$)$_s$—OH,
(11) —NO$_2$,
(12) —NH$_2$,
(13) —NH(C$_{1-6}$alkyl),
(14) —N(C$_{1-6}$alkyl)$_2$,
(15) —OC$_{1-6}$alkyl,
(16) —(CH$_2$)$_q$CO$_2$H,
(17) —(CH$_2$)$_q$CO$_2$C$_{1-6}$alkyl,
(18) —CF$_3$,
(19) —CN,
(20) —SO$_2$C$_{1-6}$alkyl, and
(21) —(CH$_2$)sCON(Re)$_2$,
wherein each CH$_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens;
each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl—OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,

(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$Rf,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl, wherein each CH$_2$ is unsubstituted or substituted with 1 or 2 substituents selected from: oxo, —OH, —CN, —N(Rh)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;

each R$^e$, R$^g$ and R$^h$ is independently selected from:
(1) hydrogen,
(2) —C$_{1-6}$alkyl, and
(3) —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^j$ is independently selected from:
(1) hydrogen,
(2) C$_{1-6}$alkyl,
(3) C$_{3-6}$cycloalkyl,
(4) —C(O)R$^i$, and
(5) —SO$_2$R$^i$, wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^f$ and R$^i$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;

n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4; and
t is 0, 1, 2, 3 or 4.

2. The compound according to claim 1 wherein:
T is N;
U is CR$^1$;
V is CR$^2$;
W is CR$^4$;
X is selected from:
(1) —O—, and
(2) —O—CH$_2$—;

Y is selected from:
(1) C$_{3-10}$cycloalkyl,
(2) C$_{3-10}$cycloalkenyl,
(3) C$_{2-10}$cycloheteroalkyl,
(4) C$_{2-10}$cycloheteroalkenyl,
(5) aryl, and
(6) heteroaryl, wherein cycloalkyl, cycloalkenyl, cycloheteroalkyl, cycloheteroalkenyl, aryl and heteroaryl are unsubstituted or substituted with 1, 2, 3 or 4 substituents selected from R$^b$;

Z is selected from:
(1) oxo,
(2) —CF$_3$,
(3) —C$_{1-6}$alkyl,
(4) —(CH$_2$)$_t$-halogen,
(5) —(CH$_2$)$_n$CO$_2$H,
(6) —(CH$_2$)$_n$OH, and
(7) —(CH$_2$)SO$_2$C$_{1-6}$alkyl, wherein each CH$_2$ is unsubstituted or substituted with 1 or 2 substituents selected from C$_{1-6}$alkyl, —OH and —NH$_2$, and wherein each alkyl is unsubstituted or substituted with 1, 2, 3 or 4 substituents selected from R$^c$;

each R$^1$ and R$^2$ is independently selected from:
(1) hydrogen,
(2) halogen,
(3) CN,
(4) CF$_3$,
(5) —C$_{1-6}$alkyl,
(6) —C$_{2-6}$alkenyl,
(7) —C$_{2-6}$alkynyl,
(8) —(CH$_2$)$_p$C$_{3-10}$cycloalkyl,
(9) —(CH$_2$)$_p$C$_{3-7}$cycloalkyl-aryl,
(10) —(CH$_2$)$_p$C$_{3-7}$cycloalkyl-heteroaryl,
(11) —(CH$_2$)$_p$C$_{4-10}$cycloalkenyl,
(12) —(CH$_2$)$_p$C$_{4-7}$cycloalkenyl-aryl,
(13) —(CH$_2$)$_p$C$_{4-7}$cycloalkenyl-heteroaryl,
(14) —(CH$_2$)$_p$C$_{2-10}$cycloheteroalkyl,
(15) —(CH$_2$)$_p$C$_{2-10}$cycloheteroalkenyl,
(16) —(CH$_2$)$_p$aryl,
(17) —(CH$_2$)$_p$aryl—C$_{3-7}$cycloalkyl,
(18) —(CH$_2$)$_p$aryl—C$_{2-7}$cycloheteroalkyl,
(19) —(CH$_2$)$_p$aryl-aryl,
(20) —(CH$_2$)$_p$aryl-heteroaryl,
(21) —(CH$_2$)$_p$heteroaryl,
(22) —C$_{2-6}$alkenyl-alkyl,
(23) —C$_{2-6}$alkenyl-aryl,
(24) —C$_{2-6}$alkenyl-heteroaryl,
(25) —C$_{2-6}$alkenyl—C$_{3-7}$cycloalkyl,
(26) —C$_{2-6}$alkenyl—C$_{3-7}$cycloalkenyl,
(27) —C$_{2-6}$alkenyl—C$_{2-7}$cycloheteroalkyl,
(28) —C$_{2-6}$alkenyl—C$_{2-7}$cycloheteroalkenyl,
(29) —C$_{2-6}$alkynyl—(CH$_2$)$_{1-3}$—O—aryl,
(30) —C$_{2-6}$alkynyl-alkyl,
(31) —C$_{2-6}$alkynyl-aryl,
(32) —C$_{2-6}$alkynyl-heteroaryl,
(33) —C$_{2-6}$alkynyl—C$_{3-7}$cycloalkyl,
(34) —C$_{2-6}$alkynyl—C$_{3-7}$cycloalkenyl,
(35) —C$_{2-6}$alkynyl—C$_{2-7}$cycloheteroalkyl,
(36) —C$_{2-6}$alkynyl—C$_{2-7}$cycloheteroalkenyl, and
(37) —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl;

each $R^4$ is independently selected from:
(1) hydrogen,
(2) halogen,
(3) —$C_{1-6}$ alkyl,
(4) —$C_{2-6}$ alkenyl,
(5) —$C_{2-6}$ alkenyl,
(6) —CN,
(7) —$CF_3$,
(8) —OH,
(9) —$OC_{1-6}$alkyl,
(10) —$NH_2$,
(11) —$NHC_{1-6}$alkyl,
(12) —$N(C_{1-6}alkyl)_2$,
(13) —$SC_{1-6}$alkyl,
(14) —$SOC_{1-6}$alkyl,
(15) —$SO_2C_{1-6}$alkyl,
(16) —$NHSO_2C_{1-6}$alkyl,
(17) —$NHC(O)C_{1-6}$alkyl,
(18) —$SO_2NHC_{1-6}$alkyl, and
(19) —$C(O)NHC_{1-6}$alkyl;

$R^5$ is selected from:
(1) hydrogen,
(2) —$C_{1-6}$alkyl,
(3) —$CH_2CO_2H$, and
(4) —$CH_2CO_2C_{1-6}$alkyl;

each $R^a$ is independently selected from the group consisting of:
(1) halogen,
(2) oxo,
(3) —$(CH_2)_m OH$,
(4) —$(CH_2)_m N(Rj)_2$,
(5) —$(CH_2)_m NO_2$,
(6) —$(CH_2)_m CN$,
(7) —$C_{1-6}$alkyl,
(8) —$(CH_2)_m CF_3$,
(9) —$(CH_2)_m OCF_3$,
(10) —$OCH_2OC_{1-6}$alkyl,
(11) —$(CH_2)_m C(O)N(Rj)_2$,
(12) —$(CH_2)_m C(=N—OH)N(Rj)_2$,
(13) —$(CH_2)_m OC_{1-6}$alkyl,
(14) —$(CH_2)_m O—(CH_2)_m—C_{3-7}$cycloalkyl,
(15) —$(CH_2)_m O—(CH_2)_m—C_{2-7}$cycloheteroalkyl,
(16) —$(CH_2)_m O—(CH_2)_m$-aryl,
(17) —$(CH_2)_m O—(CH_2)_m$-heteroaryl,
(18) —$(CH_2)_m SC_{1-6}$alkyl,
(19) —$(CH_2)_m S(O)C_{1-6}$alkyl,
(20) —$(CH_2)_m SO_2C_{1-6}$alkyl,
(21) —$(CH_2)_m SO_2C_{3-7}$cycloalkyl,
(22) —$(CH_2)_m SO_2C_{2-7}$cycloheteroalkyl,
(23) —$(CH_2)_m SO_2$-aryl,
(24) —$(CH_2)_m SO_2$-heteroaryl,
(25) —$(CH_2)_m SO_2NHC_{1-6}$alkyl,
(26) —$(CH_2)_m SO_2NHC_{3-7}$cycloalkyl,
(27) —$(CH_2)_m SO_2NHC_{2-7}$cycloheteroalkyl,
(28) —$(CH_2)_m SO_2NH$-aryl,
(29) —$(CH_2)_m SO_2NH$-heteroaryl,
(30) —$(CH_2)_m NHSO_2—C_{1-6}$alkyl,
(31) —$(CH_2)_m NHSO_2—C_{3-7}$cycloalkyl,
(32) —$(CH_2)_m NHSO_2—C_{2-7}$cycloheteroalkyl,
(33) —$(CH_2)_m NHSO_2$-aryl,
(34) —$(CH_2)_m NHSO_2NH$-heteroaryl,
(35) —$(CH_2)_m C(O)R^f$,
(36) —$(CH_2)_m C(O)N(Rj)_2$,
(37) —$(CH_2)_m N(Rj)C(O)N(Rj)_2$,
(38) —$(CH_2)_m CO_2H$,
(39) —$(CH_2)_m OCOH$,
(40) —$(CH_2)_m CO_2 Rf$,
(41) —$(CH_2)_m OCOR^f$,
(42) —$(CH_2)_m C_{3-7}$cycloalkyl,
(43) —$(CH_2)_m C_{3-7}$cycloalkenyl,
(44) —$(CH_2)_m C_{2-6}$cycloheteroalkyl,
(45) —$(CH_2)_m C_{2-6}$cycloheteroalkenyl,
(46) —$(CH_2)_m$aryl, and
(47) —$(CH_2)_m$heteroaryl,
wherein each $CH_2$ is unsubstituted or substituted with 1 or 2 substituents selected from: oxo, —$(CH_2)_{0-3}$ OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, -$SO_2C_{1-6}$ alkyl, —$C_{3-7}$cycloalkyl, phenyl, $CH2$phenyl, heteroaryl and $CH_2$heteroaryl;

each $R^b$ is independently selected from:
(1) hydrogen,
(2) —$C_{1-6}$alkyl,
(3) —$C_{3-6}$cycloalkyl,
(4) —$C_{3-6}$cycloalkenyl,
(5) —$C_{2-6}$cycloheteroalkyl,
(6) —$C_{2-6}$cycloheteroalkenyl,
(7) aryl,
(8) heteroaryl,
(9) —$(CH_2)$t-halogen,
(10) —$(CH_2)$s-OH,
(11) —$NO_2$,
(12) —$NH_2$,
(13) —$NH(C_{1-6}ablkyl)$,
(14) —$N(C_{1-6}alkyl)_2$,
(15) —$OC_{1-6}$alkyl,
(16) —$(CH_2)_q CO_2H$,
(17) —$(CH_2)_q CO_2C_{1-6}$alkyl,
(18) —$CF_3$,
(19) —CN,
(20) —$SO_2C_{1-6}$alkyl, and
(21) —$(CH_2)_s CON(R^e)_2$,
wherein each $CH_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens;

each $R^c$ is independently selected from:
(1) halogen,
(2) oxo,
(3) —$(CH_2)_r OH$,
(4) —$(CH_2)_r N(R^e)_2$,
(5) —$(CH_2)_r CN$,
(6) —$C_{1-6}$alkyl,
(7) —$CF_3$,
(8) —$C_{1-6}$alkyl—OH, (9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$Rf,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl,
wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$ alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$ alkyl, halogen, —CH$_2$F, —CHF$_2$, —CF$_3$, —CO$_2$H, —CO$_2$C$_{1-6}$ alkyl, —C$_{3-7}$cycloalkyl and heteroaryl;
each R$^e$, R$^g$ and R$^h$ is independently selected from:
(1) hydrogen,
(2) —C$_{1-6}$alkyl, and
(3) —O—C$_{1-6}$alkyl,
wherein alkyl is unsubstituted or substituted with 1, 2, 3 or 4 substituents selected from: —OH, oxo, halogen, C$_{1-6}$ alkyl, —OC$_{1-6}$ alkyl, —NH$_2$, —NH(C$_{1-6}$ alkyl), and —N(C$_{1-6}$alkyl)$_2$;
each R$^j$ is independently selected from:
(1) hydrogen,
(2) C$_{1-6}$alkyl,
(3) C$_{3-6}$cycloalkyl,
(4) —C(O)R$^i$, and
(5) —SO$_2$R$^i$,
wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH (C$_{1-6}$alkyl), and —N(C$_{1-6}$ alkyl)$_2$;
each R$^f$ and R$^i$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF2, —CF$_3$, —CO$_2$H, —CO$_2$C$_{1-6}$alkyl, —C$_{3-7}$cycloalkyl, and heteroaryl;
n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4; and
t is 0, 1, 2, 3 or 4,
or a pharmaceutically acceptable salt thereof.

3. The compound according to claim 2, wherein X is —O—; or a pharmaceutically acceptable salt thereof.

4. The compound according to claim 2, wherein Y is selected from:
(1) C$_{3-10}$cycloalkyl,
(2) C$_{2-10}$cycloheteroalkyl, and
(3) aryl,
wherein cycloalkyl, cycloheteroalkyl and aryl are unsubstituted or substituted with 1, 2, 3 or 4 substituents selected from Rb; or a pharmaceutically acceptable salt thereof.

5. The compound according to claim 4, wherein Y is selected from:
(1) C$_{3-7}$cycloalkyl,
(2) C$_{2-10}$cycloheteroalkyl, and
(3) phenyl,
wherein each cycloalkyl, cycloheteroalkyl and phenyl is unsubstituted or substituted with 1, 2, 3 or 4 substituents selected from R$_b$; or a pharmaceutically acceptable salt thereof.

6. The compound according to claim 2, wherein Z is selected from:
(1) —(CH$_2$)$_n$CO$_2$H, and
(2) —(CH$_2$)$_n$OH,
wherein each CH$_2$ is unsubstituted or substituted with 1 or 2 substituents selected from C$_{1-6}$alkyl, —OH and —NH$_2$; or a pharmaceutically acceptable salt thereof.

7. The compound according to claim 1, wherein each R$^1$ and R$^2$ is independently selected from:
(1) halogen,
(2) —C$_{4-10}$cycloalkenyl,
(3) -phenyl,
(4) -phenyl—C$_{2-8}$alkynyl—C$_{1-8}$alkyl,
(5) -phenyl—C$_{2-3}$alkynyl—C$_{3-7}$cycloalkyl,
(6) -phenyl—C$_{2-3}$alkynyl—C$_{2-10}$cycloheteroalkyl,
(7) -phenyl—C$_{3-7}$cycloalkyl,
(8) -phenyl—C$_{2-7}$cycloheteroalkyl,
(9) -phenyl—C$_{2-10}$cycloheteroalkenyl,
(10) -phenyl-aryl,
(11) -phenyl-heteroaryl,
(12) -heteroaryl, and
(13) —C$_{2-6}$alkynyl-phenyl,
and wherein each alkyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, provided that at least one of and only one of R$^1$ and R$^2$ is selected from halogen; or a pharmaceutically acceptable salt thereof.

8. The compound according to claim 7, wherein R$^1$ is independently selected from:
(1) —C$_{4-10}$cycloalkenyl,
(2) -phenyl,
(3) -phenyl—C$_2$alkynylC$_{1-5}$alkyl,
(4) -phenyl—C$_{2-3}$alkynyl- C$_{3-7}$cycloalkyl,
(5) -phenyl—C$_{2-3}$alkynyl—C$_{2-10}$cycloheteroalkyl,
(6) -phenyl—C$_{3-7}$cycloalkyl,
(7) -phenyl—C$_{2-7}$cycloheteroalkyl,
(8) -phenyl—C$_{2-10}$cycloheteroalkenyl,
(9) -phenyl-phenyl,
(10) -phenyl-heteroaryl,
(11) -heteroaryl, and
(12) —C$_{2-6}$alkynyl-phenyl,
wherein each alkyl, alkynyl, cycloalkyl, cycloalkenyl, cycloheteroalkyl, cycloheteroalkenyl, phenyl and heteroaryl is unsubstituted or substituted with 1, 2, 3 or 4 substituents independently selected from R$^a$; and
R$^2$ is selected from halogen;
or a pharmaceutically acceptable salt thereof.

9. The compound according to claim 8, wherein each R$^1$ is independently selected from:

(1) -phenyl—$C_{2-7}$cycloheteroalkyl,
(2) -phenyl—$C_{2-10}$cycloheteroalkenyl,
(3) -phenyl-phenyl, and
(4) -phenyl-heteroaryl,
wherein each cycloheteroalkyl, cycloheteroalkenyl, heteroaryl and phenyl is unsubstituted or substituted with 1, 2, 3 or 4 substituents independently selected from Ra; and R2 is halogen;
or a pharmaceutically acceptable salt thereof.

10. The compound according to claim 2, wherein each $R^1$ and $R^2$ is independently selected from:
    (1) halogen,
    (2) —$C_{4-10}$cycloalkenyl,
    (3) -phenyl,
    (4) -phenyl—$C_{3-7}$cycloalkyl,
    (5) -phenyl—$C_{2-7}$cycloheteroalkyl,
    (6) -phenyl-aryl,
    (7) -phenyl-heteroaryl,
    (8) -heteroaryl, and
    (9) —$C_{2-6}$alkynyl-phenyl,
wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloalkenyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from halogen; or a pharmaceutically acceptable salt thereof.

11. The compound according to claim 10, wherein $R^1$ is independently selected from:
    (1) —$C_{4-10}$ocycloalkenyl,
    (2) -phenyl,
    (3) -phenyl—$C_{3-7}$cycloalkyl,
    (4) -phenyl—$C_{2-7}$cycloheteroalkyl,
    (5) -phenyl-phenyl,
    (6) -phenyl-heteroaryl,
    (7) -heteroaryl, and
    (8) —C2_6alkynyl-phenyl,
wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)2$, and wherein each cycloalkyl, cycloalkenyl, cycloheteroalkyl, phenyl and heteroaryl is unsubstituted or substituted with 1, 2, 3 or 4 substituents independently selected from $R^a$; and
R2 is selected from: halogen;
or a pharmaceutically acceptable salt thereof.

12. The compound according to claim 11, wherein each R1 is independently selected from:
    (1) -phenyl—$C_{2-7}$cycloheteroalkyl, and
    (2) -phenyl-phenyl,
wherein each cycloheteroalkyl and phenyl is unsubstituted or substituted with 1, 2, 3 or 4 substituents independently selected from $R^a$, and
$R^2$ is selected from halogen;
or a pharmaceutically acceptable salt thereof.

13. The compound according to claim 2, wherein R4 is hydrogen or absent; and $R^5$ is hydrogen; or a pharmaceutically acceptable salt thereof.

14. The compound according to claim 1 wherein:
T is N;
U is —$CR^1$—;
V is —$CR^2$—;
W is —$CR4$—;
X is selected from:
    (1) —O—, and
    (2) —O—$CH_2$—;
Y is selected from:
    (1) —$C_{3-10}$ycloalkyl,
    (2) —$C_{2-10}$cycloheteroalkyl, and
    (3) -phenyl,
wherein cycloalkyl, cycloheteroalkyl and phenyl are unsubstituted or substituted with 1, 2, 3 or 4 substituents selected from $R^b$;
Z is selected from:
    (1) oxo,
    (2) —$CF_3$,
    (3) —$C_{1-6}$alkyl,
    (4) —$(CH_2)_r$-halogen,
    (5) —$(CH_2)_nCO_2H$,
    (6) —$(CH_2)_nOH$, and
    (7) —$(CH_2)_nSO_2C_{1-6}$alkyl,
wherein each $CH_2$ is unsubstituted or substituted with 1 or 2 substituents selected from $C_{1-6}$ alkyl, —OH and —$NH_2$, and wherein each alkyl is unsubstituted or substituted with 1, 2, 3 or 4 substituents selected from $R^c$;
$R^1$ is independently selected from:
    (1) —$C_{4-10}$cycloalkenyl,
    (2) -phenyl,
    (3) -phenyl—$C_2$alkynyl$C_{1-5}$alkyl,
    (4) -phenyl—$C_{2-3}$alkynyl- $C_{3-7}$cycloalkyl,
    (5) -phenyl—$C_{2-3}$alkynyl—$C_{2-10}$cycloheteroalkyl,
    (6) -phenyl—$C_{3-7}$cycloalkyl,
    (7) -phenyl—$C_{2-7}$cycloheteroalkyl,
    (8) -phenyl—$C_{2-10}$cycloheteroalkenyl,
    (9) -phenyl-phenyl,
    (10) -phenyl-heteroaryl,
    (11) -heteroaryl, and
    (12) —$C_{2-6}$alkynyl-phenyl,
wherein each alkyl, alkynyl, cycloalkyl, cycloalkenyl, cycloheteroalkyl, cycloheteroalkenyl, phenyl and heteroaryl is unsubstituted or substituted with 1, 2, 3 or 4 substituents independently selected from $R^a$;
$R^2$ is selected from halogen;
$R^4$ is hydrogen; and
$R^5$ is hydrogen;
or a pharmaceutically acceptable salt thereof.

15. The compound according to claim 2 wherein:
T is N;
U is —$CR^1$—;
V is —$CR^2$—;
W is —$CR^4$—;
X is selected from:
    (1) —O—, and
    (2) —O—$CH_2$—;
Y is selected from:
    (1) $C_{3-10}$cycloalkyl,
    (2) $C_{2-10}$cycloheteroalkyl, and
    (3) phenyl,
wherein cycloalkyl, cycloheteroalkyl and phenyl are unsubstituted or substituted with 1, 2, 3 or 4 substituents selected from $R^b$;
Z is selected from:
    (1) oxo,
    (2) $CF_3$,
    (3) —$C_{1-6}$alkyl,
    (4) —$(CH_2)_r$-halogen, (5) —(CH2)$_n$CO$_2$H, (6) —(CH2)$_n$OH, and (7) —(CH2)$_n$SO$_2$C$_{1-6}$alkyl, wherein each CH$_2$ is unsubstituted or substituted with 1 or 2 substituents selected from C$_{1-6}$ alkyl, —OH and —NH$_2$, and wherein each alkyl is unsubstituted or substituted with 1, 2, 3 or 4 substituents selected from R$^c$;

R$^1$ is independently selected from:

(1) —C$_{4-10}$cycloalkenyl, (2) -phenyl, (3) -phenyl—C$_{3-7}$cycloalkyl, (4) -phenyl—C$_{2-7}$cycloheteroalkyl, (5) -phenyl-heteroaryl, (6) -phenyl-phenyl, (7) -heteroaryl, and (8) —C$_{2-6}$alkynyl-phenyl, wherein each alkynyl is unsubstituted or substituted with 1, 2 or 3 substituents selected from:

halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, phenyl and heteroaryl is unsubstituted or substituted with 1, 2, 3 or 4 substituents independently selected from R$^a$;

R$^2$ is selected from halogen;

R$^4$ is hydrogen; and

R$^5$ is hydrogen;

or a pharmaceutically acceptable salt thereof.

16. The compound according to claim 2 wherein:

T is N;

U is —CR$^1$—;

V is —CR$^2$—;

W is —CR$^4$—;

X is —O—;

Y is selected from:

(1) C$_{3-7}$cycloalkyl, (2) C$_{2-10}$cycloheteroalkyl, and (3) phenyl, wherein each cycloalkyl, cycloheteroalkyl and phenyl is unsubstituted or substituted with 1, 2, 3 or 4 substituents selected from R$_b$;

Z is selected from:

(1) —(CH$_2$)$_n$CO$_2$H, and (2) —(CH$_2$)$_n$OH, wherein each CH2 is unsubstituted or substituted with 1 or 2 substituents selected from C$_{1-6}$alkyl and —OH;

R$^1$ is selected from:

(1) -phenyl—C$_{2-7}$cycloheteroalkyl, and (2) -phenyl-phenyl, wherein each cycloheteroalkyl and phenyl is unsubstituted or substituted with 1, 2, 3 or 4 substituents independently selected from R$^a$;

R$^2$ is selected from halogen;

R$^4$ is hydrogen; and

R$^5$ is hydrogen;

or a pharmaceutically acceptable salt thereof.

17. The compound according to claim 16, selected from:

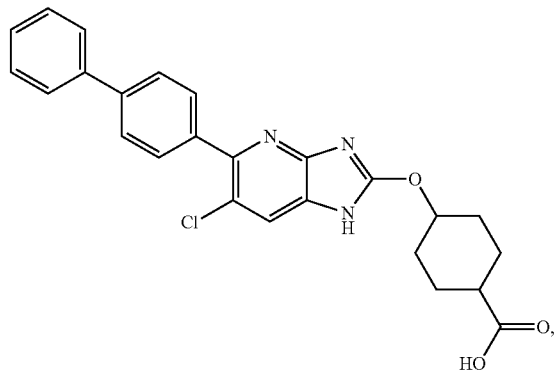

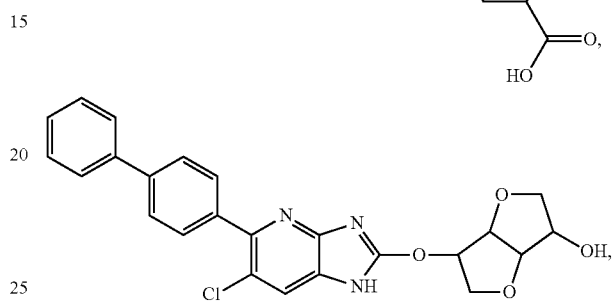

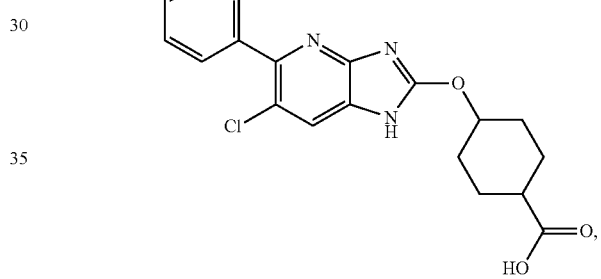

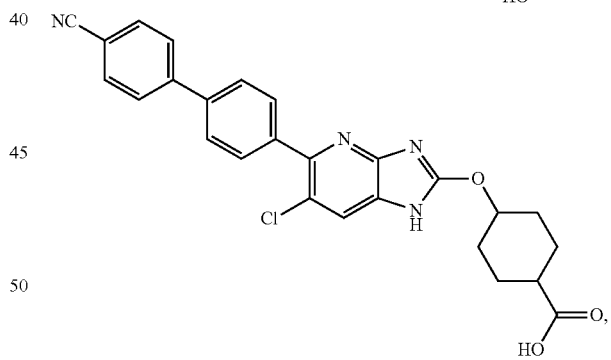

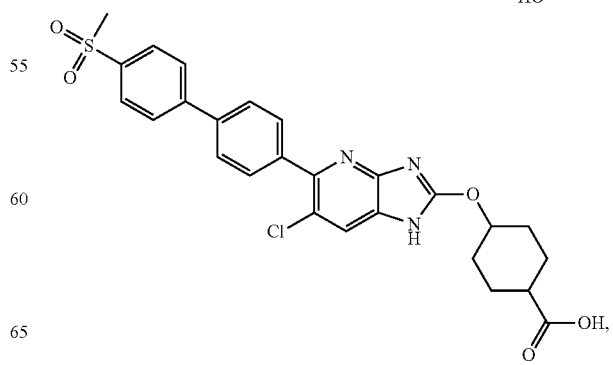

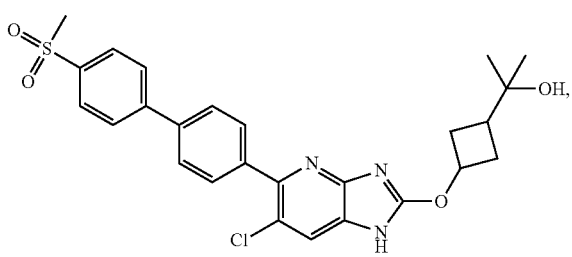

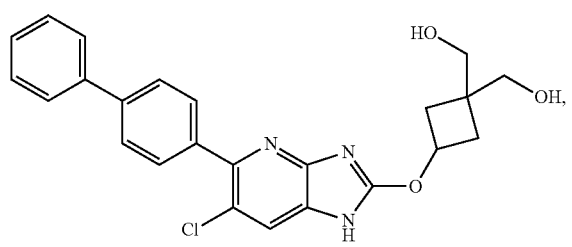

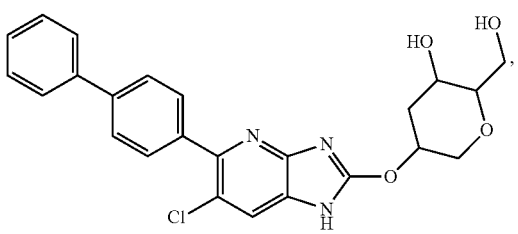

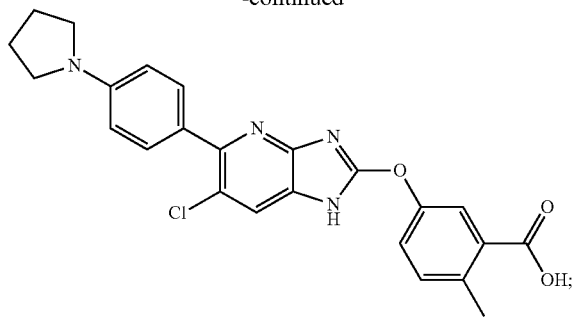

or a pharmaceutically acceptable salt thereof.

18. The compound according to claim 1 wherein:
T is N;
U is —CR$^1$—;
V is —CR$^2$—;
W is —CR$^4$—;
X is —O—;
Y is selected from C$_{2-10}$cycloheteroalkyl, wherein each cycloheteroalkyl is unsubstituted or substituted with 1, 2, 3 or 4 substituents selected from R$^b$;
Z is selected from: —(CH$_2$)$_n$ OH;
R$^1$ is independently selected from:
  (1) -phenyl—C$_{2-10}$ cycloheteroalkenyl,
  (2) -biphenyl, and
  (3) -phenyl-heteroaryl,
wherein each cycloheteroalkenyl, phenyl, biphenyl and heteroaryl is unsubstituted or substituted with 1, 2, 3 or 4 substituents independently selected from R$^a$;
R$^2$ is selected from halogen;
R$^4$ is hydrogen; and
R$^5$ is hydrogen;
or a pharmaceutically acceptable salt thereof.

19. The compound according to claim 18, selected from:

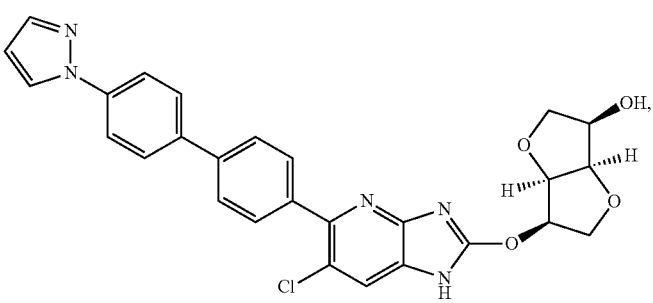

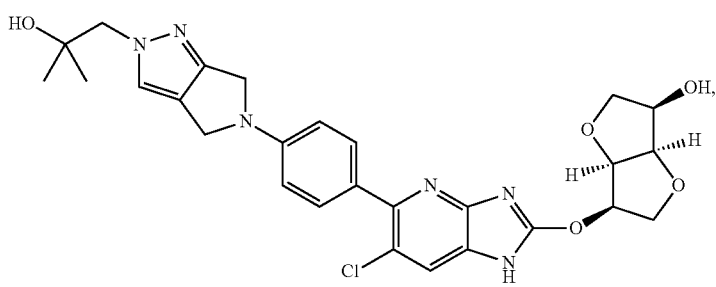

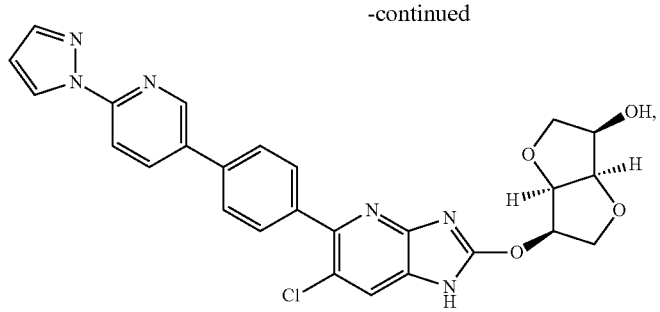

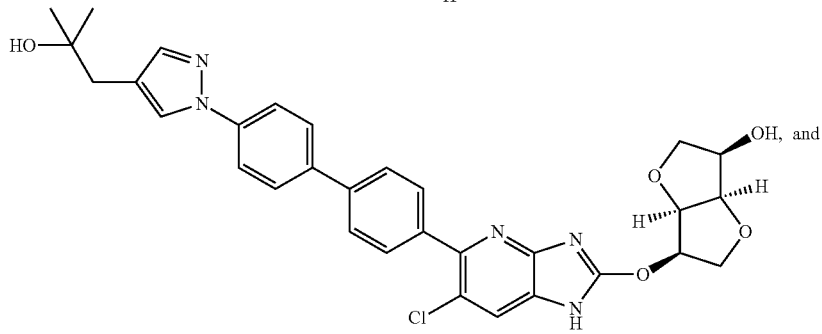

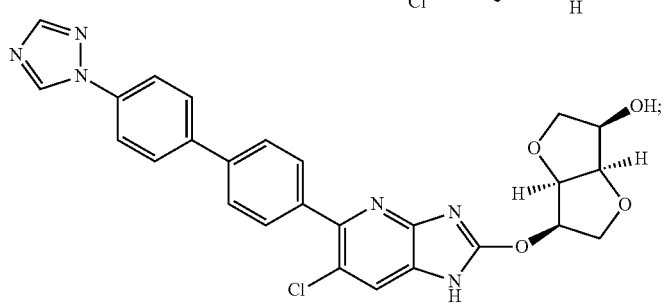

or a pharmaceutically acceptable salt thereof.

20. A composition comprising a compound according to claim 1 and a pharmaceutically acceptable carrier.

21. A composition comprising a compound according to claim 1 and a compound selected from simvastatin, ezetimibe, taranabant and sitagliptin; and a pharmaceutically acceptable carrier.

22. A method of treating a disorder, condition or disease responsive to the activation of AMP-activated protein kinase in a patient in need thereof comprising administration of a therapeutically effective amount of a compound according to claim 1, wherein the disorder, condition, or disease is selected from the group consisting of:

Type 2 diabetes, hyperglycemia, Metabolic Syndrome, obesity, hypercholesterolemia, hypertension, and cancer.

* * * * *